United States Patent [19]

Natsugari et al.

[11] Patent Number: 5,482,967
[45] Date of Patent: Jan. 9, 1996

[54] CONDENSED HETEROCYCLIC COMPOUNDS, THEIR PRODUCTION AND USE

[75] Inventors: Hideaki Natsugari, Ashiya; Hitoshi Ikeda, Higashiosaka; Takenori Ishimaru, Toyonaka; Takayuki Doi, Izumi, all of Japan

[73] Assignee: Takeda Chemical Industries, Ltd., Osaka, Japan

[21] Appl. No.: 114,841

[22] Filed: Sep. 2, 1993

[30] Foreign Application Priority Data

Sep. 4, 1992 [JP] Japan .................................. 4-237481
Apr. 28, 1993 [JP] Japan .................................. 5-103328

[51] Int. Cl.⁶ .......................... A61K 31/35; C07D 311/12
[52] U.S. Cl. .......................... 514/457; 549/399; 549/23; 549/60; 548/235; 548/203; 548/311.4; 548/364.4; 548/125; 548/127; 548/255; 548/262.2; 548/250; 546/268; 544/238; 544/333; 544/405; 514/255; 514/257; 514/247; 514/337; 514/381; 514/383; 514/385; 514/363; 514/361; 514/364; 514/403; 514/365; 514/374; 514/444
[58] Field of Search .......................... 549/399, 23, 60; 514/457, 255, 257, 247, 337, 381, 383, 385, 363, 361, 364, 403, 365, 374, 444; 548/125, 127, 203, 235, 255, 262.2, 250, 311.4, 364.4; 546/268; 544/238, 333, 405

[56] References Cited

U.S. PATENT DOCUMENTS 5,198,462  3/1993  Natsugari .......................... 514/432
5,264,454  11/1993 Meguro .......................... 514/455
5,278,186  1/1994  Meguro .......................... 514/457

Primary Examiner—C. Warren Ivy
Assistant Examiner—D. Margaret M. Mach
Attorney, Agent, or Firm—Foley & Lardner

[57] ABSTRACT

Novel compound represented by the formula:

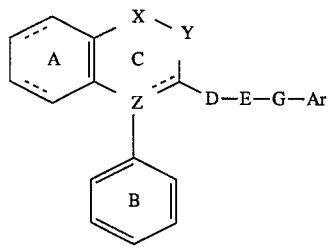

such as 6-Chloro-N-(2,6-diethoxyphenyl)-4-(2-methylphenyl-2-oxo-2H-1-benzopyran-3-acetamide:

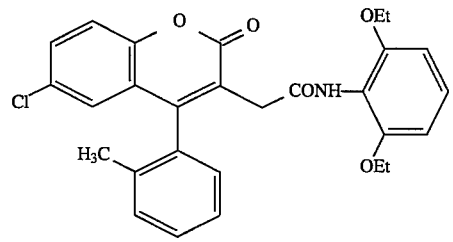

or a salt thereof. The compound has an excellent activity of inhibiting ACAT, lowering the cholesterol in blood and inhibiting tachykinin receptor. The present invention also relates to the production and use of the disclosed compound.

54 Claims, No Drawings

CONDENSED HETEROCYCLIC COMPOUNDS, THEIR PRODUCTION AND USE

The present invention relates to a new condensed heterocyclic compound which excellently inhibits the enzyme acyl-CoA: cholesterol acyl transferase (ACAT) and has a high tachykinin receptor antagonizing activity.

With respect to the compound wherein a phenyl group and a group of the formula:

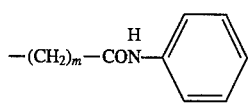

(m is 0 or 1) adjacently substitute on a heterocyclic ring resulting from condensation of a 6-membered heterocyclic ring and a benzene ring, known compounds include (1) the compound represented by the formula:

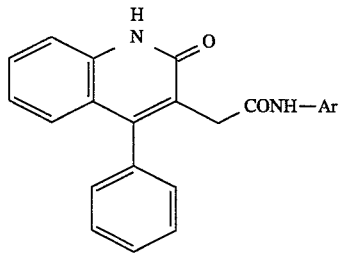

wherein Ar represents an aryl group, described in the Indian Journal of Chemistry, Section B, 26B, Vol. 8, pp. 744–747 (1987), (2) the compound represented by the formula:

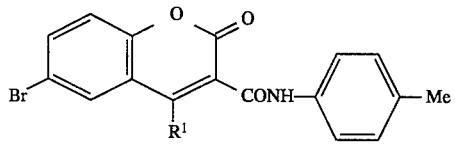

wherein $R^1$ represents an alkyl, aryl or cyclohexyl group, described in the Chemical Abstract, Vol. 107, 175835f, (3) the compound represented by the formula:

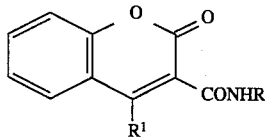

wherein R represents benzyl or 4-methylphenyl and $R^1$ represents a methyl, ethyl, naphthyl, benzyl or phenyl group, described in the Chemical Abstract, Vol. 114, 42492q, (4) the compound represented by the formula:

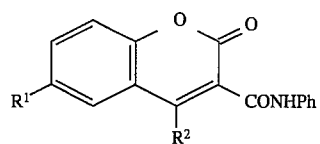

wherein Ph represents a phenyl group; $R^1$ represents an hydrogen atom or bromine; $R^2$ represents an alkyl, aryl or benzyl group, described in the Chemical Abstract, Vol. 107, 115463y, and (5) the compound represented by the formula:

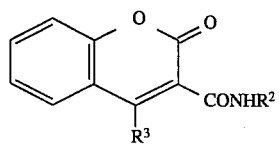

wherein $R^2$ represents a phenyl, o-, m- or p-methylphenyl or 4-chlorophenyl group; $R^3$ represents a phenyl, benzyl, allyl, ethyl, butyl, isobutyl or t-butyl group, described in the Chemical Abstract, Vol. 93, 220536q.

Also, publication (1) describes that pyrrolo[2,3-b]quinoline series compounds exhibit anti-inflammatory, antibacterial, hypotensive, antipyretic and antispasmodic actions and possess interferon-inducing activity. As for publications (2) to (5), no action is described but methods of synthesizing the respective compounds are described.

However, there have been no reports concerning whether these conventional compounds exhibit ACAT-inhibitory action, arteriosclerosis therapeutic effect, blood cholesterol lowering action and tachykinin receptor antagonizing action.

As compounds having substance P receptor antagonizing activity, the following (6) to (13) are known.

(6) In EP-A-333,174, a compound of the formula:

$$R^1-A-D-Trp(R^2)-Phe-R^3$$

wherein $R^1$ is hydrogen or an amino-protecting group; $R^2$ is hydrogen, an amino-protecting group, a carbamoyl(lower)alkyl group, a carboxy(lower)alkyl group; $R^3$ is an ar(lower)alkyl group, a group of the formula:

wherein $R^4$ and $R^5$ are each hydrogen, aryl or lower alkyl which may have suitable substituent(s), or $R^4$ and $R^5$ are linked together to form benzene-condensed lower alkylene or a group of the formula:

wherein $R^6$ is hydrogen, aryl or lower alkyl which may have suitable substituent(s); A is a single bond or one or two amino acids residue, provided when A is one amino acid residue of —D—Trp—, then $R^4$ is not hydrogen; and a salt thereof, (7) in EP-A-436,334 among others, a compound of the formula:

(8) in EP-A-429,366 among others, a compound of the formula:

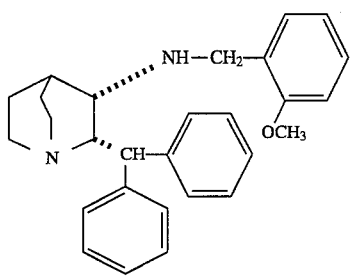

(9) in Journal of Medicinal Chemistry, 34, p1751, 1991 among others, a compound of the formula:

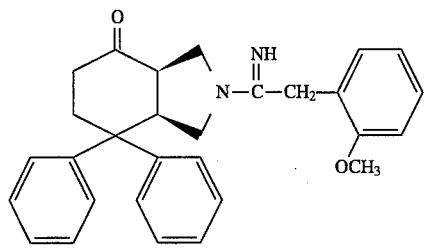

(10) in WO91/09844, a compound of the formula:

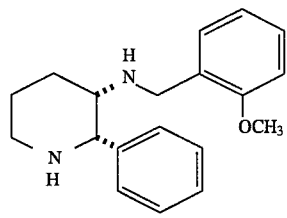

(11) in EP-A-522,808, a compound of the formula:

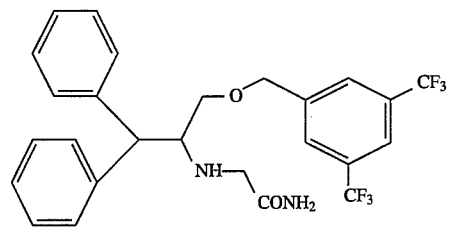

(12) in WO93/01169, a compound of the formula:

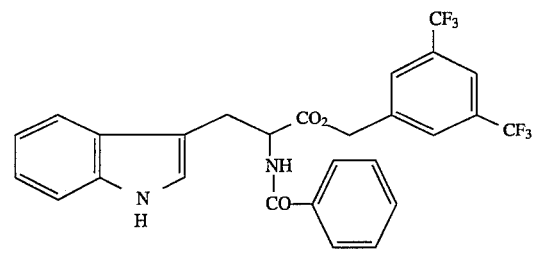

(13) in EP-A-532,456, a compound of the formula:

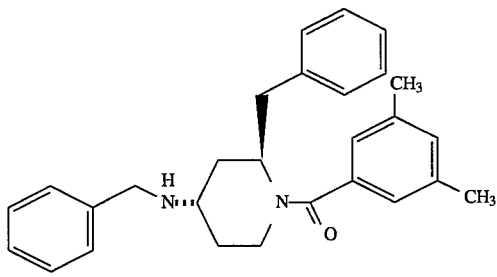

And, the following (14), (15) and (16) are known for isoquinoline derivatives. (14) in Farmaco, Edizione Scientifica, 36, 400–411 (1981), a compound of the formula:

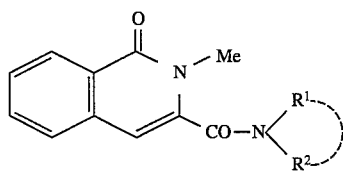

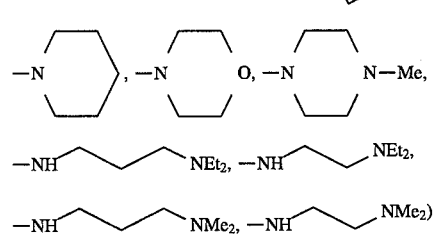

(15) in Chemical Abstract, 107, 39507 (1987), a compound of the formula:

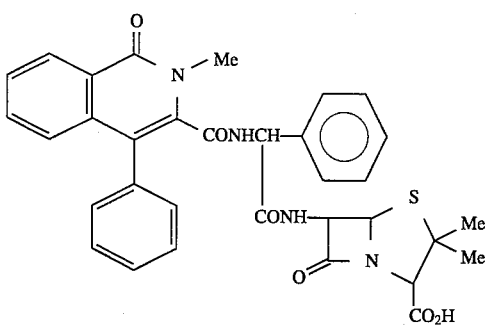

(16) Archiv der Pharmazie, 324, 809–814 (1991), a compound of the formula:

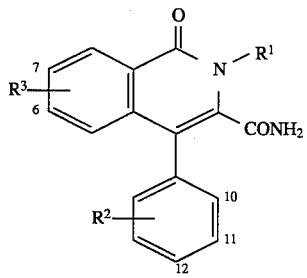

wherein R¹ represents hydrogen, methyl, n-butyl, cyclohexyl, benzyl, isopropyl; R² represents hydrogen, 10-methyl, 11-methyl, 10-chloro, 11-chloro, 12-fluoro, 12-bromo; R³ represents hydrogen, 6-chloro, 7-chloro, 6-bromo.

With respect to a bioactivity of a compounds described in (14) to (16), there is disclosure about local anesthesia action in (14), antibacterial action in (15) and anticonvulsion action in (16). However, there is no disclosure ever suggesting that these compounds have ACAT-inhibitory action, blood cholesterol lowering action and tachykinin receptor antagonizing action.

Against this background, there has been demand for the development of a compound which exhibits excellent ACAT-inhibitory action, which suppresses intestinal cholesterol absorption and arterial wall cholesterol ester accumulation in mammals, and which is useful as a prophylactic and therapeutic composition for hypercholesterolemia, atheromatous arteriosclerosis and various diseases associated therewith (e.g., ischemic heart diseases such as myocardial infarction and cerebrovascular disorders such as cerebral infarction and cerebral stroke).

And, tachykinin is a generic term denoting a group of neuropeptides. In mammalian animals, :substance P, neurokinin-A and neurokinin-B are known. It is also known that by binding their respective receptors (neurokinin-1, neurokinin-2, neurokinin-3) present in the living body, these peptides exhibit a diversity of biological activities.

Among them, substance P is a neuropeptide known for the longest time of all and studied in the greatest detail. Substance P is known to play a critical role as a transmitter substance in both the peripheral and central nervous systems. This substance is also suspected to be involved in a variety of morbid states (pain, inflammation, allergy, facilitation of micturition, mental disease, airway-diseases, etc.). Such being the case, for use as drugs for the treatment of the above-mentioned disease states, the development of compounds having potent tachykinin receptor antagonizing activity, particularly high antagonistic activity against substance P receptor, as well as other favorable properties such as safety and a sufficiently long duration of action after administration has been looked after in earnest.

This invention concerns certain heterocyclic compounds which inhibit the enzyme ACAT, pharmaceutical compositions containing these compounds, and a method of treating hypercholesterolemia and artherosclerosis and so on, and antagonize the tachykinin receptor, pharmaceutical compositions containing these compounds, and a method of treating pain, disturbances of micturition and inflammation and so on.

(1) A compound of this invention is represented by the following general formula:

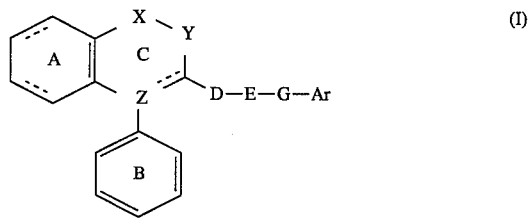

(I)

wherein ring A may be substituted;

ring B represents an optionally substituted benzene ring;

either X or Y represents —NR¹— (R¹ represents a hydrogen atom, an optionally substituted hydrocarbon group, an optionally substituted hydroxyl group or an optionally substituted amino group), —O— or —S—, the other representing —CO—, —CS— or —C(R²)R²ᵃ— (R² and R²ᵃ independently represent a hydrogen atom or an optionally substituted hydrocarbon group), or either X or Y represents —N=, the other representing =CR³— (R³ represents a hydrogen atom, a halogen atom, an optionally substituted hydrocarbon group, an optionally substituted amino group, a substituted hydroxyl group or a mercapto group substituted by an optionally substituted hydrocarbon group);

⋯⋯ represents a single or double bond;

(i) when ⋯⋯ adjacent to Z is a single bond, Z represents

(R⁴ represents a hydrogen atom, a hydroxyl group or an optionally substituted hydrocarbon group) or a nitrogen atom, or (ii) when ⋯⋯ adjacent to Z is a double bond, Z represents a carbon atom;

D represents a C₁₋₃ alkylene group which may be substituted by an oxo or thioxo group, or D and Y, taken together, may form a 5- to 7-membered ring which may be substituted by an oxo or thioxo group;

E represents —NR⁵— (R⁵ represents a hydrogen atom or an optionally substituted hydrocarbon group), —O— or —S(O)n— (n is 0,1 or 2), or R⁵ and Y, taken together, may form a 5- to 7-membered ring which may be substituted by an oxo or thioxo group;

G represents a bond or a C₁₋₃ alkylene group;

Ar represents an optionally substituted aryl group or an optionally substituted heterocyclic group, provided that, (1) when (i) —X—Y— represents —O—CO— or —CO—O—, (ii) D represents —CO— and (iii) E represents —NR⁵—, either (a) G represents a $C_{1-3}$ alkylene group and Ar represents a substituted aryl group or a substituted heterocyclic group, or (b) G represents a bond and $R^5$ represents an optionally substituted hydrocarbon group, and (2) when —X—Y— represents —NH—CO—, D represents —CO—, or a salt thereof, (2) a composition for inhibiting acyl-CoA: cholesterol acyl transferase, lowering cholesterol in blood and having tachykinin receptor antagonizing activity which comprise an effective amount of a compound of the formula:

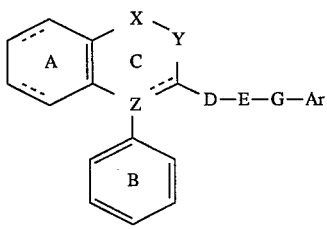
(I')

wherein the symbols are as defined above excluding for the "provided" clause, or a pharmaceutically acceptable salt and a physiologically acceptable carrier, (3) a process for producing the above compound (I) or a salt thereof which comprises reacting a compound of the formula:

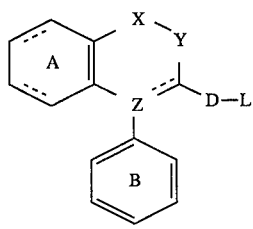
(II)

wherein L represents a leaving group; D and Y do not bind together to form a 5- to 7-membered ring; the other symbols are the same meaning as defined hereinabove or salt thereof with a compound of the formula:

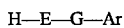
H—E—G—Ar    (III)

wherein all symbols are the same meaning as defined hereinabove or a salt thereof, (4) a process for producing the above compound (I) or a salt thereof, which comprises reacting a compound of the formula:

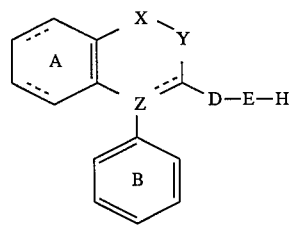
(IV)

1 wherein all symbols are the same meaning as defined hereinabove or salt thereof with a compound of the formula:

L'—G—Ar    (V)

wherein L' represents a leaving group; the other symbols are the same meaning as defined hereinabove or a salt thereof.

With respect to the above formula, the ring A represents an optionally substituted ring. The ring A represents a moiety of the formula:

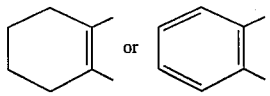

The ring B represents an optionally substituted benzene ring. Preferably, the ring A and B each is a benzene ring which may be substituted.

The substituent(s) that may be present on ring A and B include, among others, halogen atom, optionally halogenated alkyl group, optionally halogenated alkoxy group, optionally halogenated alkylthio group, $C_{1-7}$ acylamino group (e.g. formylamino, acetylamino, propionylamino, butyrylamino, benzoylamino, etc.), $C_{1-3}$ acyloxy group (e.g. formyloxy, acetoxy, propionyloxy, etc.), hydroxyl, nitro, cyano, amino, mono- or di-$C_{1-4}$ alkylamino group (e.g. methylamino, ethylamino, propylamino, dimethylamino, diethylamino, etc.), cyclic amino group (e.g., 5- to 9-membered cyclic amino which may consist 1 to 3 hetero-atoms such as oxygen and sulfur in addition to nitrogen as ring-constituent members, such as pyrrolidino, piperidino, morpholino, etc.), $C_{1-4}$ alkyl-carbonylamino group (e.g. acetylamino, propionylamino, butyrylamino, etc.), $C_{1-4}$ alkylsulfonylamino group (e.g. methylsulfonylamino, ethylsulfonylamino, etc.), $C_{1-4}$ alkoxy-carbonyl group (e.g. methoxycarbonyl, ethoxycarbonyl, propoxycarbonyl, etc.), carboxyl, $C_{1-6}$ alkyl-carbonyl group (e.g. methylcarbonyl, ethylcarbonyl, propylcarbonyl, etc.), carbamoyl, ethylcarbamoyl, etc.), mono- or di-$C_{1-4}$ alkylcarbamoyl group (e.g. methylcarbanoyl, ethylcarbamoyl, etc.:) and $C_{1-6}$ alkylsulfonyl group (e.g. methylsulfonyl, ethylsulfonyl, propylsulfonyl, etc.).

As the halogen atom, among the above-mentioned substituents, fluoro, chloro, bromo and iodo may be used and chloro or fluoro is preferred.

Examples of the optionally halogenated alkyl group include straight-chain or branched alkyl group having 1 to 6 carbon atoms and such alkyl groups substituted by 1 to 5 halogen atoms (e.g., fluorine, chlorine, bromine and iodine, preferably chlorine, bromine etc.). Specifically, commonly used alkyl group include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl, tert-butyl, pentyl, isopentyl, neopentyl, 5,5,5-trifluoropentyl, 4-trifluoromethyl-butyl, hexyl, 6,6,6-trifluorohexyl and 5-trifluoromethylpentyl. Preferably used are straight-chain or branched alkyl groups having 1 to 4 carbon atoms such as methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, 2-trifluoromethylethyl, butyl, 4,4,4-trifluorobutyl, isobutyl, sec-butyl and tert-butyl, or such alkyl groups substituted for by 1 to 3 of the above-mentioned halogen atoms.

Examples of the alkoxy group which may be substituted by halogen and the alkylthio group which may be substituted by halogen include alkoxy group which may be substituted by halogen and alkylthio groups which may be substituted for by halogen, resulting from binding of either the above-exemplified alkyl group or such alkyl group substituted for halogen and either an oxygen atom or a sulfur atom, respectively.

Examples of the optionally substituted alkoxy group include straight-chain or branched alkoxy group having 1 to 6 carbon atoms or such alkoxy group substituted by 1 to 5 of the above-mentioned halogen atoms. Specifically, commonly used alkoxy group include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentoxy and hexyloxy. Preferably used are straight-chain or branched alkoxy groups having 1 to 4 carbon atoms such as methoxy, difluoromethoxy, trifluoromethoxy, ethoxy, 2,2,2-trifluoroethoxy, propoxy, isopropoxy, butoxy, 4,4,4-trifluorobutoxy, isobutoxy and sec-butoxy, or such alkoxy group substituted for by 1 to 3 of the above-mentioned halogen atoms.

Examples of the optionally substituted alkylthio group include straight-chain or branched alkylthio group having 1 to 6 carbon atoms or such alkylthio group substituted for by 1 to 5 of the above-mentioned halogen atoms. Specifically, commonly used alkylthio groups include methylthio, difluoromethylthio, trifluoromethylthio, ethylthio, propylthio, isopropylthio, butylthio, 4,4,4-trifluorobutylthio, pentylthio and hexylthio. Preferably used are straight-chain or branched alkylthio groups having 1 to 4 carbon atoms such as methylthio, difluoromethylthio, trifluoromethylthio, ethylthio, propylthio, isopropylthio, butylthio and 4,4,4-trifluorobutylthio, or such alkylthio groups substituted for by 1 to 3 of the above-mentioned halogen atoms.

Preferable substituents on ring A and B include halogen (e.g. fluoro, chloro, bromo, etc.), optionally halogenated $C_{1-4}$ alkyl (e.g. methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, 2-trifluoromethylethyl, butyl, 4,4,4-trifluorobutyl, isobutyl, sec-butyl, tert-butyl, etc.), optionally halogenated $C_{1-4}$ alkoxy (e.g. methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, etc.), optionally substituted $C_{1-4}$ alkylthio (e.g. methylthio, difluoromethylthio, trifluoromethylthio, ethylthio, propylthio, isopropylthio, buthylthio, 4,4,4-trifluorobuthylthio, etc.), $C_{1-3}$ acyloxy (e.g. formyloxy, acetoxy, propionyloxy, etc.), hydroxyl, amino, mono-or di-$C_{1-4}$ alkylamino (e.g. methylamino, ethylamino, propylamino, dimethylamino, diethylamino, etc.), carboxyl and $C_{1-4}$ alkoxy-carbonyl (e.g. methoxycarbonyl, ethoxycarbonyl, propoxycarbonyl, etc.).

More preferable substituents on ring A and B include halogen (e.g. fluoro, chloro, bromo, etc.), optionally halogenated $C_{1-4}$ alkyl (e.g. methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, 2-trifluoromethylethyl, buthyl, 4,4,4-trifluorobutyl, isobutyl, sec-butyl, tert-butyl, etc.), optionally halogenated $C_{1-4}$ alkoxy (e.g. methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, etc.), hydroxyl, amino, mono- or di- $C_{1-4}$ alkylamino (e.g. methylamnio, ethylamino, propylamino, dimethylamino, diethylamino, etc.) and $C_{1-3}$ acyloxy (e.g. formyloxy, acetoxy, propionyloxy, etc.).

Specifically more preferable substituents on ring A and B include halogen (e.g. fluoro, chloro, bromo, etc.), optionally halogenated $C_{1-4}$ alkyl (e.g. methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, 2-trifluoromethylethyl, buthyl, 4,4,4-trifluorobutyl, isobutyl, sec-butyl, tert-butyl, etc.), optionally halogenated $C_{1-4}$ alkoxy (e.g. methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, etc.).

The substituent(s) for rings A and B may be located at any position on the ring. When two or more substituents are present, they may be identical or not, the number of substituents being 1 to 4, preferably 1 to 3, more preferably 1 or 2. Also, the adjacent carbons on ring A or B may bind with a group represented by —$(CH_2)l$— (l represents an integer of from 3 to 5) to form a 5- to 7-membered ring.

I). Some examples of ring A and B;

Ring A is preferably a benzene ring which may be substituted by one to four substituents selected from the group consisting of halogen (e.g., fluorine, chlorine, bromine, etc.), optionally halogenated $C_{1-4}$ alkyl group (e.g., methyl, ethyl, isopropyl, trifluoromethyl etc.) and optionally halogenated $C_{1-4}$ alkoxy group (e.g., methoxy trifluoromethoxy, ethoxy, etc.), specifically a benzene ring which may be substituted and which is represented by formula [A]:

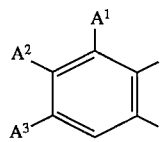

wherein $A^1$, $A^2$ and $A^3$, whether identical or not, independently represent a hydrogen, a halogen (e.g., fluorine, chlorine, etc.), an optionally halogenated $C_{1-4}$ alkyl group (e.g., methyl, trifluoromethyl, ethyl, isopropyl, etc.) or an optionally halogenated $C_{1-4}$ alkoxy group (e.g., methoxy, trifluoromethoxy, ethoxy, etc.). More preferably, for example, there may be used benzene ring which may be substituted and which is represented by the above formula [A] wherein:

(1) $A^1$, $A^2$ and $A^3$ are all hydrogen, (2) $A^1$ and $A^2$ are both hydrogen, $A^3$ being a halogen (e.g. fluorine, chlorine, etc.), an optionally halogenated $C_{1-4}$ alkyl group (e.g. methyl, trifluoromethyl, ethyl, etc.) or an optionally halogenated $C_{1-4}$ alkoxy group (e.g. methoxy, trifluoromethoxy, ethoxy, etc.), (3) $A^1$ is hydrogen, $A^2$ and $A^3$, whether identical or not, being independently a halogen (e.g. fluorine, chlorine), a $C_{1-4}$ alkyl group (e.g. methyl, ethyl, etc.) or a $C_{1-4}$ alkoxy group (e.g. methoxy, ethoxy, etc.), or (4) $A^2$ is hydrogen, $A^1$ and $A^3$, whether identical or not, being independently a $C_{1-4}$ alkyl group (e.g. methyl, ethyl, etc.).

More preferably for ring A, for example, there may be used benzene rings which may be substituted and which is represented by the above formula [A] wherein:

(a) $A^1$, $A^2$ and $A^3$ are all hydrogen, (b) $A^1$ and $A^2$ are both hydrogen, $A^3$ being chlorine, a methyl, ethyl, isopropyl, methoxy or trifluoromethyl group, (c) $A^1$ is hydrogen, $A^2$ and $A^3$ being both a methyl or methoxy group, or (d) $A^2$ is hydrogen, $A^1$ and $A^3$ being both a methyl group.

Ring B is preferably a benzene ring which may be substituted by one to four substituents selected from the group consisting of a halogen (e.g., fluorine, chlorine, etc.), an optionally halogenated $C_{1-4}$ alkyl group (e.g., methyl, trifluoromethyl, ethyl etc.) and, an optionally halogenated $C_{1-4}$ alkoxy group (e.g., methoxy, trifluoromethoxy, ethoxy etc.), specifically a benzene ring which may be substituted and which is represented by formula [B]:

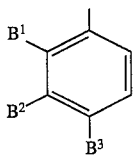

wherein $B^1$, $B^2$ and $B^3$, whether identical or not, independently represent hydrogen, a halogen (e.g., fluorine, chlorine, etc.), an optionally halogenated $C_{1-4}$ alkyl group (e.g., methyl, trifluoromethoxy, ethyl, etc.) or an optionally halogenated $C_{1-4}$ alkoxy group (e.g., methoxy, trifluoromethoxy ethoxy, etc.). More preferably, for example, there may be used benzene ring which may be substituted and which is represented by the above formula [B] wherein:

(1) $B^1$, $B^2$ and $B^3$ are all hydrogen, (2) $B^1$ is halogen (e.g. fluorine, chlorine, etc.), an optionally halogenated $C_{1-4}$ alkyl group (e.g. methyl, trifluoromethyl, ethyl, etc.) or an optionally halogenated $C_{1-4}$ alkoxy group (e.g. methoxy, trifluoromethoxy, ethoxy, etc.), $B^2$ and $B^3$ being both hydrogen, (3) $B^1$ is hydrogen, $B^2$ and $B^3$, whether identical or not, being independently an optionally halogenated $C_{1-4}$ alkoxy group (e.g. methoxy, trifluoromethoxy, ethoxy, etc.), or (4) $B^1$, $B^2$ and $B^3$, whether identical or not, are independently a $C_{1-4}$ alkoxy group (e.g. methoxy, ethoxy, etc.).

More preferably for ring B, for example, there may be used benzene rings which may be substituted for and which is represented by the above formula [B] wherein:

(a) $B^1$, $B^2$ and $B^3$ are all hydrogen, (b) $B^1$ is chlorine, fluorine, a methyl, trifluoromethyl or methoxy group, $B^2$ and $B^3$ being both hydrogen, (c) $B^1$ is hydrogen, $B^2$ and $B^3$ being both a methoxy group, or (d) $B^1$, $B^2$ and $B^3$ are all a methoxy group.

II). Other examples of ring A and B;

Referring to ring A, concrete examples of the moiety

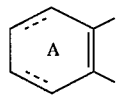

include groups of the formula:

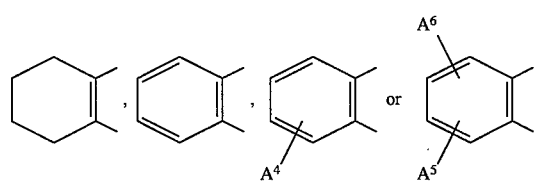

where $A^4$, $A^5$ and $A^6$ are the same or different and each means a halogen atom such as fluoro, chloro, etc., an optionally halogenated $C_{1-4}$ alkyl group such as methyl, ethyl, isopropyl trifluoromethyl, etc., or an optionally halogenated $C_{1-4}$ alkoxy group such as methoxy, trifluoromethoxy, ethoxy, etc.

Preferred examples of ring A are groups of the formula:

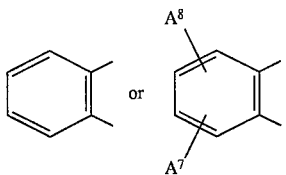

wherein $A^7$ and $A^8$ represents a halogen atom (e.g. fluorine, chlorine, etc.), an optionally halogenated $C_{1-4}$ alkyl group (e.g., methyl, trifluoromethyl, ethyl, etc.). More preferably, for example, there may be used benzene ring which may be substituted and which is represented by the above formula wherein (1) $A^4$ is a halogen (e.g. fluorine, chlorine, etc.) or an optionally halogenated $C_{1-4}$ alkyl group (e.g., methyl, trifluoromethyl, ethyl, propyl)

(2) $A^5$ and $A^6$ are an optionally halogenated a $C_{1-4}$ alkyl group (e.g., methyl, trifluoromethyl, ethyl, etc.) or a $C_{1-4}$ alkoxy group (e.g., methoxy, ethoxy, etc.), (3) $A^7$ and $A^8$ are a $C_{1-4}$ alkyl group (e.g. methyl, ethyl, etc.), (4) $A^4$ is a halogen (e.g., fluorine, chlorine, etc.), (5) $A^5$ and $A^6$ are a $C_{1-4}$ alkoxy group (e.g. methoxy, ethoxy, etc.), Referring to ring B, concrete examples of the moiety

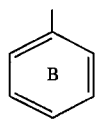

include groups of the formula:

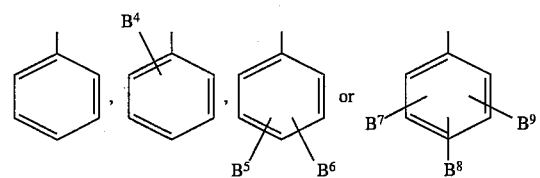

where in $B^4$, $B^5$, $B^6$, $B^7$, $B^8$ and $B^9$ are the same or different and each means a halogen atom such as chloro, fluoro, etc., an optionally halogenated $C_{1-4}$ alkyl group such as methyl, trifluoromethyl, ethyl, etc., or an optionally halogenated $C_{1-4}$ alkoxy group such as methoxy trifluoromethoxy, ethoxy, etc.

Preferred examples of the ring B are groups of the formula:

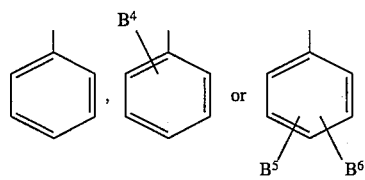

wherein $B^4$, $B^5$ and $B^6$ is the same meaning hereinbefore. Particularly preferred examples are groups of the formula:

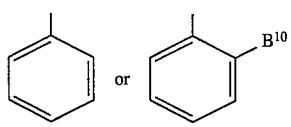

wherein $B^{10}$ is an optionally halogenated $C_{1-4}$ alkyl group (e.g., methyl, trifluoromethyl, ethyl, etc.).

More preferably, for example, there may be used benzene rings which may be substituted and which is represented by the above formula wherein:

(1) $B^4$ is a halogen (e.g., fluoro, chloro etc.) or an optionally halogenated $C_{1-4}$ alkyl group (e.g., methyl, trifluoromethyl, ethyl, etc.)

(2) $B^5$ and $B^6$, whether identical or not, being independently an optionally halogenated $C_{1-4}$ alkyl group (e.g., methyl, trifluoromethyl, ethyl, etc.).

(3) $B^4$ is an optionally halogenated $C_{1-4}$ alkoxy group (e.g., methoxy, trifluoromethoxy, ethoxy, etc.)

(4) $B^5$ and $B^6$, whether identical or not, being independently an optionally halogenated $C_{1-4}$ alkoxy group (e.g., methoxy, trifluoromethoxy, ethoxy, etc.)

With respect to the above formulas, $R^1$ represents a hydrogen atom, an optionally substituted hydrocarbon group, an optionally substituted hydroxyl group or an optionally substituted amino group.

$R^2$ and $R^{2a}$ independently represent a hydrogen atom or an optionally substituted hydrocarbon group.

$R^3$ represents a hydrogen atom, a halogen atom, an optionally substituted hydrocarbon group, an optionally substituted amino group, a substituted hydroxyl group or a mercapto group substituted by an optionally substituted hydrocarbon group.

$R^4$ represents a hydrogen atom, a hydroxyl group or an optionally substituted hydrocarbon group.

$R^5$ represents a hydrogen atom or an optionally substituted hydrocarbon group.

The hydrocarbon group described hereinabove include alkyl group, alkenyl group, alkynyl group, cycloalkyl group and aryl group. etc.

Preferable examples of hydrocarbon group are an alkyl group, a cycloalkyl group and an aryl group, and more preferable examples are an alkyl group.

The alkyl group includes a straight-chain or branched alkyl group having 1 to 6 carbon atoms such as methyl, ethyl, propyl, isopropyl, butyl, isobutyl, sec-butyl, tert-butyl, pentyl, hexyl, etc., preferably a straight-chain or branched alkyl group having 1 to 4 carbon atoms such as methyl, ethyl, propyl, isopropyl, butyl, isobutyl, sec-butyl or tert-butyl, etc.

The alkenyl group includes alkenyl group having 2 to 6 carbon atoms such as ethenyl, propenyl, isopropenyl, butenyl, isobutenyl or sec-butenyl, etc., preferably an alkenyl group having 2 to 4 carbon atoms such as ethenyl, propenyl or isopropenyl, etc.

The alkynyl group includes alkynyl group having 2 to 6 carbon atoms such as ethynyl, propynyl, isopropenyl, butynyl, isobutynyl, etc., or sec-butynyl, etc., preferably an alkynyl group having 2 to 4 carbon atoms such as ethynyl, propynyl or isopropenyl, etc.

The cycloalkyl group includes a $C_{3-8}$ cycloalkyl group such as cyclopropyl, cyclobutyl, cyclopentyl, etc., or cyclohexyl, preferably a $C_{3-6}$ cycloalkyl group such as cyclopropyl or cyclobutyl, etc.

The aryl group includes aryl group having 6 to 14 carbon atoms such as phenyl, naphthyl, anthryl or phenanthryl etc., preferably an aryl group having 6 to 10 carbon atoms such as phenyl or naphthyl, and more preferably a phenyl group.

Examples of the substituent for the optionally substituted hydrocarbon group include (i) halogen, (ii) cycloalkyl group, (iii) aryl group, (iv) amino group which may have an alkyl, alkenyl, cycloalkyl or aryl group as a substituent, (v) hydroxyl group, (vi) optionally halogenated alkoxy group (vii) acyl group, (viii) acyloxy group, (ix) cyano group, (x) optionally protected carboxyl group (xi) carbamoyl groups, (xii) mercapto group, (xiii) alkylthio group, (xiv) sulfo group and (xv) alkylsulfonyl group.

The optionally substituted hydrocarbon group may be substituted for by 1 to 4, preferably 1 or 2 of the above-mentioned substituents, whether identical or not.

The halogen atom is exemplified by fluorine, chlorine, bromine and iodine, preferably fluorine and chlorine. The cycloalkyl group is exemplified by $C_{3-6}$ cycloalkyl group such as cyclopropyl, cyclobutyl, cyclopentyl and cyclohexyl. The aryl group is exemplified by $C_{6-10}$ aryl group such as phenyl and naphthyl, and preferably a phenyl. With respect to the amino group which may have an alkyl, alkenyl, cycloalkyl or aryl group as a substituent, the alkyl group is exemplified by $C_{1-4}$ alkyl groups such as methyl, ethyl, propyl and isopropyl; the alkenyl group is exemplified by $C_{2-4}$ alkenyl group such as ethenyl, propenyl, isopropenyl and butenyl; the cycloalkyl group is exemplified by $C_{3-6}$ cycloalkyl group such as cyclopropyl, cyclobutyl, cyclopentyl and cyclohexyl; the aryl group is exemplified by $C_{6-10}$ aryl group such as phenyl and naphthyl, preferably a phenyl. Said amino group is preferably an amino group which may be substituted by one to three $C_{1-4}$ alkyl groups (e.g., methyl, ethyl, etc.), such as amino, methylamino, ethylamino, dimethylamino, trimethylamino and diethylamino. The optionally halogenated alkoxy group is exemplified by $C_{1-4}$ alkoxy group such as methoxy, difluoromethoxy, trifluoromethoxy, ethoxy, 2,2,2-trifluoroethoxy, propoxy, isopropoxy, butoxy, 4,4,4-trifluorobutoxy, isobutoxy and sec-butoxy, or such alkoxy group substituted for by 1 to 3 halogen atoms (e.g., fluorine, chlorine). The acyl group is a $C_{1-4}$ acyl group such as formyl, acetyl, propionyl, butyryl or isobutyryl. The acyloxy group is a $C_{1-4}$ acyloxy group such as formyloxy, acetyloxy, propionyloxy, butyryloxy or isobutyryloxy. The protecting group for the optionally protected carboxyl group is exemplified by $C_{1-4}$ alkyl groups such as methyl, ethyl and t-butyl groups and $C_{7-11}$ aralkyl group such as benzyl. The alkylthio group is a $C_{1-4}$ alkylthio group such as methylthio, ethylthio, propylthio, isopropylthio or butylthio. The alkylsulfonyl group is a $C_{1-4}$ alkylsulfonyl group such as a methylsulfonyl, ethylsulfonyl, propylsulfonyl, isopropylsulfonyl or butylsulfonyl group.

Preferable example of substituents for the optionally substituted hydrocarbon group include (i) halogen, (ii) cycloalkyl group, (iii) aryl group, (iv) amino group which may have an alkyl, alkenyl, cycloalkyl or aryl group as a substituent, (v) hydroxyl group, (vi) optionally halogenated alkoxy group (vii) acyl group, (viii) acyloxy group, (ix) cyano group, (x) optionally protected carboxyl group and (xi) carbamoyl group, and the term of (i) to (xi) is the same meaning described hereinabove.

More preferable examples of the substituent include the follows (1) to (3):

(1)
(i) $C_{3-6}$ cycloalkyl group such as cyclopropyl, cyclobutyl, cyclopentyl, cyclohexyl and so on,
(ii) $C_{6-10}$ aryl group such as phenyl, naphthyl and so on,
(iii) amino group which may be substituted by one to three $C_{1-4}$ alkyl groups, such as amino, methylamino, ethylamino, dimethylamino, trimethylamino, diethylamino and so on, (iv) carboxyl group which may be substituted by a $C_{1-4}$ alkyl, such as carboxyl, carboxymethyl, carboxylethyl and so on, (2) halogen such as fluoro, chloro, buromo and so on, (3)
(i) carboxyl,
(ii) $C_{1-4}$ alkyl-carbonyl such as carboxymethyl, carboxyethyl, etc. or
(iii) mono, di- or tri $C_{1-4}$ alkylamino such as amino, methylamino, dimethylamino, trimethylamino, etc.

Further, the hydrocarbon group are also preferable a $C_{1-6}$ alkyl group, $C_{3-6}$ cycloalkyl group, a $C_{3-6}$ cycloalkyl-$C_{1-4}$ alkyl group, preferably a $C_{1-6}$ alkyl group. The $C_{1-6}$ alkyl group mentioned above includes methyl, ethyl, propyl, isopropyl, butyl, isobutyl, sec-butyl, tert-butyl, pentyl, neopentyl, hexyl and so on. Preferred are $C_{1-4}$ alkyl groups such as methyl, ethyl, propyl, isopropyl, butyl, isobutyl, sec-butyl, tert-butyl and so on. The $C_{3-6}$ cycloalkyl group may for example be cyclopropyl, cyclopentyl or cyclohexyl and so on. The $C_{3-6}$ cycloalkyl-$C_{1-4}$ alkyl group includes, among others, cyclopropylmethyl and cyclopropylethyl and so on.

The substituent group(s) of the hydrocarbon group include halogen atom (e.g. fluoro, chloro, bromo, iodo, etc.), nitro, cyano, hydroxyl, $C_{1-4}$ alkoxy group (e.g. methoxy, ethoxy, propyloxy, butyloxy, isopropyloxy, etc.), $C_{1-4}$ alkylthio group (e.g. methylthio, ethylthio, propylthio etc.), amino, mono-, di or tri-$C_{1-4}$ alkylamino group (e.g. methylamino, ethylamino, propylamino, dimethylamino, diethylamino, trimethylamino etc.), cyclic amino group (e.g. 5- to 9-membered cyclic amino group which may contain 1 to 3 hetero-atoms such as oxygen and sulfur in addition to nitrogen as ring-constituent members, such as pyrrolidino, piperidino, morpholino, etc.), $C_{1-4}$ alkyl-carbonylamino group (e.g. acetylamino, propionylamino, butyrylamino, etc.), $C_{1-4}$ alkylsulfonylamino group (e.g. methylsulfonylamino, ethylsulfonylamino, etc.), $C_{1-4}$ alkoxy-carbonyl group (e.g. methoxycarbonyl, ethoxycarbonyl, propoxycarbonyl, etc.), carboxyl, $C_{1-6}$ alkyl-carbonyl group (e.g. methylcarbonyl, ethylcarbonyl, propylcarbonyl, etc.), carbamoyl, mono- or di-$C_{1-4}$ alkyl-carbamoyl group (e.g. methylcarbamoyl, ethylcarbamoyl, etc.), $C_{1-6}$ alkylsulfonyl group (e.g. methylsulfonyl, ethylsulfonyl, propylsulfonyl, etc.), phenyl, $C_{1-3}$ alkoxyphenyl (e.g. methoxyphenyl, ethoxyphenyl, etc.) and so on. 1 to 5, preferably 1 or 2, species of these substituents may be present.

Preferable examples of substituents hereinabove include a hydroxyl group, a $C_{1-4}$ alkoxy group (e.g. methoxy, ethoxy, propoxy, etc.), an amino group, a mono- or di-$C_{1-4}$ alkylamino group (e.g. methylamino, ethylamino, dimethylamino, diethylamino, etc.), a $C_{1-4}$ alkoxy-carbonyl group (e.g. methoxycarbonyl, ethoxycarbonyl, propoxycarbonyl, etc.), a carboxyl group, a carbamoyl group, a phenyl group and so on.

Specially preferable examples of substituents are a carboxyl group and a carbamoyl group.

The optionally substituted hydroxyl group described hereinabove includes a hydroxyl group, a $C_{1-4}$ alkoxy group (e.g. methoxy, ethoxy, propoxy, isopropoxy, butoxy, t-butoxy, etc.), a $C_{6-10}$ aryloxy group (e.g. phenoxy, naphthyloxy, etc.), a $C_{1-4}$ alkyl-carbonyloxy (e.g. formyloxy, acetyhyoxy, propyonyloxy, etc.) and a $C_{6-10}$ aryl-carbonyloxy group (e.g. benzoyloxy, naphthoyloxy, etc.).

Preferable examples are a hydroxyl group and a $C_{1-4}$ alkoxy group (e.g. methoxy, ethoxy, propoxy, isopropoxy, etc.)

These groups may be substituted, and the substituents include the same one as the substituents of the hydrocarbon group hereinabove, preferably a halogen atom (e.g. fluoro, chloro, bromo, etc.).

The substituted hydroxyl group include a $C_{1-4}$ alkoxy group (e.g. methoxy, ethoxy, propoxy, isopropoxy, butoxy, t-butoxy, etc.), a $C_{6-10}$ aryloxy group (e.g. phenoxy, naphthyloxy, etc.), a $C_{1-4}$ alkyl-carbonyloxy (e.g. formyloxy, acetyhyoxy, propyonyloxy, etc.), a $C_{6-10}$ aryl-carbonyloxy group (e.g. benzoyloxy, naphthoyloxy, etc.). Preferable examples are a $C_{1-4}$ alkoxy group (e.g. methoxy, ethoxy, propoxy, etc.). The substituents of a substituted hydroxyl group include the same one as the substituents of the hydrocarbon group hereinabove and so on, preferably a halogen atom (e.g. fluoro, chloro, bromo, etc.).

The halogen atom includes a fluorine, a chlorine, a bromine and so on.

The optionally substituted amino group includes an amino group which may be substituted by one to three substituents selected from the group consisting of (i) $C_{1-4}$ alkyl group (e.g. methyl, ethyl, propyl, isopropyl, etc.), (ii) $C_{1-4}$ alkylcarbonyl (e.g. acetyl, propyonyl, butynyl, etc.), (iii) $C_{1-4}$ alkoxy-carbonyl group (e.g. methoxycarbonyl, ethoxycarbonyl, propoxycarbonyl, etc.), (iv) halogen (e.g. fluoro, chloro, etc.), (v) phenyl, (vi) $C_{1-4}$ alkyl-phenyl (e.g. 4-methylphenyl, 3-methylphenyl, 2-methylphenyl, etc.), (vii) halogenated phenyl (e.g. 4-chlorophenyl, 3-chlorophenyl, 2-chlorophenyl, etc.) and (viii) $C_{1-4}$ alkoxy-phenyl (e.g. 4-methoxyphenyl, 3-methoxyphenyl, 2-methoxyphenyl, etc.) and so on.

Preferable examples of an optionally substituted amino group include an amino group or a mono- or di-$C_{1-4}$ alkylamino group (e.g. methylamino, ethylamino, propylamino, dimethylamino, diethylamino, etc.).

The optionally substituted hydrocarbon group of the mercapto group substituted by an optionally substituted hydrocarbon group are used the same one as defined hereinabove. Preferable examples of the mercapto group substituted by an optionally substituted hydrocarbon group include a $C_{1-4}$ alkylthio (e.g. methylthio, ethylthio, propylthio, etc.), and so on.

Preferable examples of $R^1$ include (i) a hydrogen atom and (ii) a $C_{1-4}$ alkyl group (e.g. methyl, ethyl, propyl, etc.) which may be substituted by (a) a mono-, di- or tri-$C_{1-4}$ alkylamino group (e.g. methylamino, ethylamino, propylamino, dimethylamino, trimethylamino, etc.), (b) a $C_{1-4}$ alkoxycarbonyl group (e.g. methoxycarbonyl, ethoxycarbonyl, propoxycarbonyl, etc.), (c) a carbamoyl group or (d) a carboxyl group.

More preferable examples of $R^1$ are a $C_{1-4}$ alkyl group (e.g. methyl, ethyl, propyl, etc.).

Preferable example of $R^2$ and $R^{2a}$ is a hydrogen atom

Preferable examples of $R^3$ include (i) a hydrogen atom, (ii) a halogen atom (e.g. fluoro, chloro, bromo, etc.), a $C_{1-4}$ alkoxy group (e.g. methoxy, ethoxy, propoxy, etc.), a $C_{1-4}$ alkyl group (e.g. methyl, ethyl, propyl, etc.), a $C_{1-4}$ alkylthio group (e.g, methylthio, ethylthio, etc.) and a mono- or di-$C_{1-4}$ alkylamino, (e.g. methylamino, ethylamino, dimethylamino, diethylamino, etc.), and (iii) a halogen atom (e.g. fluoro, chloro etc.) and mono-$C_{1-4}$ alkylamino (e.g. methylamino, ethylamino, etc.).

Preferable examples of $R^4$ include (i) a hydrogen atom and (ii) a $C_{1-4}$ alkyl group (e.g. methyl, ethyl, propyl, etc.), a hydroxyl group and halogen atom (e.g. fluoro, chloro, etc.).

Preferable examples of $R^5$ include (i) a hydrogen atom and (ii) a $C_{1-4}$ alkyl group (e.g. methyl, ethyl, propyl, etc.).

With respect to the above formula, either X or Y represents —NR$^1$— (R$^1$ represents a hydrogen atom, an optionally substituted hydrocarbon group, an optionally substituted hydroxyl group or an optionally substituted amino group), —O— or —S—, the other representing —CO—, —CS— or —C(R$^2$)R$^{2a}$— (R$^2$ and R$^{2a}$ independently represent a hydrogen atom or an optionally substituted hydrocarbon group), or ether X or Y represents —N=, the other representing =CR$^3$— (R$^3$ represents a hydrogen atom, a halogen atom, an optionally substituted hydrocarbon group, an optionally substituted amino group, a substituted hydroxyl group or a mercapto group substituted by an optionally substituted hydrocarbon group).

Preferable examples of X and Y (—X—Y—) include the following:

(i) either X or Y represents —NR$^1$— or —O—, the other representing —CO—, —CS— or —C(R$^2$)R$^{2a}$— (R$^1$, R$^2$ and R$^{2a}$ represent the same meanings as defined hereinabove), (ii) either X or Y represents —N=, the other representing =CR$^3$— (R$^3$ represents the same meaning as defined hereinabove), (iii) —NR$^1$—CO—, —NR$^1$—CH$_2$—, —CONR$^1$—, —O—CO—, —CO—O—, —N=CR$^3$— and —CR$^3$=N— (R$^1$ and R$^3$ represents the same meanings as defined hereinabove), (iv) —N(CH$_3$)—CO—, —N(C$_2$H$_5$)—CO—, —N(CH$_3$)—CH$_2$—, —N(C$_2$H$_5$)—CH$_2$, —CO—N(CH$_3$), —CO—N(C$_2$H$_5$)—, —O—CO—, —CO—O— —N=CH—, —N=C(CH$_3$)—, —N=C(OCH$_3$)—, —N=CCl—, —N=C(NHCH$_3$)—, —CH=N—, —C(Cl)=N—, —C(OCH$_3$)=N— and —C(NHCH$_3$)=C—, (v) —CONR$^1$— and —NR$^1$—CO— (R$^1$ represents the same meanings as defined hereinabove)

(vi) —O—CO—

(vii) —CO—O—

(viii) —NR$^1$—C(R$^2$)R$^{2a}$— and —C(R$^2$)R$^{2a}$—NR$^1$— (R$^1$, R$^2$ and R$^{2a}$ represent the same meaning as defined hereinabove), (ix) —N=CR$^3$— (R$^3$ represents the same meaning as defined hereinabove), (x) —CS—NR$^1$— (R$^1$ represents the same meaning as defined hereinabove).

With respect to the above formula, ⋯ represents a single or double bond; (i) when ⋯ adjacent to Z is a single bond, Z represents

—CR$^4$—
   |

(R$^4$ represents a hydrogen atom, a hydroxyl group or an optionally substituted hydrocarbon group) or a nitrogen atom, or (ii) when ⋯ adjacent to Z is a double bond, Z represents a carbon atom.

Preferable examples of ⋯ and Z include the following:

i) ⋯ on the ring A is a double bond, ii) ⋯ on the ring C is a single bond, and Z is

—CR$^4$—
   |

(R$^4$ represents the same meanings as defined hereinabove), (iii) ⋯ on the ring C is a single bond, and Z is a nitrogen atom, iv) ⋯ on the ring C is a double bond, and Z is a carbon atom.

With respect to the above formula, D represent a C$_{1-3}$ alkylene group which may be substituted by an oxo or thioxo group, or D and R$_1$, taken together, may form 5- to 7-membered ring which may be substituted by an oxo or thioxo group.

The C$_{1-3}$ alkylene group includes —CH$_2$—, —CH$_2$CH$_2$—, —CH$_2$CH$_2$CH$_2$— and —CH(CH$_3$)—CH$_2$— and so on.

D includes —CO—, —CS—, —CH$_2$—, —CH$_2$CH$_2$—, —CH$_2$CO—, —CH$_2$CS—, —CH$_2$CH$_2$C— and —CH$_2$CH$_2$CS— and so on.

Preferable examples of D include (i) a C$_{1-3}$ alkylene group which may be substituted by an oxo group, (ii) —CH$_2$—, —CH$_2$CH$_2$—, —CO—, —CH$_2$CO— and —CH$_2$CH$_2$CO—, (iii) —CO—, (iv) —CH$_2$CO— and —CH$_2$CH$_2$CO—, and (v) —CH$_2$— and —CH$_2$CH$_2$—.

Preferable examples of the compounds (I) and (I') wherein the 5- to 7-membered ring is formed by D and Y include compounds of the formula:

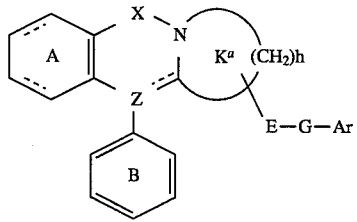

wherein ring K$^a$ may be substituted by an oxo or thioxo group; h repersents an integer of 3 to 5; and the other symbols represent the same meaning as defined hereinabove, more preferably the compounds of the formula:

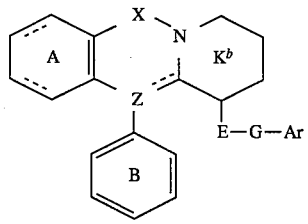

wherein ring K$^b$ may be substituted by an oxo group; and the other symbols represents the same meaning as defined hereinabove.

With respect to the above formula, E represents —NR$^5$— (R$^5$ represents a hydrogen atom or an optionally substituted hydrocarbon group), —O— or —S(O)n— (n is 0, 1 or 2), or R$^5$ and Y, taken together, may form 5- to 7-membered ring which may be substituted by an oxo or thioxo group.

Preferable examples of the compounds (I) and (I') wherein the 5- to 7-membered ring combined $R^5$ and Y include also compounds of the formula:

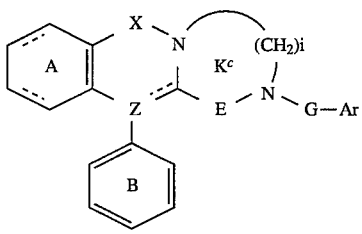

wherein the ring $K^c$ may be substituted by an oxo or thioxo group; i represents an integer of 1 to 3, the total carbon number of E and —(CH$_2$)i— being 3 to 5; and the other symbols represent the same meanings as defined hereinabove, preferably compound of the formula:

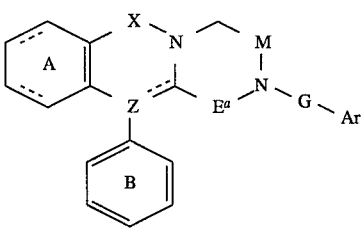

wherein $E^a$ and M represent —CH$_2$— or —CO—; and the other symbols represent the same meanings as defined hereinabove.

Preferable examples of E include —NR$^5$— (R5 represents the same meaning as defined hereinabove) and —O—, more preferably —NR$^5$— (R$^5$ represents the same meaning as defined hereinabove).

Preferable examples of G include the following:

(i) a bond, (ii) a $C_{1-3}$ alkylene group such as methylene, ethylene, propylene, etc.

Preferable examples of D, E and G include the follow:

(i) D is —CO—; E is —NR$^5$— (R$^5$ represents the same meaning as defined hereinabove); G is —CH$_2$— or —CH$_2$CH$_2$—, (ii) D is —CO—; E is —NR$^5$— (R$^5$ represents the same meaning as defined hereinabove); G is a bond, (iii) D is —CH$_2$CO— or —CH$_2$CH$_2$CO—; E is —NR$^5$— (R$^5$ represent the same meaning as defined herein); G is a bond, (iv) D is —CH$_2$CO— or —CH$_2$CH$_2$CO—; E is —NR$^5$— (R$^5$ represent the same meaning as defined hereinabove); G is —CH$_2$— or —CH$_2$CH$_2$—, (v) D is —CH$_2$— or —CH$_2$CH$_2$—; E is —O—; G is —CH$_2$— or —CH$_2$CH$_2$—, (vi) D is —CH$_2$— or —CH$_2$CH$_2$—; E is —NR$^5$— (R$^5$ represent the same meaning as defined herein); G is —CH$_2$— or —CH$_2$CH$_2$—, (vii) D is —CH$_2$— or —CH$_2$CH$_2$—; E is —S— or —SO—; G is —CH$_2$— or —CH$_2$CH$_2$—.

In the above formula, Ar represents an optionally substituted aryl group or an optionally substituted heterocyclic group. The aryl group in the "optionally substituted aryl group" represented by Ar, is preferably a $C_{6-10}$ aryl group such as phenyl or naphthyl or the like, with greater preference given to a phenyl group etc. The aryl group represented by Ar may have one to five substituents, preferably one to three substituents, whether identical or not. These substituents may be located at any position of the ring. Such substituents include an optionally halogenated $C_{1-4}$ alkyl group (e.g., methyl, chloromethyl, difluoromethyl, trichloromethyl, trifluoromethyl, ethyl, 2-bromoethyl, 2,2,2-trifluoroethyl, propyl, 3,3,3-trifluoropropyl, butyl), $C_{1-4}$ alkyl group substituted by an amino group (e.g., aminomethyl, 2-aminoethyl, etc.), $C_{1-4}$ alkyl group substituted by a mono- or di-$C_{1-4}$ alkylamino group (e.g., methylaminomethyl, dimethyl-aminomethyl), $C_{1-4}$ alkyl group substituted by a carboxyl group (e.g., carboxymethyl, carboxyethyl), $C_{1-4}$ alkyl group substituted by a $C_{1-4}$ alkoxycarbonyl group (e.g., methoxycarbonylethyl, ethoxycarbonylethyl), $C_{1-4}$ alkyl group substituted by a hydroxyl group (e.g., hydroxymethyl, hydroxyethyl), $C_{1-4}$ alkyl group substituted by a $C_{1-4}$ alkoxycarbonyl group (e.g., methoxymethyl, methoxyethyl, ethoxyethyl), $C_{3-6}$ cycloalkyl group (e.g., cyclopropyl, cyclobutyl, cyclopentyl, cyclohexyl), halogen atom (e.g., fluorine, chlorine, bromine, iodine), nitro group, cyano group, hydroxyl group, optionally halogenated $C_{1-4}$ alkoxy group (e.g., methoxy, difluoromethoxy, trifluoromethoxy, ethoxy, 2,2,2-trifluoroethoxy, propyloxy, butyloxy, isopropyloxy), optionally halogenated $C_{1-4}$ alkylthio group (e.g., methylthio, difluoromethylthio, trifluoromethylthio, ethylthio, propylthio, isopropylthio, butylthio), amino group, mono- or di-$C_{1-4}$ alkylamino group (e.g., methylamino, ethylamino, propylamino, dimethylamino, diethylamino), cyclic amino group (e.g., 5- to 9-membered cyclic amino group which may have one to three hetero atoms such as oxygen and sulfur atoms in addition to nitrogen atoms, specifically pyrrolidino, piperidino, morpholino), $C_{1-4}$ alkylcarbonylamino group (e.g., acetylamino, propionylamino, butylylamino), aminocarbonyloxy group, mono- or di-$C_{1-4}$ alkylaminocarbonyloxy group (e.g., methylaminocarbonyloxy, ethylaminocarbonyloxy, dimethylaminocarbonyloxy, diethylaminocarbonyloxy), $C_{1-4}$ alkylsulfonylamino group (e.g., methylsulfonylamino, ethylsulfonylamino, propylsulfonylamino), $C_{1-4}$ alkoxy-carbonyl group (e.g., methoxycarbonyl, ethoxycarbonyl, propoxycarbonyl, isobutoxycarbonyl), benzyloxycarbonyl group, carboxyl group, $C_{1-6}$ alkylcarbonyl group (e.g., methylcarbonyl, ethylcarbonyl, butylcarbonyl), $C_{1-6}$ cycloalkyl-carbonyl group (e.g., cyclohexylcarbonyl), carbamoyl group, mono- or di-$C_{1-4}$ alkylcarbamoyl group (e.g., methylcarbmaoyl, ethylcarbamoyl, propylcarbamoyl, butylcarbamoyl, diethylcarbamoyl, dibutylcarbamoyl) and $C_{1-6}$ alkylsulfonyl group (e.g., methylsulfonyl, ethylsulfonyl, propylsulfonyl). In addition, the below-described "optionally substituted heterocyclic group," represented by Ar, may be used as such as a substituent for the aryl group. This optionally substituted heterocyclic group is exemplified by 5- or 6-membered aromatic mono-heterocyclic group (e.g., furyl, thienyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl) which may be substituted by one to three substituents such as those selected from the group consisting of optionally halogenated $C_{1-4}$ alkyl group (e.g., methyl, chloromethyl, difluoromethyl, trichloromethyl, trifluoromethyl, ethyl, 2-bromoethyl, 2,2,2-trifluoroethyl, propyl, 3,3,3-trifluoropropyl, butyl), $C_{3-6}$ cycloalkyl group (e.g., cyclopropyl, cyclobutyl, cyclopentyl, cyclohexyl), halogen atom (e.g., fluorine, chlorine, bromine, iodine), hydroxyl group, optionally halogenated $C_{1-4}$ alkoxy group (e.g., methoxy, difluoromethoxy, trifluoromethoxy, ethoxy, 2,2,2-trifluoroethoxy, propyloxy, butyloxy, isopropyloxy), optionally halogenated $C_{1-4}$ alkylthio group (e.g., methylthio, difluoromethylthio, trifluoromethylthio, ethylthio, propylthio, isopropylthio, butylthio), amino group, mono- or di-$C_{1-4}$ alkylamino group (e.g., methylamino, ethylamino, propylamino, dimethylamino, diethylamino), $C_{1-4}$ alkoxy-carbonyl group (e.g., methoxycarbonyl, ethoxycarbonyl, propoxycarbonyl, isobutoxycarbonyl), carboxyl group and $C_{1-6}$ alkyl-carbonyl group (e.g., methylcarbonyl, ethylcarbonyl, butylcarbonyl).

Preferable examples of substituents of Ar include optionally halogenated $C_{1-4}$ alkyl group (e.g., methyl, chloromethyl, difluoromethyl, trichloromethyl, trifluoremethyl, ethyl, 2-bromoethyl, 2,2,2-trifluoroethyl, propyl, isopropyl, 3,3,3-trifluoropropyl), halogen atom (e.g., fluorine, chlorine, bromine), nitro group, hydroxyl group, optionally halogenated $C_{1-4}$ alkoxy group (e.g., methoxy, difluoromethoxy, trifluoromethoxy, ethoxy, 2,2,2-trifluoroethoxy), amino group, $C_{1-4}$ alkyl group substituted by a mono- or di-$C_{1-4}$ alkylamino group (e.g., methylaminoethyl, dimethylaminomethyl, 2-methylaminoethyl, 2-dimethylaminoethyl.), mono- or di-$C_{1-4}$ alkylamino group (e.g., methylamine, ethylamino, dimethylamino, diethylamino), $C_{1-4}$ alkoxy-carbonyl group (e.g., methoxycarbonyl, ethoxycarbonyl), carboxyl group and carbamoyl group, and optionally halogenated $C_{1-4}$ alkyl group (e.g., methyl, chloromethyl, difluoromethyl, trichloromethyl, trifluoromethyl, ethyl, 2-bromoethyl, propyl, isopropyl), halogen atom (e.g., fluorine, chlorine, bromine) and $C_{1-4}$ alkoxy group (e.g., methoxy, ethoxy, propoxy) are commonly used.

The heterocyclic group in the "optionally substituted heterocyclic group," represented by Ar, is exemplified by 5- to 9-membered, preferably 5- or 6-membered aromatic heterocyclic group which may have one to four, preferably one or two hetero atoms such as nitrogen, oxygen and sulfur atoms in addition to carbon atoms.

Such aromatic heterocyclic group include aromatic monoheterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl and aromatic condensed heterocyclic group such as benzofuranyl, isobenzofuranyl, benzo[b]thienyl, indolyl, isoindolyl, 1H-indazolyl, benzoimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenatholidinyl, phenathololinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl.

Preferable examples of the heterocyclic group include 5- or 6-membered heterocyclic groups such as furyl, thienyl, pyrrolyl, oxazolyl, isoxazolyl, imidazolyl, pyrazolyl, pyridyl, pyridazinyl, quinolyl, isoquinolyl, thiazolyl, thiadiazolyl and thiophenyl, with greater preference given to furyl, thienyl, pyridyl, etc.

The substituent in the "optionally substituted heterocyclic group," represented by Ar, is exemplified by optionally halogenated $C_{1-4}$ alkyl group(e.g., methyl, chloromethyl, difluoromethyl, trichloromethyl, trifluoromethyl, ethyl, 2,2-dibromoethyl, 2,2,2-triflu-oroethyl, propyl, 3,3,3-trifluoropropyl, butyl), $C_{3-6}$ cycloalkyl group (e.g., cyclopropyl, cyclobutyl, cyclopentyl, cyclohexyl), halogen atom (e.g., fluorine, chlorine, bromine, iodine), nitro group, cyano group, hydroxyl group, optionally halogenated $C_{1-4}$ alkoxy group (e.g., methoxy, fluoromethoxy, difluoromethoxy, trifluoromethoxy, ethoxy, 2,2,2-triflu-oroethoxy, propyloxy, butyloxy, isopropyloxy), optionally halogenated $C_{1-4}$ alkylthio group (e.g., methylthio, difluoromethylthio, trifluoromethylthio, ethylthio, propylthio, isopropylthio, butylthio), amino group, mono- or di-$C_{1-4}$ alkylamino group (e.g., methylamino, ethylamino, propylamino, dimethylamino, diethylamino), cyclic amino group (e.g., 5- to 9-membered cyclic amino groups which may have one to three hetero atoms such as oxygen and sulfur atoms in addition to nitrogen atoms, specifically pyrrolidino, piperidino, morpholino), $C_{1-4}$ alkylcarbonylamino group (e.g., acetylamino, propionylamino, butylylamino), aminocarbonyloxy group, mono- or di-$C_{1-4}$ alkylaminocarbonyloxy group (e.g., methylaminocarbony-loxy, ethylaminocarbonyloxy, dimethylaminocarbonyloxy, diethylaminocar-bonyloxy), $C_{1-4}$ alkylsulfonylamino group (e.g., methylsulfonylamino, ethylsulfonylamino, propylsulfonylamino), $C_{1-4}$ alkoxy-carbonyl group (e.g., methoxycarbonyl, ethoxycarbonyl, propoxycarbonyl, isobutoxycarbonyl), carboxyl group, $C_{1-6}$ alkyl-carbonyl group (e.g., methylcarbonyl, ethylcarbonyl, butylcarbonyl), $C_{3-6}$ cycloalkyl-carbonyl group (e.g., cyclohexylcarbonyl), carbamoyl group, mono- or di-$C_{1-4}$ alkylcarbamoyl group (e.g., methylcarbamoyl, ethylcarbamoyl, propylcarbamoyl, butylcarbamoyl, diethylcarbamoyl, dibutylcarbamoyl), $C_{1-6}$ alkylsulfonyl group (e.g., methylsulfonyl, ethylsulfonyl, propylsulfonyl), $C_{3-6}$ cycloalkylsulfonyl group (e.g., cyclopentylsulfonyl, cyclohexylsulfonyl), phenyl, naphthyl, phenoxy, benzoyl, phenoxycarbonyl, phenyl-$C_{1-4}$ alkylcarbamoyl, phenylcarbamoyl, phenyl-$C_{1-4}$ alkylcarbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino and phenylsulfonylamino group which may have one to four substituents (the substituent for each phenyl group or naphthyl group is exemplified by $C_{1-4}$ alkyl group such as methyl, ethyl, propyl, butyl and isopropyl, $C_{1-4}$ alkoxy group such as methoxy, ethoxy, n-propyloxy, i-propyloxy and n-butyloxy, halogen atom such as chlorine, bromine and iodine, hydroxyl group, benzyloxy group, amino group, mono- or di-$C_{1-4}$ alkylamino group as described above, nitro group and $C_{1-6}$ alkylcarbonyl group as described above); one to three selected from these substituents are used.

Of these substituents are preferred halogen atom (e.g., fluorine, chlorine, bromine), optionally halogenated $C_{1-4}$ alkyl group (e.g., methyl, chloromethyl, difluoromethyl, trifluoromethyl, ethyl), $C_{3-6}$ cycloalkyl group (e.g., cyclopropyl, cyclobutyl), hydroxyl group, optionally halogenated $C_{1-4}$ alkoxy group (e.g., methoxy, difluoromethoxy, trifluoromethoxy, ethoxy), optionally halogenated $C_{1-4}$ alkylthio group (e.g., methylthio, ethylthio), amino group, mono- or di-$C_{1-4}$ alkylamino group (e.g., methylamino, ethylamino, dimethylamino, diethylamino), $C_{1-4}$ alkoxy-carbonyl group (e.g., methoxycarbonyl, ethoxycarbonyl) and carboxyl group, with greater preference given to halogen atom (e.g., fluorine, chlorine), $C_{1-4}$ alkyl group (e.g., methyl, ethyl), $C_{3-6}$ cycloalkyl group (e.g., cyclopropyl, cyclobutyl), hydroxyl group, $C_{1-4}$ alkoxy group (e.g., methoxy, ethoxy) and carboxyl group, etc.

Ar is preferably a phenyl group which may have one to three substituents selected from the group consisting of halogen atom (e.g., fluorine, chlorine), optionally halogenated $C_{1-4}$ alkyl group (e.g., methyl, difluoromethyl, trifluoromethyl, ethyl, 2,2,2-trifluoroethyl, propyl, isopropyl) and optionally halogenated $C_{1-4}$ alkoxy group (e.g., methoxy, difluoromethoxy, trifluoromethoxy, ethoxy, 2,2,2-trifluoroethoxy, propoxy, isopropoxy). Also preferred are 5- or 6-membered heterocyclic groups (e.g., furyl, pyridyl, thienyl, thiazolyl, thiadiazolyl) which have one to three hetero atoms (e.g., nitrogen atoms, oxygen atoms, sulfur atoms) in addition to carbon atoms and which may be substituted by optionally halogenated $C_{1-4}$ alkyl group (e.g., methyl, trifluoromethyl, ethyl), $C_{1-4}$ alkoxy group (e.g., methoxy, ethoxy, propoxy) or $C_{3-6}$ cycloalkyl group (e.g., cyclopropyl).

Ar is preferably a phenyl group which may be substituted by one to three substituents selected from the group consisting halogen (e.g., chlorine, fluorine), optionally halogenated $C_{1-4}$ alkyl group (e.g., methyl, trifluoromethyl ethyl, isopropyl), optionally halogenated $C_{1-4}$ alkoxy group (e.g., methoxy, trifluoromethoxy, ethoxy), di-$C_{1-4}$ alkylamino group (e.g., dimethylamino), $C_{1-3}$ acyloxy group (e.g., acetoxy) and hydroxyl group, specifically a phenyl group which may be substituted for and which is represented by formula:

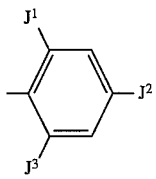

wherein $J^1$, $J^2$ and $J^3$, whether identical or not, independently represent hydrogen, a halogen (e.g., chlorine, fluorine), an optionally halogenated $C_{1-4}$ alkyl group (e.g., methyl, trifluoromethyl ethyl, isopropyl), an optionally halogenated $C_{1-4}$ alkoxy group (e.g., methoxy, trifluoromethoxy, ethoxy) or a di-$C_{1-4}$ alkylamino group (e.g., dimethylamino), or by formula:

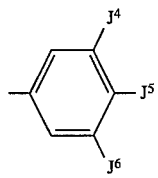

wherein $J^4$, $J^5$ and $J^6$, whether identical or not, independently represent hydrogen, an optionally halogenated $C_{1-4}$ alkyl group (e.g., methyl, trifluoromethyl isopropyl, t-butyl), a $C_{1-3}$ acyloxy group (e.g., acetoxy) or a hydroxyl group. More preferably, for example, there may be used a phenyl group which may be substituted and which is represented by the above formulas ($J^a$) and ($J^b$) wherein:

(1) $J^1$, $J^2$ and $J^3$, whether identical or not, independently represent halogen, an optionally halogenated $C_{1-4}$ alkyl group or an optionally halogenated $C_{1-4}$ alkoxy group, (2) $J^1$ and $J^2$, whether identical or not, independently represent a halogen, an optionally halogenated $C_{1-4}$ alkyl group or an optionally halogenated $C_{1-4}$ alkoxy group, $J^3$ being hydrogen, (3) $J^1$ and $J^3$, whether identical or not, independently represent a halogen, an optionally halogenated $C_{1-4}$ alkyl group or an optionally halogenated $C_{1-4}$ alkoxy group, $J^2$ being hydrogen, (4) $J^1$ and $J^3$ are hydrogen, $J^2$ being a halogen, (5) $J^4$ is a di-$C_{1-4}$ alkylamino group, $J^5$ and $J^6$ being hydrogen, (6) $J^4$ and $J^6$ are hydrogen, $J^5$ being a di-$C_{1-4}$ alkylamino group, or (7) $J^4$ and $J^6$, whether identical or not, independently represent an optionally halogenated $C_{1-4}$ alkyl group or an optionally halogenated $C_{1-4}$ alkoxy group, $J^5$ being a $C_{1-3}$ acyloxy group or a hydroxyl group.

In the above (1) to (7), the optionally halogenated $C_{1-4}$ alkyl group includes methyl, trifluoromethyl, ethyl, etc.; the optionally halogenated $C_{1-4}$ alkoxy group includes methoxy, trifluoromethoxy, ethoxy, etc.; the halogen atom includes fluoro, chloro, etc.; the di-$C_{1-4}$ alkylamino group includes N,N-dimethylamino, N,N-diethylamino, etc.; the $C_{1-3}$ acyloxy group includes formyloxy, acetoxy, etc.

More preferably for Ar, for example, there may be used a penyl group which may be substituted and which is represented by the above formulas ($J^a$) and ($J^b$) wherein:

(a) $J^1$, $J^2$ and $J^3$ are all fluorine, a methyl or methoxy group, (b) $J^1$ and $J^2$ are both chlorine, a fluorine, isopropyl or methoxy group, $J^3$ being hydrogen, (c) $J^1$ and $J^3$ are both chlorine, fluorine, a methyl, ethyl, isopropyl or methoxy group, $J^2$ being hydrogen, (d) $J^1$ is an isopropyl group, $J^2$ being hydrogen, $J^3$ being a methyl group, (e) $J^1$ and $J^3$ are hydrogen, $J^2$ being chlorine, (f) $J^1$ and $J^2$ are methyl, trifluoromethyl group, $J^3$ is a hydrogen, (g) $J^4$ is an N,N-dimethylamino group, $J^5$ and $J^6$ being hydrogen, (h) $J^4$ and $J^6$ are hydrogen, $J^5$ being an N,N-dimethylamino group, (i) $J^4$ and $J^6$ are both a methyl, trifluoromethyl or isopropyl group, $J^5$ being an acetoxy group, or (j) $J^4$ and $J^6$ are both a methyl, trifluoromethyl, isopropyl or t-butyl group, $J^5$ being a hydroxyl group.

With respect to the above formulas, two isomers exist with different relative configurations of positions 3 and 4 on the condensed ring, provided that ≈ is a single bond and Z is

($R^4$ has the same definitions as above), each of which isomers involves two isomers with different absolute configurations. Provided that ≈ is a single bond and Z is a nitrogen atom, there are two isomers with different absolute configurations of position 3. The present invention includes these isomers and mixtures thereof. In this context, the position 3 of the condensed ring indicates the position of the carbon atom to which the side is bond, the position 4 including the position of Z.

Preferable examples of the compounds (I) and (I') include compounds of the formula:

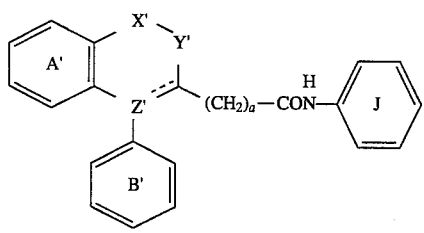 (VI)

wherein rings A', B' and J independently represent an optionally substituted benzene ring; either X' or Y' represents —NR$^{1a}$— (R$^{1a}$ represents an optionally substituted hydrocarbon group), —O— or —S—, the other representing —CO—, —CS— or —C(R$^2$)R$^{2a}$— (R$^2$ and R$^{2a}$ independently represent a hydrogen atom or an optionally substituted hydrocarbon group), or either X' or Y' represents —N═, the other representing ═CR$^{3a}$— (R$^{3a}$ represents a hydrogen atom, an optionally substituted hydrocarbon group or —OR wherein R represents an optionally substituted hydrocarbon group;  represents a single or double bond; (i) when  is a single bond, Z' represents

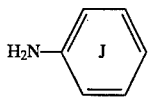

(R$^{4a}$ represents a hydrogen atom or an optionally substituted hydrocarbon group) or a nitrogen atom, or (ii) when  is a double bond, Z represents a carbon atom; α represents 0, 1 or 2, provided that when —X'—Y'— is —O—CO—, α represents 1 or 2, or a salt thereof. And, the compound (VI) can be produced by a process which comprises reacting a compound of the formula:

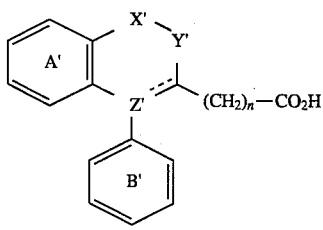 (VII)

wherein the symbols have the same definitions as above, or, a salt or reactive derivative thereof with a compound represented by general formula:

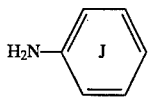 (VIII)

wherein the symbols have the same definitions as above, or a salt thereof. Further, a compound represented by general formula:

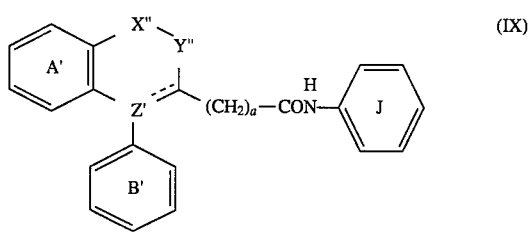 (IX)

wherein either X" or Y" represents —NR$^{1b}$— (R$^{1b}$ represents a hydrogen atom or an optionally substituted hydrocarbon group), —O— or —S—, the other representing —CO—, —CS— or —C(R$^2$)R$^{2a}$— (R$^2$ and R$^{2a}$ have the same definitions as above), or either X" or Y" represents —N═, the other representing ═CR$^{3a}$— (R$^{3a}$ has the same definition as above), the other symbols having the same definitions as above, unexpectedly exhibits potent ACAT-inhibitory action and is useful as a safe blood cholesterol lowering agent and arteriosclerosis therapeutic composition.

Preferable examples of the above symbols include the following:

(1) the substituent of the ring A', B' and J is (i) a halogen, (ii) an optionally halogenated C$_{1-6}$ alkyl group, (iii) a C$_{1-6}$ alkoxy group, (iv) a hydroxyl group, (v) an amino group which may be substituted by C$_{1-4}$ alkyl groups or (vi) a C$_{1-3}$ acyloxy group, (2) the ring A' is a benzene ring which may be substituted by one to four substituents selected from the group consisting of halogen, C$_{1-4}$ alkyl group, C$_{1-4}$ alkoxy group and halogeno-C$_{1-4}$ alkyl group, (3) the ring A' is an optionally substituted benzene ring which is represented by the formula:

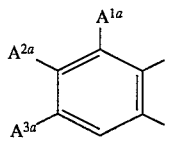

wherein A$^{1a}$, A$^{2a}$ and A$^{3a}$, whether identical or not, independently represent hydrogen, a halogen, a C$_{1-4}$ alkyl group, a C$_{1-4}$ alkoxy group or a halogeno-C$_{1-4}$ alkyl group, (4) the ring B' is benzene ring which may be substituted by one to four substituents selected from the group consisting of halogen, C$_{1-4}$ alkyl group and C$_{1-4}$ alkoxy group, (5) the ring B' is an optionally substituted benzene ring which is represented by the formula:

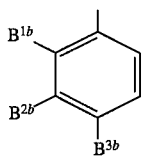

wherein B$^{1b}$, B$^{2b}$ and B$^{3b}$, whether identical or not, independently represent hydrogen, a halogen, a C$_{1-4}$ alkyl group or a C$_{1-4}$ alkoxy group, (6) the ring J is an optionally substituted benzene ring by one to four substituents selected from the group consisting of halogen, $C_{1-4}$ alkyl group, $C_{1-4}$ alkoxy group di-$C_{1-4}$ alkylamino group, $C_{1-3}$ acyloxy group and hydroxyl group, (7) the ring J is an optionally substituted benzene ring which is represented by the formula:

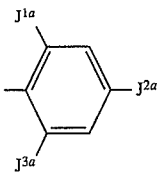

wherein $J^{1a}$, $J^{2a}$ and $J^{3a}$, whether identical or not, independently represent hydrogen, a halogen, a $C_{1-4}$ alkyl group, a $C_{1-4}$ alkoxy group or a di-$C_{1-4}$ alkylamino group or by the formula:

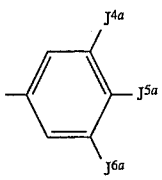

wherein $J^{4a}$, $J^{5a}$ and $J^{6a}$, whether identical or not, independently represent hydrogen, a $C_{1-4}$ alkyl group, a $C_{1-3}$ acyloxy group or a hydroxyl group, (8) the —X'—Y'— is the formula —NR$^{1a}$—CO—, —NR$^{1a}$—C(R$^2$)R$^a$—, —N=CR$^{3a}$—, —O—CO— or —CO—O— (in these formulas the symbols have the same definitions as above), (9) α is 1, In the above in (1) to (9), the halogen includes fluoro, chloro, etc; the optionally halogenated $C_{1-6}$ alkyl group includes methyl, trifluoromethyl, ethyl, propyl, etc; the $C_{1-6}$ alkoxy includes methoxy, ethoxy, propoxy, butoxy; the amino group which may be substituted by one or two $C_{1-4}$ alkyl groups includes amino, methylamino, dimethylamino, etc; the $C_{1-3}$ acyloxy includes formyloxy, acetoxy; the $C_{1-4}$ alkyl includes methyl, ethyl, propyl; the $C_{1-4}$ alkoxy includes methoxy, ethoxy, propoxy; the halogeno-$C_{1-4}$ alkyl group includes trifluoromethyl; the di-$C_{1-4}$ alkylamino includes N,N-dimethylamino.

With respect to the above formulas, rings A', B' and J independently represent a benzene ring which may have substituents. Such substituents include halogen (e.g., fluorine, chlorine, bromine and iodine, preferably chlorine, fluorine etc.), optionally halogenated alkyl group, optionally halogenated alkoxy group, optionally halogenated alkylthio group, $C_{1-7}$ acylamino group (e.g., formylamino, acetylamino, propionylamino, butyrylamino, benzoylamino), amino group which may be substituted by one or two $C_{1-4}$ alkyl groups (e.g., amino, methylamino, ethylamino, propylamino, dimethylamino, methylethylamino, methylpropylamino), $C_{1-3}$ acyloxy group (e.g., formyloxy, acetoxy., propionyloxy), hydroxyl group, cyano group and carboxyl group.

Examples of the optionally halogenated alkyl group include straight-chain or branched alkyl groups having 1 to 6 carbon atoms and such alkyl groups substituted for by 1 to 5 halogen atoms (e.g., fluorine, chlorine, bromine and iodine, preferably chlorine, bromine etc.). Specifically, commonly used alkyl groups include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl, tert-butyl, pentyl, isopentyl, neopentyl, 5,5,5-trifluoropentyl, 4-trifluoromethylbutyl, hexyl, 6,6,6-trifluorohexyl and 5-trifluoromethylpentyl. Preferably used are straight-chain or branched alkyl groups having 1 to 4 carbon atoms such as methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, 2-trifluoromethylethyl, butyl, 4,4,4-trifluorobutyl, isobutyl, sec-butyl and tert-butyl, or such alkyl groups substituted for by 1 to 3 of the above-mentioned halogen atoms.

Examples of the optionally halogenated alkoxy group and the optionally halogenated alkylthio group include alkoxy groups which may be substituted for by halogen and alkylthio groups which may be substituted for by halogen, resulting from binding of either the above-exemplified alkyl group or such alkyl group substituted for by halogen and either an oxygen atom or a sulfur atom, respectively.

Examples of the optionally halogenated alkoxy group include straight-chain or branched alkoxy groups having 1 to 6 carbon atoms or such alkoxy groups substituted for by 1 to 5 of the above-mentioned halogen atoms. Specifically, commonly used alkoxy groups include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentoxy and hexyloxy. Preferably used are linear or branched alkoxy groups having 1 to 4 carbon atoms such as methoxy, difluoromethoxy, trifluoromethoxy, ethoxy, 2,2,2-trifluoroethoxy, propoxy, isopropoxy, butoxy, 4,4,4-trifluorobutoxy, isobutoxy and sec-butoxy, or such alkoxy groups substituted for by 1 to 3 of the above-mentioned halogen atoms.

Examples of the alkylthio group which may be substituted by halogen include straight-chain or branched alkylthio groups having 1 to 6 carbon atoms or such alkylthio groups substituted for by 1 to 5 of the above-mentioned halogen atoms. Specifically, commonly used alkylthio groups include methylthio, difluoromethylthio, trifluoromethylthio, ethylthio, propylthio, isopropylthio, butylthio, 4,4,4-trifluorobutylthio, pentylthio and hexylthio. Preferably used are straight-chain or branched alkylthio groups having 1 to 4 carbon atoms such as methylthio, difluoromethylthio, trifluoromethylthio, ethylthio, propylthio, isopropylthio, butylthio and 4,4,4-trifluorobutylthio, or such alkylthio groups substituted for by 1 to 3 of the above-mentioned halogen atoms.

Preferable substituents for ring A', B' and J include (i) halogen (e.g. fluorine, chlorine, bromine), (ii) optionally halogenated $C_{1-6}$ alkyl group (e.g. methyl, trifluoromethyl, ethyl, propyl), (iii) $C_{1-6}$ alkoxy group (e.g. methoxy, ethoxy, propoxy), (iv) hydroxyl group, (v) amino group which may be substituted by one or two $C_{1-4}$ alkyl groups (e.g. methylamino, ethylamino, dimethylamino, diethylamino) and (vi) $C_{1-3}$ acyloxy group (e.g. formyloxy, acetoxy).

The substituent(s) for rings A', B' and J may be located at any position on the ring. When two or more substituents are present, they may be identical or not, the number of substituents being 1 to 4, preferably 1 to 3, more preferably 1 or 2. Also, the adjacent carbons on ring A', B' or J may bind with a group represented by —(CH$_2$)l— (l represents an integer of from 3 to 5) to form a 5- to 7-membered ring; this case is included in the desired above products.

Ring A' is preferably a benzene ring which may be substituted by one to four substituents selected from the group consisting of halogen (e.g., chlorine), optionally halogenated $C_{1-4}$ alkyl group (e.g., methyl, ethyl, isopropyl, trifluoromethyl) and $C_{1-4}$ alkoxy group (e.g., methoxy), specifically a benzene ring which may be substituted for and which is represented by formula [A]:

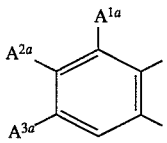

wherein $A^{1a}$, $A^{2a}$ and $A^{3a}$, whether identical or not, independently represent hydrogen, a halogen (e.g., fluorine, chlorine), a $C_{1-4}$ alkyl group (e.g., methyl, ethyl, isopropyl), a $C_{1-4}$ alkoxy group (e.g., methoxy, ethoxy) or a halogeno-$C_{1-4}$ alkyl group (e.g., trifluoromethyl). More preferably, for example, there may be used benzene rings which may be substituted for and which is represented by the above formula [A] wherein:

(1) $A^{1a}$, $A^{2a}$ and $A^{3a}$ are all hydrogen, (2) $A^{1a}$ and $A^{2a}$ are both hydrogen, $A^{3a}$ being a halogen (e.g. fluorine, chlorine), an optionally halogenated $C_{1-4}$ alkyl group (e.g. methoxy, ethoxy) or an optionally halogenated $C_{1-4}$ alkoxy group (e.g. methoxy, trifluoromethoxy, ethoxy), (3) $A^{1a}$ is hydrogen, $A^{2a}$ and $A^{3a}$, whether identical or not, being independently a halogen (e.g. fluorine, chlorine), a $C_{1-4}$ alkyl group (e.g. methyl, ethyl) or a $C_{1-4}$ alkoxy group (e.g. methoxy, ethoxy), or (4) $A^{2a}$ is hydrogen, $A^{1a}$ and $A^{3a}$, whether identical or not, being independently a $C_{1-4}$ alkyl group (e.g. methyl, ethyl).

More preferably for ring A', for example, there may be used optionally substituted benzene rings which is represented by the above formula [A] wherein:

(a) $A^{1a}$, $A^{2a}$ and $A^{3a}$ are all hydrogen, (b) $A^{1a}$ and $A^{2a}$ are both hydrogen, $A^{3a}$ being chlorine, a methyl, ethyl, isopropyl, methoxy or trifluoromethyl group, (c) $A^{1a}$ is hydrogen, $A^{2a}$ and $A^{3a}$ being both a methyl or methoxy group, or (d) $A^{2a}$ is hydrogen, $A^{1a}$ and $A^{3a}$ being both a methyl group.

Ring B' is preferably an optionally substituted benzene ring by one to four substituents selected from the group consisting of halogen (e.g., fluorine trifluoromethyl, ethyl) and $C_{1-4}$ alkoxy group (e.g., methoxy, ethoxy), specifically an optionally substituted benzene ring which is represented by formula [B]:

wherein $B^{1b}$, $B^{2b}$ and $B^{3b}$, whether identical or not, independently represent hydrogen, a halogen (e.g., chlorine, fluorine), an optionally halogenated $C_{1-4}$ alkyl group (e.g., methyl, trifluoromethyl, ethyl) or a $C_{1-4}$ alkoxy group (e.g., methoxy, ethoxy). More preferably, for example, there may be used benzene rings which may be substituted for and which is represented by the above formula [B] wherein:

(1) $B^{1b}$, $B^{2b}$ and $B^{3b}$ are all hydrogen, (2) $B^{1b}$ is halogen, an optionally halogenated $C_{1-4}$ alkyl group (e.g. methyl, trifluoromethyl, ethyl) or an optionally halogenated $C_{1-4}$ alkoxy group (e.g. methoxy, trifluoromethoxy, ethoxy), $B^{2b}$ and $B^{3b}$ being both hydrogen, (3) $B^{1b}$ is hydrogen, $B^{2b}$ and $B^{3b}$, whether identical or not, being independently an optionally halogenated $C_{1-4}$ alkoxy group (e.g. methoxy, trifluoromethoxy, ethoxy), or (4) $B^{1b}$, $B^{2b}$ and $B^{3b}$, whether identical or not, are independently an optionally halogenated $C_{1-4}$ alkoxy group (e.g. methoxy, trifluoromethoxy, ethoxy).

More preferably for ring B', for example, there may be used optionally substituted benzene rings which is represented by the above formula [B] wherein:

(a) $B^{1b}$, $B^{2b}$ and $B^{3b}$ are all hydrogen, (b) $B^{1b}$ is chlorine, fluorine, a methyl, trifluoromethyl or methoxy group, $B^{2b}$ and $B^{3b}$ being both hydrogen, (c) $B^{1b}$ is hydrogen, $B^{2b}$ and $B^{3b}$ being both a methoxy group, or (d) $B^{1b}$, $B^{2b}$ and $B^{3b}$ are all a methoxy group.

Ring J may be preferably a benzene ring which may be substituted by one to four substituents selected from the group consisting of halogen (e.g., chlorine, fluorine, bromine), optionally halogenated $C_{1-4}$ alkyl group (e.g., methyl, trifluoromethyl, ethyl, isopropyl, t-butyl), $C_{1-4}$ alkoxy group (e.g., methoxy), di-$C_{1-4}$ alkylamino group (e.g., N,N-dimethylamino, N,N-diethylamino), $C_{1-3}$ acyloxy group (e.g., formyloxy, acetoxy) and hydroxyl group, specifically an optionally substituted benzene ring which is represented by formula [J]:

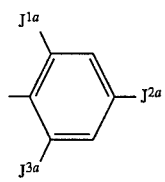

wherein $J^{1a}$, $J^{2a}$ and $J^{3a}$, whether identical or not, independently represent hydrogen, a halogen (e.g., chlorine, fluorine), an optionally halogenated $C_{1-4}$ alkyl group (e.g., methyl, trifluoromethyl, ethyl, isopropyl), a $C_{1-4}$ alkoxy group (e.g., methoxy) or a di-$C_{1-4}$ alkylamino group (e.g., N,N-dimethylamino), or by formula [J']:

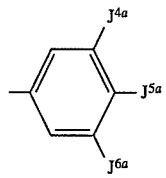

wherein $J^{4a}$, $J^{5a}$ and $J^{6a}$, whether identical or not, independently represent hydrogen, an optionally halogenated $C_{1-4}$ alkyl group (e.g., methyl, trifluoromethyl, isopropyl, t-butyl), a $C_{1-3}$ acyloxy group (e.g., acetoxy) or a hydroxyl group. More preferably, for example, there may be used a benzene ring which may be substituted and which is represented by the above formula [J] or [J'] wherein:

(1) $J^{1a}$, $J^{2a}$ and $J^{3a}$, whether identical or not, independently represent halogen, a $C_{1-4}$ alkyl group or a $C_{1-4}$ alkoxy group, (2) $J^{1a}$ and $J^{2a}$, whether identical or not, independently represent a halogen, a $C_{1-4}$ alkyl group or a $C_{1-4}$ alkoxy group, $J^{3a}$ being hydrogen, (3) $J^{1a}$ and $J^{3a}$, whether identical or not, independently represent a halogen, a $C_{1-4}$ alkyl group or a $C_{1-4}$ alkoxy group, $J^{2a}$ being hydrogen, (4) $J^{1a}$ and $J^{3a}$ are hydrogen, $J^{2a}$ being a halogen, (5) $J^{4a}$ is a di-$C_{1-4}$ alkylamino group, $J^{5a}$ and $J^{6a}$ being hydrogen, (6) $J^{4a}$ and $J^{6a}$ are hydrogen, $J^{5a}$ being a di-$C_{1-4}$ alkylamino group, or (7) $J^{4a}$ and $J^{6a}$, whether identical or not, independently represent a $C_{1-4}$ alkyl group or a $C_{1-4}$ alkoxy group, $J^{5a}$ being a $C_{1-3}$ acyloxy group or a hydroxyl group.

In the above (1) to (7), the $C_{1-4}$ alkyl group includes methyl, ethyl, propyl, isopropyl, etc.; the halogen atom includes fluorine, chlorine, bromine, etc.; the $C_{1-4}$ alkoxy group includes methoxy, ethoxy, propoxy, etc.; the di-$C_{1-4}$ alkylamino group includes N,N-dimethylamino, N,N-diethylamino, etc.; the $C_{1-3}$ acyloxy group includes formyloxy, acetoxy, etc.

More preferably for ring J, for example, there may be used optionally substituted benzene rings which is represented by the above formula [J] or [J'] wherein:

(a) $J^{1a}$, $J^{2a}$ and $J^{3a}$ are all fluorine, a methyl or methoxy group, (b) $J^{1a}$ and $J^{2a}$ are both chlorine, a fluorine, isopropyl or methoxy group, $J^{3a}$ being hydrogen, (c) $J^{1a}$ and $J^{3a}$ are both chlorine, fluorine, a methyl, ethyl, isopropyl or methoxy group, $J^{2a}$ being hydrogen, (d) $J^{1a}$ is an isopropyl group, $J^{2a}$ being hydrogen, $J^{3a}$ being a methyl group, (e) $J^{1a}$ and $J^{3a}$ are hydrogen, $J^{2a}$ being chlorine, (f) $J^{4a}$ is an N,N-dimethylamino group, $J^{5a}$ and $J^{6a}$ being hydrogen, (g) $J^{4a}$ and $J^{6a}$ are hydrogen, $J^{5a}$ being an N,N-dimethylamino group, (h) $J^{4a}$ and $J^{6a}$ are both a methyl or isopropyl group, $J^{5a}$ being an acetoxy group, or (i) $J^{4a}$ and $J^{6a}$ are both a methyl, isopropyl or t-butyl group, $J^{5a}$ being a hydroxyl group.

With respect to the above formulas, $R^{1a}$ and R independently represent an optionally hydrocarbon group; $R^{1b}$, $R^2$, $R^{2a}$, $R^{3a}$ and $R^{4a}$ independently represent a hydrogen atom or an optionally substituted hydrocarbon group. Such hydrocarbon group include alkyl group, alkenyl group, alkynyl group, cycloalkyl group and aryl group, preferably a alkyl group.

The alkyl group is a straight-chain or branched one having 1 to 6 carbon atoms such as methl, ethyl, propyl, isopropyl, butyl, isobutyl, sec-butyl, tert-butyl, pentyl, isopentyl, hexyl, etc., preferably a straight-chain or branched alkyl group having 1 to 4 carbon atoms such as methyl, ethyl, propyl, isopropyl, butyl, isobutyl, sec-butyl or tert-butyl.

The alkenyl group is one having 2 to 6 carbon atoms such as ethenyl, propenyl, isopropenyl, butenyl, isobutenyl or sec-butenyl, preferably an alkenyl group having 2 to 4 carbon atoms such as ethenyl, propenyl or isopropenyl.

The alkynyl group is one having 2 to 6 carbon atoms such as ethynyl, propynyl, isopropenyl, butynyl, isobutynyl or sec-butynyl, preferably an alkenyl group having 2 to 4 carbon atoms such as ethynyl, propynyl or isopropenyl.

The cycloalkyl group is a $C_{3-8}$ cycloalkyl group such as cyclopropyl, cyclobutyl, cyclopentyl or cyclohexyl, preferably a $C_{3-6}$ cycloalkyl group such as cyclopropyl or cyclobutyl.

The aryl group is one having 6 to 14 carbon atoms such as phenyl, naphthyl, anthryl or phenanthryl, preferably an aryl group having 6 to 10 carbon atoms such as phenyl or naphthyl, more preferably phenyl.

Examples of the substituent for the optionally substituted hydrocarbon group include (i) halogen, (ii) cycloalkyl group, (iii) aryl group, (iv) amino groups which may have an alkyl, alkenyl, cycloalkyl or aryl group as a substituent, (v) hydroxyl group, (vi) optionally halogenated alkoxy group, (vii) acyl group, (viii) acyloxy group, (ix) cyano group, (x) optionally protected carboxyl group, (xi) carbamoyl group, (xii) mercapto group, (xiii) alkylthio group, (xiv) sulfo group, and (xv) alkylsulfonyl group.

The optionally substituted hydrocarbon group which may be substituted for may be substituted for by 1 to 4, preferably 1 or 2 of the above-mentioned substituents, whether identical or not.

The halogen atom is exemplified by fluorine, chlorine, bromine and iodine, preferably fluorine and chlorine. The cycloalkyl group is exemplified by $C_{3-6}$ cycloalkyl groups such as cyclopropyl, cyclobutyl, cyclopentyl and cyclohexyl. The aryl group is exemplified by $C_{6-10}$ aryl groups such as phenyl and naphthyl. With respect to the amino group which may have an alkyl, alkenyl, cycloalkyl or aryl group as a substituent, the alkyl group is exemplified by $C_{1-4}$ alkyl group such as methyl, ethyl, propyl and isopropyl; the alkenyl group is exemplified by $C_{2-4}$ alkenyl group such as ethenyl, propenyl, isopropenyl and butenyl; the cycloalkyl group is exemplified by $C_{3-6}$ cycloalkyl group such as cyclopropyl, cyclobutyl, cyclopentyl and cyclohexyl; the aryl group is exemplified by $C_{6-10}$ aryl group such as phenyl and naphthyl. Said amino group is preferably an amino group which may be substituted by a $C_{1-4}$ alkyl group, such as an amino, methylamino, ethylamino, dimethylamino or diethylamino group. The optionally halogenated alkoxy group is exemplified by $C_{1-4}$ alkoxy group such as methoxy, difluoromethoxy, trifluoromethoxy, ethoxy, 2,2,2-trifluoroethoxy, propoxy, isopropoxy, butoxy, 4,4,4-trifluorobutoxy, isobutoxy and sec-butoxy, or such alkoxy group substituted for by 1 to 3 halogen atoms (e.g., fluorine, chlorine). The acyl group is a $C_{1-4}$ acyl group such as formyl, acetyl, propionyl, butyryl or isobutyryl. The acyloxy group is a $C_{1-4}$ acyloxy group such as formyloxy, acetyloxy, propionyloxy, butyryloxy or isobutyryloxy. The protecting group for the optionally protected carboxyl group is exemplified by $C_{1-4}$ alkyl groups such as methyl, ethyl and t-butyl groups and $C_{7-11}$ aralkyl group such as benzyl. The alkylthio group is a $C_{1-4}$ alkylthio group such as methylthio, ethylthio, propylthio, isopropylthio or butylthio. The alkylsulfonyl group is a $C_{1-4}$ alkylsulfonyl group such as a methylsulfonyl, ethylsulfonyl, propylsulfonyl, isopropylsulfonyl or butylsulfonyl group.

Example preferable substituents for the hydrocarbon group which may be substituted for include (i) halogen, (ii) cycloalkyl group, (iii) aryl group, (iv) amino group which may have an alkyl, alkenyl, cycloalkyl or aryl group as a substituent, (v) hydroxyl group, (vi) optionally halogenated alkoxy groups, (vii) acyl group, (viii) acyloxy group, (ix) cyano group, (x) optionally protected carboxyl group and (xi) carbamoyl group, with greater preference given to (a) $C_{3-6}$ cycloalkyl group, (b) $C_{6-10}$ aryl group, (c) amino group which may be substituted by $C_{1-4}$ alkyl group, and (d) carboxyl group which may be substituted by $C_{1-4}$ alkyl group.

The definition of substituents as described in (i) to (x) and (a) to (d) is the same meaning as defined in the above hydrocarbon group.

Examples of preferable groups for $R^{1a}$, $R^{1b}$ and R in —OR include a $C_{1-6}$ alkyl (e.g. methyl, ethyl, propyl, isopropyl, butyl, sec-butyl, tert-butyl) or $C_{3-6}$ cycloalkyl group (e.g. cyclopropyl) which may be substituted by a (i) $C_{6-10}$ aryl (e.g. phenyl), (ii) amino which may be substituted by one or two $C_{1-4}$ alkyl groups (e.g. amino, methylamino, dimethylamino), (iii) hydroxyl, (iv) optionally protected carboxyl (e.g. $C_{1-6}$ alkoxy-carbonyl such as methoxycarbonyl, ethoxycarbonyl, t-butoxycarbonyl) or (v) $C_{3-6}$ cycloalkyl (e.g. cyclopropyl), preferably, methyl, ethyl, propyl, isopropyl, butyl, sec-butyl, tert-butyl, cyclopropyl, cyclopropylmethyl, benzyl, 2,2-dimethylaminoethyl, 2,2-diethylaminoethyl, 2-hydroxyethyl, carboxymethyl, methoxycarbonylmethyl, ethoxycarbonylmethyl and t-butoxycarbonylmethyl. Hydrogen is also preferable for $R^{1b}$.

Preferable groups for $R^2$, $R^{2a}$, $R^{3a}$ and $R^{4a}$ include hydrogen atom and $C_{1-4}$ alkyl group (e.g. methyl, ethyl, propyl, isopropyl, etc.), with greater preference given to hydrogen atoms, methyl, ethyl, propyl and isopropyl groups.

With respect to the above formulas, α represents 0, 1 or 2, with preference given to 1.

In the above formulas, ═ represents a single or double bond; Z' represents $$-\underset{|}{CR^4}-$$

(the symbols have the same definitions as above) or a nitrogen atom, provided that ═ is a single bond, or a carbon atom, provided that ═ is a double bond.

In the above formulas, either X' or Y' represents —$NR^{1a}$— (the symbols have the same definitions as above), —O— or —S—, the other representing —CO—, —CS— or —$C(R^2)R^{2a}$— (the symbols have the same definitions as above), or either X' or Y' represents —N═, the other representing ═$CR^{3a}$— (the symbols have the same definitions as above). —X'—Y'— is preferably exemplified by —$NR^{1a}$—CO—, —$NR^{1a}$—$CH_2$—, —CO—$NR^{1a}$—, —O—CO—, —CO—O— and N═$CR^{3a}$— (the symbols have the same definitions as above), more preferably —$N(CH_3)$—CO—, —$N(C_2H_5)$—CO—, —$N(CH_3)$—$CH_2$—, —$N(C_2H_5)$—$CH_2$, —CO—$N(CH_3)$—, —CO—$N(C_2H_5)$—, —O—CO—, —CO—O—, —N═CH—, —N═$C(CH_3)$—, —N═$C(OCH_3)$— and —N═$C(OC_2H_5)$—.

In the above formulas, either X" or Y" represents —$NR^{1b}$— (the symbols have the same definitions as above), —O— or —S—, the other representing —CO—, —CS— or —$C(R^2)R^{2a}$— (the symbols have the same definitions as above), or either X" or Y" represents —N═, the other representing ═$CR^{3a}$— (the symbols have the same definitions as above). —X"—Y"— is preferably exemplified by —$NR^{1b}$— CO—, —$NR^{1b}$—$CH_2$—, —CO—$NR^{1b}$—, —O—CO—, —CO—O— and —N═$CR^{3a}$— (the symbols have the same definitions as above), more preferably —NHCO—, —$N(CH_3)$—CO—, —$N(C_2H_5)$—CO—, —$N(CH_3)$—$CH_2$—, —$N(C_2H_5)$—$CH_2$—, —CONH—, —CO—$N(CH_3)$—, —CO—$N(C_2H_5)$—, —O—CO—, —CO—O—, —N═CH—, —N═$C(CH_3)$—, —N═$C(OCH_3)$— and —N═$C(OC_2H_5)$—.

With respect to the above formulas, two isomers exist with different relative configurations of positions 3 and 4 on the condensed ring, provided that ═ is a single bond and Z' is $$-\underset{|}{CR^{4a}}-$$

($R^{4a}$ has the same definitions as above), each of which isomers involves two isomers with different absolute configurations. Provided that ═ is a single bond and Z' is a nitrogen atom, there are two isomers with different absolute configurations of position 3. The present invention includes these isomers and mixtures thereof. In this context, the position 3 of the condensed ring indicates the position of the carbon atom to which

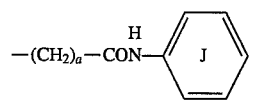

is bound, the position 4 indicating the position of Z'.

Preferable examples of (I) and (I') include also compounds of the formula:

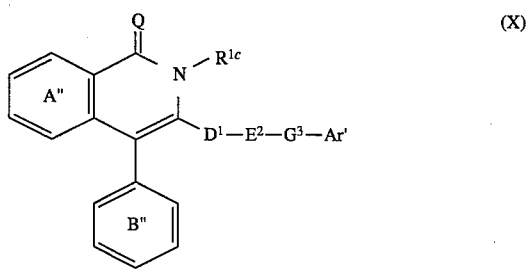

wherein rings A" and B" are an optionally substituted benzene ring; $R^{1c}$ represents a hydrogen atom, a hydroxyl group, an optionally substituted hydrocarbon group, an optionally substituted alkoxy group or an optionally substituted amino group; Q represents an oxygen atom or a sulfur atom; $D^1$ represents a $C_{1-3}$ alkylene group which may be substituted by an oxo or thioxo group; provided that $D^1$ is an unsubstituted $C_{1-3}$ alkylene group, it may cooperate with $R^{1C}$ to form a 5- to 7-membered ring which may be substituted by an oxo or thioxo group; $E^2$ represents —$NR^{5a}$— ($R^{5a}$ represents a hydrogen atom or an optionally substituted hydrocarbon group), —O— or —S—; $R^5$ and $R^{1c}$, taken together, may form a 5- to 7-membered ring which may be substituted by an oxo or thioxo group; $G^3$ represents a bond or a $C_{1-3}$ alkylene group; Ar' represents an optionally substituted aryl group or an optionally substituted heterocyclic group; provided that, when —$D^1$—$E^2$— is —$(CH_2)_\beta$—CONH— (β is 0, 1 or 2), $G^3$ represents a $C_{1-3}$ alkylene group, or a salt thereof.

And, the compound (X) can be produced by a process which comprises reacting a compound of the formula:

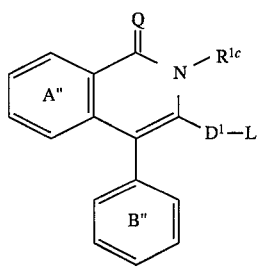

(XI)

wherein L represents a leaving group; $D^1$ and $R^{1c}$ do not bind together to form a 5- to 7- membered ring; the other symbols are the same meaning as defined hereinabove or salt thereof with a compound of the formula:

$$H—E^2—G^3—Ar'\qquad(XII)$$

wherein all symbols are the same meanings as defined hereinabove or a salt thereof.

Further the compound (X) can be produced by a process which comprises reacting a compound of the formula:

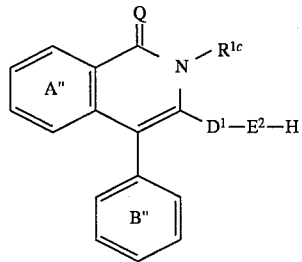

(XIII)

wherein L' represents a leaving group; the other symbols are the same meaning as defined hereinabove or salt thereof, with a compound, of the formula:

$$L'—G^3—Ar'\qquad(XIV)$$

wherein all symbols are the same meaning as defined hereinabove or a salt thereof.

Preferable examples of the above symbols include the following:

(1) rings A" and B" are a benzene ring which may be substituted by one to four substituents selected from the group consisting of halogen (e.g. fluorine, chlorine, bromine), optionally halogenated $C_{1-4}$ alkyl group (e.g. methyl, trifluoromethyl, ethyl, propyl, isopropyl), hydroxyl group, optionally halogenated $C_{1-4}$ alkoxy group (e.g. methoxy, trifluoromethoxy, ethoxy, propoxy, butoxy), optionally halogenated $C_{1-4}$ alkylthio group (e.g. mercapto, methylthio, trifluoromethylthio, ethylthio), amino group, mono- or di-$C_{1-4}$ alkylamino group (e.g. methylamino, ethylamino, dimethylamino), carboxyl group and $C_{1-4}$ alkoxy-carbonyl group (e.g. methoxycarbonyl, ethoxycarbonyl), (2) ring A" is represented by the general formula:

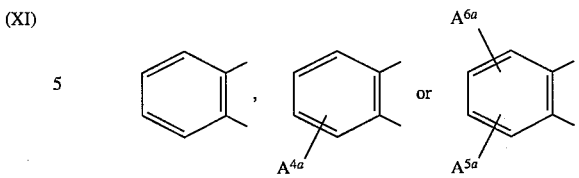

wherein $A^{4a}$, $A^{5a}$ and $A^{6a}$, whether identical or not, independently represent a halogen atom (e.g. fluorine, chlorine, bromine), an optionally halogenated $C_{1-4}$ alkyl group (e.g. methyl, trifluoromethyl, ethyl, propyl, isopropyl) or an optionally halogenated $C_{1-4}$ alkoxy group (e.g. methoxy, trifluoromethoxy, ethoxy, propoxy, butoxy), (3) ring B" is represented by the general formula:

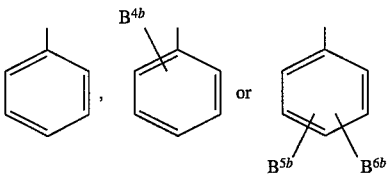

wherein $B^{4b}$, $B^{5b}$ and $B^{6b}$, whether identical or not, independently represent a halogen atom, an optionally halogenated $C_{1-4}$ alkyl group (e.g. methyl, trifluoromethyl, ethyl, propyl, isopropyl) or an optionally halogenated $C_{1-4}$ alkoxy group (e.g. methoxy, trifluoromethoxy, ethoxy, propoxy, butoxy), (4) $R^{1c}$ is a hydrogen atom or a $C_{1-4}$ alkyl group (e.g. methyl, ethyl, propyl) which may be substituted by one or two substituents selected from the group consisting of hydroxyl group, $C_{1-4}$ alkoxy group (e.g. methoxy, ethoxy), amino group, mono- or di-$C_{1-4}$ alkylamino group (e.g. methylamino, ethylamino, dimethylamino, diethylamino), $C_{1-4}$ alkoxy-carbonyl group (e.g. methoxycarbonyl, ethoxycarbonyl), carboxyl group, carbamoyl group and phenyl group, (5) $R^{1c}$ is a hydrogen atom or a $C_{1-4}$ alkyl group (e.g. methyl, ethyl, propyl), (6) $R^{5a}$ is a hydrogen atom or a $C_{1-4}$ alkyl group (e.g. methyl, ethyl, propyl) which may be substituted for by one or two substituents selected from the group consisting of hydroxyl group, $C_{1-4}$ alkoxy group (e.g. methoxy, ethoxy, propoxy), amino group, mono- or di-$C_{1-4}$ alkylamino group (e.g. methylamino, ethylamino, dimethylamino, diethylamino), $C_{1-4}$ alkoxycarbonyl group (e.g. methoxycarbonyl, ethoxycarbonyl), carboxyl group, carbamoyl group and phenyl group, (7) $R_{5a}$ is a hydrogen atom or a $C_{1-4}$ alkyl group (e.g. methyl, ethyl, propyl), (8) the optionally substituted aryl group represented by Ar', is a $C_{6-10}$ group (e.g. phenyl, naphthyl) which may have one to three substituents selected from the group consisting of an optionally halogenated $C_{1-4}$ alkyl group (e.g. methyl, trifluoromethyl, ethyl, propyl, isopropyl), halogen atom (e.g. fluorine, chlorine, bromine), nitro group, hydroxyl group, optionally halogenated $C_{1-4}$ alkoxy group (e.g. methoxy, trifluoromethoxy, ethoxy, butoxy), amino group, mono- or di-$C_{1-4}$ alkylamino group (e.g. Methylamino, ethylamino, dimethylamino, diethylamino), $C_{1-4}$ alkoxy-carbonyl group (e.g. methoxycarbonyl, ethoxycarbonyl), carboxyl group and carbamoyl group, (9) the optionally substituted aryl group represented by Ar', is a phenyl group which may have one to three substituents selected from the group consisting of an optionally halogenated $C_{1-4}$ alkyl group (e.g. methyl, trifluoromethyl, ethyl, propyl, isopropyl), halogen atom (e.g. fluorine, chlorine, bromine) and $C_{1-4}$ alkoxy group (e.g. methoxy, ethoxy, propoxy),

(10) the optionally substituted heterocyclic group represented by Ar', is furyl, thienyl, pyrrolyl, oxazolyl, isoxazolyl, imidazolyl, pyrazolyl, pyridyl, pyridazinyl, quinolyl, isoquinolyl, thiazolyl, thiadiazolyl or thiophenyl which may have one to three substituents selected from the group consisting of halogen atom (e.g. fluorine, chlorine, bromine), optionally halogenated, $C_{1-4}$ alkyl group (e.g. methyl, trifluoromethyl, ethyl, propyl, isopropyl), $C_{3-6}$ cycloalkyl group (e.g. cyclopropyl), hydroxyl group, $C_{1-4}$ alkoxy group (e.g. methoxy, ethoxy, propoxy), $C_{1-4}$ alkylthio group (e.g. methylthio, ethylthio, propylthio), amino group, mono- or di-$C_{1-4}$ alkylamino group (e.g. methylamino, ethylamino, dimethylamino, diethylamino), $C_{1-4}$ alkoxycarbonyl group (e.g. methoxycarbonyl, ethoxycarbonyl) and carboxyl group,

(11) the heterocyclic group represented by Ar', is furyl, thienyl or pyridyl which may have one to three substituents selected from the group consisting of halogen atom (e.g. fluorine, chlorine, bromine), $C_{1-4}$ alkyl group (e.g. methyl, ethyl, propyl) and $C_{1-4}$ alkoxy group (e.g. methoxy, ethoxy, propoxy),

(12) Q is an oxygen atom.

(13) $D^1$ is —CO—, —CS—, —CH$_2$—, —CH$_2$CH$_2$—, —CH$_2$CO— or —CH$_2$CH$_2$CO—,

(14) $D^1$ is —CO— or —CH$_2$CO—,

(15) $D^1$ is —CH$_2$— or —CH$_2$CH$_2$—,

(16) $D^1$ is —CO— or —CH$_2$—,

(17) $E^2$ is —NR$^{5c}$— (R$^{5c}$ is a hydrogen atom or a $C_{1-4}$ alkyl group (e.g. methyl, ethyl, propyl)),

(18) $E^2$ is —O—,

(19) $G^3$ is —CH$_2$— or —CH$_2$CH$_2$—, (20). ring A" is a benzene ring which may be substituted by two $C_{1-4}$ alkyl group (e.g. methyl, ethyl, propyl); ring B is a benzene ring which may be substituted by a $C_{1-4}$ alkyl group (e.g. methyl, ethyl, propyl); $R^{1c}$ is a $C_{1-4}$ alkyl group (e.g. methyl, ethyl, propyl), $R^{5a}$ is a hydrogen atom or a $C_{1-4}$ alkyl group (e.g. methyl, ethyl, propyl), $D^1$ is —CO—; $E^2$ is —NR$^{5c}$— (R$^{5c}$ represents a hydrogen atom or a $C_{1-4}$ alkyl group (e.g. methyl, ethyl, propyl)), $G^3$ is —CH$_2$—; Ar' is a phenyl group substituted by one to three optionally halogenated $C_{1-4}$ alkyl groups (e.g. methyl, trifluoromethyl, ethyl),

(21) N-(3,5-bistrifluoromethyl)benzyl-1,2-dihydro-2-methyl-4-(2 -methylphenyl)-1-oxo-3-isoquinolinecarboxamide, N-(3,5-bistrifluoromethyl)benzyl-1,2-dihydro-N,2-dimethyl-4-(2-methylphenyl)-1 -oxo-3-isoquinolinecarboxamide or N-[3,5-bis(trifluoromethyl)benzyl]-1,2 -dihydro-N,2,6,7-tetra methyl-1-oxo-4-phenyl-3-isoquinolinecarboxamide, The terms of ring A" and B" are the same meaning as defined above in the ring A and B of (I) and (I').

Preferable substituents on ring A" and B" include halogen (e.g. fluoro, chloro, bromo, etc.), optionally halogenated $C_{1-4}$ alkyl (e.g. methyl, chloromethyl, difluoromethyl, trichloromethyl, trifluoromethyl, ethyl, 2-bromoethyl, 2,2,2-trifluoroethyl, propyl, 3,3,3-trifluropropyl, isopropyl, 2-trifluoromethylethyl, butyl, 4,4,4-trifluorobutyl, isobutyl, sec-butyl, tert-butyl, etc.), optionally halogenated $C_{1-4}$ alkoxy (e.g. methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, etc.), optionally substituted $C_{1-4}$ alkylthio (e.g. methylthio, difluoromethylthio, trifluoromethylthio, ethylthio, propylthio, isopropylthio, buthylthio, 4,4,4-trifluorobuthylthio, etc.), hydroxyl, amino, mono-or di-$C_{1-4}$ alkylamino (e.g. methylamino, ethylamino, propylamino, dimethylamino, diethylamino, etc.), carboxyl and $C_{1-4}$ alkoxy-carbonyl (e.g. methoxycarbonyl, ethoxycarbonyl, propoxycarbonyl, etc.).

More preferable substituents on ring A" and B" include halogen (e.g. fluoro, chloro, bromo, etc.), optionally halogenated $C_{1-4}$ alkyl (e.g. methyl, chloromethyl, difluoromethyl, trichloromethyl, trifluoromethyl, ethyl; 2-bromoethyl, 2,2,2-trifluoroethyl, propyl, 3,3,3-trifluoropropy isopropyl, 2-trifluoromethylethyl, buthyl, 4,4,4-trifluorobutyl, isobutyl, sec-butyl, tert-butyl, etc.), optionally halogenated $C_{1-4}$ alkoxy (e.g. methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, etc.), hydroxyl, amino and mono- or di-$C_{1-4}$ alkylamino (e.g. methylamino, ethylamino, propylamino, dimethylamino, diethylamino, etc.).

Specifically more preferable substituents on ring A" and B" include halogen (e.g. fluoro, chloro, bromo, etc.), optionally halogenated $C_{1-4}$ alkyl (e.g. methyl, chloromethyl, difluoromethyl, trichloromethyl, trifluoromethyl, ethyl, 2-bromoethyl, 2,2,2-trifluoroethyl, propyl, 3,3,3-trifluoropropy isopropyl, 2-trifluoromethylethyl, buthyl, 4,4,4-trifluorobutyl, isobutyl, sec-butyl, tert-butyl, etc.), optionally halogenated $C_{1-4}$ alkoxy (e.g. methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, etc.). The substituent(s) for rings A" and B" may be located at any position on the ring. When two or more substituents are present, they may be identical or not, the number of substituents being 1 to 4, preferably 1 to 3, more preferably 1 or 2. Also, the adjacent carbons on ring A" or B" may bind with a group represented by —(CH$_2$)l— (l represents an integer of from 3 to 5) to form a 5- to 7-membered ring.

Referring to ring A", concrete examples of the moiety

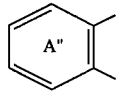

include groups of the formula:

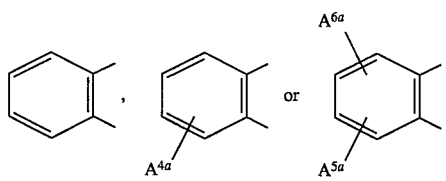

where $A^{4a}$, $A^{5a}$ and $A^{6a}$ are the same or different and each means a halogen atom such as chloro, fluoro, etc., an optionally halogenated $C_{1-4}$ alkyl group such as methyl, ethyl, isopropyl trifluoromethyl, etc., or an optionally halogenated $C_{1-4}$ alkoxy group such as methoxy, trifluoromethoxy, ethoxy, etc.

In $A^{4a}$, $A^{5a}$ and $A^{6a}$, preferably a $C_{1-4}$ alkyl group (e.g. methyl, ethyl, etc.).

Referring to ring B", concrete examples of the moiety

include groups of the formula:

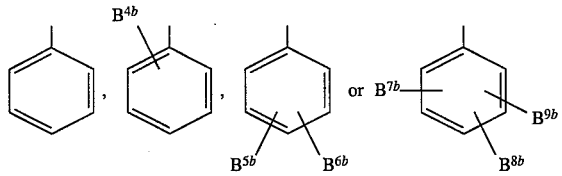

where $B^{4b}$, $B^{5b}$, $B^{6b}$, $B^{7b}$, $B^{8b}$ and $B^{9b}$ are the same or different and each means a halogen atom such as chloro, fluoro, etc., an optionally halogenated $C_{1-4}$ alkyl group such as methyl, trifluoromethyl, ethyl, etc., or an optionally halogenated $C_{1-4}$ alkoxy group such as methoxy trifluoromethoxy, ethoxy, etc.

Preferred examples of the ring B" are groups of the formula:

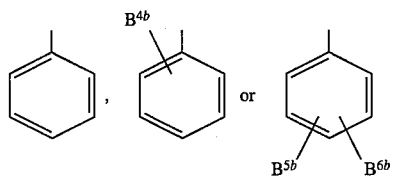

wherein $B^{4b}$, $B^{5b}$ and $B^{6b}$ is the same meaning hereinbefore.

In $B^{4b}$, $B^{5b}$ and $B^{6b}$, preferably a $C_{1-4}$ alkyl group (e.g. methyl, ethyl, etc.) and a $C_{1-4}$ alkoxy group (e.g. methoxy, ethoxy, etc.).

With respect to the above formula, $R^{1c}$ represents a hydrogen atom, hydroxyl group, optionally substituted hydrocarbon group, optionally substituted alkoxy group or optionally substituted amino group. The "hydrocarbon group" of "optionally substituted hydrocarbon group" represented by $R^{1c}$ is used, for example, $C_{1-6}$ alkyl group, $C_{3-6}$ cycloalkyl group or $C_{3-6}$ cycloalkyl-$C_{1-4}$ alkyl group and so on. The $C_{1-6}$ alkyl group includes, for example, methyl, ethyl, propyl, isopropyl, butyl, isobutyl, sec-butyl, tert-butyl, pentyl, neopentyl, hexyl, etc., preferably a $C_{1-4}$ alkyl group such as methyl, ethyl, propyl, isopropyl, butyl, isobutyl, sec-butyl, tert-butyl, etc. The $C_{3-6}$ cycloalkyl group includes, for example, cyclopropyl, cyclopentyl or cyclohexyl, etc. The $C_{3-6}$ cycloalkyl-$C_{1-4}$ alkyl group includes, for example, cyclopropylmethyl, cyclopropylethyl, etc.

The preferable substituent of the hydrocarbon group hereinabove is commonly used a $C_{1-4}$ alkyl group such as methyl, ethyl, propyl, isopropyl, butyl and so on.

The substituent of the hydrocarbon group is used one to five, preferably one to three, more preferable one or two substituent(s) selected from the group consisting of halogen atom (e.g. fluoro, chloro, bromo, etc.), nitro, cyano, hydroxyl, $C_{1-4}$ alkoxy group (e.g. methoxy, ethoxy, propoxy, butoxy, isopropoxy, etc.), $C_{1-4}$ alkylthio group (e.g. methylthio, ethylthio, propylthio, etc.), amino, mono- or di-$C_{1-4}$ alkylamino group (e.g. methylamino, ethylamino, propylamino, dimethylamino, diethylamino, etc.), cyclic amino group (e.g., 5- to 9-membered cyclic amino which may contain 1 to 3 heteroatoms such as oxygen and sulfur in addition to nitrogen as ring-constituent members, such as pyrrolidino, piperidino, morpholino, etc.), $C_{1-4}$ alkylcarbonylamino group (e.g. acetylamino, propionylamino, butyrylamino, etc.), $C_{1-4}$ alkylsulfonylamino group (e.g. methylsulfonylamino, ethylsulfonylamino, etc.), $C_{1-4}$ alkoxycarbonyl group (e.g. methoxycarbonyl, ethoxycarbonyl, propoxycarbonyl, etc.), carboxyl, $C_{1-6}$ alkyl-carbonyl group (e.g. methylcarbonyl, ethylcarbonyl, propylcarbonyl, etc.), carbamoyl, ethylcarbamoyl, etc.), mono- or di-$C_{1-4}$ alkylcarbamoyl (e.g. methylcarbamoyl, ethylcarbamoyl, etc.), $C_{1-6}$ alkylsulfonyl group (e.g. methylsulfonyl, ethylsulfonyl, propylsulfonyl, etc.), and phenyl group which may be substituted by $C_{1-3}$ alkoxy group (e.g. methoxyphenyl, ethoxyphenyl, etc.).

As the halogen atoms, among the above-mentioned substituents, fluoro, chloro, bromo and iodo may be reckoned and chloro or fluoro is preferred.

Preferable examples of substituent of hydrocarbon group include hydroxyl group, $C_{1-4}$ alkoxy group (e.g. methoxy, ethoxy, propoxy, etc.), amino group, mono- or di-$C_{1-4}$ alkylamino group (e.g. methylamino, ethylamino, dimethylamino, diethylamino, etc.), $C_{1-4}$ alkoxy-carbonyl group (e.g. methoxycarbonyl, ethoxycarbonyl, propoxycarbonyl, etc.), carboxyl group, carbamoyl group, phenyl group, more preferably carboxyl group and carbamoyl group.

Preferable examples of $R^{1c}$ include a hydrogen atom and a $C_{1-4}$ alkyl group (e.g. methyl, ethyl, n-propyl, n-butyl, etc.), more preferably a $C_{1-4}$ alkyl group (e.g. methyl, ethyl, n-propyl, etc.), The "alkoxy group" of the "optionally substituted alkoxy group" represented by $R^{1c}$ is, for example, $C_{1-4}$ alkoxy group (e.g. methoxy, ethoxy, propoxy, isopropoxy, butoxy, t-butoxy, etc.) and so on. The substituent of the "alkoxy group" is the same meaning as defined in the substituent of "hydrocarbon group".

The substituent of the "optionally substituted amino group" represented by $R^{1c}$ includes (i) $C_{1-4}$ alkyl group (e.g. methyl, ethyl, propyl, isopropyl, etc.), (ii) $C_{1-4}$ alkyl-carbonyl group (e.g. acetyl, propyonyl, butyril, etc.), (iii) $C_{1-4}$ alkoxy-carbonyl (e.g. methoxycarbonyl, ethoxycarbonyl, propoxycarbonyl, etc.), (iv) halogen atom (e.g. fluoro, chloro, etc.) and (v) phenyl group which may be substituted by a $C_{1-4}$ alkyl (e.g. methyl, ethyl, etc.), a $C_{1-4}$ alkoxy group (e.g. methoxy, ethoxy, etc.) or a halogen atom (e.g. fluoro, chloro, etc.) such as phenyl, 4-chlorophenyl, 3-chlorophenyl, 2-chlorophenyl, 4-methylphenyl, 3-methylphenyl, 2-methylphenyl, 4-methoxyphenyl, 3-methoxyphenyl, 2-methoxyphenyl, etc. The optionally substituted amino group maybe substituted by one or two substituent(s).

With respect to the above formula, Q represents an oxygen atom and a sulfur atom, preferably an oxygen atom.

With respect to the above formula, $D^1$ represents a $C_{1-3}$ alkylene group which may be substituted by an oxo or thioxo group.

The $C_{1-3}$ alkylene group includes, for example, —$CH_2$—, —$CH_2CH_2$—, —$CH_2CH_2CH_2$— and —$CH(CH_3)$—$CH_2$— and so on.

Preferable examples of $D^1$ include —CO—, —CS—, —$CH_2$—, —$CH_2CH_2$—, —$CH_2CO$—, —$CH_2CS$—, —$CH_2CH_2CO$— and —$CH_2CH_2CS$—, more preferably —CO—, —$CH_2$—, —$CH_2CH_2$— and —$CH_2CO$—, specially —CO— and —$CH_2$— are more preferable.

Provided that $D^1$ is an unsubstituted $C_{1-3}$ alkylene group, its carbon atoms may cooperate with $R^{1c}$ to form a 5- to 7-membered ring which may be substituted by an oxo or thioxo group. Specifically, the compound (X) is represented by the formula:

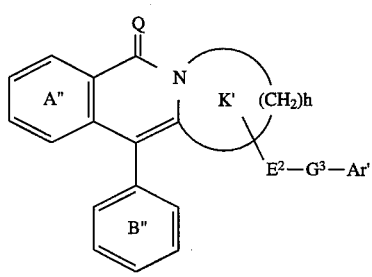
(I-A)

wherein ring K' is a 5- to 7-membered ring which may be substituted by an oxo or thioxo group; h represents an integer from 3 to 5; the other symbols have the same definitions as above, or a salt thereof, preferably represented by the formula:

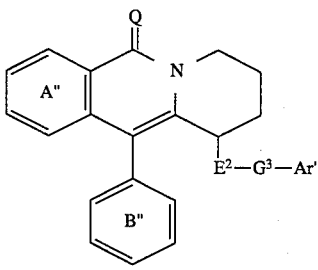

wherein the symbols have the same definitions as above or below.

With respect to the above formulas, $E^2$ represents —$NR^{5a}$— ($R^{5a}$ represents a hydrogen atom or an optionally substituted hydrocarbon group), —O— or —S—. The hydrocarbon group represented by $R^{5a}$ is preferably a $C_{1-6}$ alkyl group, a $C_{3-6}$ cycloalkyl group, a $C_{3-6}$ cycloalkyl-$C_{1-4}$ alkyl group or the like, more preferably a $C_{1-4}$ alkyl group (e.g. methyl, ethyl, propyl). The $C_{1-6}$ alkyl group is exemplified by methyl, ethyl, propyl, isopropyl, butyl, isobutyl, sec-butyl, tert-butyl, pentyl, neopentyl and hexyl, with preference given to $C_{1-4}$ alkyl groups such as methyl, ethyl, propyl, isopropyl, butyl, isobutyl, sec-butyl and tert-butyl. The $C_{3-6}$ cycloalkyl group is exemplified by cyclopropyl, cyclopentyl and cyclohexyl. The $C_{3-6}$ cycloalkyl-$C_{1-4}$ alkyl group is exemplified by cyclopropylmethyl and cyclopropylethyl. $R^{5a}$ is preferably a hydrogen atom or a $C_{1-4}$ alkyl grou (e.g., methyl, ethyl, propyl, butyl), with greater preference given to $C_{1-4}$ alkyl groups (e.g., methyl, ethyl, propyl, isopropyl). The substituent the alkyl group may have is exemplified by the same groups as the "substituents" for the "optionally halogenated hydrocarbon group" represented by $R^{1c}$. Preferable substituents for the hydrocarbon group represented by $R^{5a}$ are the same as specified for substituents for the hydrocarbon group represented by $R^{1c}$; $C_{1-3}$ alkoxy group (e.g., methoxy, ethoxy), mono- or di-$C_{1-2}$ alkylamino group (e.g., dimethylamino), carbamoyl group, carboxyl group etc. are used commonly. The number of substituents is preferably 1 or 2. Preferable examples or $E^2$ are —NH— or —O—.

Also, $R^{5a}$ and $R^{1c}$ may bind together to form a 5- to 7-membered ring which may be substituted by an oxo or thioxo group. Specifically, the compound (X) is represented by the general formula:

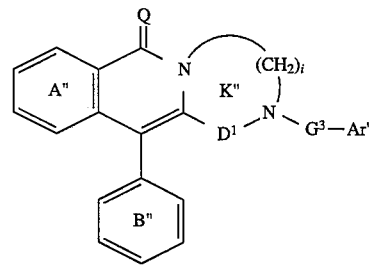
(I-B)

wherein ring K" is a 5- to 7-membered ring which may be substituted by an oxo or thioxo group; i represents an integer from 1 to 3, the total carbon number of $D^1$ and —$(CH_2)_i$— being 3 to 5; the other symbols have the same definitions as above or below. Preferably, it is represented by the formula:

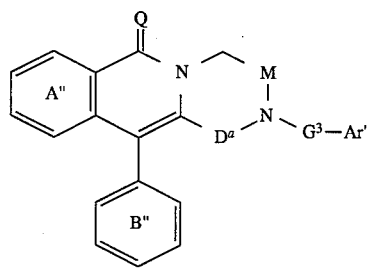

wherein $D^a$ and M independently represent —$CH_2$— or —CO—; the other symbols have the same definitions as above or below.

In the above formulas, Ar' represents an aryl group which may have an optionally substituted substituent or an optionally substituted heterocyclic group. The optionally substituted aryl group is the same meaning as defined in Ar.

Preferable examples of substituent of the aryl group represented by Ar' include optionally halogenated $C_{1-4}$ alkyl group (e.g., methyl, chloromethyl, difluoromethyl, trichloromethyl, trifluoromethyl, ethyl, 2-bromoethyl, 2,2,2-trifluoroethyl, propyl, isopropyl, 3,3,3-trifluoropropyl), halogen atom (e.g., fluorine, chlorine, bromine), nitro group, hydroxyl group, optionally halogenated $C_{1-4}$ alkoxy group (e.g., methoxy, difluoromethoxy, trifluoromethoxy, ethoxy, 2,2,2-trifluoroethoxy), amino group, mono- or di-$C_{1-4}$ alkylamino group (e.g., methylamino, ethylamino, dimethylamino, diethylamino), $C_{1-4}$ alkoxy-carbonyl group (e.g., methoxycarbonyl, ethoxycarbonyl), carboxyl group and carbamoyl group, more preferably, optionally halogenated $C_{1-4}$ alkyl group (e.g., methyl, chloromethyl, difluoromethyl, trichloromethyl, trifluoromethyl, ethyl, 2-bromoethyl), halogen atom (e.g., fluorine, chlorine, bromine) and $C_{1-4}$ alkoxy group (e.g., methoxy, ethoxy, propoxy).

The heterocyclic group represented by Ar', is exemplified by 5- to 9-membered, preferably 5- or 6-membered aromatic heterocyclic groups which may have one to four, preferably one or two hetero atoms such as nitrogen, oxygen and sulfur atoms in addition to carbon atoms.

Such aromatic heterocyclic group is the same meaning as defined in Ar.

Preferable example of the heterocyclic group represented by Ar' include 5- or 6-membered heterocyclic groups such as furyl, thienyl, pyrrolyl, oxazolyl, isoxazolyl, imidazolyl, pyrazolyl, pyridyl, pyridazinyl, quinolyl, isoquinolyl, thiazolyl, thiadiazolyl and thiophenyl, with greater preference given to furyl, thienyl, pyridyl etc.

The substituent in the "optionally substituted heterocyclic group,", represented by Ar', is the same meaning as defined in Ar.

Preferable examples of substituent of the heterocyclic ring represented by Ar' include halogen atom (e.g., fluorine, chlorine, bromine), optionally halogenated $C_{1-4}$ alkyl group (e.g., methyl, chloromethyl, difluoromethyl, trifluoromethyl, ethyl), $C_{3-6}$ cycloalkyl group (e.g., cyclopropyl, cyclobutyl), hydroxyl groups, optionally halogenated $C_{1-4}$ alkoxy group (e.g., methoxy, difluoromethoxy, trifluoromethoxy, ethoxy), optionally halogenated $C_{1-4}$ alkylthio group which may be halogenated (e.g., methylthio, ethylthio), amino group, mono- or di-$C_{1-4}$ alkylamino group (e.g., methylamino, ethylamino, dimethylamino, diethylamino), $C_{1-4}$ alkoxycarbonyl groups (e.g., methoxycarbonyl, ethoxycarbonyl) and carboxyl group, with greater preference given to halogen atom (e.g., fluorine, chlorine), $C_{1-4}$ alkyl group (e.g., methyl, ethyl), $C_{3-6}$ cycloalkyl group (e.g., cyclopropyl, cyclobutyl), hydroxyl group, $C_{1-4}$ alkoxy group (e.g., methoxy, ethoxy) and carboxyl groups etc.

Ar' is preferably a phenyl group which may have one to three substituents selected from the group consisting of halogen atom (e.g., fluorine, chlorine), optionally halogenated $C_{1-4}$ alkyl group (e.g., methyl, difluoromethyl, trifluoromethyl, ethyl, 2,2,2-trifluoroethyl, propyl, isopropyl) and optionally halogenated $C_{1-4}$ alkoxy group (e.g., methoxy, difluoromethoxy, trifluoromethoxy, ethoxy, 2,2,2-trifluoroethoxy, propoxy, isopropoxy). Also preferred are 5- or 6-membered heterocyclic group (e.g., furyl, pyridyl, thienyl, thiazolyl, thiadiazolyl) which have one to three hetero atom (e.g., nitrogen atoms, oxygen atoms, sulfur atoms) in addition to carbon atoms and which may be substituted by an optionally halogenated $C_{1-4}$ alkyl group (e.g., methyl, trifluoromethyl, ethyl), a $C_{1-4}$ alkoxy group (e.g., methoxy, ethoxy, propoxy) or a $C_{3-6}$ cycloalkyl group (e.g., cyclopropyl).

$G^3$ represents a bond or a $C_{1-3}$ alkylene group. The $C_{1-3}$ alkylene group include —$CH_2$—, —$CH_2CH_2$—, —$CH_2CH_2CH_2$— and —$CH(CH_3)CH_2$—. $G^3$ is preferably —$CH_2$— or —$CH_2CH_2$—, —$CH_2$— being commonly used.

In the above formula, L represents a leaving group. This group is exemplified by hydroxyl group, halogen atom (e.g., chlorine, bromine, iodine), substituted sulfonyloxy group (e.g., methanesulfonyloxy and p-toluenesulfonyloxy groups), acyloxy group (e.g., acetoxy and benzoyloxy groups), and oxy group substituted by a heterocyclic group or an aryl group (e.g., succinimide, benzotriazole, quinoline or 4-nitrophenyl group).

In the above formula, L' and L" represents a leaving group. This leaving group is exemplified by halogen atom and substituted sulfonyloxy group among the leaving groups exemplified for L above.

When compound (I) and (I') of the present invention has a basic group such as an amino group or a substituted amino group, it may form a physiologically acceptable acid addition salt. Such salts include those with inorganic acids (e.g., hydrochloric acid, phosphoric acid, hydrobromic acid, sulfuric acid) and those with organic acids (e.g., acetic acid, formic acid, propionic acid, fumaric acid, maleic acid, succinic acid, tartaric acid, citric acid, maleic acid, oxalic acid, benzoic acid, methanesulfonic acid, benzenesulfonic acid). When compound (I) and (I') of the present invention has an acidic group such as —COOH, it may form a salt with an inorganic base (e.g., alkali metals or alkaline earth metals such as sodium, potassium and magnesium, ammonia) or an organic base (e.g., tri-$C_{1-3}$ alkylamine such as triethylamine).

Production methods for compound (I) and (I') or a salt thereof of the present invention are described below.

Compound (I) and (I') or a salt thereof of the present invention can, for example, be produced by the following methods ① and ②. Specifically, compound (I) and (I') or a salt thereof is produced by ① reacting a heterocyclic compound or a salt thereof having a leaving group L, represented by general formula (II) and a compound or a salt thereof represented by formula (III), or by ② reacting a heterocyclic compound or a salt thereof represented by general formula (IV) and a compound or a salt thereof represented by formula (v).

Methods ① and ② are hereinafter described in detail.

Method ①

This method generally affords two options: i) acylation, conducted when the L-linked methylene group in D is substituted by an oxo or thioxo group, and ii) alkylation, conducted when the L-linked methylene group in D is unsubstituted.

i) Acylation:

When the leaving group L of compound (II) is a hydroxyl group, it is preferable to use an appropriate condensing agent or to convert the leaving hydroxyl group to another leaving group as appropriate (e.g., an acyloxy group as described above, or an oxy group substituted by a heterocyclic group or aryl group) and then react it with compound (III) or a salt thereof. Such condensing agents include dicyclohexylcarbodiimide (DCC), diethyl cyanophosphate (DEPC) and diphenylphosphorylazide (DPPA). When these condensing agents are used, the reaction is preferably carried out in a solvent (e.g., ethers, esters, hydrocarbons, amides, sulfoxides) such as tetrahydrofuran, dioxane, dimethoxyethane, ethyl acetate, benzene, toluene, N,N-dimethylformamide and dimethylsulfoxide. This reaction may be accelerated in the presence of a base, and is carried out at about −10° to 100° C., preferably about 0° to 60° C. Reaction time is normally 5 minutes to 96 hours, preferably 0.5 to 72 hours. The mount of compound (III) or a salt thereof or condensing agent used is 1 to 5 mol equivalents, preferably 1 to 3 mol equivalents per mol of compound (II) or a salt thereof. Examples of bases which can be used include alkylamines such as triethylamine and cyclic mines such as N-methylmorpholine and pyridine, their amount being 1 to 5 mol equivalents, preferably 1 to 3 mol equivalents per mol of compound (II) or a salt thereof.

Compound (II) as a reactive derivative is preferably an acid halide (e.g., chloride, bromide), acid anhydride, mixed acid anhydride (e.g., anhydride with methylcarbonic acid, anhydride with ethylcarbonic acid, anhydride with isobutylcarbonic acid), active ester (e.g., ester with hydroxysuccinimide, ester with 1-hydroxybenzotriazole, ester with N-hydroxy-5-norbornane-2,3-dicarboxymide, ester with p-nitrophenol, ester with 8-oxyquinoline), with preference given to acid halides. The reaction of compound (III) or a salt thereof and compound (II) is normally carried out in a solvent (e.g., halogenated hydrocarbons ethers, esters, hydrocarbons, amides such as chloroform, dichloromethane, ethyl ether, tetrahydrofuran, dioxane, dimethoxyethane, ethyl acetate, benzene, toluene, pyridine, and N,N-dimethylformamide). This reaction may be accelerated in the presence of a base. Reaction temperature is normally about −10° to 120° C., preferably about 0° to 100° C. Reaction time is normally 5 minutes to 48 hours, preferably 0.5 to 24 hours. The amounts of compound (III) used is 1 to 5 mol equivalents, preferably 1 to 3 mol equivalents per mol of compound (II) or a salt thereof. Examples of bases which can be used include alkylamines such as triethylamine, cyclic mines such as N-methyl-morpholine and pyridine, aromatic amines such as N,N-dimethylaniline and N,N-diethylaniline, alkali metal carbonates such as sodium carbonate and potassium carbonate and alkali metal hydrogen carbonates such as sodium hydrogen carbonate and potassium hydrogen carbonate, their amount being 1 to 5 mol equivalents, preferably 1 to 3 mol equivalents per mol of compound (III) or a salt thereof. Also, when a water-immiscible solvent is used for the reaction, the reaction system may consist of two phases including water.

ii) Alkylation:

In the reaction with compound (III), the leaving group L of compound (II) is preferably one of the above-mentioned halogen atoms or substituted sulfonyloxy groups.

Although compound (III) may be used as such in a free form, it may be converted to a salt such as with an alkali metal such as lithium, sodium or potassium before being tested in the reaction. The amount of compound (III) or a salt thereof reacted is 1 to 10 mol equivalents, preferably 1 to 5 mol equivalents per mol of compound (II). This reaction is normally carried out in a solvent. Preferable solvents include halogenated hydrocarbons such as dichloromethane and chloroform, nitriles such as acetonitrile, ethers such as dimethoxyethane and tetrahydrofuran, and dimethylformamide, dimethylsulfoxide and hexamethylphosphoramide. Addition of a base promotes the reaction. Bases preferred for this purpose include sodium hydrogen carbonate, potassium hydrogen carbonate, sodium carbonate, potassium carbonate, sodium hydride, potassium hydride, sodium amide, sodium methoxide, triethylamine, diisopropylethylamine and pyridine. Also, in this reaction, compound (III) may be converted to one of the above-mentioned alkali metal salts, alkaline earth metal salts etc. and then reacted with compound (II), in place of using a base. When E of compound (III) is —NR$^5$—, compound (III) itself may be used as a base, in place of using one of the above bases. Varying depending on types of compounds (II) and (III) and solvent and other reaction conditions, the amount of base used is normally 1 to 10 mol equivalents, preferably 1 to 5 mol equivalents per mol of compound (III). Reaction temperature is about −50° to 200° C., preferably −20° to 150° C. Varying depending on type of compound (III) or a salt thereof, reaction temperature and other factors, reaction time is 1 to 72 hours, preferably 1 to 24 hours.

Method ②

This method is carried out in the same manner as the alkylation described in term ii), method ②. Specifically, the same procedures as those of the method described in term ii) is followed, using compound (V) in place of compound (II) and using compound (IV) or a salt thereof in place of compound (III) or a salt thereof.

Of the compounds represented by formula (I), a compound or a salt thereof represented by the general formula (I$^a$):

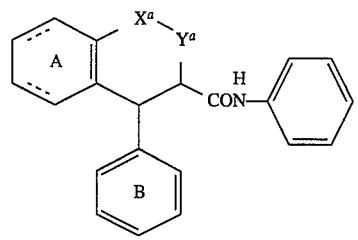

wherein either of X$^a$ and Y$^a$ is —NR$^{1a}$— (R$^{1a}$ had the same definition as above) or —O—, the other representing —CO—; the other symbols have the same definitions as above, can be produced by subjecting to reduction a compound or a salt thereof represented by formula (I$^b$):

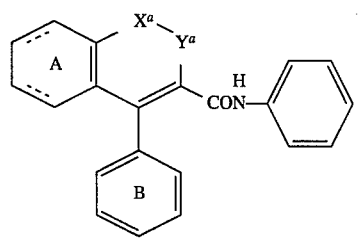

wherein the symbols have the same definitions as above.

This reaction, wherein an amide compound represented by general formula (I$^b$) is reduced to convert its double bond to a single bond, is carried out by various methods. For example, it is preferable to use a method wherein the starting material is reduced in the presence of a metal catalyst for catalytic reduction. Examples of the catalysts for this catalytic reduction method include platinum catalysts such as platinum black, platinum oxide and platinum carbon, palladium catalysts such as palladium black, palladium oxide, palladium barium sulfate and palladium carbon, and nickel catalysts such as reduced nickel, oxidized nickel, Raney nickel and Urushibara nickel. This reaction is normally carried out in a solvent. An organic acid such as formic acid, acetic acid or propionic acid is used as the solvent, or an alcohol such as methanol, ethanol, propanol or isopropanol, an ether such as tetrahydrofuran or dioxane, or an ester such as ethyl acetate, is used as the solvent in the presence of the above organic acid or an inorganic acid such as phosphoric acid, sulfuric acid or hydrochloric acid. Reaction temperature is normally 0° to 200° C., preferably 20° to 110° C. Reaction time is normally 0.5 to 48 hours, preferably 1 to 16 hours. Although the reaction is normally carried out under normal pressure, it may be carried out under increased pressure (3 to 10 atm) as necessary. Varying depending on catalyst type, the mount of catalyst used is normally 0.1 to 10% (w/w), relative to compound (I$^b$).

Of the compounds represented by formula (I), a compound represented by the general formula (I$^c$):

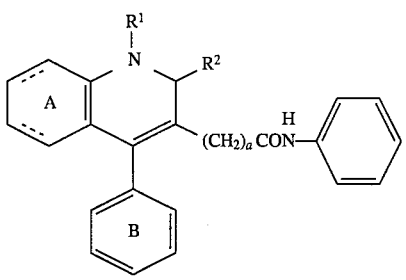

wherein the symbols have the same definitions as above or a salt thereof can be produced by reacting a compound represented by general formula ($I^d$):

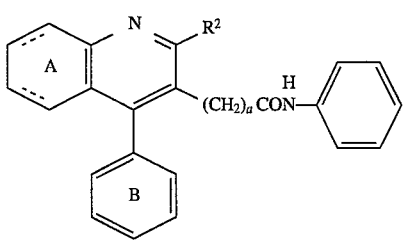

wherein the symbols have the same definitions as above, or a salt thereof with an alkylating agent represented by the formula $R^1$—L ($R^1$ has the same definition as above; L represents a leaving group) to produce a compound represented by general formula ($I^e$):

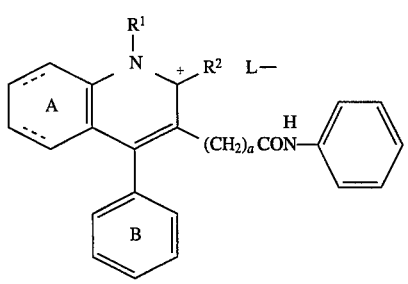

wherein the symbols have the same definitions as above or a salt thereof, which is then subjecting to a reducing reaction.

This reaction, wherein a quinolineamide compound represented by general formula ($I^d$) is reacted with an alkylating agent represented by $R^1$—L to a quaternary salt ($I^e$), which is then reduced to produce a compound represented by general formula ($I^c$). Examples of the alkylating agent $R^1$—L used to convert formula ($I^d$) to ($I^e$) include alkane halides (e.g., chloride, bromide, iodide), sulfates and sulfonates (e.g., methanesulfonate, p-toluenesulfonate, benzenesulfonate), with preference given to alkyl halides. The amount of alkylating agent used is 1 to 100 mol equivalents, preferably 1 to 30 mol equivalents per mol of compound ($I^d$). This reaction is normally carried out in a solvent. Examples of the solvent include alcohols such as methanol, ethanol, propanol and isopropanol, ethers such as tetrahydrofuran and dioxane, esters such as ethyl acetate, and halogenated hydrocarbons such as dichloromethane and 1,2-dichloroethane. The alkylating agent itself may be used as the solvent. Reaction temperature is normally 10° to 200° C., preferably 20° to 110° C. Reaction time is normally 0.5 to 24 hours, preferably 1 to 16 hours.

The thus-obtained quaternary salt ($I^e$) is normally reduced to ($I^c$) in an inert solvent in the presence of a metal hydride. Examples of metal hydrides which can be used for this purpose include sodium borohydride, lithium borohydride, zinc borohydride, sodium cyanoborohydride and lithium cyanoborohydride, with preference given to sodium borohydride. Reaction solvents which can be used include lower alcohols such as methanol and ethanol, ethers such as dioxane and tetrahydrofuran and hydrocarbons such as benzene and toluene. These solvents may be used singly or in combination. Reaction temperature is normally about −100° to 40° C., preferably about −80° to 25° C. Reaction time is normally 5 minutes to 10 hours, preferably 10 minutes to 5 hours. The amount of reducing agent used is normally 1 to 2 mol equivalents per mol of compound (II). Also, of the compounds represented by formula (I) and (I'), a compound represented by the general formula:

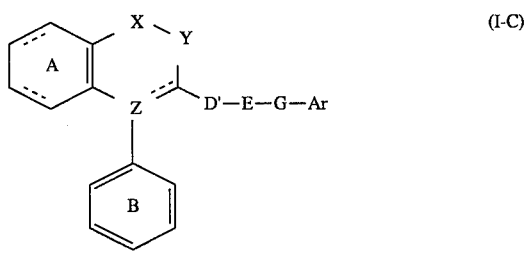

wherein D' represents a $C_{1-3}$ alkylene group; the other symbols have the same definitions as above or a salt thereof, can also be produced by a reaction of a compound represented by the general formula:

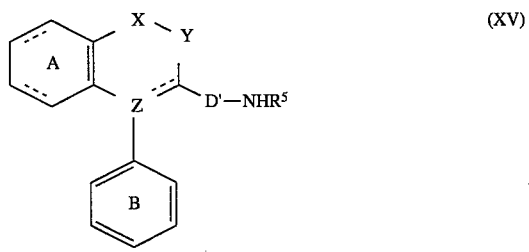

wherein the symbols have the same definitions as above or a salt thereof, and a compound represented by the general formula:

$$Ar—G'—CHO \qquad (XVI)$$

wherein G' represents a bond or a $C_{1-2}$ alkylene group; the other symbols have the same definitions as above, in the presence of a reducing agent. This reaction is carried out by various methods; for example, the reducing reaction described by R. F. Borch et al. in the Journal of American Chemical Society, Vol. 93, pp. 2897–2904 (published 1971) or a method based thereon is preferably used. Also, a compound of general formula (I) and (I') wherein D is a $C_{1-3}$ alkylene group and E is —NH— can be reacted with a carbonyl compound represented by the general formula:

wherein $R^{5p}$ and $R^{5q}$, whether identical or not, independently represent hydrogen or an optionally substituted hydrocarbon group, in the presence of a reducing agent, for example, the above-mentioned method of Borch et al. or a method based thereon, to yield a compound or a salt thereof represented by the general formula:

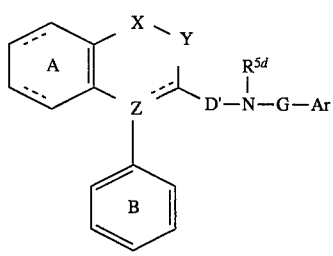

wherein $R^{5d}$ represents an optionally substituted hydrocarbon group; the other symbols have the same definitions as above.

A compound of general formula (I-B), one of the desired compounds described above, which has a tricyclic structure, can, for example, be produced by the following methods a) and b).

Method a)

A compound represented by the general formula:

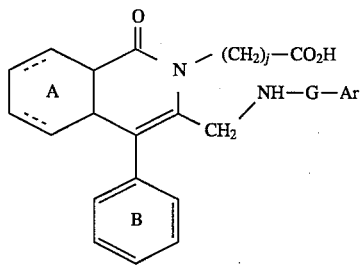

wherein j represents an integer from 0 to 2; the other symbols have the same definitions as above or a salt thereof or a reactive derivative thereof derivatized at the carboxyl group thereof (included in the desired compound of the present invention and produced by the above Method ① or ② is cyclized by intramolecular amidation to yield a compound represented by the general formula:

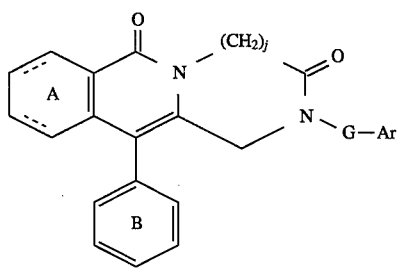

wherein the symbols have the same definitions as above or a salt thereof.

Method b)

A compound represented by the general formula:

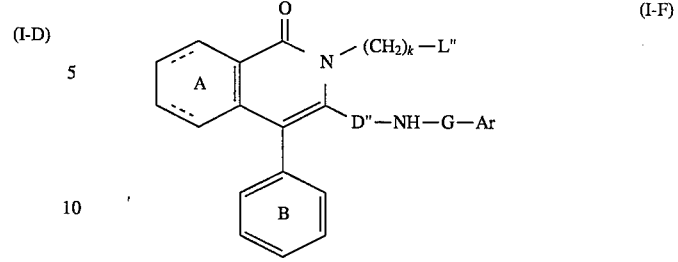

wherein D" represents —CH$_2$— or —CO—; L" represents a leaving group; k represents an integer from 1 to 3; the other symbols have the same definitions as above (included in the desired compound of the present invention and produced by the above method ① or ②) or a salt thereof, is cyclized by intramolecular alkylation to yield a compound or salt thereof represented by the general formula:

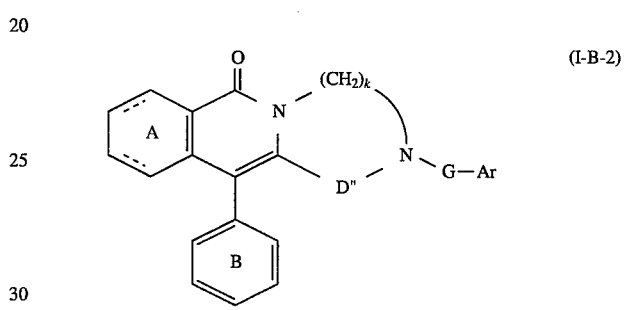

wherein the symbols have the same definitions as above or a salt thereof.

The above Method a), based on amide bond forming reaction, is carried out by various procedures. For example, the same procedures as described in method ①-i) may be used. Method b), based on alkylation, is carried out by the same procedures as described in method ①-ii) or method ② may be used.

It is also possible to produce a compound of formula (I) wherein E is —NR$^{5d}$— (the symbols have the same definitions as above) by alkylating a compound of formula (I) and (I') wherein E is —NH— with an alkylating agent represented by the formula R$^{5e}$—L" (R$^{5e}$ represents an optionally substituted alkyl group; L" represents a leaving group) by the same method as described in method ①-ii).

(iii) Of the compounds represented by the formula (I), a quinoline or an isoquinoline compound represented by the general formula: wherein —X$^b$—Y$^b$— represents —N=CR$^3$— or —CR$^3$=N— (R$^3$ represents the same meaning as defined above), E' represents —NR$^{5f}$—(R$^{5f}$ represents an optionally

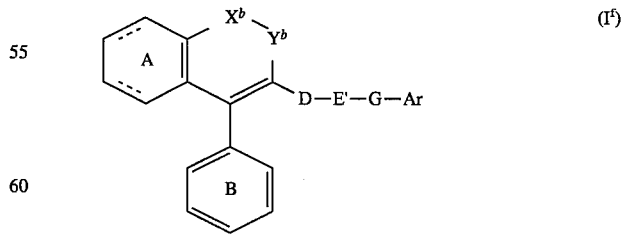

substituted hydrocarbon group), —O— or —S(O)n— (n is 0,1 or 2) and the other symbols are the same meaning as defined above, can be produced from a quinolone or an isoquinolone compound represented by the general formula:

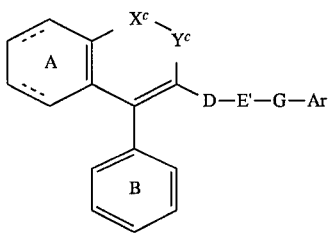

(I<sup>g</sup>)

wherein —X<sup>c</sup>—Y<sup>c</sup>— represents —NH—CO— or —CO—NH—, the other symbols are the same meaning as defined above. This reaction is first conducted, preferably, by converting the amide moiety of (Ig) into the imino halide group, yielding the compound (I<sup>f</sup>) where $R^3$ is a halogen atom (e.g. Cl, Br). The reagent used in the reaction is, for example, phosphorus halides such as phosphorus oxychloride, phosphorus pentachloride, and thionyl halides such as thionyl chloride, thionyl bromide, etc.. The amount of the reagent is 1 to 100 mol equivalents relative to the compound (Ig). The reaction is generally carried out in an inert solvent (e.g., ethers such as tetrahydrofurane, dioxane, hydrocarbons such as benzene, toluene, xylene), and the reagent itself may be used as the solvent. The reaction temperature is generally about 20° C. to 200° C. and preferably 50° C. to 150° C. The reaction time, which depends on the species of starting , compound, reagent, solvent and temperature, is generally 30 minutes to 12 hours. The imino halide thus obtained can be converted to the compounds having various $R^3$-substituent, i.e., a hydrogen atom, an optionally substituted hydrocarbon group, an optionally substituted amino group, a substituted hydroxyl group, or a mercapto group substituted by an optionally substituted hydrocarbon group. The compound (I<sup>f</sup>) where $R^3$ is a hydrogen atom can be prepared from (I<sup>f</sup>;$R^3$=Cl, Br) by using catalytic reduction. The reduction can be carried out by a method similar to that used in the conversion of (I<sup>b</sup>) to (I<sup>a</sup>). The compound (I<sup>f</sup>) where $R^3$ is an optionally substituted amino group can be prepared from (I<sup>f</sup>;$R^3$=Cl) by reacting an optionally substituted amine under conditions similar to those used in the reaction of (XI) and (XII) (Method 1-ii). Similarly, the compound (I<sup>f</sup>) where $R^3$ is an optionally substituted hydrocarbon group, a substituted hydroxyl group or a mercapto group substituted by an optionally substituted hydrocarbon group can be prepared from (I<sup>f</sup>R<sup>3</sup>=Cl) by reacting a Grignard reagent (e.g., MeMgBr, EtMgBr), an alkaline metal (e.g., lithium, sodium, potassium) salt of alcohol (e.g., methanol, ethanol) or an alkaline metal (e.g., lithium, sodium, pottasium) salt of thiol (e.g., methanethiol, ethanethiol), respectively, under conditions similar to (Method 1-ii).

Of compound (I) and (I') of the present invention, a compound wherein X or Y is a —CS— group and/or D contains a thioxo group can be produced by reacting a compound wherein X or Y is a —CO— group and/or D contains an oxo group with an appropriate sulfur containing reagents. Examples of such reagents include phosphorus pentasulfide and Lowesson's reagent. This reaction is normally carried out in a solvent such as dichloromethane, chloroform, dioxane, tetrahydrofuran, benzene or toluene uunder water-free conditions. The amount of sulfide used is not less than 1 mol equivalent, preferably 2 to 5 mol equivalents, reaction temperature being between 20° C. and 120° C. Varying depending on kind of starting material or sulfide, reaction temperature etc., reaction time is normally 1 to 8 hours.

When compound (I) and (I') or a salt thereof produced by the above methods contains a lower ($C_{1-6}$) alkoxy group on ring A (wherein ═══ is a double bond), ring B or the benzene ring in the group represented by Ar, it may be converted to a hydroxyl group as necessary by reaction with, for example, boron tribromide. This reaction is normally carried out in a solvent (e.g., halogenated hydrocarbons such as dichloromethane, chloroform, carbon tetrachloride, benzene and toluene, and hydrocarbons) at about −20° to 80° C., preferably about 0° to 30° C. The mount of boron tribromide used is about 1 to 10 mol equivalents, preferably about 1 to 5 mol equivalents per mol of lower alkoxy group. Reaction time is normally 15 minutes to 24 hours, preferably 30 minutes to 12 hours. Also, when compound (I) and (I') or a salt thereof produced by the above methods contains a hydroxyl group on ring A, ring B or the benzene ring in the group represented by Ar, it may be converted to an alkoxy or acyloxy group by alkylation or acylation as necessary. This alkylation,m is carried out by a reaction with an alkylating agent such as a halide (e.g., chloride, bromide, iodide) of an alkane which may have a substituent or a sulfate ester or sulfonate ester (e.g., methanesulfonate, p-toluenesulfonate, benzenesulfon-ate) in a solvent (e.g., alcohols such as methanol, ethanol and propanol, ethers such as dimethoxyethane, dioxane and tetrahydrofuran, ketones such as acetone and amides such as N,N-dimethylformamide) in the presence of a base (e.g., organic bases such as trimethylamine, triethylamine, N-methylmorpholine, pyridine, picoline and N,N-dimethylaniline, and inorganic bases such as potassium carbonate, sodium carbonate, potassium hydroxide and sodium hydroxide). Reaction temperature is normally −10° to 100° C., preferably about 0° to 80° C. The amount of these alkylating agents used is about 1 to 5 mol equivalents, preferably 1 to 3 mol equivalents per mol of starting material phenolic derivative. Reaction time is normally 15 minutes to 24 hours, preferably 30 minutes to 12 hours.

Acylation is carried out by using the appropriate carboxylic acid or a reactive derivative thereof. Although varying depending on type of acylating agent and type of starting material phenolic derivative, this reaction is normally carried out in a solvent (e.g., hydrocarbons, ethers, esters, halogenated hydrocarbons, amides, aromatic amines such as benzene, toluene, ethyl ether, ethyl acetate, chloroform, dichloromethane, dioxane, tetrahydrofuran, N,N-dimethylformamide and pyridine); appropriate bases (e.g., hydrogen carbonates such as sodium hydrogen carbonate and potassium hydrogen carbonate, carbonates such as sodium carbonate and potassium carbonate, acetates such as sodium acetate, tertiary amines such as triethylamine, aromatic amines such as pyridine) may be added to accelerate the reaction. Such reactive derivatives of carboxylic acid include acid anhydrides, mixed acid anhydrides and acid halides (e.g., chloride, bromide). The amount of these acylating agents used is 1 to 5 mol equivalents, preferably 1 to 3 mol equivalents per mol of starting material phenolic derivative. Reaction temperature is normally about 0° to 150° C., preferably about 10° to 100° C. Reaction time is normally 15 minutes to 12 hours, preferably 30 minutes to 6 hours.

Also, known amide compounds of formula (I) and (I') can be synthesized by, for example, (1) the method described in the Indian Journal of Chemistry, Section B, 26B, Vol. 8, pp. 744–747 (published 1987), (2) the method described in the Chemical Abstract, Vol. 107, 175835f, (3) the method described in the Chemical Abstract, Vol. 114, 42492q, (4) the method described in the Chemical Abstract, Vol. 107, 115463y, (5) the method described in the Chemical Abstract, Vol. 93, 220536q, a method based thereof, or by the above-described production method for the compounds represented by formula (I) and (I') or methods based thereon.

When compound (I) and (I') is obtained in a free form by one of the above methods, it may be prepared as a salt with an inorganic acid (e.g., hydrochloric acid, sulfuric acid, hydrobromic acid), an organic acid (e.g., methanesulfonic acid, benzenesulfonic acid, toluenesulfonic acid, oxalic acid, fumaric acid, maleic acid, tartaric acid), an inorganic base (e.g., alkali metals such as sodium and potassium, alkaline earth metals such as calcium and magnesium, aluminum or ammonium), or an organic base (e.g., trimethylamine, triethylamine, pyridine, picoline, ethanolamine, diethanolamine, triethanolamine, dicyclohexylamine or N,N'-dibenzylethylenediamine). When compound (I) is obtained in the form of a salt, it can be converted to the free form or another salt, in accordance with a conventional method.

The thus-obtained desired compound (I) and (I') or salt thereof can be purified and separated by a known means of separation and purification (e.g., concentration, solvent extraction, column chromatography or recrystallization).

Starting material (VII), or a salt thereof, used to produce the inventive compound (I) and (I') or a salt thereof can industrially advantageously produced by, for example, the following methods 1) to 3) or methods based thereon.

1) Compounds represented by the general formulas:

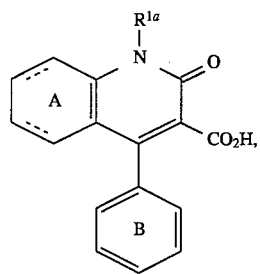
(VII-1)

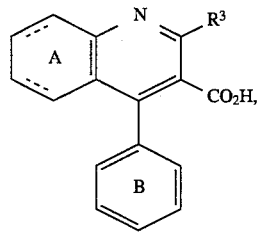
(VII-2)

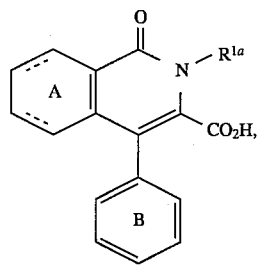
(VII-3)

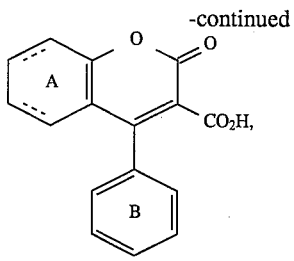
(VII-4)

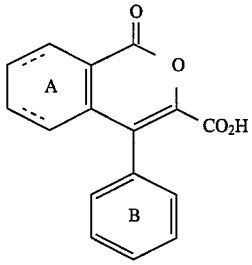
(VII-5)

wherein the symbols have the same definitions as above, or esters thereof can be synthesized by methods (or methods based thereon) such as those described in European Patent Publication No. 421456 (published Apr. 11, 1991), European Patent Publication No. 354994 (published Feb. 21, 1990), European Patent Publication No. 481383 (published Apr. 22, 1992), PCT International Patent Publication No. WO9112249 (published Aug. 22, 1991), and Bolletino Chimico Farmaceutico, vol. 125 pp. 437–440 (published 1986, describe by N. A. Santagati et al.).

The compound (VII-3) can also be produced via an amide compound of (VII-3). An amide compound of (VII-3) is produced by the method described by K. Unverferth et al. in Archiv der Pharmazie, Vol. 324 pp. 809–814 (published 1991) or a method based thereon. This amide compound may be reacted under, for example, diazotizing conditions (e.g., reacted with sodium nitrite at about 0° to 50° C. in an acidic solvent such as acetic acid or hydrochloric acid) to yeild compound (VII-3).

2) Compounds represented by the general formulas:

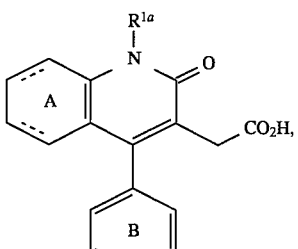
(VII-6)

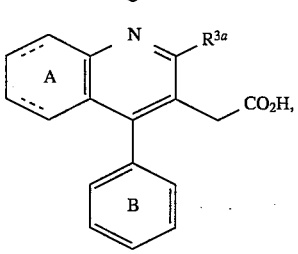
(VII-7)

-continued

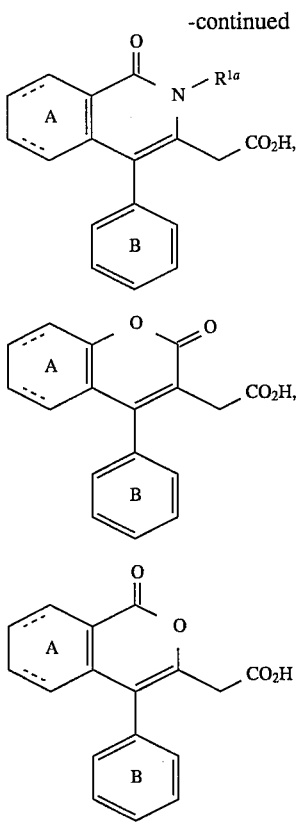

wherein the symbols have the same definitions as above, can be synthesized by, for example, the following methods 2-A) and 2-B) or methods based thereon.

Method 2-A)

The carboxyl group of (VII-1) to (VII-5) is treated with diazomethane to add one carbon atom to the carboxyl group by a reaction generally known as the Arndt-Eistert reaction (F. Arndt et al.: Chemische Berichte, Vol. 68, page 200 (published 1935)) to yield (VII-6) to (VII-10), respectively. For example, a method is known wherein a compound of formula (VII-5) whose ring A is not substituted for and whose ring B is not substituted for or has substituent methyl for $R^3$ in the above formula is converted to a corresponding compound of formula (II-10) having a substituent (I.N. Chatterjea et al.: Liebigs Ann. Chem., 1974, page 1126); by this method or a method based thereon, (VII-6) to (VII-10) can be produced. In this method, the desired compound may be isolated as a carboxylic acid ester (methyl ester, ethyl ester etc.), which ester is then converted to a carboxylic acid by hydrolysis. This hydrolyzing reaction is normally carried out in a solvent (e.g., alcohols such as methanol, ethanol and propanol, organic acids such as acetic acid) in the presence of an aqueous solution of a mineral acid (e.g., hydrochloric acid, hydrobromic acid, sulfuric acid) or a metal hydroxide (e.g., sodium hydroxide, potassium hydroxide) at a treatment temperature of about 15° to 130° C.

Method 2-B)

One carbon atom is also added to the carboxyl group of (VII-1) to (VII-5) by the following method:

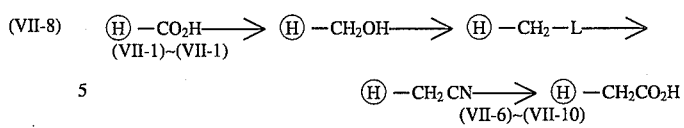

wherein H represents the heterocyclic moiety of (VII-1) to (VII-10); L represents a leaving group. In this method, the carboxyl group is first reduced to yield an alcohol. This reduction is carried out by converting the carboxyl group to a reactive derivative thereof (acid halide, mixed acid anhydride, active ester, ester etc.) and then treated at a reaction temperature of about 0° to 100° C. in a solvent (ether such as tetrahydrofuran or dimethoxyethane) in the presence of a reducing agent (sodium borohydride, lithium aluminum hydride). The hydroxyl group of the thus-obtained alcohol is converted to a leaving group (—OH→—L). The leaving group L is preferably a halogen (chlorine, bromine, iodine etc.), a $C_{1-4}$ alkanesulfonyloxy group (e.g., methanesulfonyloxy group, ethanesulfonyloxy group) or a $C_{6-10}$ arylsulfonyloxy group (e.g., benzenesulfonyloxy group, p-toluenesulfonyloxy group). This converting reaction is normally carried out by a treatment with, for example, thionyl chloride, thionyl bromide, methanesulfonyl chloride or benzenesulfonyl chloride in a solvent (e.g., benzene, toluene, dichloromethane, 1,2-dichloroethane, chloroform, tetrahydrofuran, ethyl acetate) at a treatment temperature of about 0° to 100° C. The leaving group of the compound is then converted to a nitrile group (—L→—CN). This reaction is normally carried out by a treatment with, for a cyanogen compound such as sodium cyanide, potassium cyanide or copper cyanide in a solvent (e.g., dimethylsulfoxide, dimethylformamide, acetone) at a treatment temperature of 0° to 100° C. The resulting nitrile compound is hydrolyzed to carboxylic acids (VII-6) to (VII-10). This hydrolyzing reaction is normally carried out in a solvent (alcohol such as methanol, ethanol or propanol, or acetic acid) in the presence of an aqueous solution of a mineral acid (e.g., hydrochloric acid, hydrobromic acid, sulfuric acid) or a metal hydroxide (e.g., sodium hydroxide, potassium hydroxide) at a treatment temperature of about 15° to 130° C. Compounds (VII-6) and (VII-7) can also be produced by the method described by H. Kohl et al. in the Journal of Pharmaceutical Sciences, Vol. 62, page 2028 (published 1973) or a method based thereon.

3) Compounds represented by the general formulas:

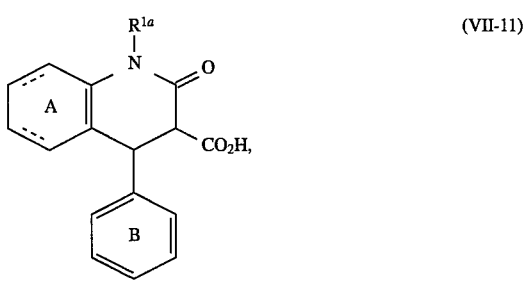

-continued

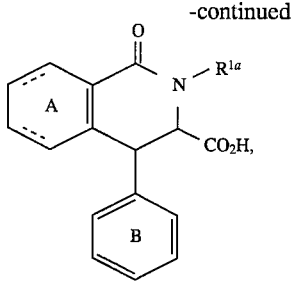 (VII-12)

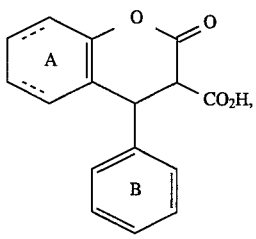 (VII-13)

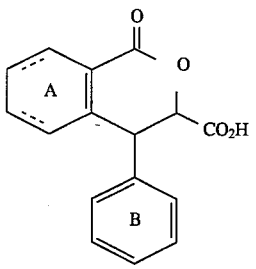 (VII-14)

wherein the symbols have the same definitions as above, can be produced from the above compounds (VII-1), (VII-3), (VII-4), (VII-5) or esters thereof, respectively, by reducing the double bond at the positions 3 and 4 to single bond. This method can, for example, be carried out by the above-described method used to convert ($I^a$) to ($I^b$) or a method based thereon. When an ester is used as the starting material, esters of (VII-11) to (VII-14) are produced, which may be hydrolyzed as described in Method 2-A) to carboxylic acids. Compound (VII-11) or an ester thereof can also be produced using a reducing agent such as lithium aluminum hydride. This reaction is normally carried out in a solvent (ethers such as tetrahydrofuran, dioxane and dimethoxyethane) at a temperature of about 0° to 100° C.

4) A compound represented by the general formula:

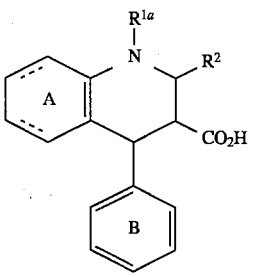 (VII-15)

wherein the symbols have the same definitions as above, can be produced from, for example, compound (VII-2A) by the following method:

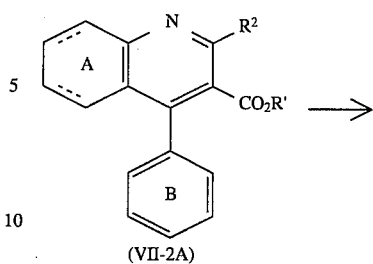
(VII-2A)

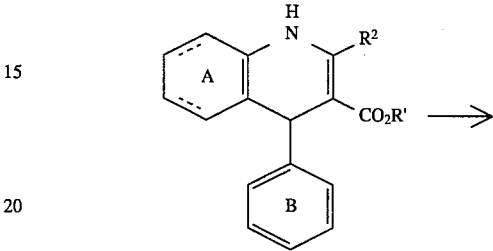

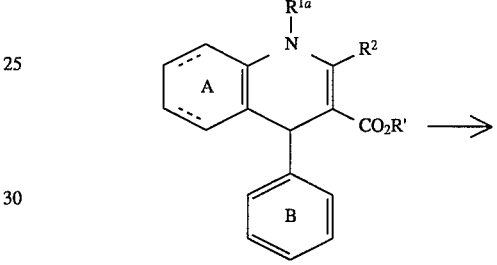

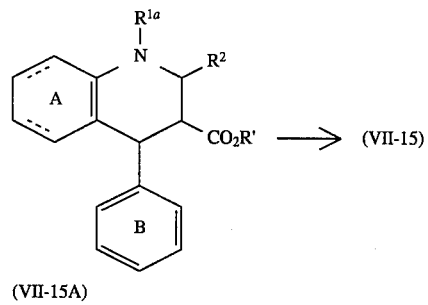
(VII-15A)

wherein R' represents a lower alkyl group (e.g. methyl, ethyl, etc.), the other symbols having the same definitions as above.

In this method, (VII-2A) is first reduced, at the positions 1 and 4, to a 1,4-dihydro derivative. This reducing reaction is carried out using a reducing agent such as sodium borohydride or sodium cyanoborohydride. The reaction is normally carried out in a solvent (alcohols such as methanol, ethanol and propanol, ethers such as tetrahydrofuran, dioxane and dimethoxyethane) at a temperature of about 15° to 100° C. The position 1 of this 1,4-dihydro derivative is then alkylated by a reaction with an alkylating agent represented by the general formula R'—L (the symbols have the same definitions as above). The alkylating reaction is normally carried out in a solvent (ethers such as tetrahydrofuran, dioxane and dioxane, amides such as dimethylformamide), preferably in the presence of a base (e.g., sodium hydride, potassium hydride, sodium methylate, sodium ethylate, sodium amide, potassium t-butoxide). The reaction is normally carried out at a temperature of about −10° to 100° C. The thus-obtained 1-alkyl-1,4-dihydro derivative is reduced to a 1,2,3,4-tetrahydro derivative (VII-15A). This reducing reaction is carried out using a reducing agent such as sodium cyanoborohydride, sodium borohydride or lithium aluminum hydride. The reaction is normally carried out in a solvent at a temperature of about 0° to 100° C. Varying depending on the kinds of reducing agent and substrate used, it is possible to use the same solvents as used in the above-described reducing reaction of (VII-2A) to 1,4-dihydro derivative. Conversion of (VII-15A) to (VII-15) is achieved by a hydrolyzing reaction as described in Method 2-A).

5) Compounds represented by the general formulas:

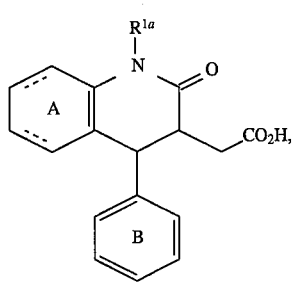 (VII-16)

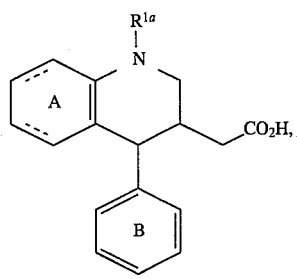 (VII-17)

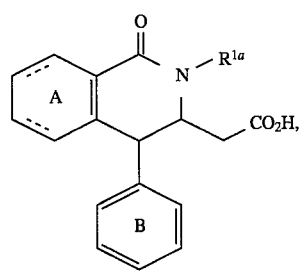 (VII-18)

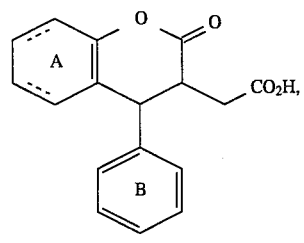 (VII-19)

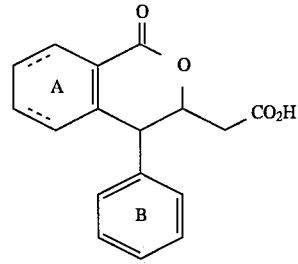 (VII-20)

wherein the symbols have the same definitions as above, can be produced from the above-mentioned compounds (VII-11) to (VII-15) by adding one carbon atom. This method can be carried out in the same manner as the above-described Method 2-A) or 2-B) or a method based thereon. (VII-16) and (VII19) can also be produced by the following method:

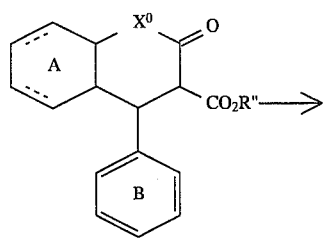

(VII-11A):$X^0$= —$NR^{1a}$—,
(VII-13A):$X^0$= —O—,

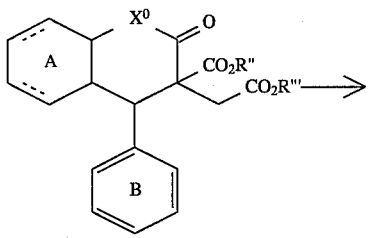

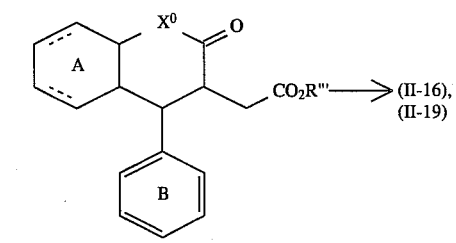 (II-16), (II-19)

(VII-16A):$X^0$= —$NR^{1a}$—,
(VII-19A):$X^0$= —O—, wherein $X^0$ represents —$NR^{1a}$— ($R^{1a}$ represents the same meaning as defined hereinabove) or —O—; R" and R'" independently represent a protecting group for the carboxyl group; the other symbols have the same definitions as above.

With respect to the above formula, the carboxyl group protecting groups R" and R'" is exemplified by ester-forming protecting groups such as methyl, ethyl, methoxyethyl, methoxyethoxymethyl, benzyloxymethyl, tert-butyl, benzyl, p-methoxybenzyl, p-nitrobenzyl, o-nitrobenzyl, benzhydryl, trityl, 2,2,2-trichloroethyl, 2-trimethylsilylethyl and allyl, and silyl-ester-forming protective groups such as trimethylsilyl, triethylsilyl, tert-butyldimethylsilyl, isopropyldimethylsilyl and dimethylphenylsilyl. In the above method, the position 3 of (VII-11A) or (VII-13A) is first alkylated with an alkylating agent represented by the general formula R'"OCOCH$_2$—L (the symbols have the same definitions as above). This reaction can be carried out under the same conditions as for the position 1 alkylation in 4) above. The resulting alkyl derivative, after removal of the protecting group R", may be decarboxylated to (VII-16A) or (VII-19A). Varying depending on the type of protecting group used, the protecting group R" can be removed by hydrolysis by the method described in Method 2-A) above when R" is a lower alkyl group such as methyl or ethyl. In this case, when R'" is similarly a lower alkyl group such as methyl or ethyl, it may also be removed to leave and isolate a dicarboxylic acid. While heating, the R"-removed carboxylic acid may be further decarboxylated to yield compound (VII-16A) or (VII-19A). In the case of a dicarboxylic acid wherein both R'' and R''' have been removed, this decarboxylation immediately results in the production of (VII-16) or (VII-19). This decarboxylation is normally carried out in a solvent (e.g., pyridine, picoline, benzene, toluene, dimethylsulfoxide, dimethylformamide, acetic acid) at a temperature of about 40° to 200° C. The thus-obtained compounds (VII-16A) and (VII-19A) can be converted to compounds (VII-16) and (VII-19), respectively, by removing their R''' by a deprotecting reaction according to the type thereof.

6) A compound represented by the general formula:

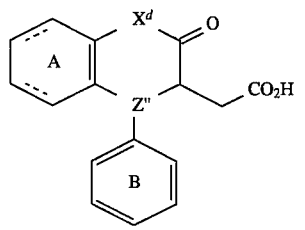

(VII-21):Z'' = —CR$^{4a}$—, (VII-22):Z$^a$ = —N— wherein X$^d$ represents —NR$^{1a}$— (R$^{1a}$ represents the same meaning as defined hereinabove), —O— or —S—; Z'' represents —CR$^{4a}$— (R$^{4a}$ is an optionally substituted hydrocarbon group) or —N—; the other symbols have the same definitions as above, is produced by alkylating a compound represented by the general formula:

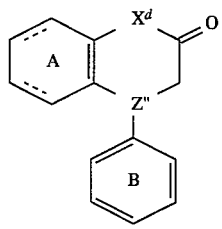

wherein the symbols have the same definitions as above, with the alkylating agent used above 5), represented by the formula R'''OCOCH$_2$—L, and then removing the protecting group R'''. The alkylating and deprotecting reactions can be carried out under the same conditions as described above.

7) Compounds (VII'-23) and (VII'-24), represented by the general formula: wherein the symbols have the same definitions as above, and having —NR$^{1a}$— for X$^d$ and hydrogen for at least one of R$^2$ and R$^{2a}$, can be produced by the following method:

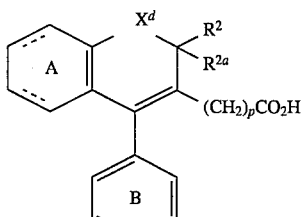

(VII-23):p = 0, (VII-24):p = 1

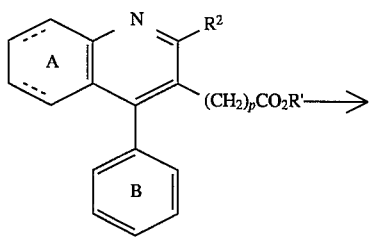

(VII-2A):p = 0
(VII-7A):p = 1

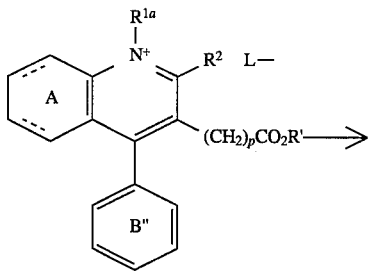

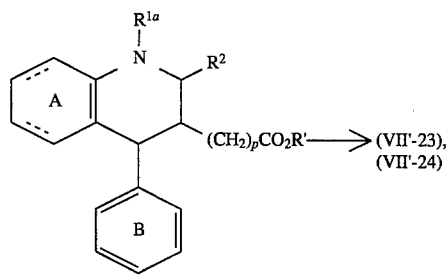

(VII'-23A)
(VII'-24A)

wherein the symbols have the same definitions as above. In this method, (VII-2A) or (VII-7A) is first alkylated to a quaternary salt, which is then reduced to a 1,2-dihydro derivative (VII-23A) or (VII-24A), respectively. This converting reaction can be carried out in the same manner as the converting reaction of compound (I$^d$)→(I$^e$)→(I$^c$). The thus-obtained compounds (VII-23A) and (VII-24A) may be subjected to the above-described Method 2-A) to remove R' to yield (VII-23) and (VII-24), respectively.

Alternatively, (II-23) can be produced by the following method:

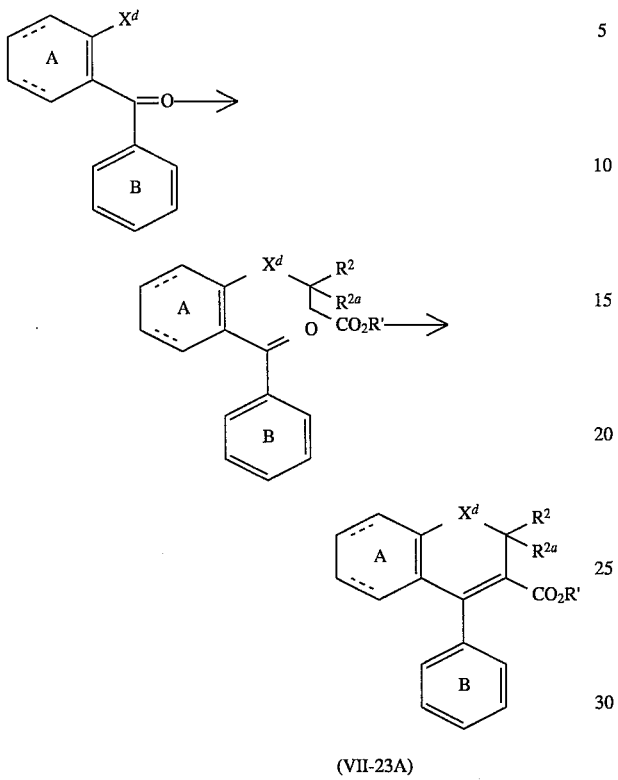

(VII-23A)

wherein the symbols have the same definitions as above. In this method, a benzophenone derivative, as the starting material, is reacted with, for example, a propionic acid derivative represented by the following formula:

wherein the symbols have the same definitions as above, to a substituted benzophenone derivative. Upon dehydrating reaction, this compound yields a cyclized derivative (VII-23A). (VII-23A) may be subjected to the above-described Method 2-A) to remove R' to yield (VII-23).

(VII-23) may be subjected to the above-described Method 2-A) or 2-B) to add one carbon atom to yield (VII-24).

8) Compounds represented by the general formula:

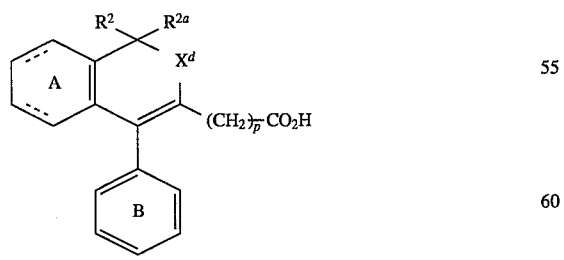

(VII-25):p = 0, (VII-26):p = 1 wherein the symbols have the same definitions as above, and having S for $X^d$, hydrogen for each of $R^2$ and $R^{2a}$ and 0 for p, include known compounds; for example, Natsugari et al. describe in European Patent Publication No. 481383 (published Apr. 22, 1992) a method of synthesizing these compounds as intermediates. Another compound (VII-25) wherein p=0 can also be produced in accordance with this method. (VII-25) may be treated in the same manner as the above-described Method 2-A) or 2-B) to add one carbon atom to yield (VII-26).

9) A compound represented by the general formula:

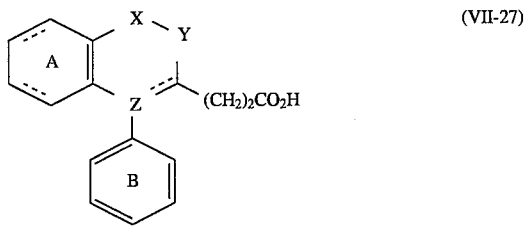

(VII-27)

wherein the symbols have the same definitions as above, can be produced from, for example, compounds of formulas (VII-6) to (VII-10), (VII-16) to (VII-22), (VII-24) and (VII-26) by adding one carbon atom by the above-described reaction Method 2-A) or 2-B).

10) In accordance with the above-described methods 1) through 3), 5) and 9), compounds of general formula (VII) wherein either X' or Y'— is S, the other being —CO—, can be produced. Also, compounds of general formula (VII) wherein either X' or Y' is —CO— can be converted to those wherein either is —CS— by a thioxo-derivatizing reaction with phosphorus pentasulfide etc.

11) A compound represented by the general formula:

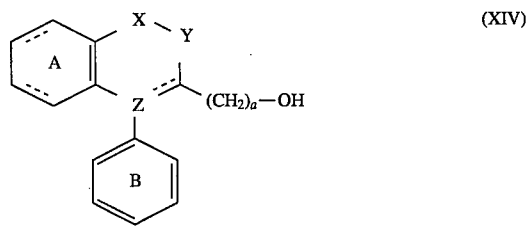

(XIV)

wherein α represents an integral from 1 to 3, the other symbols representing the same definition as above, can be produced from the corresponding carboxylic acid by subjecting reduction as described in Method 2B).

12) A compound represented by the general formula:

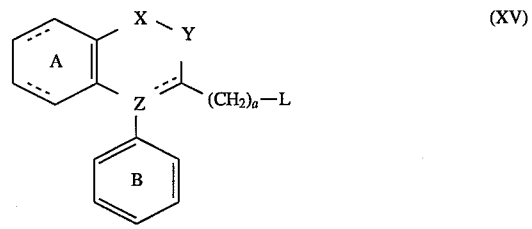

(XV)

wherein the symbols represent the same definition as above can be produced from the corresponding hydroxyl compound (XIV) by subjecting the conversion (—OH→—L) reaction described in Method 2B).

13) A compound represented by the general formula:

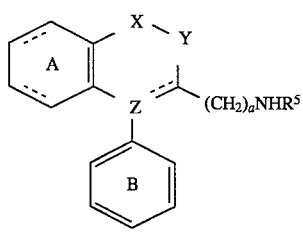

wherein the symbols represent the same definition as above can be produced from (XV) by reacting an amine represented by the formula $R^5-NH_2$ (the symbols have the same definition as above). This reaction can be carried out using the same conditions as those described in the alkylation reaction of (II) with (II) (Method ①-ii).

When the substituent in these compounds thus prepared contains a functional group, it can be converted to another appropriate functional group by various known methods. For example, when the substituent is a group containing a carboxyl group, up or ester thereof, it can be converted to an amide group by reaction with, for example, an amine or to a hydroxymethyl group or another group by reduction, for a starting material for synthesis of compound (I) and (I').

Starting materials for production of compound (I-A) or a salt thereof include compounds represented by the formulas (S-1) and (S-2). These compounds can be produced by the method schematized in the following reaction scheme 1 or a method based thereon.

Reaction scheme 1

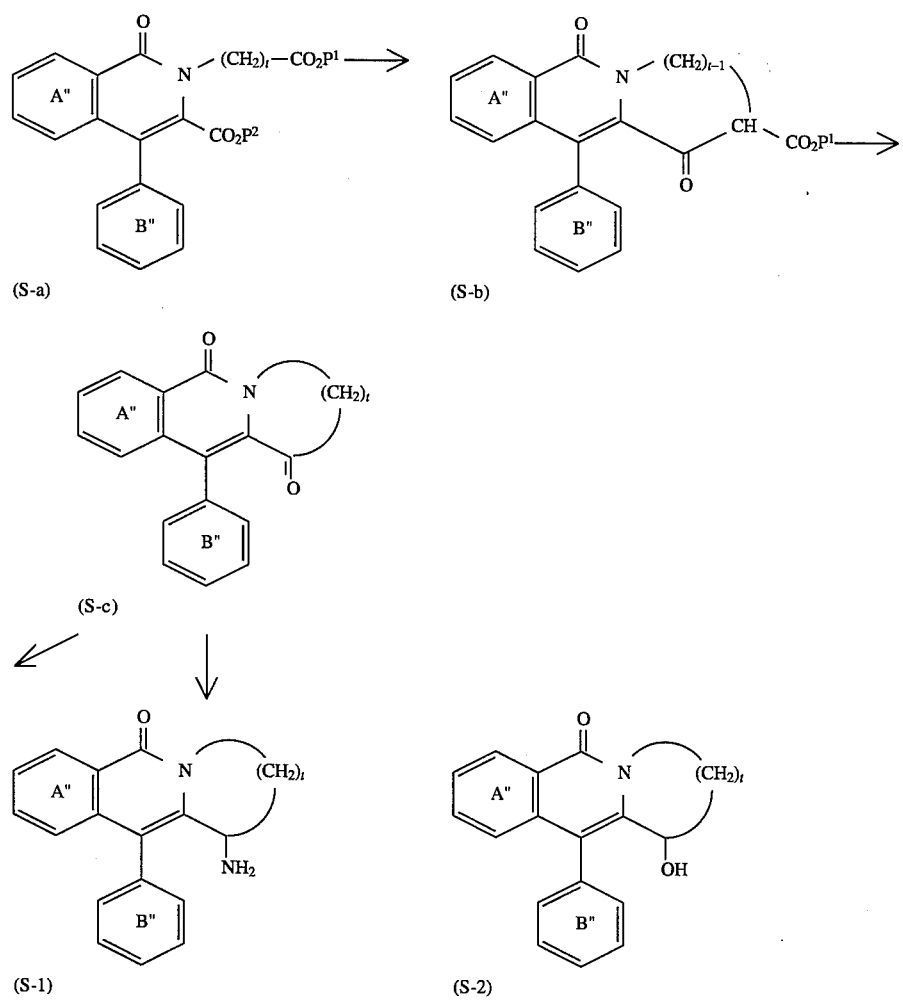

wherein $P^1$ and $P^2$ independently represent a protecting group for the carboxyl group; t represent an integer from 2 to 4; the other symbols have the same definitions as above.

With respect to the above formulas, the carboxyl group protecting groups $P^1$ and $P^2$ are exemplified by ester-forming protecting groups such as methyl, ethyl, methoxymethyl, methoxyethoxymethyl, benzyloxymethyl, tert-butyl, benzyl, p-methoxybenzyl, p-nitrobenzyl, o-nitrobenzyl, benzhydryl, trityl, 2,2,2-trichloroethyl, 2-trimethylsilylethyl and allyl, and silylester-forming protective groups such as trimethylsilyl, triethylsilyl, tert-butyldimethylsilyl and isopropyldimethylsilyl.

In the above method, compound (S-a) is first intramolecularly cyclized to compound (S-b). This cyclization is carried out by a reaction generally known as Dieckmann Condensation [J. P. Schaefer et al.: Organic Reactions, Vol. 15, pp. 1–203 (published 1967)] in a solvent inert to the reaction (e.g., tetrahydrofuran, dioxane, dimethoxyethane) in the presence of a base (e.g., sodium hydride, sodium ethoxide, sodium methoxide, sodium amide, potassium tert-butoxide). The mount of base used is not less than 1 mol equivalent, preferably 1.5 to 3 mol equivalents per mol of (S-a), reaction temperature being between about 0° C. and 130° C. Varying depending on type of starting material compound, reaction temperature and other factors, reaction time is normally about 0.5 to 5 hours.

The protected carboxyl group of compound (S-b) is removed to yield ketone compound (S-c). This reaction can be carried out under various sets of conditions depending on type of the protecting group $P^1$ used; when $P^1$ is a lower alkyl group such as methyl or ethyl, acidic or alkaline hydrolytic conditions are preferably used, under which decarboxylation usually takes place simultaneously with the removal of $P^1$, yielding compound (S-c). This reaction is carried out in a solvent (e.g., alcohols such as methanol, ethanol and propanol, ethers such as tetrahydrofuran, dioxane and dimethoxyethane, and mixtures thereof) under alkaline conditions with an alkali such as sodium hydroxide or barium hydroxide or an alkaline earth metal hydroxide or under acidic conditions with an inorganic acid such as hydrochloric acid, bromide acid or sulfuric acid or with an organic acid such as formic acid or acetic acid, or a mixture of these acids. Reaction temperature is normally about 0° to 150° C., preferably about 15° to 110° C., reaction time being about 0.5 to 24 hours, preferably about 1 to 10 hours.

Conversion of compound (S-c) to amino compound (S-1) is preferably achieved by a method of oxime derivative reduction. In this method, compound (S-c) is first reacted with hydroxylamine to yield an oxime compound by a conventional method (e.g., reacted at 20° to 70° C. in ethanol in the presence of hydroxylamine hydrochloride and sodium acetate). This oxime compound is then reduced to compound (S-1). This reducing reaction is carried out by, for example, the method described by C. A. Buehler et al. in the Survey of Organic Syntheses, pp. 423–424 (1970, published by Wiley-Interscience). For example, a reducing reaction with zinc powder is conducted under acidic conditions (e.g., in acetic acid solvent) or basic conditions (e.g., in a mixed solvent of ethanol and aqueous ammonia in the presence of ammonium acetate).

Hydroxyl compound (S-2) is produced by reducing compound (S-c). For this reducing reaction, a reducing agent such as sodium cyanoborohydride or sodium borohydride is preferably used. The reaction is carried out in a solvent (e.g., methanol, ethanol, tetrahydrofuran, dioxane, dimethoxyethane) at a temperature of about 0° to 50° C., the reaction time being about 15 minutes to 5 hours.

Each of the above compounds thus prepared as the starting material may form a salt. Such salts include those with inorganic acids (e.g., hydrochloric acid, phosphoric acid, hydrobromic acid, sulfuric acid) and those with organic acids (e.g., acetic acid, formic acid, propionic acid, fumaric acid, maleic acid, succinic acid, tartaric acid, citric acid, maleic acid, oxalic acid, benzoic acid, methanesulfonic acid, benzenesulfonic acid). When these compounds have an acidic group such as —COOH, they may form a salt with an inorganic base (e.g., alkali metal or alkaline earth metals such as sodium, potassium, calcium and magnesium, ammonia) or with an organic base (e.g., tri-$C_{1-3}$ alkylamines such as triethylamine).

The compounds obtained by the above methods may be purified and collected by known methods of purification such as concentration, liquid phase conversion, re-dissolution, solvent extraction, column chromatography, crystallization and recrystallization, or may be used in the form of a mixture as such for the subsequent reaction.

When the starting material compound used in the above reactions contains an amino group, a carboxyl group or a hydroxyl group as a substituent, these groups may have incorporated a protecting group generally used in peptide chemistry and other fields; the desired compound can be obtained by removing the protecting group as necessary after completion of the reaction.

Amino group protecting groups include $C_{1-6}$ alkylcarbonyl groups which may have a substituent (e.g., formyl, methylcarbonyl, ethylcarbonyl), phenylcarbonyl groups, $C_{1-6}$ alkyl-oxycarbonyl groups (e.g., methoxycarbonyl, ethoxycarbonyl), phenyloxycarbonyl groups (e.g., benzoxycarbonyl), $C_{7-10}$ aralkyl-carbonyl groups (e.g., benzyloxycarbonyl), trityl and phthaloyl. Substituents for these protecting groups include halogen atoms (e.g., fluorine, chlorine, bromine, iodine), $C_{1-6}$ alkyl-carbonyl groups (e.g., methylcarbonyl, ethylcarbonyl, butylcarbonyl) and nitro groups, the number of substituents being 1 to 3.

Carboxyl group protecting groups include $C_{1-6}$ alkyl groups which may have a substituent (e.g., methyl, ethyl, n-propyl, i-propyl, n-butyl, tert-butyl), phenyl, trityl and silyl. Substituents for these protecting groups include halogen atoms (e.g., fluorine, chlorine, bromine, iodine), $C_{1-6}$ alkylcarbonyl groups (e.g., formyl, methylcarbonyl, ethylcarbonyl, butylcarbonyl) and nitro groups, the number of substituents being 1 to 3.

Hydroxyl group protecting groups include $C_{1-6}$ alkyl groups which may have a substituent (e.g., methyl, ethyl, n-propyl, i-propyl, n-butyl, tert-butyl), phenyl groups, $C_{7-10}$ aralkyl groups (e.g., benzyl), $C_{1-6}$ alkylcarbonyl groups (e.g., formyl, methylcarbonyl, ethylcarbonyl), phenyloxycarbonyl groups (e.g., benzoxycarbonyl), $C_{7-10}$ aralkyl-carbonyl groups (e.g., benzyloxycarbonyl), pyranyl groups, furanyl groups and silyl groups. Substituents for these protecting groups include halogen atoms (e.g., fluorine, chlorine, bromine, iodine), $C_{1-6}$ alkyl groups, phenyl groups, $C_{7-10}$ aralkyl groups and nitro groups, the number of substituents being 1 to 4.

Protecting groups can be removed by known methods or those based thereon, including treatments with acids, bases, reducing agents, ultraviolet rays, hydrazine, phenylhydrazine, sodium N-methyldithiocarbamate, tetrabutylammonium fluoride, palladium acetate etc.

The thus-obtained compound (I) and (I') can be isolated and purified by ordinary means of separation such as recrystallization, distillation and chromatography. When compound (I) and (I') is obtained as a free form, it can be converted to a salt by a known method or a method based thereon (e.g., neutralization). Contrarily, when it is obtained as a salt, it can be converted to a free form or another salt by a known method or a method based thereon.

When compound (I) and (I') has a chiral center(s), it can be resolved to d- and l-configurations by conventional methods of optical resolution.

The compound (I) and (I') or a salt thereof is low in acute toxicity (Mice are dosed at 300 mg/kg, p.o. and 100 mg/kg, i.p. for observation of acute toxic symptoms or autonomic effects during the subsequent 72 hours; the response is no effect) and chronic toxicity, thus being a medicinally useful and safe substance.

The compounds (I) and (I') or a pharmacologically acceptable salt thereof (e.g., the above-mentioned salts with inorganic or organic bases and salts with inorganic or organic acids) exhibit excellent inhibitory action against acyl-CoA-:cholesterol acyl transferase (ACAT), and is pharmaceutically safe with low acute and chronic toxicities. ACAT, an enzyme involved in the higher fatty acid esterification of cholesterol in cells, is known to play a key role in cholesterol ester absorption in the digestive tract and cholesterol ester accumulation in various peripheral organs and cells (e.g., arterial walls, macrophages). ACAT-inhibiting substances can therefore inhibit intestinal absorption of food cholesterols to suppress blood cholesterol level rise and suppress intracellular cholesterol ester accumulation in arteriosclerosis lesions, thus preventing progress of atherosclerosis. The objected compounds or salt thereof of the present invention, exhibiting such excellent ACAT-inhibitory action and excellent cholesterol-lowering activity, is therefore useful as a safe preventive/therapeutic agent for hypercholesterolemia, atheromatous arteriosclerosis and diseases associated therewith (e.g. ischemic diseases such as myocardial infarction and cerebrovascular diseases such as cerebral infarction and cerebral stroke) in mammals (e.g., mice, rats, hamsters, rabbits, cats, dogs, horses, bovines, sheep, monkeys, humans).

Also, the compounds (I) and (I') or salt thereof include those which exhibit suppressing action against lipid peroxide production (antioxidant action) (e.g., compound of the above formula wherein at least one of rings A, B and Ar is a benzene ring substituted by an amino or hydroxyl group which may be substituted by a $C_{1-4}$ alkyl group). Lipid peroxidation in vivo is known to be closely associated with the onset of arteriosclerosis and ischemic diseases in the brain and cardiovascular system. Accordingly, the objected compound (I) and (I') or salt thereof, which exhibits both ACAT inhibitory and antioxidant actions, is highly useful as a pharmaceutical, because it can prevent and treat various vascular lesions due to these changes for both blood cholesterol and peroxide lipid.

When the compounds (I) and (I') or a pharmacologically acceptable salt thereof is used as a pharmaceutical as described above, it can be orally or non-orally administered in the form of powder, fine subtilaes, granules, tablets, capsules, injectable solutions or other dosage forms by conventional methods in a mixture with appropriate pharmacologically acceptable carriers, excipients (e.g., starch, lactose, sucrose, calcium carbonate, calcium phosphate), binders (e.g., starch, gum arabic, carboxymethyl cellulose, hydroxypropyl cellulose, crystalline cellulose, alginic acid, gelatin, polyvinylpyrrolidone), lubricants (e.g., stearic acid, magnesium stearate, calcium stearate, talc), disintegrating agents (e.g., carboxymethyl cellulose calcium, talc), diluents (e.g., physiological saline) and other additives. However, for inhibiting cholesterol absorption, oral administration is preferred. Varying depending on type of the objected compound or salt thereof, route of administration, symptoms, patient's age etc., daily dose is about 0.005 to 50 mg, preferably about 0.05 to 10 mg, more preferably about 0.2 to 4 mg per kg body weight for oral administration in adult hypercholesterolemia patients. This daily dose is preferably administered in one to three portions.

The compounds (I) and (I') of the present invention or a salt thereof exhibit excellent ACAT-inhibitory action and excellent cholesterol-lowering activity. The results of a pharmacologic test thereof are given below.

The following data of (I) to (III) are the experimental data showing the pharmacological efficacy of the compound (I) and (I') or salts thereof of the present invention.

(I) Inhibitory action against acyl-CoA:cholesterol acyl transferase (ACAT)

Method of Experiment

An ACAT enzyme preparation was prepared from a small intestine mucosal microsome fraction of a 6-week-old male Sprague-Dawley rat, previously fasted for 20 hours, in accordance with the method described by Heider et al. in the Journal of Lipid Research, Vol. 24, page 1127 (1982).

ACAT activity was determined by measuring the amount of labeled cholesterol ester produced from [$1$-$^{14}$C]-oleoyl-CoA and endogenous cholesterol, in accordance with the method of Helgerud et al. [Journal of Lipid Research, Vol. 22, page 271 (1981)].

Results (1) Table 1 shows data on the inhibitory rate (%) of formation of labeled cholesterol ester inhibitory rate (%), as an index of ACAT-inhibitory action, obtained when the compound was added at $10^{-6}$M.

TABLE 1

| Subject Compound (Example No.) | ACAT Inhibitory Rate (%) $10^{-6}$M |
| --- | --- |
| 9 | 90.3 |
| 10 | 93.3 |
| 13 | 93.8 |
| 15 | 90.2 |
| 18 | 97.3 |
| 19 | 99.1 |
| 20 | 97.8 |
| 21 | 99.3 |
| 22 | 97.9 |
| 23 | 99.4 |
| 25 | 96.9 |
| 27 | 92.0 |
| 29 | 98.4 |
| 31 | 97.5 |
| 32 | 96.0 |
| 33 | 98.9 |
| 36 | 98.8 |
| 42 | 96.6 |
| 43 | 98.2 |
| 45 | 99.5 |
| 47 | 90.3 |
| 48 | 99.2 |
| 49 | 92.8 |
| 50 | 95.7 |
| 51 | 98.1 |
| 52 | 90.4 |
| 53 | 99.7 |
| 54 | 98.4 |
| 55 | 97.9 |
| 56 | 98.1 |
| 57 | 99.3 |
| 60 | 99.9 |
| 64 | 99.5 |

TABLE 1-continued

| Subject Compound (Example No.) | ACAT Inhibitory Rate (%) $10^{-6}$M |
|---|---|
| 74 | 99.5 |
| 76 | 99.3 |
| 79 | 99.1 |
| 82 | 99.3 |
| 83 | 99.4 |
| 84 | 99.5 |
| 85 | 99.5 |
| 87 | 99.3 |
| 88 | 99.7 |
| 89 | 98.2 |
| 92 | 98.2 |
| 93 | 99.0 |
| 94 | 98.6 |
| 95 | 99.1 |
| 96 | 99.3 |
| 99 | 97.0 |

Table 1 shows that compound (I) or a salt thereof exhibits excellent ACAT-inhibitory action.

(II) Hypocholesterolemic activity (Cholesterol-lowering activity)

Method of Experiment

Groups of 6 ICR mice (2 subgroups of 3 mice) were made hypercholesterolemic by being fed a high cholesterol-cholic acid diet for 7 days and administered with test compounds orally on the last two days. One-half of the total does was given on day 6 followed by the other half on day 7. After fasting overnight (16 hours after the last dose), the animals were sacrificed and sera were collected together for the each subgroup for measuring the levels of cholesterol and heparin precipitating lipoproteins (HPL). Both cholesterol and HPL levels were measured with autonalyzer by the enzymatic CHOD-PAP method for the former and by the turbidimetric method of Shurr et. al. [in C. E. Dau ed. Atherosclerosis Drug Discovery, Plenum Publishing, New York, pp. 215–229 & 231–249, 1976.] for the latter.

Table 2 shows reduction % (compared to control groups) of cholesterol and HPL.

Results

TABLE 2

| Test compounds (Example No.) | Dose (po) mg/kg | Reduction % cholesterol | HPL |
|---|---|---|---|
| 48 | 10 | 32 | 39 |
|  | 3 | 27 | 26 |
| 74 | 10 | 33 | 37 |
|  | 3 | 29 | 32 |
| 82 | 10 | 40 | 50 |
|  | 3 | 31 | 37 |
| 84 | 10 | 33 | 47 |
|  | 3 | 15 | 28 |

From Table 2, it is clear that compound (I) or a salt thereof exhibits excellent hypocholesterolemic activity Also, the compounds (I) and (I') and a salt thereof according to the invention has excellent tachykinin receptor antagonizing activity, particularly potent antagonistic activity against substance P (hereinafter sometimes referred to briefly as SP), and is low in acute toxicity and chronic toxicity, thus being a medicinally useful and safe substance.

Substance P (SP) is a neuropeptide discovered in an equine intestinal canal extract in 1931 and its structure, consisting of 11 amino acids, was established in 1971. SP is broadly distributed in the central and peripheral nervous systems and, in addition to being a primary sensory neurotransmitter, has various physiological activities such as vasodilating activity augmentation of vascular permeability, smooth muscle contracting activity, neuronal excitatory activity, sialogogue activity, facilitation of micturition and immunomodulatory effect. It is known particularly that SP released by a pain impulse at the terminal of the cornu posterius of the spinal cord transmits pain information to secondary neurons and that SP released from the peripheral nerve terminal induces an inflammatory response in the nociceptive field. Moreover, SP is suspected to be involved in Alzheimer type dementia. Therefore, the objected compounds or salts thereof having potent SP receptor antagonizing activity are of value as a safe prophylactic/therapeutic drug for pain, inflammation, allergy airway diseases such as asthma and cough, disturbances of micturition such as pollakiuria and incontinence dementia in mammalian animals (e.g. mouse, rat, hamster, rabbit, cat, dog, bovine, sheep, monkey, man, etc.).

The dosage is dependent on the species of the objected compound or salts thereof, route of administration, disease condition, and patient's age and other background factors. However, for oral administration to an adult patient, for instance, a daily dose of about 0.005 to 50 mg, preferably about 0.05 to 10 mg, more preferably about 0.2 to 4 mg, per kg body weight is administered in 1 to 3 divided doses.

(III) Radioligand receptor binding inhibitory assay using receptor from human lymphoblast cells (IM-9)

The method of A. Margaret et al. [Molecular Pharmacology 42, 458 (1992)] was modified and used. The receptor was prepared from human lymphoblast cells (IM-9). IM-9 cells were grown in 175 cm$^2$ tissue culture flasks (100 ml×10) at a density approximately $2\times10^5$/ml of RPMI 1640 with L-glutamine, 10% (V/V) heat inactivated fetal calf serum, penicillin (100 u/ml), and streptomycin (100 μg/ml) at 37° C. in 5% $CO_2$/95% air for 3 days. IM-9 cells were obtained by centrifugation at 500×g for 5 minutes at 5° C. The pellet obtained was washed once with phosphate buffer (Flow Laboratories, CAT No. 28-103-05), homogenized using Polytron homogenizer (Kinematika, Germany) in 30 ml of 50 mM Tris-HCl buffer containing 120 mM NaCl, 5 mM KCl, 2 μg/ml phenylmethyl sulfonyl fluoride, and 1 mM ethylenediamine tetra-acetic acid and then centrifuged at 40,000×g for 20 minutes. The residue was washed twice with 30 ml of buffer described above, and preserved frozen (−80° C.).

The above specimen was suspended in a reaction buffer (50 mM Tris-HCl buffer (pH 7.4), 0.02% bovine serum albumin, 1 mM phenylmethylsulfonyl fluoride, 2 μg/ml chymostatin, 40 μg/ml bacitracin, 3 mM manganese chloride) at a protein concentration of 1.5 mg/ml and a 100 μl portion of the suspension was used in the reaction. After addition of the sample and 125I-BHSP (0.46 KBq), the reaction was conducted in 0.2 ml of reaction buffer at 25° C. for 30 minutes. The amount of nonspecific binding was determined by adding substance P at a final concentration of $2\times10^{-6}$M. After the reaction, using a cell harvester (290PHD, Cambridge Technology, Inc., England), rapid filtration was carried out through a glass filter (GF/B, Whatman, U.S.A.) to stop the reaction. After washing three times with 250 μl of 50 mM Tris-HCl buffer (pH 7.4) containing 0.02% bovine serum albumin, the radioactivity remaining on the filter was measured with a gamma counter.

Before use, the filter was immersed in 0.1% polyethyleneimine for 24 hours and air-dried.

The antagonistic activity of each test substance, in terms of the concentration necessary to cause 50% inhibition [IC$_{50}$] under the above conditions, was expressed in nM (Table 3).

TABLE 3

| Test Compounds Example No. | IC50 (nM) | Test Compounds Example No. | IC50 (nM) |
|---|---|---|---|
| 101 | 2.5 | 182 | 2 |
| 102 | 1.3 | 184 | 17 |
| 103 | 34 | 185 | 32 |
| 104 | 16 | 186 | 1.8 |
| 105 | 19 | 187 | 1.4 |
| 106 | 30 | 188 | 1.2 |
| 107 | 34 | 189 | 1.7 |
| 108 | 30 | 190 | 13 |
| 109 | 50 | 191 | 28 |
| 110 | 90 | 205 | 22 |
| 111 | 98 | 207 | 110 |
| 112 | 8.4 | 208 | 140 |
| 122 | 82 | 211 | 23 |
| 123 | 46 | 212 | 30 |
| 127 | 8.8 | 216 | 62 |
| 128 | 88 | 218 | 23 |
| 130 | 38 | 221 | 130 |
| 131 | 86 | 224 | 68 |
| 156 | 6.1 | 225 | 94 |
| 157 | 1.2 | 233 | 44 |
| 158 | 78 | 239 | 80 |
| 159 | 12 | 240 | 2 |
| 165 | 24 | 241 | 60 |
| 166 | 0.35 | 242 | 8.6 |
| 170 | 19 | 243 | 0.9 |
| 171 | 20 | 244 | 1.6 |
| 172 | 0.5 | 245 | 59 |
| 173 | 24 | 246 | 0.61 |
| 174 | 3.4 | 247 | 5.2 |
| 175 | 6.2 | 248 | 16 |
| 176 | 0.7 | 249 | 17 |
| 177 | 13 | 250 | 0.9 |
| 178 | 0.14 | 251 | 60 |
| 179 | 80 | 254 | 0.36 |
| 180 | 9.1 | 255 | 1.3 |
| 181 | 31 | 256 | 4.4 |

| Test Compounds Example No. | IC$_{50}$ (nM) | Test Compounds Example No. | IC50 (nM) |
|---|---|---|---|
| 258 | 3.1 | | |
| 260 | 1 | | |
| 261 | 63 | | |
| 262 | 2 | | |
| 263 | 46 | | |
| 264 | 16 | | |
| 265 | 0.52 | | |
| 266 | 8.2 | | |
| 267 | 0.68 | | |
| 269 | 1.4 | | |
| 270 | 10 | | |
| 271 | 1.9 | | |
| 272 | 23 | | |
| 273 | 2 | | |
| 274 | 2.3 | | |
| 275 | 1.9 | | |
| 276 | 3 | | |
| 277 | 54 | | |
| 278 | 10 | | |
| 279 | 34 | | |
| 280 | 58 | | |
| 281 | 36 | | |
| 282 | 22 | | |
| 285 | 9.4 | | |

It is apparent from Table 3 that the objected compound and salts thereof of the present invention have excellent substance P receptor antagonizing activity.

[EXAMPLES]

The present invention is hereinafter described in more detail by means of the following reference examples and working examples. The following Reference Examples and Examples are further descriptive of the present invention. It should be understood that these are merely illustrative and by no means definitive of the invention and that many changes and modifications can be made within the scope of the invention.

Elution in column chromatography in the reference and working examples was conducted with observation by TLC (Thin Layer Chromatography), unless otherwise stated. In the TLC observations, a TLC plate of Merck 60F$_{254}$ was used, in which the developing solvent was the same as the column chromatography eluent and the detector was a UV detector. Silica gel used for column chromatography was Merck Silica gel 60 (70–230 mesh). Room temperature is generally defined to be between about 10° C. and 35° C.

Extracts were dried over sodium sulfate or magnesium sulfate.

The abbreviations in the working and reference examples are defined as follows:

DMF for dimethylformamide, THF for tetrahydrofuran, DMSO for dimethyl sulfoxide, Hz for Herz, J for coupling constant, m for multiplet, q for quartet, t for triplet, d for doublet, s for singlet and b for broad.

Example 1

6-Chloro-N-(2,4-difluorophenyl)-1-oxo-4-phenyl-1H-2-benzopyran-3-carboxamide

Method A

To a solution of 6-chloro-1-oxo-4-phenyl-1H-2-benzopyran-3-carboxylic acid (450 mg) in dichloromethane (20 ml) were added oxalyl chloride (0.22 ml) and DMF (one drop) at room temperature, followed by stirring for 1 hour. After the solvent was distilled off, the residue was dissolved in anhydrous THF (20 ml). To this solution was added a solution of 2,4-difluoroaniline (0.30 ml) and triethylamine (0.27 ml) in anhydrous THF, followed by stirring at room temperature for 1.5 hours. After the solvent was distilled off, ethyl acetate was added to the residue, which was then washed successively with water, dilute hydrochloric acid, water, aqueous sodium hydrogen carbonate and water and then dried, after which the solvent was distilled off, to yield the title compound as colorless crystals (520 mg).

Method B

To a solution of 6-chloro-1-oxo-4-phenyl-1H-2-benzopyran-3-carboxylic acid (300 mg) in 1,2-dichloroethane (10 ml) were added 1-hydroxybenzotriazole (135 mg) and 1,3-dicyclohexylcarbodiimide (220 mg), followed by stirring at room temperature for 0.5 hours. To this mixture was added 2,4-difluoroaniline (0.20 ml), followed by stirring at room temperature for 16 hours. After the reaction mixture was concentrated, ethyl acetate was added to the residue, and the precipitated crystals were separated by filtration. The filtrate was washed successively with dilute hydrochloric acid, water, aqueous potassium carbonate and water and then dried, after which the solvent was distilled off, to yield the title compound as colorless crystals (350 mg).

Melting point: 189°–191° C. (recrystallized from ethyl acetate-ethyl ether) NMR(200 MHz, CDCl$_3$) ppm: 6.70–6.93 (2H, m), 7.08 (1H, d, J=2.2Hz), 7.24–7.63 (6H, m), 8.10 (1H, m), 8.39 (1H, d, J=8.6 Hz), 8.68 (1H, b) Elemental analysis (for C$_{22}$H$_{12}$NO$_3$ClF$_2$): Calculated (%): C, 64.17; H, 2.94; N, 3.40 Found (%): C, 63.91; H, 2.84; N, 3.44

In the working examples 2 to 97 below, unless otherwise specified, the desired compound was obtained in substantially the same method as Method A or Method B in Example 1, using the carboxylic acid and aniline corresponding thereto as starting materials. For the compounds of respective examples, the method of synthesis (Method A or Method B) is specified with (A) or (B) after the name of the compound.

Example 2

4-(4-Fluorophenyl)-6-methyl-1-oxo-N-(2,4,6-trimethoxyphenyl)-1H-2-benzopyran-3-carboxamide (A)

Melting point: 228°–229° C. (recrystallized from ethanol) NMR (200 MHz, CDCl$_3$) ppm: 2.39 (3H, s), 3.76 (6H, s), 3.77 (3H, s), 6.10 (2H, s), 6.88 (1H, s), 7.10–7.30 (4H, m), 7.44 (1H, d, J=8.0 Hz), 7.90 (1H, s) 8.31 (1H, d, J=8.0 Hz) Elemental analysis (for C$_{26}$H$_{22}$NO$_6$F): Calculated (%): C, 67.38; H, 4.78; N, 3.02 Found (%): C, 67.21; H, 4.92; N, 3.13

Example 3

N-(2,4-Difluorophenyl)-4-(4-fluorophenyl)-6-(1-methylethyl)-2-oxo-2H-1-benzopyran-3-carboxamide (A)

Melting point: 175°–176° C. (recrystallized from ethyl acetate-isopropyl ether) NMR (200 MHz, CDCl$_3$) ppm: 1.17 (6H, d, J=7.0 Hz), 2.87 (1H, m), 6.70–6.90 (2H, m), 6.96 (1H, d, J=2.0 Hz), 7.18–7.57 (6H, m), 8.12 (1H, m), 9.74 (1H, b) Elemental analysis (for C$_{25}$H$_{18}$NO$_3$F$_3$): Calculated (%): C, 68.65; H, 4.15; N, 3.20 Found (%): C, 68.68; H, 4.00; N, 3.141

Example 4

N-[2,6-Bis(1-methylethyl)phenyl]-4-(4-fluorophenyl)-6-(1-methylethyl)-2-oxo-2H-1-benzopyran-3-carboxamide (A)

Melting point: 220°–222° C. (recrystallized from ethyl acetate-hexane) NMR (200 MHz, CDCl$_3$) ppm: 1.11 (12H, d, J=6.8 Hz), 1.18 (6H, d, J=6.8 Hz), 2.87 (1H, m), 2.97 (2H, m), 6.97 (1H, d, J=1.4 Hz), 7.10–7.55 (9H, m) 8.18 (1H, b) Elemental analysis (for C$_{31}$H$_{32}$NO$_3$F): Calculated (%): C, 76.68; H, 6.64; N, 2.88 Found (%): C, 76.30; H, 6.60; N, 2.84

Example 5

N-[2,6-Bis(1-methylethyl)phenyl]-4-(2-chlorophenyl)-6,7-dimethyl-2-(1-methylethyloxy)-3-quinolinecarboxamide (A)

Melting point: 176°–178° C. (recrystallized from ethyl ether-hexane) NMR (200 MHz, CDCl$_3$) ppm: 1.04 (12H, bs), 1.46 (3H, d, J=6.4 Hz), 1.51 (3H, d, J=6.2 Hz), 2.26 (3H, s), 2.43 (3H, s), 2.60–3.80 (2H, bs), 5.78 (1H, m), 6.82 (1H, s), 7.00–7.65 (8H, m), 7.67 (1H, s) Elemental analysis (for C$_{33}$H$_{37}$N$_2$O$_2$Cl): Calculated (%): C, 74.91; H, 7.05; N, 5.29 Found (%): C, 74.98; H, 7.09; N, 5.35

Example 6

4-[3,5-Bis-(1,1-dimethylethyl)-4-hydroxyphenyl]-N-[2,6-bis(1-methylethyl)phenyl]-1,2-dihydro-2-methyl-1-oxo-3-isoquinolinecarboxamide (A)

Melting point: 334°–338° C. (recrystallized from acetone-methanol) NMR (200 MHz, CDCl$_3$) ppm: 1.24 (12H, d, J=7.0 Hz), 1.64 (18H, s), 2.35 (1H, s), 2.74 (1H, m), 3.97 (3H, s), 5.59 (1H, s), 7.09–7.13 (1H, m), 7.29–7.50 (5H, m), 7.67–7.73 (2H, m), 8.66–8.71 (1H, m) Elemental analysis (for C$_{37}$H$_{46}$N$_2$O$_3$.1/4 H$_2$O): Calculated (%): C, 77.79; H, 8.20; N, 4.90 Found (%): C, 77.75; H, 8.22; N, 4.75

Example 7

N-[2,6-Bis(1-methylethyl)phenyl]-4-(2-chlorophenyl)-1-ethyl-6,7-dimethyl-2-oxo-3-quinolinecarboxamide (A)

Melting point: 217°–222° C. (recrystallized from acetone-hexane) NMR (200 MHz, CDCl$_3$) ppm: 1.11 (12H, d, J=6.2 Hz), 1.50 (3H, t, J=7.2 Hz), 2.19 (3H, s), 2.44 (3H, s), 3.10 (2H, bs), 4.38–4.68 (2H, m), 6.79 (1H, s), 7.02–7.50 (8H, m), 9.79 (1H, s) Elemental analysis (for C$_{32}$H$_{35}$N$_2$O$_2$Cl): Calculated (%): C, 74.62; H, 6.85; N, 5.44 Found (%): C, 74.70; H, 7.06; N, 5.41

Example 8

N-(2,5-Dimethoxyphenyl)-4-(4-fluorophenyl)-1-oxo-1H-2-benzopyran-3-carboxamide (A)

Melting point: 186°–187° C. (recrystallized from acetone-ethyl ether) NMR (200 MHz, CDCl$_3$) ppm: 3.72 (3H, s), 3.90 (3H, s), 6.59 (1H, dd, J=12.0, 3.0 Hz), 6.81 (1H, d, J=8.8 Hz), 7.10–7.30 (5H, m), 7.60–7.72 (2H, m), 7.96 (1H, d, J=2.8 Hz), 8.44 (1H, dd, J=7.2, 1.0 Hz), 9.23 (1H, b) Elemental analysis (for C$_{24}$H$_{18}$O$_5$F): Calculated (%): C, 63.73; H, 4.33; N, 3.34 Found (%): C, 68.66; H, 4.37; N, 3.47

Example 9

3,4-trans-4-(4-Fluorophenyl)-1,2,3,4-tetrahydro-2-methyl-N-(3-methylphenyl)-1-oxo-3-isoquinolinecarboxamide (A)

Melting point: 273°–275° C. (recrystallized from chloroform) NMR (200 MHz, DMSO-d$_6$) ppm: 2.25 (3H, s), 2.88 (3H, s), 4.54 (1H, s), 4.65 (1H, s), 6.83–7.43 (11H, m), 7.96–8.00 (1H, m) Elemental analysis (for C$_{24}$H$_{21}$N$_2$O$_2$F): Calculated (%): C, 74.21; H, 5.45; N, 7.21 Found (%): C, 73.75; H, 5.20; N, 7.32

Example 10

3,4-trans-4-(2-Chlorophenyl)-N-(2,4-difluorophenyl)-1,2,3,4-tetrahydro-1,6,7-trimethyl-2-oxo-3-quinolinecarboxamide (A)

Melting point: 230°–233° C. (recrystallized from ethyl acetate-isopropyl ether) NMR (200 MHz, CDCl$_3$) ppm: 2.19 (3H, s), 2.29 (3H, s), 3.44 (3H, s), 4.00 (1H, d, J=1.6 Hz), 5.30 (1H, s like), 6.57–6.65 (1H, m), 6.72–6.90 (2H, m), 6.98 (1H, s), 7.00–7.23 (2H, m), 7.01 (1H, s), 7.37–7.45 (1H, m), 8.11–8.26 (1H, m), 8.43 (1H, bs) Elemental analysis (for C$_{25}$H$_{21}$N$_2$O$_2$ClF$_2$): Calculated (%): C, 66.01; H, 4.65; N, 6.16 Found (%): C, 65.98; H, 4.85; N, 6.03

Example 11

3,4-trans-N-[2,6-Bis(1-methylethyl)phenyl]-6-chloro-1,2,3,4-tetrahydro-1-methyl-2-oxo-4-phenyl-3-quinolinecarboxamide (A)

Melting point: 201°–203° C. (recrystallized from ethyl acetate-isopropyl ether) NMR (200 MHz, CDCl$_3$) ppm: 0.98 (6H, d, J=6.2 Hz), 1.08 (6H, d, J=6.6 Hz), 2.68 (2H, m), 3.45 (3H, s), 4.02 (1H, d, J=4.0 Hz), 4.49 (1H, d, J=3.6 Hz), 6.90–7.50 (12H, m) Elemental analysis (for $C_{29}H_{31}N_2O_2Cl$): Calculated (%): C, 73.33; H, 6.58; N, 5.90 Found (%): C, 73.06; H, 6.61; N, 5.92

Example 12

3,4-cis-4-[3,5-Bis(1,1-dimethylethyl)-4-hydroxyphenyl]-N-[2,6-bis(1-methylethyl)phenyl]-1,2,3,4-tetrahydro-2-methyl-1-oxo-3-isoquinolinecarboxamide A mixture of the compound obtained in Example 6 (300 mg), acetic acid (8 ml) and 10% palladium-carbon (50% hydrated) (150 mg) was stirred at 90° to 100° C. in a hydrogen atmosphere for 15 hours. After cooling, the mixture was filtered, the filtrate being distilled to remove the solvent. The residue was dissolved in ethyl acetate and washed successively with water, aqueous sodium hydrogen carbonate and water and then dried, after which the solvent was distilled off, to yield the title compound as colorless crystals (160 mg).

Melting point: 268°–270° C. (recrystallized from acetone-ethyl ether) NMR (200MHz, CDCl$_3$) ppm: 0.87 (6H, d, J=6.8 Hz), 1.00 (6H, d, J=6.8 Hz), 1.39 (18H, s), 2.41 (1H, m), 3.41 (3H, s), 4.40 (1H, d, J=5.6 Hz), 4.93 (1H, d, J=5.6 Hz), 5.22 (1H, s), 6.82 (1H, s), 7.02–7.53 (8H, m), 8.16–8.20 (1H, m) Elemental analysis (for $C_{37}H_{48}N_2O_3$): Calculated (%): C, 78.13; H, 8.51; N, 4.92 Found (%): C, 77.94; H, 8.60; N, 4.83

Example 13

3,4-trans-N-[2,6-Bis(1-methylethyl)phenyl]-4-(4-fluorophenyl)-3,4-dihydro-6-(1-methylethyl)-2-oxo-2H-1-benzopyran-3-carboxamide The compound obtained in Example 4 was reacted in substantially the same manner as in Example 12 to yield the title compound as colorless crystals. Melting point: 223°–225° C. (recrystallized from ethyl acetate-isopropyl ether) NMR (200 MHz, CDCl$_3$) ppm: 0.98, 1.06 (each 6H, d, J=7.0 Hz), 1.16, 1.17 (each 3H, d, J=7.0 Hz), 2.65 (2H, b), 2.82 (1H, m), 3.98 (1H, d, J=7.0 Hz), 5.00 (1H, d, J=7.0 Hz), 6.86–7.29(10H, m) Elemental analysis (for $C_{31}H_{34}NO_3F$): Calculated (%): C, 76.36; H, 7.03; N, 2.87 Found (%): C, 76.06; H, 7.14; N, 3,08

Example 14

N-(2,5-Dimethoxyphenyl)-4-(4-fluorophenyl)-3,4-dihydro-1-oxo-1H-2-benzopyran-3-carboxamide The compound obtained in Example 8 was reacted in substantially the same manner as in Example 12 to yield the title compound as colorless crystals.

Melting point: 133°–136° C. (recrystallized from acetone-ethyl ether) NMR (200 MHz, CDCl$_3$) ppm: 3.72 (3H, s), 3.78 (3H, s), 4.83 (1H, d, J=3.5 Hz), 5.35 (1H, d, J=3.5 Hz), 6.57 (1H, dd, J=12.0, 2.8 Hz), 6.73 (1H, d, J=9.0 Hz), 6.83–7.07 (4H, m), 7.31 (1H, d, J=7.2 Hz), 7.50–7.70 (2H, m), 7.8 (1H, d, J=2.6 Hz), 8.25 (1H, d, J=7.6 Hz), 8.49 (1H, b) Elemental analysis (for $C_{24}H_{20}NO_5F.1/3 H_2O$): Calculated (%): C, 67.94; H, 4.91; N, 3.30 Found (%): C, 67.73; H, 4.98; N, 3.30

Example 15

3,4-trans-N-[2,6-Bis(1-methylethyl)phenyl]-4-(2-chlorophenyl)-1,2,3,4 -tetrahydro-1,6,7-trimethyl-3-quinolinecarboxamide (A)

Melting point: 145°–146° C. (recrystallized from ethyl ether-hexane) NMR (200 MHz, CDCl$_3$) ppm: 1.06 (12H, d like, J=6.6 Hz), 2.07 (3H, s), 2.24 (3H, s), 2.71 (2H, m), 3.01 (3H, s), 3.11 (1H, m), 3.25–3.52 (2H, m), 4.90 (1H, d, J=3.2 Hz), 6.62 (2H, s), 6.80–6.90 (1H, m), 7.05–7.30 (5H, m), 7.40–7.50 (1H, m), 7.56 (1H, bs) Elemental analysis (for $C_{31}H_{37}N_2OCl$): Calculated (%): C, 76.13; H, 7.62; N, 5.73 Found (%): C, 75.95; H, 7.74; N, 5.80

Example 16

N-[2,6-Bis(1-methylethyl)phenyl]-1,2,3,4-tetrahydro-1-methyl-2-oxo-4-phenyl-3-quinolineacetamide (trans:cis=about 3:1 mixture) (A)

Melting point: 214°–216° C. (recrystallized from ethyl acetate-isopropyl ether) NMR (200 MHz, CDCl$_3$) ppm: 0.90–1.30, 1.17 (total 12H, m, d, J=7.0 Hz), 2.06, 2.35–3.05 (total 2H, d, J=5.8 Hz, m), 2.90–3.20 (2H, m), 3.35–3.70 (1H, m), 3.38, 3.46, 3.51 (total 3H, each s), 4.30, 4.33, 4.41 (1H, each d, J=6.2 Hz, J=11.0 Hz, J=8.0 Hz), 6.55–7.60(13H, m) Elemental analysis (for $C_{30}H_{34}N_2O_2$): Calculated (%): C, 79.26; H, 7.54; N, 6.16 Found (%): C, 79.10; H, 7.65; N, 6.30

Example 17

4-(2-Chlorophenyl)-1,2,3,4-tetrahydro-1-methyl-N-(3-methylphenyl)-2-oxo-3-quinolineacetamide (trans:cis=about 3:1 mixture) (A)

Melting point: 161°–162° C. (recrystallized from ethyl acetate-isopropyl ether) NMR (200 MHz, CDCl$_3$) ppm: 2.25–2.55 (1H, m), 2.31 (3H, s), 2.60–2.80 (1H, m), 3.40–3.65 (0.75H, m), 3.47 (2.25H, s), 3.50 (0.75H, s), 3.70–3.85 (0.25H, m), 4.76(0.75H,d,J=13Hz), 5.05 (0.25H, d, J=7.0Hz), 6.63 (0.75H, d, J=7.8 Hz), 6.85–7.50 (11.25H, m), 7.85 (0.25H, bs), 8.11 (0.75H, bs) Elemental analysis (for $C_{25}H_{23}N_2O_2Cl.0.2 H_2O$): Calculated (%): C, 71.07; H, 5.58; N, 6.63 Found (%): C, 71.07; H, 5.56; N, 6.53

Example 18

N-[2,6-Bis(1-methylethyl)phenyl]-1,2,3,4-tetrahydro-6,7-dimethoxy-1 -methyl-2-oxo-4-phenyl-3-quinolineacetamide (trans:cis=about 4:1 mixture) (A)

Melting point: 205°–207° C. (recrystallized from ethyl acetate-isopropyl ether) NMR (200 MHz, CDCl$_3$) ppm: 0.85–1.35, 1.17 (total 12H, m, d, J=6.8 Hz), 2.04, 2.55–2.80 (total 2H, d, J=5.2 Hz, m), 3.06 (2H, m), 3.30–3.55 (1H, m), 3.36, 3.42, 3.45 (total 3H, each s), 3.62, 3.65 (total 3H, each s), 3.89, 3.90, 3.94 (total 3H, each s), 4.24, 4.33 (total 1H, each d, J=10 Hz, J=11 Hz), 6.21, 6.30 (total 1H, each s), 6.56, 6.66 (total 1H, each s), 7.00–7.50 (9H, m) Elemental analysis (for $C_{32}H_{38}N_2O_4$): Calculated (%): C, 74.68; H, 7.44; N, 5.44 Found (%): C, 74.82; H, 7.50; N, 5.36

Example 19

N-[2,6-Bis-(1-methylethyl)phenyl]-6-chloro-1,2,3,4-tetrahydro-1,4 -dimethyl-2-oxo-4-phenyl-3-quinolineacetamide (A)

Melting point: 236°–237° C. (recrystallized from ethyl acetate-isopropyl ether) NMR (200 MHz, CDCl$_3$) ppm: 1.13 (12H, d, J=6.6 Hz), 1.49 (3H, s), 2.01 (1H, dd, J=14.4 Hz, J=2.0 Hz), 2.88 (1H, dd, J=14.4 Hz, J=9.6 Hz), 3.00 (2H m), 3.40, 3.45 (total 3H, each s), 3.86 (1H, d, J=9.8 Hz), 6.53 (1H, d, J=2.4 Hz), 6.9–7.5(10H, m) Elemental analysis (for $C_{31}H_{35}N_2O_2Cl$): Calculated (%): C, 74.01; H, 7.01; N, 5.57 Found (%): C, 73.71; H, 6.89; N, 5.87

Example 20

3,4-trans-N-[2,6-Bis(1-methylethyl)phenyl]-4-(2-chlorophenyl)-1,2,3,4 -tetrahydro-1,6,7-trimethyl-2-oxo-3-quinolineacetamide (A)

Melting point: 213°–215° C. (recrystallized from ethyl acetate-isopropyl ether) NMR (200 MHz, CDCl$_3$) ppm: 0.95–1.30, 1.16 (total 12H, m, d, J=6.8 Hz), 2.06, 2.13 (total 3H, each s), 2.24, 2.30 (total 3H, each s), 2.56 (1H, dd, J=15.0, 3.8 Hz), 2.79 (1H, dd, J=15.0, 7.8 Hz), 3.06 (2H, m), 3.39, 3.45 (total 3H, each s), 3.40–3.60 (1H, m), 4.69, 4.85 (total 1H, each d, J=10.0 Hz, J=13.0 Hz), 6.23, 6.47 (total 1H, each s), 6.79, 6.90 (total 1H, each s), 7.00–7.30, 7.40–7.55, 7.55 (total 8H, m, m, s) Elemental analysis (for C$_{32}$H$_{37}$N$_2$O$_2$Cl): Calculated (%): C, 74.33; H, 7.21; N, 5.42 Found (%): C, 74.13; H, 7.09; N, 5.83

Example 21

3,4-trans-N-[2,6-Bis(1-methylethyl)phenyl]-6-chloro-4-(2-chlorophenyl)-1,2,3,4-tetrahydro-1-methyl-2-oxo-3-quinolineacetamide (A)

Melting point: 231°–234° C. (recrystallized from ethyl acetate-isopropyl ether-ethanol) NMR (200 MHz, CDCl$_3$) ppm: 1.00–1.30, 1.16 (total 12H, m, d, J=6.8 Hz), 2.55 (1H, dd, J=15.0, 4.0 Hz), 2.76 (1H, dd, J=15.0, 7.4 Hz), 3.06 (2H, m), 3.39, 3.45 (total 3H, each s), 3.40–3.70 (1H, m), 4.83, 4.96 (total 1H, each d, J=12.0 Hz, J=14.0 Hz), 6.46, 6.62 (total 1H, each s), 6.90–7.56 (10H, m) Elemental analysis (for C$_{30}$H$_{32}$N$_2$O$_2$Cl$_2$.0.2CH$_3$CO$_2$C$_2$H$_5$): Calculated (%): C, 68.37; H, 6.26; N, 5.18 Found (%): C, 68.14; H, 6.42; N, 5.24

Example 22

3,4-cis-6-Chloro-1,2,3,4-tetrahydro-1-methyl-N-[2-methyl-6-(1-methylethyl)phenyl]-2-oxo-4-phenyl-3-quinolineacetamide To a solution of 6-chloro-1,2,3,4-tetrahydro-1-methyl-2-oxo-4-phenyl-3-quinolineacetic acid (trans:cis=about 4:1 mixture, described in Reference Example 12) (220 mg) in anhydrous THF (7 ml) were added oxalyl chloride (0.11 ml) and DMF (one drop) at room temperature, followed by stirring for 0.5 hours. After the solvent was distilled off, the residue was dissolved in anhydrous THF (10 ml). To this solution was added a solution of 2-isopropyl-6-methylaniline (0.135 ml) and triethylamine (0.11 ml) in anhydrous THF (5 ml), followed by stirring at room temperature for 0.5 hours. After the solvent was distilled off, ethyl acetate was added to the residue, which was then washed successively with water, dilute hydrochloric acid, water, aqueous sodium hydrogen carbonate and water and then dried, followed by concentration, to yield the compound of Example 23 as colorless crystals (120 mg). After the filtrate was distilled to remove the solvent, the residue was subjected to silica gel column chromatography (eluted with hexane:ethyl acetate= 1:0→3:1); the title compound, as colorless crystals (35 mg), was obtained in the first fraction, the compound of Example 23 described below, as additional colorless crystals (25 mg), was obtained in the second fraction.

Melting point: 162°–164° C. (recrystallized from isopropyl ether) NMR (200 MHz, CDCl$_3$) ppm: 1.17 (3H, d, J=7.2 Hz), 1.20 (3H, d, J=7.2 Hz), 2.23 (3H, s), 2.37 (1H, dd, J=15.1, 4.8 Hz), 2.91 (1H, dd, J=15.1, 7.8 Hz), 3.09 (1H, m), 3.48 (3H, s), 3.65 (1H, m), 4.25 (1H, d, J=6.7 Hz), 7.01–7.37 (11H, M) Elemental analysis (for C$_{28}$H$_{29}$N$_2$O$_2$Cl): Calculated (%): C, 72.95; H, 6.34; N, 6.08 Found (%): C, 72.64; H, 6.57; N, 6.19

Example 23

3,4-trans-6-Chloro-1-methyl-N-[2-methyl-6-(1-methylethyl)phenyl]-2-oxo-4-phenyl-1,2,3,4-tetrahydro-3-quinolineacetamide The title compound, along with the compound of Example 22, was obtained as colorless crystals by the method described in Example 22.

Melting point: 238°–240° C. (recrystallized from ethyl acetate-ethyl ether) NMR (200 MHz, CDCl$_3$+DMSO-d$_6$) ppm: 1.16 (3H, d, J=7.0 Hz), 1.17 (3H, d, J=7.0 Hz), 2.21 (3H, s), 2.57–2.64 (2H, m), 3.10 (1H, m), 3.39 (3H, s), 3.34–3.50 (1H, m), 4.35 (1H, d, J=8.8 Hz), 6.79 (1H, d, J=2.4 Hz), 7.01–7.40 (10H, m), 8.48 (1H, s) Elemental analysis (for C$_{28}$H$_{29}$N$_2$O$_2$Cl): Calculated (%): C, 72.95; H, 6.34; N, 6.08 Found (%): C, 72.64; H, 6.40; N, 6.15

The compounds of Examples 24 through 33 were obtained in the same reaction as in Example 22, using the carboxylic acid used in Example 22 and respective corresponding anilines.

Example 24

3,4-cis-6-Chloro-1,2,3,4-tetrahydro-1-methyl-2-oxo-4-phenyl-N-(2,4,6-trimethoxyphenyl)-3-quinolineacetamide Melting point: 160°–162° C. (recrystallized from ethyl acetate-isopropyl ether) NMR (200 MHz, CDCl$_3$) ppm: 2.20 (1H, dd, J=14.4 Hz, J=2.0 Hz), 3.10 (1H, dd, J=14.4 Hz, J=9.6 Hz), 3.39, 3.46 (total 3H, each s), 3.81 (3H, s), 3.84 (6H, s), 4.34 (1H, d, J=7.0 Hz), 6.17 (2H, s), 6.65 (1H, s), 6.9–7.3 (7H, m) Elemental analysis (for C$_{27}$H$_{27}$N$_2$O$_5$Cl): Calculated (%): C, 65.52; H, 5.50; N, 5.66 Found (%): C, 65.51; H, 5.84; N, 5.84

Example 25

3,4-trans-6-Chloro-1,2,3,4-tetrahydro-1-methyl-2-oxo-4-phenyl-N-(2,4,6-trimethoxyphenyl)-3-quinolineacetamide Melting point: 157°–158° C. (recrystallized from ethyl acetate-isopropyl ether) NMR (200 MHz, CDCl$_3$)ppm: 2.58 (1H, d, J=6.2 Hz), 3.32, 3.40 (total 3H, each s), 3.66, 3.79 (total 9H, each s), 4.37 (1H, d, J=7.6 Hz), 6.14 (2H, s), 6.85 (1H, d, J=2.4Hz), 6.7–7.4(7H, m) Elemental analysis (for C$_{27}$H$_{27}$N$_2$O$_5$Cl): Calculated (%): C, 65.52; H, 5.50; N, 5.66 Found (%): C, 65.47; H, 5.60; N, 5.74

Example 26

3,4-cis-6-Chloro-N-(2,4-difluorophenyl)-1,2,3,4-tetrahydro-1-methyl-2-oxo-4-phenyl-3-quinolineacetamide Melting point: 198°–200° C. (recrystallized from ethyl acetate-isopropyl ether) NMR (200 MHz, CDCl$_3$) ppm: 2.34 (1H, dd, J=15.0 Hz, J=4.8 Hz), 2.81 (1H, dd, J=15.0 Hz, J=4.0 Hz), 3.47 (3H, s), 3.61 (1H, m), 4.19 (1H, d, J=6.6 Hz), 6.8–7.3 (9H, m), 7.96 (1H, bs), 8.21 (1H, m) Elemental analysis (for C$_{24}$H$_{19}$N$_2$O$_2$ClF$_2$): Calculated (%): C, 65.38; H, 4.34; N, 6.35 Found (%): C, 65.32; H, 4.41; N, 6.37

Example 27

3,4-trans-6-Chloro-N-(2,4-difluorophenyl)-1,2,3,4-tetrahydro-1-methyl-2-oxo-4-phenyl-3-quinolineacetamide Melting point: 165°–168° C. (recrystallized from ethyl acetate-isopropyl ether) NMR (200 MHz, CDCl$_3$) ppm: 2.55 (1H, m), 3.43 (3H, s), 3.43 (1H, m), 4.18 (1H, d, J=13.2 Hz), 6.60 (1H, m), 6.86 (2H, m), 6.97 (1H, d, J=8.6 Hz), 7.2–7.5 (7H, m), 7.8 (1H, bs), 8.2 (1H, m) Elemental analysis (for C$_{24}$H$_{19}$N$_2$O$_2$ClF$_2$): Calculated (%): C, 65.38; H, 4.34; N, 6.35 Found (%): C, 65.51; H, 4.34; N, 6.36

Example 28

3,4-cis-6-Chloro-N-(2,6-dimethylphenyl)-1,2,3,4-tetrahydro-1-methyl-2-oxo-4-phenyl-3-quinolineacetamide Melting point: 203°–205° C. (recrystallized from ethyl acetate-isopropyl ether) NMR (200 MHz, CDCl$_3$) ppm: 2.30 (6H, s), 2.37 (1H, dd, J=15.2 Hz, J=4.8 Hz), 2.87 (1H, dd, J=15.0 Hz, J=8.2 Hz), 3.47 (3H, s), 3.64 (1H, m), 4.24 (1 H, d, J=6.6 Hz), 7.0–7.4 (1H, m) Elemental analysis (for C$_2$H$_{25}$N$_2$O$_2$Cl): Calculated (%): C, 72.13H, 5.82; N, 6.47 Found (%): C, 71.75; H, 5.84; N, 6.55

Example 29

3,4-trans-6-Chloro-N-(2,6-dimethylphenyl)-1,2,3,4-tetrahydro-1-methyl-2-oxo-4-phenyl-3-quinolineacetamide Melting point: 201°–203° C. (recrystallized from ethyl acetate-isopropyl ether) NMR (200 MHz, CDCl$_3$) ppm: 2.20 (6H, s), 2.59 (2H, m), 3.38 (1H, m), 3.43 (3H, s), 4.29 (1H, d, J=12.0 Hz), 6.64 (1H, m), 6.9–7.4 (10H, m) Elemental analysis (for C$_{26}$H$_{25}$N$_2$O$_2$Cl): Calculated (%): C, 72.13; H, 5.82; N, 6.47 Found (%): C, 71.57; H, 5.76; N, 6.65

Example 30

3,4-cis-6-Chloro-1,2,3,4-tetrahydro-1-methyl-2-oxo-4-phenyl-N-(2,4,6-trimethylphenyl)-3-quinolineacetamide Melting point: 224°–227° C. (recrystallized from ethyl acetate-isopropyl ether) NMR (200 MHz, CDCl$_3$) ppm: 2.19 (6H, s), 2.25 (3H, s), 2.35 (1H, dd, J=15.2 Hz, J=4.8 Hz), 2.86 (1H, dd, J=15.4 Hz, J=7.8 Hz), 3.47 (3H, s), 3.63 (1H, M), 4.24 (1H, d, J=6.6 Hz), 6.88 (1H, s), 7.0–7.3 (9H, m) Elemental analysis (for C$_{27}$H$_{27}$N$_2$O$_2$Cl): Calculated (%): C, 72.55; H, 6.09; N, 6.27 Found (%): C, 72.33; H, 6.27; N, 6.44

Example 31

3,4-trans-6-Chloro-1,2,3,4-tetrahydro-1-methyl-2-oxo-4-phenyl-N-(2,4,6-trimethylphenyl)-3-quinolineacetamide Melting point: 191°–193° C. (recrystallized from ethyl acetate-isopropyl ether) NMR (200 MHz, CDCl$_3$) ppm: 2.16 (6H, s), 2.24 (3H, s), 2.58 (2H, m), 3.4 (1H, m), 3.42 (3H, s), 4.29 (1H, d, J=11.8 Hz), 6.65 (1H, m), 6.86 (2H, s), 6.98 (1H, d, J=8.6 Hz), 7.1–7.5 (6H, m) Elemental analysis (for C$_{27}$H$_{27}$N$_2$O$_2$Cl): Calculated (%): C, 72.55; H, 6.09; N, 6.27 Found (%): C, 72.64; H, 6.11; N, 6.36

Example 32

3,4-cis-N-[2,6-Bis(1-methylethyl)phenyl]-6-chloro-1,2,3,4-tetrahydro-1-methyl-2-oxo-4-phenyl-3-quinolineacetamide Melting point: 208°–210° C. (recrystallized from ethyl acetate-isopropyl ether) NMR (200 MHz, CDCl$_3$) ppm: 1.18 (12H, t like, J=6.8 Hz), 2.37 (1H, dd, J=15.0, 5.4 Hz), 2.96 (1H, dd, J=15.0, 7.6 Hz), 3.08 (2H, m), 3.48 (3H, s), 3.55–3.70 (1H, m), 4.27 (1H, d, J=6.6 Hz), 7.00–7.35 (12H, m) Elemental analysis (for C$_{30}$H$_{33}$N$_2$O$_2$Cl): Calculated (%): C, 73.68; H, 6.80; N, 5.73 Found (%): C, 73.75: H, 6.86; N, 5.68

Example 33

3,4-trans-N-[2,6-Bis(1-methylethyl)phenyl]-6-chloro-1,2,3,4-tetrahydro-1-methyl-2-oxo-4-phenyl-3-quinolineacetamide Melting point: 259°–260° C. (recrystallized from ethyl acetate-isopropyl ether) NMR (200 MHz, DMSO-d$_6$) ppm: 1.11 (12H, d, J=7.0 Hz), 1.83 (1H, dd, J=15.0, 9.0 Hz), 2.37 (1H, dd, J=15.0, 5.2 Hz), 2.67 (1H, m), 2.90–3.20 (2H, m), 2.96 (3H, s), 3.32 (3H, s), 4.19 (1H, d, J=4.8 Hz), 6.68–6.82 (2H, m), 7.00–7.40 (9H, m), 9.17 (1H, s) Elemental analysis (for C$_{30}$H$_{33}$N$_2$O$_2$Cl): Calculated (%): C, 73.68; H, 6.80; N, 5.73 Found (%): C, 73.72; H, 6.92; N, 5.63

Example 34

3,4-cis-N-[2,6-Bis-(1-methylethyl)phenyl]-6-chloro-3,4-dihydro-2-oxo-4-phenyl-2H-1-benzopyran-3-acetamide (A)

Melting point: 229°–232° C. (recrystallized from ethyl acetate-isopropyl ether) NMR (200 MHz, CDCl$_3$) ppm: 1.18 (12H, d, J=7.0 Hz), 2.42 (1H, dd, J=15.8 Hz, J=6.2 Hz), 2.85 (1H; dd, J=16.0 Hz, J=7.0 Hz), 3.08 (2H, m), 3.84 (1H, m), 4.39 (1H, d, J=7.0 Hz), 6.5 (1H, bs), 7.1–7.4 (10H, m) Elemental analysis (for C$_{29}$H$_{30}$NO$_3$Cl): Calculated (%): C, 73.17; H, 6.35; N, 2.94 Found (%): C, 73.06; H, 6.48; N, 2.97

Example 35

3,4-trans-N-[2,6-Bis-(1-methylethyl)phenyl]-3,4-dihydro-6-methyl-2-oxo-4-phenyl-2H-1-benzopyran-3-acetamide (A)

Melting point: 245°–247° C. (recrystallized from ethyl acetate-isopropyl ether) NMR (200 MHz, CDCl$_3$) ppm: 1.17 (12H, d, J=6.8 Hz), 2.17, 2.21 (total 3H, each s), 2.63 (1H, m), 3.06 (2H, m), 3.58 (2H, m), 4.44 (1H, d, J=11.2 Hz), 6.49 (1H, bs), 6.78 (1H, bs), 7.0–7.5 (6H, m) Elemental analysis (for C$_{30}$H$_{33}$NO$_3$): Calculated (%): C, 79.09; H, 7.30; N, 3.07 Found (%): C, 79.06; H, 7.39; N, 3.07

Example 36

3,4-cis-N-[2,6-Bis(1-methylethyl)phenyl]-6-chloro-1,2,3,4-tetrahydro-1-methyl-4-phenyl-3-quinolineacetamide (B)

Melting point: 239°–241° C. (recrystallized from ethyl acetate-isopropyl ether) NMR (200 MHz, DMSO-d$_6$) ppm: 1.11 (12H, d, J=6.6 Hz), 2.25–2.35 (2H, m), 3.02 (2H, m), 3.20–3.40 (3H, m), 3.32 (3H, s), 4.30 (1H, d, J=6.6 Hz), 6.88 (1H, d, J=2.2 Hz), 7.00–7.50 (10H, m), 9.20 (1H, s) Elemental analysis (for C$_{30}$H$_{35}$N$_2$OCl): Calculated (%): C, 75.85; H, 7.43; N, 5.90 Found (%): C, 76.17; H, 7.52; N, 5.77

Example 37

3,4-cis-6-Chloro-1,2,3,4-tetrahydro-1-methyl-4-phenyl-N-(2,4,6-trimethoxyphenyl)-3-quinolineacetamide (B)

Melting point: 179°–180° C. (recrystallized from ethyl acetate-isopropyl ether) NMR (200 MHz, CDCl$_3$)ppm: 1.96 (1H, dd, J=15, 8.2 Hz), 2.21 (1H, dd, J=15, 6.2 Hz), 2.86 (1H, m), 2.99 (3H, s), 3.15–3.30 (2H, m), 3.81 (9H, s), 4.21 (1H, d, J=4.6 Hz), 6.15 (2H, s), 6.34 (1H, s), 6.58 (1H, d, J=8.8 Hz), 6.84 (1H, s like), 7.00–7.35 (6H, m) Elemental analysis (for C$_{27}$H$_{29}$N$_2$O$_4$Cl): Calculated (%): C, 67.42; H, 6.08; N, 5.82 Found (%): C, 67.36; H, 6.20; N, 5.67

Example 38

3,4-cis-6-Chloro-N-(2,4-difluorophenyl)-1,2,3,4-tetrahydro-1-methyl-4-phenyl-3-quinolineacetamide (B)

Melting point: 161°–162° C. (recrystallized from ethyl acetate-isopropyl ether) NMR (200 MHz, CDCl$_3$) ppm: 1.99 (1H, dd, J=15, 8.2 Hz), 2.24 (1H, dd, J=15, 6.4 Hz), 2.88 (1H, m), 2.97 (3H, s), 3.15–3.25 (2H, m), 4.21 (1H, d, J=4.8 Hz), 6.61 (1H, d, J=8.8 Hz), 6.80–7.35 (10H, m), 8.15–8.30 (1H, m) Elemental analysis (for C$_{24}$H$_{21}$N$_2$OClF$_2$.0.2CH$_3$CO$_2$C$_2$H$_5$): Calculated (%): C, 67.01; H, 5.12; N, 6.30 Found (%): C, 66.71; H, 4.96; N, 6.61

Example 39

3,4-trans-N-[2,6-Bis(1-methylethyl)phenyl]-1,2,3,4-tetrahydro-1-oxo-4-phenyl-2,6,7-trimethyl-3-isoquinolineacetamide (A)

Melting point: 280°–282° C. (recrystallized from ethyl acetate-isopropyl ether) NMR (200 MHz, CDCl$_3$) ppm: 1.00–1.35, 1.23 (total 12H, m, d, J=7.0 Hz), 2.22, 2.24, 2.28, 2.33 (total 6H, each s), 2.58 (1H, dd, J=15.0, 10.0 Hz), 2.75, 2.96 (total 3H, each s), 2.89 (1H, dd, J=15.0, 4.6 Hz), 3.08 (2H, m), 4.05–4.35 (1H, m), 4.21, 4.23 (total 1H, each s), 6.85–7.40 (10H, m), 7.76, 7.94 (total 1H, each s) Elemental analysis (for C$_{32}$H$_{38}$N$_2$O$_2$): Calculated (%): C, 79.63; H, 7.94; N, 5.80 Found (%): C, 79.56; H, 8.03; N, 5.74

Example 40

3,4-trans-1,2,3,4-Tetrahydro-1-oxo-4-phenyl-N-(2,4,6-trimethoxyphenyl)-2,6,7-trimethyl-3-isoquinolineacetamide (A)

Melting point: 213°–214° C. (recrystallized from ethyl acetate-isopropyl ether) NMR (200 MHz, CDCl$_3$) ppm: 2.23, 2.27, 2.34 (total 6H, each s), 2.50 (1H, dd, J=14.0, 10.0 Hz), 2.78 (1H, dd, J=14.0, 4.8 Hz), 2.79, 2.98 (total 3H, each s), 3.67, 3.82 (total 9H, each s), 3.90–4.30 (1H, m), 4.23, 4.33 (total 1H, s), 6.02, 6.17 (total 2H, each s), 6.32, 6.41 (total 1H, each s), 6.85–7.30 (6H, m), 7.80, 7.96 (total 1H, each s) Elemental analysis (for C$_{29}$H$_{32}$N$_2$O$_5$): Calculated (%): C, 71.29; H, 6.60; N, 5.73 Found (%): C, 71.19; H, 6.62; N, 5.68

Example 41

3,4-trans-N-(2,4-Difluorophenyl)-1,2,3,4-tetrahydro-2,6,7-trimethyl-1-oxo- 4-phenyl-3-isoquinolineacetamide (A)

Melting point: 176°–177° C. (recrystallized from ethyl acetate-isopropyl ether) NMR (200 MHz, CDCl$_3$) ppm: 2.26 (3H, s), 2.32 (3H, s), 2.61 (1H, dd, J=15.0, 8.8 Hz), 2.77 (1H, dd, J=15.0, 5.0 Hz), 2.94 (3H, s), 4.15–4.30 (1H, m), 4.17 (1H, s), 6.80–7.30 (8H, m), 7.41 (1H, bs), 7.92 (1H, s), 8.10–8.30 (1H, m) Elemental analysis (for C$_{26}$H$_{24}$N$_2$O$_2$F$_2$): Calculated (%): C, 71.87; H, 5.57; N, 6.45 Found (%): C, 71.63; H, 5.68; N, 6.24

Example 42

N-[2,6-Bis(1-methylethyl)phenyl]-6-chloro-1,2,3,4-tetrahydro-1-methyl- 2-oxo-4-phenyl-3-quinoxalineacetamide (A)

Melting point: 205°–206° C. (recrystallized from ethyl ether-hexane) NMR (200 MHz, CDCl$_3$) ppm: 1.09 (6H, d, J=6.8 Hz), 1.16 (6H, d, J=7.0 Hz), 2.63(1H, dd, J=15.0, 8.6 Hz), 2.84 (1H, dd, J=15.0,4.6 Hz), 3.02(2H, m), 3.44 (3H, s), 5.15 (1H, dd, J=8.6, 4.6 Hz), 6.90–7.35 (12H, m) Elemental analysis (for C$_{29}$H$_{32}$N$_3$O$_2$Cl): Calculated (%): C, 71.08; H, 6.58; N, 8.57 Found (%): C, 71.29; H, 6.61; N, 8.81

Example 43

6-Chloro-1,2,3,4-tetrahydro-1-methyl-2-oxo-4-phenyl-N-(2,4,6-trimethoxyphenyl)- 3-quinoxalineacetamide (A)

Melting point: 236°–238° C., (recrystallized from THF-isopropyl ether) NMR (200 MHz, CDCl$_3$) ppm: 2.51 (1H, dd, J=14.0, 9.6 Hz), 2.73 (1H, dd, J=14.0, 3.8 Hz), 3.43 (3H, s), 3.65 (6H, s), 3.79 (3H, s), 5.10 (1H, dd, J=9.6, 3.8 Hz), 6.11 (2H, s), 6.57 (1H, s), 6.90–7.35 (8H, m) Elemental analysis (for C$_{26}$H$_{26}$N$_3$O$_5$Cl): Calculated (%): C, 62.97; H, 5.28; N, 8.47 Found (%): C, 62.61; H, 5.48; N, 8.20

Example 44

6-Chloro-N-(2,4-difluorophenyl)-1,2,3,4-tetrahydro-1-methyl-2-oxo-4-phenyl- 3-quinoxalineacetamide (A)

Melting point: 160°–161° C. (recrystallized from ethyl ether-hexane) NMR (200 MHz, CDCl$_3$) ppm: 2.68 (1H, dd, J=15.0, 7.0 Hz), 2.80 (1H, dd, J=15.0, 5.8 Hz), 3.45 (3H, s), 4.99 (1H, t like, J=6.3 Hz), 6.78–7.42 (10H, m), 7.76 (1H, m), 8.10–8.30 (1H, m) Elemental analysis (for C$_{23}$H$_{18}$N$_3$O$_2$ClF$_2$): Calculated (%): C, 62.52; H, 4.11; N, 9.51 Found (%): C, 62.57; H, 4.23; N, 9.74

Example 45

N-[2,6-Bis(1-methylethyl)phenyl]-6-chloro-1,2-dihydro-1-methyl-2-oxo- 4-phenyl-3-quinolineacetamide To a solution of the compound obtained in Reference Example 18 (100 ml) in 1,2-dichloroethane (5 ml) were added 1-hydroxybenzotriazole (45 mg) and 1,3-dicyclohexylcarbodiimide (90 mg), followed by stirring at room temperature for 0.5 hours. To this mixture was added 2,6-diisopropylaniline (0.5 ml), followed by heating under reflux for 10 hours. After the reaction mixture was concentrated, ethyl acetate was added to the residue, the precipitated crystals were separated by filtration. The filtrate was washed successively with hydrochloric acid, water, aqueous potassium carbonate and water and then dried, after which the solvent was distilled off, to yield the title compound as colorless crystals (105 mg).

Melting point: 237°–238° C. (recrystallized from acetone-ethyl ether) NMR (200 MHz, CDCl$_3$) ppm: 1.09 (12H, d, J=6.8 Hz), 2.98 (1H, m), 3.62 (2H, s), 3.88 (3H, s), 7.09–7.60 (11H, m), 8.53 (1H, s) Elemental analysis (for C$_{30}$H$_{31}$N$_2$O$_2$Cl): Calculated (%): C, 73.98; H, 6.42; N, 5.75 Found (%): C, 73.75; H, 6.64; N, 5.72

Example 46

6-Chloro-N-(2,4-difluorophenyl)-1,2-dihydro-1-methyl-2-oxo-4-phenyl-3-quinolineacetamide (B)

Melting point: 217°–218° C. (recrystallized from acetone-ethyl ether) NMR (200 MHz, CDCl$_3$) ppm: 3.54 (2H, s), 3.87 (3H, s), 6.77–6.87 (2H, m), 7.15 (1H, d, J=2.4 Hz), 7.29–7.58 (9H, m), 8.19 (1H, m), 9.28 (1H, b) Elemental analysis (for C$_{24}$H$_{17}$N$_2$O$_2$ClF$_2$): Calculated (%): C, 65.68; H, 3.90; N, 6.38 Found (%): C, 65.81; H, 4.16; N, 6.44

Example 47

N-[2,6-Bis(1-methylethyl)phenyl]-1,2-dihydro-2,6,7-trimethyl-1-oxo-4-phenyl- 3-isoquinolineacetamide (A)

Melting point: 265°–270° C. (recrystallized from ethyl acetate-isopropyl ether) NMR (200 MHz, CDCl$_3$) ppm: 1.00–1.30, 1.12 (total 12H, m, d, J=6.8 Hz), 2.18, 2.24 (total 3H, each s), 2.34, 2.38 (total 3H, each s), 2.83 (2H, m), 3.03, 3.14 (total 2H, each s), 3.77, 3.78 (total 3H, each s), 6.55–6.80 (2H, m), 7.10–7.60 (8H, m), 8.15–8.30 (1H, m) Elemental analysis (for C$_{32}$H$_{36}$N$_2$O$_2$.0.25CH$_3$CO$_2$C$_2$H$_5$): Calculated (%): C, 78.85; H, 7.62; N, 5.57 Found (%): C, 78.82: H, 7.37; N, 5.56

Example 48

N-[2,6-Bis(1-methylethyl)phenyl]-6-chloro-1-oxo-4-phenyl-1H-2-benzopyran- 3-acetamide (B)

Melting point: 183°–184° C. (recrystallized from ethyl acetate-ethyl ether) NMR (200 MHz, CDCl$_3$) ppm: 1.16 (12, d, J=6.8 Hz), 3.03 (2H, m), 3.54 (2H, s), 6.94–7.55 (11H, m), 8.31 (1H, d, J=8.6 Hz) Elemental analysis (for $C_{29}H_{28}N)_3Cl$): Calculated (%): C, 73.49; H, 5.95; N, 2.96 Found (%): C, 73.37; H, 6.15; N, 2.89

Example 49

6-Chloro-N-(2,4-difluorophenyl)-1-oxo-4-phenyl-1H-2-benzopyran-3-acetamide (B)

Melting point: 244°–245° C. (recrystallized from ethyl acetate-ethyl ether) NMR (200 MHz, CDCl$_3$) ppm: 3.50 (2H, s), 6.81–6.90 (2H, m), 7.01 (1H, d, J=1.6 Hz), 7.34–7.54 (6H, m), 8.25 (1H, m), 8.28 (1H, d, J=8.4 Hz) Elemental analysis (for $C_{23}H_{14}NO_3ClF_2$): Calculated (%): C, 64.88; H, 3.31; N, 3.29 Found (%): C, 64.82; H, 3.49; N, 3.26

Example 50

N-[2,6-Bis(1-methylethyl)phenyl]-6-chloro-2-oxo-4-phenyl-2H-1-benzopyran- 3-acetamide (A)

Melting point: 252°–255° C. (recrystallized from ethyl acetate-isopropyl ether) NMR (200 MHz, CDCl$_3$) ppm: 1.15 (12H, d, J=7.0 Hz), 3.03 (2H, m), 3.52 (2H, s), 7.0–7.6 (11H, m) Elemental analysis (for $C_{29}H_{28}NO_3Cl$): Calculated (%): C, 73.49; H, 5.95; N, 2.96 Found (%): C, 73.36; H, 5.85; N, 3.26

Example 51

6-Chloro-2-oxo-4-phenyl-N-(2,4,6-trimethoxyphenyl)-2H-1-benzopyran- 3-acetamide (A)

Melting point: 257°–259° C. (recrystallized from chloroform-ethyl acetate-isopropyl ether) NMR (200 MHz, CDCl$_3$) ppm: 3.49 (2H, s), 3.79 (9H, s), 6.12 (2H, s), 7.0–7.6–7.6 (9H, m) Elemental analysis (for $C_{26}H_{22}NO_6Cl$): Calculated (%): C, 65.07; H, 4.62; N, 2.92 Found (%): C, 64.81; H, 4.44; N, 3.02

Example 52

6-Chloro-N-(2,4-difluorophenyl)-2-oxo-4-phenyl-2H-1-benzopyran-3-acetamide (A)

Melting point: 225°–227° C. (recrystallized from ethyl acetate-isopropyl ether) NMR (200 MHz, CDCl$_3$) ppm: 3.49 (2H, s), 6.8–6.9 (2H, m), 7.05 (1H, d, J=2.4 Hz), 7.3–7.6 (6H, m), 8.1–8.3 (2H, m) Elemental analysis (for $C_{23}H_{14}NO_3ClF_2$): Calculated (%): C, 64.88; H, 3.31; N, 3.29 Found (%): C, 64.26; H, 3.54; N, 3.00

Example 53

N-[2,6-Bis(1-methylethyl)phenyl]-6-methyl-2-oxo-4-phenyl-2H-1-benzopyran- 3-acetamide (A)

Melting point: 257°–258° C. (recrystallized from ethyl acetate-isopropyl ether) NMR (200 MHz, CDCl$_3$) ppm: 1.14 (12H, d, J=7.0 Hz), 2.29 (3H, s), 2.03 (2H, m), 3.51 (2H, s), 6.85 (1H, s), 7.1–7.7 (10H, m) Elemental analysis (for $C_{30}H_{31}NO_3$): Calculated (%): C, 79.44; H, 6.89; N, 3.09 Found (%): C, 79.15; H, 6.75; N, 3.14

Example 54

6-Methyl-2-oxo-4-phenyl-N-(2,4,6-trimethoxyphenyl)-2H-1-benzopyran- 3-acetamide

Melting point: 256°–257° C. (recrystallized from chloroform-ethyl acetate-isopropyl ether) NMR (200 MHz, CDCl$_3$) ppm: 2.27 (3H, s), 3.47 (2H, s), 3.76 (3H, s), 3.78 (6H, s), 6.11 (2H, s), 6.83 (1H, s), 7.2–7.6 (7H, m) Elemental analysis (for $C_{27}H_{25}NO_6$): Calculated (%): C, 70.58; H, 5.48; N, 3.05 Found (%): C, 70.22; H, 5.60; N, 2.95

Example 55

N-(2,4-Difluorophenyl)-6-methyl-2-oxo-4-phenyl-2H-1-benzopyran-3-acetamide (A)

Melting point: 168°–170° C. (recrystallized from ethyl acetate-isopropyl ether) NMR (200 MHz, CDCl$_3$) ppm: 2.28 (3H, s), 3.47 (2H, s), 6.8–6.9 (3H, m), 7.3– 7.5 (4H, m), 7.5–7.6 (3H, m), 8.1–8.3 (1H, m), 8.45 (1H, bs) Elemental analysis (for $C_{24}H_{17}NO_3F_2$): Calculated (%): C, 71.11; H, 4.23; N, 3.46 Found (%): C, 70.84; H, 4.25; N, 3.54

Example 56

N-[2,6-Bis(1-methylethyl)phenyl]-4-(2-methoxyphenyl)-1-oxo-1H-2-benzopyran- 3-acetamide (B)

Melting point: 250°–252° C. (recrystallized from acetone-ethyl ether) NMR (200 MHz, CDCl$_3$) ppm: 1.08, 1.15 (total 12H, each d, J=6.6 Hz), 2.96 (2H, m), 3.47 (1H, d, J=15.4 Hz), 3.60 (1H, d, J=15.4 Hz), 3.62 (3H, s), 6.91– 7.67 (10H, m), 8.38 (1H, dd, J=7.8, 1.7 Hz) Elemental analysis (for $C_{30}H_{31}NO_4$): Calculated (%): C, 76.73; H, 6.65; N, 2.98 Found (%): C, 76.53; H, 6.79; N, 3.00

Example 57

N-[2,6-Bis(1-methylethyl)phenyl]-6-chloro-4-phenyl-3-quinolineacetamide (B)

Melting point: 262°–263° C. (recrystallized from ethyl acetate-isopropyl ether) NMR (200 MHz, CDCl$_3$) ppm: 1.12 (12H, d, J=6.8 Hz), 2.87 (2H, m), 3.80 (2H, s), 6.45 (1H, s), 7.10–7.70 (10H, m), 8.11 (1H, d, J=9.0 Hz), 9.05 (1H, s) Elemental analysis (for $C_{29}H_{29}N_2OCl$): Calculated (%): C, 76.22; H, 6.40; N, 6.13 Found (%): C, 75.93; H, 6.65; N, 6.44

Example 58

3,4-cis-N-(2,4-Difluorophenyl)-3,4-dihydro-6-methyl-2-oxo-4-phenyl-2H-1-benzopyran-3-acetamide (A)

Melting point: 194°–196° C. (recrystallized from ethyl acetate-isopropyl ether)

Example 59

3,4-cis-6-Chloro-N-(2,4-difluorophenyl)-3,4-dihydro-2-oxo-4-phenyl-2H-1-benzopyran-3-acetamide (A)

Melting point: 182°–184° C. (recrystallized from ethyl acetate-isopropyl ether)

Example 60

3,4-trans-N-[2,6-Bis(1-methylethyl)phenyl]-1,2,3,4-tetrahydro-1,6-dimethyl- 2-oxo-4-phenyl-3-quinolineacetamide (A)

Melting point: 251°–252° C. (recrystallized from ethyl acetate-isopropyl ether) NMR (200 MHz, CDCl$_3$) ppm: 0.90–1.30, 1.17 (total 12H, m, d, J=7.0 Hz), 2.17, 2.21 (total 3H, each s), 2.61 (1H, dd, J=15, 6.2 Hz), 2.71 (1H, dd, J=15, 5.4 Hz), 3.06 (2H, m), 3.30–3.50 (1H, m), 3.35, 3.43 (total 3H, each s), 4.27, 4.38 (total 1H, each d, J=10 Hz, J=11 Hz), 6.46, 6.59 (total 1H, each s), 6.80– 7.40 (11H, m)

Example 61

3,4-trans-N-[2,6-Bis(1-methylethyl)phenyl]-3-(6-chloro-1,2,3,4-tetrahydro- 1-methyl-2-oxo-4-phenylquinolin-3-yl)propionamide (A)

Melting point: 178°–180.5° C. (recrystallized from ethyl acetate-hexane) NMR (200 MHz, CDCl$_3$) ppm: 1.13 (6H, d, J=4.0 Hz), 1.16 (6H, d, J=3.2 Hz), 1.70–2.30 (2H, m), 2.45–2.58 (2H, m), 2.92–3.20 (3H, m), 3.41 (3H, s), 4.01 (1H, d, j=4.8 Hz), 6.90–7.40 (11H, m), 7.54 (1H, bs)

Example 62

3,4-trans-3-(6-Chloro-1,2,3,4-tetrahydro-1-methyl-2-oxo-4-phenylquinolin- 3-yl)-N-(2,4,6-trimethoxyphenyl)propionamide (A)

A white foam

NMR (200 MHz, CDCl₃) ppm: 1.67–2.20 (2H, m), 2.36–2.70 (2H, m), 3.20– 3.50 (1H, m), 3.39 (3H, s), 3.66 (6H, s), 3.79 (3H, s), 3.98 (1H, bd), 6.11 (2H, s), 6.90–7.40 (9H, m)

Example 63

N-(2,4-Difluorophenyl)-1,2,3,4-tetrahydro-1,6-dimethyl-2-oxo-4-phenyl- 3-quinoxalineacetamide (A)

Melting point: 94.5°–95.0° C. (recrystallized from ethyl ether-hexane) NMR (200 MHz, CDCl₃) ppm: 2.26 (3H, s), 2.60 (1H, dd, J=15, 8.5 Hz), 2.77 (1H, dd, J=15, 5.5 Hz), 3.43 (3H, s), 5.01 (1H, dd, J=8.5, 5.5 Hz), 6.76–7.32 (10H, m), 7.87 (1H, bs), 8.25 (1H, m)

Example 64

N-[2,6-Bis(1-methylethyl)phenyl]-1,2,3,4-tetrahydro-1,6-dimethyl-2-oxo- 4-phenyl-3-quinoxalineacetamide (A)

Melting point: 186.5°–187.5° C. (recrystallized from ethyl ether-hexane) NMR (200 MHz, CDCl₃) ppm: 1.08 (6H, d, J=6.6 Hz), 1.15 (6H, d, J=7.0 Hz), 2.28 (3H, s), 2.59 (1H, dd, J=15, 9.4 Hz), 2.81 (1H, dd, J=15, 4.6 Hz), 3.06 (2H, m), 3.42 (3H, s), 5.16 (1H, dd, J=9.4, 4.6 Hz), 6.90–7.30 (12H, m)

Example 65

1,2,3,4-Tetrahydro-1,6-dimethyl-2-oxo-4-phenyl-N-(2,4,6-trimethoxyphenyl)- 3-quinoxalineacetamide (A)

Melting point: 237°–238° C. (recrystallized from THF-isopropyl ether) NMR (200 MHz, CDCl₃) ppm: 2.26 (3H, s), 2.49 (1H, dd, J=14, 10 Hz), 2.71 (1H, dd, J=14, 3.6 Hz), 3.41 (3H, s), 3.63 (6H, s), 3.79 (3H, s), 5.11 (1H, dd, J=10, 3.6 Hz), 6.11 (2H, s), 6.68 (1H, bs), 6.87–7.28 (8H, m)

Example 66

N-(2,6-Dimethoxyphenyl)-1,2,3,4-tetrahydro-1,6-dimethyl-2-oxo-4-phenyl- 3-quinoxalineacetamide (A)

Melting point: 139.5°–140.5° C. (recrystallized from ethyl acetate-isopropyl ether) NMR (200 MHz, CDCl₃) ppm: 2.26 (3H, s), 2.40–2.80 (2H, m), 3.41 (3H, s), 3.67 (6H, s), 5.10 (1H, bdd), 6.54 (2H, d, J=8.4 Hz), 6.80–7.30 (10 H, m)

Example 67

6-Chloro-N-(2,6-dimethoxyphenyl)-1,2,3,4-tetrahydro-1-methyl-2-oxo-4-phenyl-3-quinoxalineacetamide (A)

Melting point: 212.5°–213.2° C. (recrystallized from ethyl acetate-isopropyl ether) NMR (200 MHz, CDCl₃) ppm: 2.35–2.90 (2H, m), 3.41 (3H, s), 3.69 (6H, s), 5.08 (1H, m), 6.53 (2H, d, J=8.0 Hz), 6.72 (1H, bs), 6.95–7.30 (9H, m)

Example 68

N-[2,6-Bis(1-methylethyl)phenyl]-6-chloro-1,2-dihydro-2-oxo-4-phenyl-3-quinolineacetamide (A)

Melting point: 333°–337° C. (recrystallized from methanol-chloroform-isopropyl ether) NMR (200 MHz, CDCl₃-DMSO-d₆) ppm: 1.11 (12H, d, J=7.0 Hz), 3.54 (2H, s), 7.0–7.6 (11H, m), 8.84 (1H, b), 12.2 (1H, b)

Example 69

1,2-Dihydro-1,6-dimethyl-2-oxo-4-phenyl-N-(2,4,6-trimethoxyphenyl)-3-quinolineacetamide (A)

Melting point: 275.5°–277.0° C. (recrystallized from ethyl acetate-isopropyl ether) NMR (200 MHz, CDCl₃) ppm: 2.28 (3H, s), 3.54 (2H, s), 3.73 (3H, s), 3.77 (6H, s), 3.86 (3H, s), 6.10 (2H, s), 6.96 (1H, bs), 7.25–7.55 (8H, m)

Example 70

N-(2,6-Dimethoxyphenyl)-1,2-dihydro-1,6-dimethyl-2-oxo-4-phenyl-3-quinolineacetamide (A)

Melting point: 212.0°–213.5° C. (recrystallized from ethyl acetate-isopropyl ether) NMR (200 MHz, CDCl₃) ppm: 2.28 (3H, s), 3.54 (2H, s), 3.76 (6H, s), 3.86 (3H, s), 6.53 (2H, d, J=8.4 Hz), 6.96 (1H, bs), 7.10 (1H, t, J=8.4 Hz), 7.30–7.60 (8H, m)

Example 71

N-[2,6-Bis(1-methylethyl)phenyl]-6-chloro-2-methoxy-4-phenyl-3-quinolineacetamide (A)

Melting point: 256°–259° C. (recrystallized from ethyl acetate-hexane) NMR (200 MHz, CDCl₃) ppm: 1.14 (12H, d, J=7.0 Hz), 3.69 (2H, s), 4.19 (3H, s), 7.1–7.2 (2H, m), 7.2–7.4 (5H, m), 7.5–7.6 (3H, m), 7.84 (1H, m)

Example 72

6-Chloro-N-(2,6-dimethoxyphenyl)-2-methoxy-4-phenyl-3-quinolineacetamide (A)

Melting point: 220°–222° C. (recrystallized from ethyl acetate-hexane) NMR (200 MHz, CDCl₃) ppm: 3.63 (2H, b), 3.79 (6H, s), 4.18 (3H, s), 6.55 (2H, d, J=8.6 Hz), 7.15 (1H, m), 7.28 (1H, m), 7.3–7.5 (2H, m), 7.5–7.6 (4H, m), 7.83 (1H, d, J=9.0 Hz)

Example 73

N-(2,4-Difluorophenyl)-4-(2-methoxyphenyl)-1-oxo-1H-2-benzopyran-3-acetamide (A)

Melting point: 214°–216° C. (recrystallized from ethyl acetate-isopropyl ether) NMR (200 MHz, CDCl₃) ppm: 3.51 (2H, s), 3.70 (3H, s), 6.8–6.9 (2H, m), 6.96 (1H, d, J=10.4 Hz), 7.0–7.2 (2H, m), 7.26 (1H, m), 7.4–7.7 (3H, m), 7.75 (1H, b), 8.15 (1H, m), 8.36 (1H, dd, J=7.6 Hz, 1.2 Hz)

Example 74

N-(2,6-Dimethoxyphenyl)-4-(2-methoxyphenyl)-1-oxo-1H-2-benzopyran- 3-acetamide (A)

Melting point: 210°–213° C. (recrystallized from ethyl acetate-isopropyl ether) NMR (200 MHz, CDCl₃) ppm: 3.46 (2H, m), 3.68 (3H, s), 3.77 (6H, s), 6.54 (2H, d, J=8.4 Hz), 6.93 (1H, d, J=8.2 Hz), 7.0–7.2 (3H, m), 7.35 (1H, dd, J=7.4 Hz, 1.6 Hz), 7.4–7.6 (3H, m), 8.35 (1H, m)

Example 75

4-(2-Methoxyphenyl)-1-oxo-N-(2,4,6-trimethoxyphenyl)-1H-2-benzopyran- 3-acetamide (A)

Melting point: 229°–231° C. (recrystallized from ethyl acetate-chloroformisopropyl ether) NMR (200 MHz, CDCl₃) ppm: 3.47 (2H, m), 3.67 (3H, s), 3.76 (3H, s), 3.78

(6H, s), 6.11 (2H, s), 6.9–7.2 (3H, m), 7.35 (1H, d, J=6.8 Hz), 7.4–7.6 (3H, m), 8.36 (1H, m)

Example 76

6-Chloro-N-(2,6-dimethoxyphenyl)-1-oxo-4-phenyl-1H-2-benzopyran-3-acetamide (A)

Melting point: 245°–247° C. (recrystallized from chloroform-isopropyl ether) NMR (200 MHz, CDCl$_3$) ppm: 3.45 (2H, m), 3.78 (6H, s), 6.54 (2H, d, J=8.4 Hz), 7.01 (1H, d, J=1.4 Hz), 7.18 (1H, t, J=8.6 Hz), 7.4–7.6 (6H, m), 8.27 (1H, d, J=8.4 Hz)

Example 77

6-Chloro-N-(2,6-ethoxyphenyl)-1-oxo-4-phenyl-1H-2-benzopyran-3-acetamide (B)

Melting point: 209°–210° C. (recrystallized from ethanol) NMR (200 MHz, CDCl$_3$) ppm: 1.31 (6H, t, J=7 Hz), 3.44 (2H, b), 4.01 (4H, q, J=7 Hz), 6.52 (2H, d, J=8.4 Hz), 7.02–7.52 (9H, m), 8.27 (1H, d, J=8.4 Hz)

Example 78

6-Chloro-N-[4-(N,N-dimethylamino)phenyl]-2-oxo-4-phenyl-2H-1-benzopyran- 3-acetamide (A)

Melting point: 220°–222° C. (recrystallized from ethyl acetate-chloroformisopropyl ether) NMR (200 MHz, CDCl$_3$) ppm: 2.90 (6H, s), 3.42 (2H, s), 6.68 (2H, d, J=9.0 Hz), 7.04 (1H, d, J=2.0 Hz), 7.3–7.6 (9H, m), 7.95 (1H, b)

Example 79

6-Chloro-N-(2,6-dimethoxyphenyl)-2-oxo-4-phenyl-2H-1-benzopyran-3-acetamide (A)

Melting point: 245°–247° C. (recrystallized from chloroform-isopropyl ether) NMR (200 MHz, CDCl$_3$) ppm: 3.47 (2H, b), 3.78 (6H, s), 6.55 (2H, d, J=8.4 Hz), 7.03 (1H, d, J=1.8 Hz), 7.16 (1H, t, J=8.4 Hz), 7.3–7.5 (4H, m), 7.5–7.6 (3H, m)

Example 80

N-[4-(N,N-Dimethylamino)phenyl]-6-methyl-2-oxo-4-phenyl-2H-1-benzopyran- 3-acetamide (A)

Melting point: 227°–228° C. (recrystallized from ethyl acetate-chloroformisopropyl ether) NMR (200 MHz, CDCl$_3$) ppm: 2.27 (3H, s), 2.89 (6H, s), 3.41 (2H, s), 6.68 (2H, d, J=8.8 Hz), 6.84 (1H, s), 7.3–7.4 (6H, m), 7.5–7.6 (3H, m), 8.18 (1H, b)

Example 81

N-(2,6-Dimethoxyphenyl)-6-methyl-2-oxo-4phenyl-2H-1-benzopyran-3-acetamide (A)

Melting point: 257°–258° C. (recrystallized from chloroform-isopropyl ether) NMR (200 MHz, CDCl$_3$) ppm: 2.27 (3H, s), 3.46 (2H, b), 3.77 (6H, s), 6.54 (2H, d, J=8.4 Hz), 6.83 (1H, s), 7.14 (1H, t, J=8.4 Hz), 7.2–7.3 (2H, m), 7.4–7.6 (5H, m)

Example 82

N-[2,6-Bis(1-methylethyl)phenyl]-6-chloro-4-(2-methylphenyl)-2-oxo-2H-1-benzopyran-3-acetamide (A)

Melting point: 241°–243° C. (recrystallized from acetone-methanol) NMR (200 MHz, CDCl$_3$) ppm: 1.13 (total 12H, d, J=6.8 Hz, 1.0–1.1, m), 2.03, 2.09 (total 3H, each s), 3.00 (2H, m), 3.38 (1H, d, J=13.8 Hz), 3.58 (1H, d, J=13.8 Hz), 6.85 (1H, d, J=2.4 Hz), 7.1–7.2 (3H, m), 7.3–7.5 (6H, m)

Example 83

6-Chloro-N-(2,4-difluorophenyl)-4-(2-methylphenyl)-2-oxo-2H-1-benzopyran- 3-acetamide (A)

Melting point: 186°–188° C. (recrystallized from chloroform-isopropyl ether) NMR (200 MHz, CDCl$_3$) ppm: 2.09 (3H, s), 3.35 (1H, d, J=14.1 Hz), 3.50 (1H, d, J=13.9 Hz), 6.7–6.9 (3H, m), 7.17 (1H, m), 7.3–7.5 (5H, m), 8.0–8.2 (2H, m)

Example 84

6-Chloro-N-(2,6-dimethoxyphenyl)-4-(2-methylphenyl)-2-oxo-2H-1-benzopyran- 3-acetamide (A)

Melting point: 196°–198° C. (recrystallized from ethyl acetate-isopropyl ether) NMR (200 MHz, CDCl$_3$) ppm: 2.09 (3H, s), 3.4 (2H, m), 3.75 (6H, s), 6.53 (2H, d, J=8.4 Hz), 6.82 (1H, d, J=2.2 Hz), 7.14 (1H, t, J=8.4 Hz), 7.2(1H, m), 7.3–7.5 (5H, m)

Example 85

6-Chloro-4-(2-methylphenyl)-2-oxo-N-(2,4,6-trimethoxyphenyl)-2H-1-benzopyran- 3-acetamide (A)

Melting point: 183°–185° C. (recrystallized from ethyl acetate-isopropyl ether) NMR (200 MHz, CDCl$_3$) ppm: 2.08 (3H, s), 3.4 (2H, m), 3.74 (3H, s), 3.78 (6H, s), 6.09 (2H, s), 6.81 (1H, m), 7.2–7.5 (6H, m)

Example 86

6-Chloro-N-(2,6-dimethylphenyl)-4-(2-methylphenyl)-2-oxo-2H-1-benzopyran- 3-acetamide (A)

Melting point: 235°–238° C. (recrystallized from ethyl acetate-isopropyl ether) NMR (200 MHz, CDCl$_3$) ppm: 2.10 (3H, s), 2.17 (6H, s), 3.36 (1H, d, J=13.8 Hz), 3.54 (1H, d, J=14.0 Hz), 6.86 (1H, d, J=2.4 Hz), 7.04 (3H, m), 7.2–7.3 (1H, m), 7.3–7.5 (5H, m)

Example 87

6-Chloro-4-(2-methylphenyl)-2-oxo-N-(2,4,6-trimethylphenyl)-2H-1-benzopyran-3-acetamide (A)

Melting point: 238°–241° C. (recrystallized from ethyl acetate-acetone-isopropyl ether) NMR (200 MHz, CDCl$_3$) ppm: 2.10 (3H, s), 2.12 (6H, s), 2.23 (3H, s), 3.34 (1H, d, J=14.0 Hz), 3.52 (1H, d, J=13.8 Hz), 6.85 (3H, m), 7.2–7.3 (1H, m), 7.3–7.5 (5H, m)

Example 88

6-Chloro-N-(2,6-diethoxyphenyl)-4-(2-methylphenyl)-2-oxo-2H-1-benzopyran- 3-acetamide (A)

Melting point: 200°–202° C. (recrystallized from ethyl acetate-isopropyl ether) NMR (200 MHz, CDCl$_3$) ppm: 1.29 (6H, t, J=7.0 Hz), 2.08 (3H, s), 3.44 (2H, b), 3.98 (4H, q, J=7.0 Hz), 6.50 (2H, d, J=8.4 Hz), 6.82 (1H, m), 7.09 (1H, t, J=8.6 Hz), 7.2–7.5 (6H, m)

Example 89

6-Chloro-N-(2,6-diethoxy-4-fluorophenyl)-4-(2-methylphenyl)-2-oxo-2H-1-benzopyran-3-acetamide (A)

Melting point: 208°–209° C. (recrystallized from ethyl acetate-isopropyl ether) NMR (200 MHz, CDCl$_3$) ppm: 1.29 (6H, t, J=7.0 Hz), 2.08 (3H, s), 3.32 (1H, bd), 3.53 (1H, bd), 3.93 (4H, q, J=7.0 Hz), 6.23 (2H, d, J=11 Hz), 6.83 (2H, bs), 7.19–7.50 (7H, m)

Example 90

N-[3,5-Bis(trifluoromethyl)phenyl]-6-chloro-4-(2-methylphenyl)-2-oxo-2H- 1-benzopyran-3-acetamide (A)

Melting point: 205°–206° C. (recrystallized from ethyl acetate-isopropyl ether)

Example 91

N-[2,6-Bis(1-methylethyl)phenyl]-6-chloro-4-(2-methylphenyl)-1-quinolineacetamide (B)

Melting point: 208°–210° C. (recrystallized from ethyl acetate-isopropyl ether) NMR (200 MHz, CDCl$_3$) ppm: 1.11 (6H, d, J=7.0 Hz), 1.13 (6H, d, J=7.0 Hz), 1.97 (3H, s), 2.85 (2H, m), 3.60 (1H, d, J=16 Hz), 3.79 (1H, d, J=16 Hz), 6.43 (1H, bs), 7.00–7.70 (8H, m), 8.12 (1H, d, J=8.8 Hz), 9.08 (1H, s)

Example 92

N-[2,6-Bis(1-methylethyl)phenyl]-6-chloro-4-(2-methoxyphenyl)-2-oxo-2H- 1-benzopyran-3-acetamide (A)

Melting point: 303°–305° C. (recrystallized from chloroform) NMR (200 MHz, CDCl$_3$) ppm: 1.13 (dd, 12H, J=2.4, 6.8 Hz), 2.90–3.05 (m, 2H), 3.38 (d, 1H, J=13.8 Hz), 3.65 (d, 1H, J=14.0 Hz), 3.71 (s, 3H), 6.95 (d, 1H, J=2.4 Hz), 7.06–7.18 (m, 4H), 7.22–7.30 (m, 2H), 7.37 (d, J=8.8 Hz), 7.44–7.58 (m, 2H)

Example 93

6-Chloro-N-(2,6-diethoxyphenyl)-4-(2-methoxyphenyl)-2-oxo-2H-1-benzopyran- 3-acetamide (A)

Melting point: 226°–227° C. (recrystallized from ethyl acetate-methanol) NMR (200 MHz, CDCl$_3$) ppm: 1.29 (6H, t, J=7.0 Hz), 3.20–3.38 (1H, m), 3.56– 3.70 (1H, m), 3.69 (3H, s), 3.98 (4H, q, J=7.0 Hz), 6.51 (2H, d, J=8.4 Hz), 6.92 (1H, d, J=2.2 Hz), 7.00–7.18 (3H, m), 7.28–7.56 (4H, m)

Example 94

N-[2,6-Bis(1-methylethyl)phenyl]-6-chloro-2-oxo-4-(2-trifluoromethylphenyl)- 2H-1-benzopyran-3-acetamide (A)

Melting point:246°–247° C. (recrystallized from ethyl acetate) NMR (200 MHz, CDCl$_3$) ppm: 1.12 (12H, t, J=6.4 Hz), 2.88–3.06 (2H, m), 3.07 (1H, d, J=14.0 Hz), 3.79 (1H, d, J=13.8 Hz), 6.72 (1H, d, J=2.4 Hz), 7.13 (1H, d, J=7.0 Hz), 7.20–7.30 (1H, m), 7.32–7.50 (4H, m), 7.64–7.74 (2H, m), 7.84–7.92 (1H, m)

Example 95

6-Chloro-N-(2,6-diethoxyphenyl)-2-oxo-4-(2-trifluoromethylphenyl)- 2H-1-benzopyran-3-acetamide (A)

Melting point: 197°–199° C. (recrystallized from ethyl ether-ethyl acetate) NMR (200 MHz, CDCl$_3$) ppm: 1.27 (6H, t, J=7.0 Hz), 2.94–3.08 (1H, m), 3.70– 3.88 (1H, m), 3.97 (4H, q, J=7.0 Hz), 6.50 (2H, d, j=8.4 Hz), J=8.4 Hz),6.68 (1H, s), 7.09 (1H, t, J=8.0 Hz), 7.32 (2H, d, J=8.6 Hz), 7.44 (1H, dd, J=2.2, 8.6 Hz), 7.46–7.58 (1H, m), 7.58–7.76 (2H, m), 7.86 (1H, d, J=7.6 Hz)

Example 96

6-Chloro-N-(2,6-diethoxy-4-fluorophenyl)-2-oxo-4-(2-trifluoromethylphenyl)- 2H-1-benzopyran-3-acetamide (A)

Melting point: 199°–200° C. (recrystallized from ethyl ether-hexane) NMR (200 MHz, CDCl$_3$) ppm: 1.28 (6H, t, J=7.0 Hz), 3.01 (1H, bd), 3.75 (1H, bd), 3.93 (4H, q, J=7.0 Hz), 6.23 (2H, d, J=11 Hz), 6.69 (1H, bs), 7.18–7.90 (7H, m)

Example 97

6-Chloro-4-(2-methoxyphenyl)-2-oxo-N-(2,4,6-trifluolophenyl)-2H-1-benzopyran- 3-acetamide (A)

Melting point: 243°–245° C. (recrystallized from ethyl acetate) NMR (200 MHz, CDCl$_3$) ppm: 3.41 (1H, d, J=14.2 Hz), 3.55 (1H, d, J=14.0 Hz), 3.73 (3H, s), 6.70 (2H, ddd, J=2.0, 7.6, 8.8 Hz), 6.97 (1H, d, J=2.4 Hz), 7.09 (1H, d, J=8.6 Hz), 7.17 (1H, d, J=7.0 Hz), 7.21 (1H, dd, J=2.0, 4.2 Hz), 7.36 (1H, d, J=8.8 Hz), 7.48 (1H, dd, J=2,4 Hz), 7.54 (1H, ddd, J=2.2, 7.0, 8.4 Hz), 7.75 (1H, bs)

Example 98

6-Chloro-N-(2,6-dimethoxybenzyl)-4-(2-methylphenyl)-2-oxo-2H-1-benzopyran- 3-acetamide 6-Chloro-4-(2-methylphenyl)-2-oxo-2H -1-benzopyran-3-acetic acid was reacted with 2,6-dimethoxybenzylamine by a method similar to Example 1(A) to yield the title compound.

Melting point: 194°–196° C. (recrystallized from ethyl acetate-methanol-isopropyl ether) NMR (200 MHz, CDCl$_3$) ppm: 2.05 (3H, s), 3.11 (1H, d, J=14.0 Hz), 3.27 (1H, d, J=14.0 Hz), 3.81 (6H, s), 4.49 (2H, d, J=5.4 Hz), 6.35 (1H, b), 6.54 (2H, d, J=8.4 Hz), 6.81 (1H, d, J=2.2 Hz), 7.2–7.5 (7H, m)

Example 99

N-[2,6-Bis(1-methylethyl)phenyl]-6-chloro-1,2-dihydro-1-methyl-4-phenyl- 3-quinolineacetamide A mixture of the compound obtained in Example 57 (150 mg), dioxane (5 ml) and methyl iodide (1.5 ml) was refluxed for 2 hours while heating. Upon solvent removal by distillation, a quaternary salt (iodide), resulting from 1-methylation of the compound of Example 57, was obtained as yellow crystals. To a solution of this quaternary salt in methanol (5 ml) was added sodium borohydride (30 mg) at 0° C., followed by stirring for 20 minutes. The reaction mixture was acidified with dilute hydrochloric acid and then alkalinized with aqueous potassium carbonate, followed by extraction with ethyl acetate. The extract was washed with water and dried, after which the solvent was distilled off, to yield the title compound as colorless crystals (90 mg).

Melting point: 192°–194° C. (recrystallized from ethyl acetate-isopropyl ether) NMR (200 MHz, CDCl$_3$) ppm: 1.15 (12H, d, J=6.6 Hz), 2.86 (3H, s), 2.95 (2H, m), 3.17 (2H, s), 4.08 (2H, s), 6.45–6.58 (2H, m), 7.00–7.50 (10H, m) Elemental analysis (for $C_{30}H_{33}N_2OCl.0.2i-Pr_2O$): Calculated (%): C, 75.94; H, 7.31; N, 5.68 Found (%): C, 75.71; H, 7.13; N, 6.02

Example 100

N-[2,6-Bis(1-methylethyl)phenyl]-6-chloro-1,2-dihydro-1-methyl-4-(2-methylphenyl)- 3-quinolineacetamide N-[2,6-Bis(1-methylethyl)phenyl]-6-chloro-4-(2-methylphenyl)-3-quinolineacetamide (Example 91) was reacted by a method similar to Example 99 to yield the title compound.

Melting point: 159.5°–160.5° C. (recrystallized from ethyl acetate-isopropyl ether) NMR (200 MHz, CDCl$_3$) ppm: 1.14 (6H, d, J=3.6 Hz), 1.17 (6H, d, J=3.6 Hz), 2.15 (3H, s), 2.87 (3H, s), 2.95 (2H, m), 3.05 (2H, m), 4.11 (2H, s), 6.36 (1H, d, J=2.2 Hz), 6.53 (1H, d, J=8.8 Hz), 6.97 (1H, bs), 7.00–7.40 (8H, m)

Example 101

N-[3,5-Bis(trifluoromethyl)benzyl]-1,2-dihydro-2-methyl-4-(2-methylphenyl)- 1-oxo-3-isoquinolinecarboxamide To a solution of 2-methyl-4-(2-methylphenyl)-1(2H)-isoquinolinone-3-carboxylic acid (293 mg) in THF (10 ml) were added oxalyl chloride (0.104 ml) and DMF (one drop) at room temperature, followed by stirring for 1 hour. After the solvent was distilled off, the residue was dissolved in dichloromethane (10 ml). To this solution was added a solution of 3,5-bis(trifluoromethyl)benzylamine (340 mg) and triethylamine (0.154 ml) in dichloromethane (5 ml), followed by stirring at room temperature for 5 hours. After the solvent was distilled off, ethyl acetate was added to the residue. This mixture was washed successively with water, dilute hydrochloric acid, water, aqueous sodium hydrogen carbonate and water and then dried, after which the solvent was distilled off, to yield the title compound as colorless crystals (250 mg).

Melting point: 168.5°–170.0° C. (recrystallized from ethyl acetate-hexane) NMR (200 MHz, CDCl$_3$) ppm: 2.02 (3H, s), 3.59 (3H, s), 4.24 (1H, dd, J=14.6, 5.6 Hz), 4.42 (1H, dd, J=14.6, 5.6 Hz), 6.15 (1H, b, NH), 6.89 (1H, m), 7.09 (4H, m), 7.50 (4H, m), 7.79 (1H, s), 8.44 (1H, m) Elemental analysis (for C$_{27}$H$_{20}$N$_2$O$_2$F$_6$): Calculated: C, 62.55; H, 3.89; N, 5.40 Found: C, 62.29; H, 4.12; N, 5.68

Example 102

N-[3,5-Bis(trifluoromethyl)benzyl]-1,2-dihydro-N,2-dimethyl-4-(2-methylphenyl)- 1-oxo-3-isoquinolinecarboxamide

Method C

A mixture of the compound (156 mg) obtained in Example 101, sodium hydride (60% in oil) (12 mg) and DMF (5 ml) was stirred at room temperature for 30 minutes, and methyl iodide (0.5 ml) was added, followed by stirring at room temperature for 1 hour. The reaction mixture was poured into water and extracted with ethyl acetate, and the extract was washed with water and then dried, followed by solvent removal by distillation, to yield the title compound as colorless crystals (156 mg).

Method D

Using N-[3,5-bis(trifluoromethyl)benzyl]methylamine in place of 3,5-bis(trifluoromethyl)benzylamine, 2-methyl-4-(2-methylphenyl)-1(2H)-isoquinolinone- 3-carboxylic acid was amidated in substantially the same manner as in Example 101 to yield the title compound as colorless crystals.

Melting point: 76°–78° C. (recrystallized from hexane) NMR (200 MHz, CDCl$_3$) ppm: 2.01 (1.5H, s), 2.12 (1.5H, s), 2.77 (1.5H, s), 2.97 (1.5H, s), 3.58 (1.5H, s), 3.60 (1.5H, s), 4.10 (0.5H, d, J=14.4 Hz), 4.26 (0.5H, d, J=14.4 Hz), 4.78 (0.5H, d, J=14.4 Hz), 4.96 (0.5H, d, J=14.4 Hz), 6.86–7.02 (2H, m), 7.12–7.32 (3H, m), 7.48–7.57 (4H, m), 7.79 (1H, s), 8.51 (1H, m) Elemental analysis (for C$_{28}$H$_{22}$N$_2$O$_2$F$_6$): Calculated: C, 63.16; H, 4.16; N, 5.26 Found: C, 63.40; H, 4.37; N, 5.02

The compounds of Examples 103 to 188 were obtained by reacting 1(2H)-isoquinoline-3-carboxylic acids having respective corresponding substituents with amines in the same manner (amidation) as in Example 101 or method D of Example 102, or by reacting amide compounds having respective corresponding substituents with alkylating agents in the same manner (alkylation) as method C of Example 102. With respect to Examples 103 to 188, the name of the compound is followed by the symbol [C] when the compound was produced by alkylation, other production examples being based on amidation.

Example 103

N-Benzyl-1,2-dihydro-N,2-dimethyl-4-(2-methylphenyl)-1-oxo-3-isoquinolinecarboxamide Melting point: 172°–173.5° C. (recrystallized from ethyl acetate) NMR (200 MHz, CDCl$_3$) ppm: 2.22 (3H, s), 2.86 (3H, s), 3.60 (3H, s), 3.96 (1H, d, J=14.6 Hz), 5.05 (1H, d, J=14.6 Hz), 6.66 (1H, dd, J=8.0, 2.0 Hz), 6.92–7.56 (11H, m), 8.53 (1H, m) Elemental analysis (for C$_{26}$H$_{24}$N$_2$O$_2$.0.2H$_2$O): Calculated: C, 78.05; H, 6.15; N, 7.00 Found: C, 78.25; H, 6.11; N, 7.00

Example 104

1,2-Dihydro-N-(2-methoxybenzyl)-N,2-dimethyl-4-(2-methylphenyl)-1-oxo- 3-isoquinolinecarboxamide [C]

Melting point: 153°–154.5° C. (recrystallized from ethyl acetate) NMR (200 MHz, CDCl$_3$) ppm: 2.04 (1.5H, s), 2.19 (1.5H, s), 2.74 (1.5H, s), 2.89 (1.5H, s), 3.59 (1.5H, s), 3.62 (1.5H, s), 3.77 (1.5H, s), 3.78 (1.5H, s), 4.35 (1H, dd, J=15.2, 7.6 Hz), 4.73 (1H, dd, J=15.0, 5.8 Hz), 6.08 (0.5H, d, J=7.2 Hz), 6.24(0.5H, d, J=7.6 Hz), 6.56–7.56 (10H, m), 8.51 (1H, m) Elemental analysis (for C$_{27}$H$_{26}$N$_2$O$_3$): Calculated: C, 76.03; H, 6.14; N, 6.57 Found: C, 75.66; H, 6.20; N, 6.56

Example 105

N-(2-Chlorobenzyl)-1,2-dihydro-N,2-dimethyl-4-(2-methylphenyl)-1-oxo- 3-isoquinolinecarboxmide [C]

Melting point: 143°–144° C. (recrystallized from ethyl acetate) NMR (200 MHz, CDCl$_3$) ppm: 2.05 (1.5H, s), 2.20 (1.5H, s), 2.79 (1.5H, s), 2.94 (1.5H, s), 3.63 (1.5H, s), 3.65 (1.5H, s), 4.26 (1H, d, J=15.4 Hz), 5.08 (1H, d, J=16.2 Hz), 5.92 (0.5H, d, J=8.0 Hz), 6.07 (0.5H, d, J=8.0 Hz), 6.89–7.59 (10H, m), 8.53 (1H, m) Elemental analysis (for C$_{26}$H$_{23}$N$_2$O$_2$Cl): Calculated: C, 72.47; H, 5.38; N, 6.50 Found: C, 72.46; H, 5.37; N, 6.73

Example 106

1,2-Dihydro-N-(3,5-dimethylbenzyl)-N,2-dimethyl-4-(2-methylphenyl)-1-oxo- 3-isoquinolinecarboxamide [C]

Melting point: 135°–136° C. (recrystallized from ethyl acetate-hexane) NMR (200 MHz, CDCl$_3$) ppm: 2.01 (1.5H, s), 2.20 (1.5H, s), 2.25 (6H, s), 2.66 (1.5H, s), 2.84 (1.5H, s), 3.58 (1.5H, s), 3.61 (1H, s), 4.08 (1H, dd, J=14.0, 8.8 Hz), 4.71 (1H, t, J=12.8 Hz), 6.45 (1H, s), 6.52 (1H, s), 6.87–7.55 (8H, m), 8.52 (1H, m) Elemental analysis (for C$_{28}$H$_{28}$N$_2$O$_2$): Calculated: C, 79.22; H, 6.65; N, 6.60 Found: C, 78.85; H, 6.68; N, 6.64

Example 107

N-Ethyl-1,2-dihydro-N-(2-methoxybenzyl)-2-methyl-4-(2-methylphenyl)- 1-oxo-3-isoquinolinecarboxamide [C]

Melting point: 119°–120° C. (recrystallized from ethyl ether-hexane) NMR (200 MHz, CDCl$_3$) ppm: 0.97 (0.9H, t, J=7.2 Hz), 1.12 (2.1H, t, J=7.2 Hz), 2.01 (0.9H, s), 2.19 (2.1H, s), 2.85–3.20 (2H, m), 3.62 (2.1H, s), 3.63 (0.9H, s), 3.79 (3H, s), 4.30 (0.7H, d, J=15.8 Hz), 4.35 (0.3H, d, J=15.8 Hz), 4.87 (0.3H, d, J=15.8 Hz), 4.93 (0.7H, d, J=15.8 Hz), 5.88 (1H, m), 6.56–7.58 (10H, m), 8.53 (1H, m) Elemental analysis (for C$_{28}$H$_{28}$N$_2$O$_3$): Calculated: C, 76.34; H, 6.41; N, 6.36 Found: C, 76.57; H, 6.48; N, 6.51

Example 108

1,2-Dihydro-N-(2-methoxybenzyl)-N,2-dimethyl-1-oxo-4-phenyl-3-isoquinolinecarboxamide [C]

Melting point: 146.5°–147.5° C. (recrystallized from ethyl acetate) NMR (200 MHz, CDCl$_3$) ppm: 2.72 (3H, s), 3.62 (3H, s), 3.77 (3H, s), 4.40 (1H, d, J=15.2 Hz), 4.64 (1H, d, J=15.2 Hz), 6.23 (1H, d, J=6.2 Hz), 6.69 (1H, t, J=7.4 Hz), 6.78 (1H, d, J=8.4 Hz), 7.15–7.31 (3H, m), 7.41–7.60 (6H, m), 8.52 (1H, m) Elemental analysis (for $C_{26}H_{24}N_2O_3$): Calculated: C, 75.71; H, 5.86; N, 6.79 Found: C, 75.43; H, 5.83; N, 6.90

Example 109

1,2-Dihydro-N-(4-methoxybenzyl)-2,6,7-trimethyl-1-oxo-4-phenyl-3-isoquinolinecarboxamide Melting point: 240°–242.5° C. (recrystallized from THF-isopropyl ether) NMR (200 MHz, CDCl$_3$) ppm: 2.22 (3H, s), 2.34 (3H, s), 3.53 (3H, s), 3.79 (3H, s), 4.17 (2H, d, J=5.4 Hz), 6.15 (1H, bt, J=5.4 Hz), 6.72 (4H, s), 6.89 (1H, s), 7.30–7.50 (5H, m), 8.14 (1H, s) Elemental analysis (for $C_{27}H_{26}N_2O_3$): Calculated: C, 76.03; H, 6.14; N, 6.57 Found: C, 75.70; H, 6.32; N, 6.47

Example 110

1,2-Dihydro-N-(2-methoxybenzyl)-2,6,7-trimethyl-1-oxo-4-phenyl-3-isoquinolinecarboxamide Melting point: 229°–231.5° C. (recrystallized from THF-ethyl ether) NMR (200 MHz, CDCl$_3$) ppm: 2.23 (3H, s), 2.36 (3H, s), 3.57 (3H, s), 3.75 (3H, s), 4.24 (2H, d, J=6.4 Hz), 6.21 (1H, bt), 6.70–6.90 (3H, m), 6.93 (1H, s), 7.15–7.30 (6H, m), 8.21 (1H, s) Elemental analysis (for $C_{27}H_{26}N_2O_3$): Calculated: C, 76.03; H, 6.14; N, 6.57 Found: C, 75.95; H, 6.18; N, 6.53

Example 111

1,2-Dihydro-N-(2-methoxybenzyl)-N,2,6,7-tetramethyl-1-oxo-4-phenyl-3-isoquinolinecarboxamide [C]

Melting point: 123°–124° C. (recrystallized from ethyl acetate-isopropyl ether) NMR (200 MHz, CDCl$_3$) ppm: 2.26 (3H, s), 2.40 (3H, s), 2.70 (3H, s), 3.60 (3H, s), 3.77 (3H, s), 4.38 (1H, d, J=15 Hz), 4.64 (1H, d, J=15 Hz), 6.20 (1H, dd, J=7.2, 1.4 Hz), 6.69 (1H, dt, J=1.0, 7.6 Hz), 6.79 (1H, d, J=7.4 Hz), 6.97 (1H, s), 7.10–7.35 (2H, m), 7.35–7.55 (4H, m), 8.27 (1H, s) Elemental analysis (for $C_{28}H_{28}N_2O_3$): Calculated: C, 76.34; H, 6.41; N, 6.36 Found: C, 76.00; H, 6.70; N, 6.00

Example 112

N-[3,5-Bis(trifluoromethyl)benzyl]-1,2-dihydro-N,2,6,7-tetramethyl-1-oxo- 4-phenyl-3-isoquinolinecarboxamide [C]

Melting point: 148°–149° C. (recrystallized from ethyl ether-hexane) NMR (200 MHz, CDCl$_3$) ppm: 2.26 (3H, s), 2.40 (3H, s), 2.76 (3H, s), 3.58 (3H, s), 4.26 (1H, d, J=15 Hz), 4.74 (1H, d, J=15 Hz), 6.94 (1H, s), 7.15–7.45 (5H, m), 7.50 (2H, s), 7.80 (1H, s), 8.27 (1H, s) Elemental analysis (for $C_{29}H_{24}N_2O_2F_6$): Calculated: C, 63.73; H, 4.43; N, 5.13 Found: C, 63.98; H, 4.59; N, 5.13

Example 113

1,2-Dihydro-N-(2-methoxybenzyl)-2-methyl-1-oxo-4-phenyl-3-isoquinolinecarboxamide Melting point: 220°–221° C. (recrystallized from ethyl acetate)

Example 114

1,2-Dihydro-N-(2-methoxybenzyl)-2-methyl-4-(2-methylphenyl)-1-oxo-3-isoquinolinecarboxamide Melting point: 237°–239° C. (recrystallized from ethyl acetate)

Example 115

N-(2-Chlorobenzyl)-1,2-dihydro-2-methyl-4-(2-methylphenyl)-1-oxo-3-isoquinolinecarboxamide Melting point: 230°–231° C. (recrystallized from ethyl acetate)

Example 116

1,2-Dihydro-N-(3,5-dimethylbenzyl)-2-methyl-4-(2-methylphenyl)-1-oxo- 3-isoquinolinecarboxamide Melting point: 176.5°–177.5° C. (recrystallized from ethyl acetate)

Example 117

N-Benzyl-1,2-dihydro-N-(2-methoxybenzyl)-2-methyl-4-(2-methylphenyl)- 1-oxo-3-isoquinolinecarboxamide [A]

Melting point: 118°–120° C. (recrystallized from ethyl ether-hexane)

Example 118

1,2-Dihydro-N-(4-methoxybenzyl)-2-methyl-4-(2-methylphenyl)-1-oxo-3-isoquinolinecarboxamide Melting point: 178°–179.5° C. (recrystallized from ethyl acetate)

Example 119

N-Benzyl-1,2-dihydro-2-methyl-4-(2-methylphenyl)-1-oxo-3-isoquinolinecarboxamide Melting point: 170°–172° C. (recrystallized from ethyl acetate)

Example 120

N-Benzyl-4-(2-ethylphenyl)-1,2-dihydro-2-methyl-1-oxo-3-isoquinolinecarboxamide

Melting point: 177°–179° C. (recrystallized from ethyl acetate)

Example 121

4-(2-Ethylphenyl)-1,2-dihydro-N-(4-methoxybenzyl)-2-methyl-1-oxo-3isoquinolinecarboxamide Melting point: 195°–196° C. (recrystallized from ethyl acetate)

Example 122

N-[3,5-Bis(trifluoromethyl)benzyl]-1,2-dihydro-2-methyl-4-(2,6-dimethylphenyl)- 1-oxo-3-isoquinolinecarboxamide Melting point: 225.5°–226.5° C. (recrystallized from ethyl acetate) Elemental analysis (for $C_{28}H_{22}N_2O_2F_6$): Calculated: C, 63.16; H, 4.16; N, 5.26 Found: C, 62.94; H, 4.18; N, 5.15

Example 123

N-[3,5-Bis(trifluoromethyl)benzyl]-1,2-dihydro-4-(2,6-dimethylphenyl)-N, 2-dimethyl-1-oxo-3-isoquinolinecarboxamide [C]

Melting point: 121°–124° C. (recrystallized from ethyl ether)

Example 124

1,2-Dihydro-N-(2-methoxybenzyl)-2-methyl-4-(2,6-dimethylphenyl)-1-oxo- 3-isoquinolinecarboxamide Melting point: 175°–177° C. (recrystallized from ethyl acetate)

Example 125

1,2-Dihydro-4-(2,6-dimethylphenyl)-N-(2-methoxybenzyl)-N,2-dimethyl- 1-oxo-3-isoquinolinecarboxamide [C]

Melting point: 192°–194° C. (recrystallized from ethyl acetate-ethyl ether)

Example 126

1,2-Dihydro-2,6,7-trimethyl-1-oxo-4-phenyl-N-(2-phenylethyl)-3-isoquinolinecarboxamide Melting point: 225°–226.5° C. (recrystallized from ethyl acetate-isopropyl ether)

Example 127

1,2-Dihydro-2,6,7-trimethyl-N-(4-methylbenzyl)-1-oxo-4-phenyl-3-isoquinolinecarboxamide Melting point: 240°–242° C. (recrystallized from ethyl acetate-isopropyl ether)

Example 128

1,2-Dihydro-N-(3-methoxybenzyl)-2,6,7-trimethyl-1-oxo-4-phenyl-3-isoquinolinecarboxamide Melting point: 201°–203° C. (recrystallized from THF-ethyl ether)

Example 129

N-(4-Chlorobenzyl)-1,2-dihydro-2,6,7-trimethyl-1-oxo-4-phenyl-3-isoquinolinecarboxamide Melting point: 243.7°–245.7° C. (recrystallized from THF-isopropyl ether)

Example 130

N-(3-Chlorobenzyl)-1,2-dihydro-2,6,7-trimethyl-1-oxo-4-phenyl-3-isoquinolinecarboxamide Melting point: 213°–214° C. (recrystallized from THF-ethyl ether)

Example 131

N-(2-Chlorobenzyl)-1,2-dihydro-2,6,7-trimethyl-1-oxo-4-phenyl-3-isoquinolinecarboxamide Melting point: 259.5°–260.5° C. (recrystallized from THF-ethyl ether)

Example 132

1,2-Dihydro-N,2,6,7-tetramethyl-N-(4-methylbenzyl)-1-oxo-4-phenyl-3-isoquinolinecarboxamide [C]

Melting point: 169.8°–170.8° C. (recrystallized from ethyl acetate-isopropyl ether)

Example 133

1,2-Dihydro-N-(4-methoxybenzyl)-N,2,6,7-tetramethyl-1-oxo-4-phenyl-3-isoquinolinecarboxamide [C]

Melting point: 201°–202° C. (recrystallized from ethyl acetate-isopropyl ether)

Example 134

N-(4-Chlorobenzyl)-1,2-dihydro-N,2,6,7-tetramethyl-1-oxo-4-phenyl-3-isoquinolinecarboxamide [C]

Melting point: 175°–176° C. (recrystallized from ethyl acetate-isopropyl ether)

Example 135

N-[3,5-Bis(trifluoromethyl)benzyl]-1,2-dihydro-2,6,7-trimethyl-1-oxo-4-phenyl-3-isoquinolinecarboxamide Melting point: 92°–93° C. (recrystallized from ethyl acetate-isopropyl ether)

Example 136

1,2-Dihydro-N-[2-(2-methoxyphenyl)ethyl]-2,6,7-trimethyl-1-oxo-4-phenyl- 3- isoquinolinecarboxamide Melting point: 214°–216° C. (recrystallized from ethyl acetate-isopropyl ether)

Example 137

1,2-Dihydro-N-[2-(2-methoxyphenyl)ethyl]-N,2,6,7-tetramethyl-1-oxo-4-phenyl-3-isoquinolinecarboxamide [C]

Melting point: 110°–111° C. (recrystallized from ethyl ether-hexane)

Example 138

N-[2-(3,4-Dimethoxyphenyl)ethyl]-2,6,7-trimethyl-1-oxo-4-phenyl-3-isoquinolinecarboxamide Melting point: 185°–187° C. (recrystallized from THF-isopropyl ether)

Example 139

6-Chloro-1,2-dihydro-N-(4-methoxybenzyl)-2-methyl-4-(2-methylphenyl)- 1-oxo-3-isoquinolinecarboxamide Melting point: 181°–183° C. (recrystallized from ethyl acetate)

Example 140

6-Chloro-1,2-dihydro-N-(4-methoxybenzyl)-N,2-dimethyl-4-(2-methylphenyl)- 1-oxo-3-isoquinolinecarboxamide [C]

Melting point: 159°–160.5° C. (recrystallized from ethyl acetate)

Example 141

N-Benzyl-6-chloro-1,2-dihydro-N,2-dimethyl-4-(2-methylphenyl)-1-oxo- 3-isoquinolinecarboxamide Melting point: 151°–153° C. (recrystallized from ethyl acetate)

Example 142

7-Chloro-1,2-dihydro-N-(4-methoxybenzyl)-2-methyl-4-(2-methylphenyl)- 1-oxo-3-isoquinolinecarboxamide Melting point: 204°–205.5° C. (recrystallized from ethyl acetate)

Example 143

N-Benzyl-7-chloro-1,2-dihydro-N,2-dimethyl-4-(2-methylphenyl)-1-oxo- 3-isoquinolinecarboxamide
  Melting point: 171°–172° C. (recrystallized from ethyl acetate)

Example 144

6-Chloro-1,2-dihydro-N-(2-methoxybenzyl)-2-methyl-4-(2-methylphenyl)- 1-oxo-3-isoquinolinecarboxamide
  Melting point: 200.5°–202.5° C. (recrystallized from ethyl acetate)

Example 145

7-Chloro-1,2-dihydro-N-(2-methoxybenzyl)-2-methyl-4-(2-methylphenyl)- 1-oxo-3-isoquinolinecarboxamide
  Melting point: 187°–188° C. (recrystallized from ethyl acetate)

Example 146

N-Benzyl-1,2-dihydro-N,2,6,7-tetramethyl-4-(2-methylphenyl)-1-oxo-3-isoquinolinecarboxamide
  Melting point: 177°–178° C. (recrystallized from ethyl acetate)

Example 147

N-Benzyl-1,2-dihydro-4-(2,6-dimethylphenyl)-N,2,6,7-tetramethyl-1-oxo- 3-isoquinolinecarboxamide
  Melting point: 186°–187.5 ° C. (recrystallized from ethyl acetate)

Example 148

1,2-Dihydro-N-furfuryl-2,6,7-trimethyl-1-oxo-4-phenyl-3-isoquinolinecarboxamide
  Melting point: 224°–225° C. (recrystallized from THF-isopropyl ether)

Example 149

1,2-Dihydro-2,6,7-trimethyl-1-oxo-4-phenyl-N-(2-pyridyl)methyl-3-isoquinolinecarboxamide
  Melting point: 218°–220° C. (recrystallized from THF-ethyl ether)

Example 150

1,2-Dihydro-2,6,7-trimethyl-1-oxo-4-phenyl-N-(2-thienyl)methyl-3-isoquinolinecarboxamide
  Melting point: 256.5°–258.0° C. (recrystallized from tetrahydrofuran-isopropyl ether)

Example 151

1,2-Dihydro-N-(4-methoxybenzyl)-N,2-dimethyl-4-(2-methylphenyl)-1-oxo- 3-isoquinolinecarboxamide [C]
  Melting point: 147°–150° C. (recrystallized from hexane-ethyl acetate)

Example 152

1,2-Dihydro-N-[2-(2-methoxyphenyl)ethyl]-2-methyl-4-(2-methylphenyl)- 1-oxo-3-isoquinolinecarboxamide
  Melting point: 217°–219° C. (recrystallized from ethyl acetate)

Example 153

1,2-Dihydro-N-[2-(2-methoxyphenyl)ethyl]-N,2-dimethyl-4-(2-methylphenyl)- 1-oxo-3-isoquinolinecarboxamide [C]
  Melting point: 123°–125° C. (recrystallized from ethyl ether)

Example 154

1,2-dihydro-N-(2-methoxyphenyl)-2-methyl-4-(2-methylphenyl)-1-oxo-3-isoquinolinecarboxamide
  Melting point: 142°–145° C. (recrystallized from ethyl ether)

Example 155

1,2-Dihydro-2-methyl-4-(2-methylphenyl)-1-oxo-N-(3,4,5-trimethoxyphenyl)- 3-isoquinolinecarboxamide
  Melting point: 222.5°–224° C. (recrystallized from ethyl acetate)

Example 156

N-[3,5-Bis(trifluoromethyl)benzyl]-1,2-dihydro-2-methyl-1-oxo-4-phenyl- 3- isoquinolinecarboxamide
  Melting point: 150°–152° C. (recrystallized from ethyl acetate-ethyl ether) NMR (200 MHz, CDCl$_3$) ppm: 3.55 (3H,s), 4.34 (2H,d,J=6.2 Hz), 6.68 (1H,bt), 7.12–7.50 (8H, m), 7.52 (2H,s), 7.78 (1H,s), 8.37 (1H,m)

Example 157

N-[3,5-Bis(trifluoromethyl)benzyl]-1,2-dihydro-N,2-dimethyl-1-oxo-4-phenyl- 3-isoquinolinecarboxamide [C]
  Melting point: 144.5°–146° C. (recrystallized from ether) NMR (200 MHz, CDCl$_3$) ppm: 2.78 (3H,s), 3.61 (3H,s), 4.26 (1H,d,J=14.2 Hz), 4.75 (2H,d,J=14.2 Hz), 7.19–7.40 (6H,m), 7.51 (2H,s), 7.53–7.58 (2H,m), 7.81 (1H,s), 8.52 (1H,m)

Example 158

N-[3,5-Bis(trifluoromethyl)benzyl]-1,2-dihydro-4-(2-methoxyphenyl)-2-methyl-1-oxo-3-isoquinolinecarboxamide
  Melting point: 236°–238° C. (recrystallized from ethyl acetate)

Example 159

N-[3,5-Bis(trifluoromethyl)benzyl]-1,2-dihydro-4-(2-methoxyphenyl)-N,2-dimethyl- 1-oxo-3-isoquinolinecarboxamide [C]
  Melting point: 171°–173° C. (recrystallized from ethyl ethyl acetate-ether)

Example 160

1,2-Dihydro-N-(2-methoxybenzyl)-4-(2-methoxyphenyl)-2-methyl-1-oxo- 3-isoquinolinecarboxamide
  Melting point: 191°–193° C. (recrystallized from ethyl acetate)

Example 161

1,2-Dihydro-N-(2-methoxybenzyl)-4-(2-methoxyphenyl)-N,2-dimethyl-1-oxo-3-isoquinolinecarboxamide [C]
  Melting point: 146°–148.5° C. (recrystallized from ethyl acetate-ethyl ether)

Example 162

N-Benzyl-4-(2-ethylphenyl)-1,2-dihydro-N,2-dimethyl-1-oxo-3-isoquinolinecarboxamide [C]

A colorless oily substance

NMR (200 MHz, CDCl₃) ppm: 1.04 (3H, t, J=7.6 Hz), 2.63 (2H, m), 2.83 (3H, s), 3.61 (3H, s), 3.94 (1H, d, J=14.2 Hz), 5.06 (1H, d, J=14.2 Hz), 6.60–6.65 (2H, m), 6.95–7.55 (10H, m), 8.52 (1H, m)

Example 163

4-(2-Ethylphenyl)-1,2-dihydro-N-(4-methoxybenzyl)-N,2-dimethyl-1-oxo- 3-isoquinolinecarboxamide [C]

A colorless oily substance

NMR (200 MHz, CDCl₃) ppm: 1.04 (3H, t, J=7.6 Hz), 2.66 (2H, m), 2.80 (3H, s), 3.59 (3H, s), 3.80 (3H, s), 3.91 (1H, d, J=14.4 Hz), 4.94 (1H, d, J=14.4 Hz), 6.57–6.72 (4H, m), 6.94–7.19 (3H, m), 7.36–7.55 (4H, m), 8.51 (1H, m)

Example 164

N-Benzyl-4-(2-ethylphenyl)-1,2-dihydro-N,2,6,7-tetramethyl-1-oxo-3-isoquinolinecarboxamide A white powder NMR (200 MHz, CDCl₃) ppm: 1.26 (3H, t, J=7.0 Hz), 2.23 (3H, s), 2.39 (3H, s), 2.65 (2H, m), 2.73 (3H, s), 3.57 (3H, s), 3.79 (1H, d, J=14.0 Hz), 4.92 (1H, d, J=14.0 Hz), 6.50–7.40 (10H, m), 8.26 (1H, s)

Example 165

N-[3,5-Bis(trifluoromethyl)benzyl]-4-(4-fluorophenyl)-1,2-dihydro-2-methyl- 1-oxo-3-isoquinolinecarboxamide Melting point: 184°–186° C. (recrystallized from ethyl ether) NMR (200 MHz, CDCl₃) ppm: 3.59 (3H,s), 4.39 (2H, d, J=5.8 Hz), 6.32 (1H, bt, NH), 6.95 (1H, t, J=8.4 Hz), 7.10–7.37 (5H, m), 7.51 (1H, m), 7.56 (2H, s), 7.83 (1H, s), 8.45 (1H, m)

Example 166

N-[3,5-Bis(trifluoromethyl)benzyl]-4-(4-fluorophenyl)-1,2-dihydro-N,2-dimethyl- 1-oxo-3-isoquinolinecarboxamide (C)

Melting point: 99°–101° C. (recrystallized from isopropyl ether-hexane) NMR (200 MHz, CDCl₃) ppm: 2.83 (3H, s), 3.60 (3H, s), 4.28 (1H, d, J=14.4 Hz), 4.78 (1H, d, J=14.4 Hz), 6.93–7.02 (2H, m), 7.13–7.39 (3H, m), 7.52– 7.61 (4H, m), 7.84 (1H, s), 8.52 (1H, m)

Example 167

1,2-Dihydro-2-methyl-4-(2-methylphenyl)-1-oxo-N-(3,4,5-trimethoxybenzyl)- 3-isoquinolinecarboxamide Melting point: 227°–228° C. (recrystallized from ethyl acetate)

Example 168

1,2-Dihydro-N,2-dimethyl-4-(2-methylphenyl)-1-oxo-N-(3,4,5-trimethoxybenzyl)- 3-isoquinolinecarboxamide (C)

Melting point: 178°–179.5° C. (recrystallized from ethyl acetate)

Example 169

1,2-Dihydro-2-methyl-N-(4-methylbenzyl)-4-(2-methylphenyl)1oxo-3-isoquinolinecarboxamide Melting point: 165°–166° C. (recrystallized from ethyl acetate-ethyl ether)

Example 170

1,2-Dihydro-2-methyl-N-(4-methylbenzyl)-1-oxo-4-phenyl-3isoquinolinecarboxamide

Melting point: 216°–217° C. (recrystallized from ethyl acetate-ethyl ether) NMR (200 MHz, CDCl₃) ppm: 2.32 (3H, s), 3.54 (3H, s), 4.19 (2H, d, J=5.4 Hz), 6.10 (1H, bt), 6.68 (2H, d, J=8.0 Hz), 7.02 (2H, d, J=8.0 Hz), 7.20 (1H, d, J=7.8 Hz), 7.31–7.56 (7H, m), 8.37 (1H, dd, J=7.2, 1.0 Hz)

Example 171

1,2-Dihydro-2-methyl-1-oxo-4-phenyl-N-[4-(trifluoromethyl)benzyl]-3-isoquinolinecarboxamide Melting point: 200°–201° C. (recrystallized from ethyl acetate-isopropyl ether) NMR (200 MHz, CDCl₃) ppm: 3.51 (3H, s), 4.35 (2H, d, J=5,8 Hz), 6.49 (1H, bt), 6.87 (2H, d, J=8.0 Hz), 7.16 (1H, d, J=8.0 Hz), 7.30–7.56 (9H, m), 8.36 (1H, dd, J=7.9, 1.7 Hz)

Example 172

N-[3,5-Bis(trifluoromethyl)benzyl]-1,2-dihydro-N-methyl-1-oxo-4-phenyl- 3-isoquinolinecarboxamide Melting point: 224°–225° C. (recrystallized from ethyl acetate-hexane) NMR (200 MHz, CDCl₃) ppm: 2.73 (3H, s), 7.20–7.70 (11H, m), 7.80 (1H, s), 8.53 (1H, d, J=8.4 Hz)

Example 173

N-[3,5-Bis(trifluoromethyl)benzyl]-6-chloro-1,2-dihydro-2-methyl-1-oxo- 4-phenyl-3-isoquinolinecarboxamide Melting point: 164°–165° C. (recrystallized from ethyl acetate-isopropyl ether) NMR (200 MHz, CDCl₃) ppm: 3.55 (3H, s), 4.34 (2H, d, J=6.0 Hz), 6.54 (1H, b), 7.08 (1H, m), 7.20–7.95 (6H, m), 7.52 (2H, s), 7.80 (2H, s), 8.28 (1H, d, J=8.6 Hz)

Example 174

N-[3,5-Bis(trifluoromethyl)benzyl]-6-chloro-1,2-dihydro-N,2-dimethyl-1-oxo-4-phenyl-3-isoquinolinecarboxamide Melting point: 165°–166° C. (recrystallized from ethyl acetate-ethyl ether) NMR (200 MHz, CDCl₃) ppm: 2.77 (3H, s), 3.59 (3H, s), 4.25 (1H, d, J=14.6 Hz), 4.74 (1H, d, J=14.6 Hz), 7.10–7.60 (9H, m), 7.80 (1H, s), 8.44 (1H, d, J=8.0 Hz)

Example 175

N-[3,5-Bis(trifluoromethyl)benzyl]-4-(4-fluoro-2-methylphenyl)-1,2-dihydro- 2-methyl-1-oxo-3-isoquinolinecarboxamide Melting point: 189°–190° C. (recrystallized from ethyl acetate-isopropyl ether) NMR (200 MHz, CDCl₃) ppm: 2.02 (3H, s), 3.41 (3H, s), 4.33 (1H, dd, J=15.0, 5.4 Hz), 4.50 (1H, dd, J=15.0, 5.4 Hz), 6.65–6.95 (4H, m), 7.12 (1H, dd, J=8.4 Hz, 5.4 Hz), 7.48 (2H, m), 7.84 (1H, s), 8.34 (1H, d, J=7.6 Hz)

Example 176

N-[3,5-Bis(trifluoromethyl)benzyl]-4-(4-fluoro-2-methylphenyl)-1,2-dihydro-N,2-dimethyl- 1-oxo-3-isoquinolinecarboxamide Melting point: 142°–143° C. (recrystallized from ethyl acetate-ethyl ether) NMR (200 MHz, CDCl$_3$) ppm: 2.11 (3H, s), 2.99 (3H, s), 3.58 (3H, s), 4.11 (1H, d, J=14.7 Hz), 4.97 (1H, d, J=14.7 Hz), 6.65 (1H, m), 6.80–7.63 (7H, m), 7.83 (1H, s), 8.51 (1H, m)

Example 177

N-[3,5-Bis(trifluoromethyl)benzyl]-6-chloro-1,2-dihydro-N-methyl-1-oxo- 4-phenyl-3-isoquinolinecarboxamide Melting point: 251°–253° C. (recrystallized from ethyl acetate-hexane) NMR (200 MHz, CDCl$_3$) ppm: 2.73 (3H, s), 4.0–5.0 (2H, b), 7.33–7.56 (9H, m), 7.81 (1H, s), 8.35 (1H, d, J=8.4 Hz)

Example 178

N-[3,5-Bis(trifluoromethyl)benzyl]-4-(4-fluorophenyl)-1,2-dihydro-N-methyl- 1-oxo-3-isoquinolinecarboxamide Melting point: 225°–226° C. (recrystallized from ethyl acetate-isopropyl ether) NMR (200 MHz, CDCl$_3$) ppm: 2.81 (3H, s), 4.1–5.1 (2H, b), 6.99–7.80 (9H, m), 7.83 (1H, s), 8.46 (1H, d, J=7.4 Hz)

Example 179

N-[3,5-Bis(trifluoromethyl)benzyl]-2-(2-ethoxycarbonylethyl)-1,2-dihydro- 1-oxo-4-phenyl-3-isoquinolinecarboxamide Melting point: 155°–156° C. (recrystallized from ethyl acetate-isopropyl ether)

Example 180

N-[3,5-Bis(trifluoromethyl)benzyl]-2-(2-ethoxycarbonylethyl)-1,2-dihydro-N-methyl- 1-oxo-4-phenyl-3-isoquinolinecarboxamide A white powder NMR (200 MHz, CDCl$_3$) ppm: 1.26 (3H, t, J=7.0 Hz), 2.80 (3H, s), 2.97 (2H, t, J=7.2 Hz), 3.83 (1H, m), 4.00–4.27 (3H, m), 4.68 (1H, m), 4.48 (1H, d, J=14.2 Hz), 7.05–7.65 (10H, m), 7.80 (1H, s), 8.50 (1H, m)

Example 181

N-[3,5-Bis(trifluoromethyl)benzyl]-1,2-dihydro-2-methyl-1-oxo-4-(2-trifluoromethylphenyl)- 3-isoquinolinecarboxamide Melting point: 176.5°–177.5° C. (recrystallized from ethyl acetate-ethyl ether)

Example 182

N-[3,5-Bis(trifluoromethyl)benzyl]-1,2-dihydro-N,2-dimethyl-1-oxo-4-(2-trifluoromethylphenyl)-3-isoquinolinecarboxamide (C)

Melting point: 159°–160° C. (recrystallized from ethyl acetate-ethyl ether) NMR (200 MHz, CDCl$_3$) ppm: 2.89 (3H, s), 3.58 (3H, s), 4.11 (1H, d, J=14.6 Hz), 4.98 (1H, d, J=14.6 Hz), 6.86 (1H, m), 7.43 (2H, s), 7.46–7.56 (5H, m), 7.65 (1H, d, J=7.8 Hz), 7.78 (1H, s), 8.50 (1H, m)

Example 183

N-[3,5-Bis(trifluoromethyl)benzyl]-2-[2-(N,N-dimethylamino)ethyl]-1,2-dihydro-1-oxo-4-phenyl-3-isoquinolinecarboxamide Melting point: 148°–149° C. (recrystallized from ethyl acetate-isopropyl ether)

Example 184

N-[3,5-Bis(trifluoromethyl)benzyl]-2-[2-(N,N-dimethylamino)ethyl]-1,2-dihydro-N-methyl-1-oxo-4-phenyl-3-isoquinolinecarboxamide hydrochloride Melting point: 167°–168° C. (recrystallized from ethyl acetate-isopropyl ether) NMR (200 MHz, CDCl$_3$) ppm: 2.87 (3H, s), 2.92 (3H, s), 3.04 (3H, s), 3.23–3.52 (1H, b), 3.62–3.85 (1H, b), 3.99 (1H, d, J=16.0 Hz), 4.30–4.60 (1H, b), 4.75–5.00 (1H, b), 5.66 (1H, d, J=16.0 Hz), 7.08–7.35 (6H, m), 7.42 (2H, s), 7.58 (2H, m), 7.77 (1H, s), 8.45 (1H, m)

Example 185

N-[3,5-Bis(trifluoromethyl)benzyl]-1,2,5,6,7,8-hexahydro-2-methyl-1-oxo- 4-phenyl-3-isoquinolinecarboxamide Melting point: 224°–225° C. (recrystallized from ethyl acetate-isopropyl ether)

Example 186

N-[3,5-Bis(trifluoromethyl)benzyl]-1,2,5,6,7,8-hexahydro-N-2-dimethyl- 1-oxo-4-phenyl-3-isoquinolinecarboxamide Melting point: 200°–201° C. (recrystallized from ethyl acetate-hexane) NMR (200 MHz, CDCl$_3$) ppm: 1.40–2.70 (8H, m), 2.74 (3H, s), 3.50 (3H, s), 4.17 (1H, d, J=14.6 Hz), 4.73 (1H, d, J=14.4 Hz), 7.04 (1H, m), 7.22 (5H, m), 7.46 (2H, s), 7.78 (1H, m)

Example 187

N-[3,5-Bis(trifluoromethyl)benzyl]-1,2-dihydro-N-ethyl-2-methyl-1-oxo- 4-phenyl-3-isoquinolinecarboxamide (C)

Melting point: 99°–100° C. (recrystallized from ethyl acetate-hexane) NMR (200 MHz, CDCl$_3$) ppm: 1.02 (3H, t, J=7.2 Hz), 2.95 (1H, m), 3.45 (1H, m), 3.61 (3H, s), 4.20 (1H, d, J=14.7 Hz), 4.87 (1H, d, J=14.7 Hz), 7.2–7.26 (10H, m), 7.78 (1H, s), 8.49–8.54 (1H, m)

Example 188

N-[3,5-Bis(trifluoromethyl)benzyl]-5-fluoro-4-(4-fluorophenyl)-N,2-dimethyl- 1-oxo-3-isoquinolinecarboxamide Melting point: 96°–98° C. (recrystallized from isopropyl ether-ethyl acetate) NMR (200 MHz, CDCl$_3$) ppm: 2.83 (3H, s), 3.57 (3H, s), 4.26 (1H, d, J=14.0 Hz), 4.67 (1H, d, J=14.6 Hz), 6.80–6.96 (2H, m), 7.06–7.40 (2H, m), 7.42–7.54 (1H, m), 7.56 (2H, s), 7.83 (1H, d, J=1.2 Hz), 8.35 (1H, dd, J=1.0, 8.0 Hz)

Example 189

N-[3,5-Bis(trifluoromethyl)benzyl]-1,2-dihydro-2-ethyl-N-methyl-1-oxo- 4-phenyl-3-isoquinolinecarboxamide The compound obtained in Example 172 was reacted with ethyl iodide by a method similar to Example 102(C) to yield the title compound.

Melting point: 105°–106° C. (recrystallized from ethyl acetate-hexane) NMR (200 MHz, CDCl$_3$) ppm: 1.39 (3H, t, J=7.0 Hz), 2.75 (3H, s), 3.85 (1H, m), 4.32 (1H, m), 4.45 (2H, s), 7.2–7.6 (10H, m), 7.80 (1H, s), 8.49–8.54 (1H, m)

Example 190

1,2-Dihydro-N-(2-methoxybenzyl)-2,6,7-trimethyl-1-oxo-4-phenyl-3-isoquinolinemethylamine To a solution of the compound (300 mg) obtained in Reference Example 52 in THF (5 ml) was added 2-methoxybenzylamine (0.51 ml), followed by heating at 130° C.

in a sealed tube for 2 hours. After ethyl acetate was added, the reaction mixture was washed by successively with of aqueous potassium carbonate and aqueous sodium chloride and then dried, after which the solvent was distilled off. The residue was subjected to column chromatography using silica gel (hexane:ethyl acetate=1:1) to yield the title compound as colorless crystals (301 mg).

Melting point: 159°–160° C. (recrystallized from ethyl acetate-isopropyl ether) NMR (200 MHz, CDCl$_3$) ppm: 2.20 (3H, s), 2.36 (3H, s), 3.46 (2H, s), 3.64 (2H, s), 3.79 (3H, s), 3.82 (3H, s), 6.69 (1H, s), 6.80 (1H, d, J=7.8 Hz), 6.84 (1H, d, J=6.0 Hz), 7.03 (1H, d, J=6.0 Hz), 7.12–7.30 (3H, m), 7.35–7.50 (3H, m), 8.22 (1H, s) Elemental analysis (for $C_{27}H_{28}N_2O_2$): Calculated: C, 78.61; H, 6.84; N, 6.79 Found: C, 78.47; H, 6.88; N, 6.69

1(2H)-Isoquinoline derivatives having respective corresponding substituents were reacted with amines in the same manner as in Example 190 to yield the compounds of Example 191 to 206.

Example 191

N-(3,5-Dimethylbenzyl)-1,2-dihydro-2,6,7-trimethyl-1-oxo-4-phenyl-3-isoquinolinemethylamine Melting point: 129°–130° C. (recrystallized from ethyl ether-hexane) NMR (200 MHz, CDCl$_3$) ppm: 2.21 (3H, s), 2.27 (6H, s), 2.37 (3H, s), 3.48 (2H, s), 3.56 (2H, s), 3.82 (3H, s), 6.70 (1H, s), 6.79 (2H, s), 6.86 (1H, s), 7.15–7.30 (2H, m), 7.40–7.50 (3H, m), 8.24 (1H, s) Elemental analysis (for $C_{28}H_{30}N_2O$): Calculated: C, 81.91; H, 7.37; N, 6.82 Found: C, 82.05; H, 7.37; N, 6.82

Example 192

N-(2-Chlorobenzyl)-1,2-dihydro-N,2,6,7-tetramethyl-1-oxo-4-phenyl-3-isoquinolinemethylamine Melting point: 117°–118° C. (recrystallized from ethyl ether-hexane)

Example 193

N-(2-Chlorobenzyl)-1,2-dihydro-2,6,7-trimethyl-1-oxo-4-phenyl-3-isoquinolinemethylamine Melting point: 141°–142° C. (recrystallized from ethyl acetate-isopropyl ether)

Example 194

1,2-Dihydro-N-[2-(2-methoxyphenyl)ethyl]-2,6,7-trimethyl-1-oxo-4-phenyl- 3-isoquinoline methylamine Melting point: 119°–120° C. (recrystallized from ethyl acetate-isopropyl ether)

Example 195

N-[3,5-Bis(trifluoromethyl)benzyl]-1,2-dihydro-2,6,7-trimethyl-1-oxo- 4-phenyl-3-isoquinolinemethylamine hydrochloride A white powder NMR (200 MHz, DMSO-d$_6$) ppm: 2.19 (3H, s), 2.36 (3H, s), 3.74 (3H, s), 4.05 (2H, bs), 4.14 (2H, bs), 6.63 (1H, s), 7.30–7.50 (5H, m), 8.12 (1H, s), 9.9 (2H, bs) Elemental analysis (for $C_{28}H_{25}N_2OClF_6$): Calculated: C, 60.60; H, 4.54; N, 5.05 Found: C, 60.78; H, 4.63; N, 4.78

Example 196

1,2-Dihydro-N-(2-methoxybenzyl)-N,2,6,7-tetramethyl-1-oxo-4-phenyl-3-isoquinolinemethylamine Melting point: 91°–92° C. (recrystallized from ethyl ether-hexane)

Example 197

1,2-Dihydro-N-(2-methoxybenzyl)-2-methyl-1-oxo-4-phenyl-3-isoquinolinemethylamine Melting point: 212°–214° C. (recrystallized from ethyl ethyl acetate-ether)

Example 198

1,2-Dihydro-N-(3-methoxybenzyl)-2-methyl-1-oxo-4-phenyl-3-isoquinolinemethylamine Melting point: 95°–96° C. (recrystallized from ethyl acetate-isopropyl ether)

Example 199

1,2-Dihydro-N-(4-methoxybenzyl)-2-methyl-1-oxo-4-phenyl-3-isoquinolinemethylamine Melting point: 94°–95° C. (recrystallized from ethyl acetate-isopropyl ether)

Example 200

N-[3,5-Bis(trifluoromethyl)phenyl]-1,2-dihydro-2-methyl-1-oxo-4-phenyl- 3-isoquinolinemethylamine Melting point: 241°–242° C. (recrystallized from ethyl acetate-isopropyl ether)

Example 201

N-[3,5-Bis(trifluoromethyl)benzyl]-1,2-dihydro-N,2-dimethyl-1-oxo-4-phenyl- 3-isoquinolinemethylamine Melting point: 135°–136° C. (recrystallized from ethyl acetate-isopropyl ether)

Example 202

1,2-Dihydro-2-methyl-1-oxo-4-phenyl-N-(2-pyridyl)methyl-3-isoquinolinemethylamine Melting point: 145°–146° C. (recrystallized from ethyl acetate-isopropyl ether)

Example 203

1,2-Dihydro-N-(2-methoxybenzyl)-2-methyl-4-(2-methylphenyl)-1-oxo-3-isoquinolinemethylamine Melting point: 91°–92° C. (recrystallized from ethyl acetate-isopropyl ether)

Example 204

N-[3,5-Bis(trifluoromethyl)benzyl]-1,2-dihydro-2-methyl-4-(2-methylphenyl)- 1-oxo-3-isoquinolinemethylamine hydrochloride A white powder NMR (200 MHz, DMSO-d$_6$) ppm: 1.95 (3H, s), 3.77 (3H, s), 3.50–4.50 (4H, m), 6.70–6.85 (1H, m), 7.20–7.45 (4H, m), 7.50–7.70 (2H, m), 8.07 (3H, s), 8.30–8.40 (1H, m), 9.60–10.60 (1H, m)

Example 205

1,2-Dihydro-2-methyl-1-oxo-4-phenyl-N-(3,4,5-trimethoxybenzyl)-3-isoquinolinemethylamine Melting point: 131°–132° C. (recrystallized from ethyl acetate-isopropyl ether) NMR (200 MHz, CDCl$_3$) ppm: 3.54 (2H, s), 3.59 (2H, s), 3.82 (9H, s), 3.86 (3H, s), 6.45 (2H, s), 6.96 (1H, m), 7.20–7.28 (2H, m), 7.42–7.50 (5H, m), 8.49 (1H, m)

Example 206

4-(2-Ethylphenyl)-1,2-dihydro-N-(2-methoxybenzyl)-2-methyl-1-oxo-3-isoquinolinemethylamine hydrochloride A white powder NMR (200 MHz, CDCl$_3$) ppm: 0.98 (3H, t, J=7.5 Hz), 2.30 (2H, q, J=7.5 Hz), 3.40 (1H, d, J=13 Hz), 3.49 (1H, d, J=13 Hz), 3.65(2H, s), 3.78 (3H, s), 3.85 (3H, s), 6.73–6.88 (3H, m), 7.00–7.29 (4H, m), 7.33–7.48 (4H, m), 8.48 (1H, m)

Example 207

1,2-Dihydro-2,6,7-trimethyl-1-oxo-4-phenyl-3-isoquinolinemethyl 2-(2-methoxyphenyl)ethyl ether A mixture of 2-methoxyphenethyl alcohol (0.125 ml), sodium hydride (60% in oil) (50 mg) and DMF (5 ml) was stirred at room temperature for 30 minutes. After this mixture was cooled to 0° C., the compound (200 mg) obtained in Reference Example 52 was added, followed by stirring at room temperature for 30 minutes. After dilute hydrochloric acid was added, the mixture was extracted with ethyl acetate. The extract was washed with aqueous potassium carbonate and water and then dried, after which the solvent was distilled off. The residue was subjected to column chromatography using silica gel (hexane:ethyl acetate=3:2) to yield the title compound as colorless crystals (101 mg).

Melting point: 114°–115° C. (recrystallized from ethyl acetate-isopropyl ether) NMR (200 MHz, CDCl$_3$) ppm: 2.22 (3H, s), 2.38 (3H, s), 2.83 (2H, t, J=7.0 Hz), 3.53 (2H, t, J=7.0 Hz), 3.67 (3H, s), 3.76 (3H, s), 4.22 (2H, s), 6.78–6.92 (3H, m), 7.05–7.30 (4H, m), 7.38–7.50 (3H, m), 8.25 (1H, s) Elemental analysis (for C$_{28}$H$_{29}$NO$_3$): Calculated: C, 78.66; H, 6.84; N, 3.28 Found: C, 78.60; H, 6.91; N, 3.19

1(2H)-Isoquinolinone derivatives having respective corresponding substituents were reacted with alcohols in the same manner as in Example 207 to yield the compounds of Examples 208 to 216.

Example 208

1,2-Dihydro-2,6,7-trimethyl-1-oxo-4-phenyl-3-isoquinolinemethyl 3,5-dimethylbenzyl ether Melting point: 99°–100° C. (recrystallized from ethyl acetate-isopropyl ether) NMR (200 MHz, CDCl$_3$) ppm: 2.23 (3H, s), 2.28 (6H, s), 2.38 (3H, s), 3.78 (3H, s), 4.28 (2H, s), 4.30 (2H, s), 6.81 (1H, s), 6.84 (2H, s), 6.91 (1H, s), 7.25–7.35 (2H, m), 7.40–7.50 (3H, m), 8.26 (1H, s) Elemental analysis (for C$_{28}$H$_{29}$NO$_2$): Calculated: C, 81.72; H, 7.10; N, 3.40 Found: C, 81.64; H, 7.29; N, 3.25

Example 209

Benzyl 1,2-dihydro-2,6,7-trimethyl-1-oxo-4-phenyl-3-isoquinolinemethyl ether

Melting point: 127°–128° C. (recrystallized from ethyl acetate-isopropyl ether)

Example 210

1,2-Dihydro-2,6,7-trimethyl-1-oxo-4-phenyl-3-isoquinolinemethyl 2-methoxybenzyl ether Melting point: 105°–106° C. (recrystallized from ethyl acetate-isopropyl ether)

Example 211

3,5-Bis(trifluoromethyl)benzyl 1,2-dihydro-2-methyl-1-oxo-4-phenyl-3-isoquinolinemethyl ether Melting point: 133°–134° C. (recrystallized from ethyl acetate-isopropyl ether) NMR (200 MHz, CDCl$_3$) ppm: 3.83 (3H, s), 4.42 (2H, s), 4.48 (2H, s), 7.00–7.10 (1H, m), 7.20–7.30 (2H, m), 7.35–7.60 (5H, m), 7.67 (2H, s), 7.79 (1H, s), 8.45–8.60 (1H, m)

Example 212

3,5-Bis(trifluoromethyl)benzyl 1,2-dihydro-2-methyl-4-(2-methylphenyl)-1-oxo-3-isoquinoline methyl ether A colorless oily substance NMR (200 MHz, CDCl$_3$) ppm: 2.02 (3H, s), 3.85 (3H, s), 4.28 (1H, d, J=12 Hz), 4.45 (1H, d, J=12 Hz), 4.48 (2H, s), 6.85–7.00 (1H, m), 7.10–7.35 (4H, m), 7.45–7.55 (2H, m), 7.66 (2H, s), 7.79 (1H, s), 8.50–8.60 (1H, m)

Example 213

1,2-Dihydro-2-methyl-1-oxo-4-phenyl-3-isoquinolinemethyl 2-(2methoxyphenyl)ethyl ether Melting point: 145°–147° C., (recrystallized from ethyl acetate-isopropyl ether) NMR (200 MHz, CDCl$_3$) ppm: 2.83 (2H, t, J=6.8 Hz), 3.54 (2H, t, J=6.8 Hz), 3.68 (3H, s), 3.75 (3H, s), 4.25 (2H, s), 6.78–6.92 (2H, m), 7.04–7.30 (5H, m), 7.38–7.52 (5H, m), 8.46–8.54 (1H, m)

Example 214

1,2-Dihydro-2,6,7-trimethyl-1-oxo-4-phenyl-3-isoquinolinemethyl 4-methoxybenzyl ether Melting point: 123°–124° C. (recrystallized from ethyl acetate-isopropyl ether)

Example 215

2-(1,2-Dihydro-2,6,7-trimethyl-1-oxo-4-phenylisoquinoline-3-yl)ethyl 3,5-dimethylbenzyl ether Melting point: 150°–151° C. (recrystallized from ethyl-ether-hexane)

Example 216

3,5-Bis(trifluoromethyl)benzyl 4-(2-ethylphenyl)-1,2-dihydro-2-methyl- 1-oxo-3-isoquinolinemethyl ether A colorless oil NMR (200 MHz, CDCl$_3$) ppm: 0.99 (3H, t, J=7.7 Hz), 2.34 (2H, q, J=7.7 Hz), 3.82 (3H, s), 4.27 (1H, d, J=12 Hz), 4.45 (1H, d, J=12 Hz), 4.48 (2H, s) 6.93 (1H, m), 7.10–7.57 (6H, m), 7.67 (2H, s), 7.79 (1H, s), 8.51 (1H, m)

Example 217

3,5-Bis(trifluoromethyl)benzyl 1,2-dihydro-2-methyl-4-(2-methylphenyl)- 1-oxo-3-isoquinolinemethyl sulfide The compound obtained in Reference Example 68 was reacted with 3,5-bis(trifluoromethyl)benzyl bromide in DMF in the presence of sodium hydride by a method similar to Example 207 to yield the title compound as colorless crystals.

Melting point: 178°–179° C. (recrystallized from ethyl acetate-isopropyl ether)

Example 218

3,5-Bis(trifluoromethyl)benzyl 1,2-dihydro-2-methyl-4-(2-methylphenyl)- 1-oxo-3-isoquinolinemethyl sulfoxide A mixture of the compound obtained in Reference Example 217, m-chloroperbenzoic acid (purity 70%) (50 mg) and dichloromethane (20 ml) was stirred for 30 minutes with ice cooling. After evaporation of the solvent, the residue was dissolved in ethyl acetate, washed successively with water, diluted hydrochloric acid and aqueous sodium hydrogen carbonate, dried and evaporated. The residue was subjected to silica gel column chromatography (ethyl acetate) to yield the title compound as colorless crystals (60.3 mg).

Melting point: 173°–174° C. (recrystallized from ethyl acetate-isopropyl ether) NMR (200 MHz, $CDCl_3$) ppm: 1.97, 2.00 (total 3H, each s), 3.65–3.95 (4H, m), 3.80, 3.81 (total 3H, each s), 6.83 (1H, m), 7.10 (1H, m), 7.19–7.35 (3H, m), 7.45–7.55 (4H, m), 7.84 (1H, s), 8.50 (1H, m)

Example 219

N-Benzyl-1,2-dihydro-2,6,7-trimethyl-1-oxo-4-phenyl-3-isoquinolineacetamide 1,2-Dihydro-2,6,7-trimethyl-1-oxo-4-phenyl-3-isoquinolineacetic acid (Reference Example 56) and benzylamine were reacted (amidation) and treated in substantially the same manner as in Example 101 to yield the title compound as colorless crystals.

Melting point: 222°–222.5° C. (recrystallized from ethyl acetate-isopropyl ether) NMR (200 MHz, $CDCl_3$) ppm: 2.19 (3H, s), 2.34 (3H, s), 3.54 (2H, s), 3.66 (3H, s), 4.41 (2H, d, J=6.0 Hz), 5.87 (1H, bt), 6.68 (1H, s), 7.10–7.45 (10H, m), 8.18 (1H, s) Elemental analysis (for $C_{27}H_{26}N_2O_2 \cdot 0.1H_2O$): Calculated: C, 78.65; H, 6.40; N, 6.79 Found: C, 78.46; H, 6.40; N, 6.94

Isoquinolineacetic acid derivatives having respective corresponding substituents were reacted with amines in the same manner as in Example 219 to yield the compounds of Example 220 to 223.

Example 220

1,2-Dihydro-N-(4-methoxybenzyl)-2,6,7-trimethyl-1-oxo-4-phenyl-3-isoquinolineacetamide Melting point: 214°–215° C., (recrystallized from ethyl acetate-isopropyl ether)

Example 221

N-(2-Chlorobenzyl)-1,2-dihydro-N,2,6,7-tetramethyl-1-oxo-4-phenyl-3-isoquinolineacetamide Melting point: 191°–192° C. (recrystallized from ethyl acetate-isopropyl ether)

Example 222

N-[3,5-Bis(trifluoromethyl)benzyl]-6-chloro-1,2-dihydro-N,2-dimethyl-1-oxo-4-phenyl-3-isoquinolineacetamide Melting point: 156°–157° C. (recrystallized from ethyl acetate-hexane)

Example 223

N-[3,5-Bis(trifluoromethyl)phenyl]-6-chloro-1,2-dihydro-2-methyl-1-oxo-4-phenyl-3-isoquinolineacetamide Melting point: 288°–289° C. (recrystallized from methanol-ethyl acetate)

Example 224

N-[3,5-Bis(trifluoromethyl)phenyl]-1,2-dihydro-N,2-dimethyl-1-oxo-4-phenyl-3-isoquinolineacetamide A mixture of the compound obtained in Example 222 (250 mg), methanol (8 ml), THF (2 ml), 10% palladium-carbon (50% hydrated) (130 mg) and sodium acetate (60 mg) was stirred in a hydrogen atmosphere for 1 hour at room temperature. The catalyst was filtered off, and the filtrate was evaporated. The residue was dissolved in ethyl acetate, washed with water, dried and evaporated to yield the title compound as colorless crystals (160 mg).

Melting point: 198°–194° C. (recrystallized from ethyl acetate-isopropyl ether)

Example 225

N-[3,5-Bis(trifluoromethyl)benzyl]-2-carbamoylmethyl-1,2-dihydro-6,7-dimethyl-1-oxo-4-phenyl-3-isoquinolinecarboxamide To a solution of the compound (190 mg) obtained in Reference Example 59 in dichloromethane (10 ml) were added oxalyl chloride (0.052 ml) and DMF (one drop), followed by stirring at room temperature for 1 hour. After the solvent was distilled off, the residue was dissolved in dichloromethane (10 ml). To this solution was added a solution of 3,5-bis(trifluoromethyl)benzylamine (170 mg) and triethylamine (0.077 ml) in dichloromethane (5 ml), followed by stirring at room temperature for 5 hours. After the solvent was distilled off, ethyl acetate was added to the residue. This mixture was washed successively with water, dilute hydrochloric acid, water, aqueous sodium hydrogen carbonate and water and then dried, after which the solvent was distilled off. The residue was dissolved in methanol (5 ml), and 15% ammonia-methanol (10 ml) was added at room temperature, followed by stirring for 15 hours and then solvent removal by distillation, to yield the title compound as colorless crystals (125 mg).

Melting point: 235°–237° C. (recrystallized from methanol) Elemental analysis (for $C_{29}H_{23}N_3O_3F_6$): Calculated: C, 60.52; H, 4.03; N, 7.30 Found: C, 60.72; H, 4.11; N, 7.52

The compound obtained in Reference Example 59 and benzylamines having respective corresponding substituents were reacted and treated in the same manner as in Example 225 to yield the compounds of Examples 226 and 227.

Example 226

2-Carbamoylmethyl-1,2-dihydro-6,7-dimethyl-N-(3,5-dimethylbenzyl)-1-oxo-4-phenyl-3-isoquinolinecarboxamide Melting point: 253°–254° C. (recrystallized from ethanol)

Example 227

2-Carbamoylmethyl-1,2-dihydro-N-(2-methoxybenzyl)-6,7-dimethyl-1-oxo-4-phenyl-3-isoquinolinecarboxamide Melting point: 234.5°–236° C. (recrystallized from ethanol)

Example 228

1,2,3,4-Tetrahydro-2-(2-methoxybenzyl)-8,9-dimethyl-3,6-dioxo-11-phenyl-6H-pyrazino[1,2-b]isoquinoline To a solution of 2-ethoxycarbonylmethyl-1,2-dihydro-3-hydroxymethyl-6,7-dimethyl-1-oxo-4-phenylisoquinoline (Reference Example 51) (183 mg) in dichloromethane (10 ml) were added methanesulfonyl chloride (0.037 ml) and triethylamine (0.084 ml) with ice cooling, followed by stirring for 30 minutes. The reaction mixture was poured into water and extracted with dichloromethane. The extract was washed with water and then dried, after which the solvent was distilled off. The residue was mixed with 2-methoxybenzylamine (0.196 ml) and THF (5 ml), followed by heating at 130° C. in a sealed tube for 3 hours. The reaction mixture was poured into aqueous sodium hydrogen carbonate and extracted with ethyl acetate. The extract was washed with water and then dried, after which the solvent was distilled off. The residue was subjected to silica gel column chromatography (hexane:acetone=1:1) to yield the title compound as colorless crystals (110 mg).

Melting point: 211°–214° C. (recrystallized from ethyl acetate-hexane) NMR (200 MHz, CDCl$_3$) ppm: 2.22 (3H, s), 2.37 (3H, s), 3.54 (3H, s), 4.15 (2H, s), 4.60 (2H, s), 4.88 (2H, s), 6.76–6.98 (5H, m), 7.13–7.28 (2H, m), 7.36–7.42 (3H, m), 8.23 (1H, s) Elemental analysis (for C$_{28}$H$_{26}$N$_2$O$_3$): Calculated: C, 76.67; H, 5.97; N, 6.39 Found: C, 76.41; H, 6.05; N, 6.40

Example 229

1,2,3,4-Tetrahydro-1-(4-methoxybenzyloxy)-8,9-dimethyl-6-oxo-11-phenyl- 6H-benzo[b]quinolizine To a solution of the compound (160 mg) obtained in Reference Example 65 in DMF (5 ml) was added sodium hydride (60% in oil) (22 mg), followed by stirring at room temperature for 15 minutes. While ice cooling the solution, 4-methoxybenzyl chloride (0.075 ml) was added, followed by stirring at room temperature for 4 hours. The reaction mixture was poured into water and extracted with ethyl acetate. The extract was washed successively with dilute hydrochloric acid, water, aqueous sodium hydrogen carbonate and water and then dried, after which the solvent was distilled off. The residue was subjected to silica gel column chromatography (hexane:ethyl acetate=5:1) to yield the title compound as colorless crystals (170 mg).

Melting point: 145°–146° C. (recrystallized from ethyl ether-hexane) Elemental analysis (for C$_{29}$H$_{29}$NO$_3$): Calculated: C, 79.24; H, 6.65; N, 3.19 Found: C, 79.30; H, 6.85; N, 3.14

The compound obtained in Reference Example 65 and benzyl chlorides having respective corresponding substituents were reacted (alkylation) and treated in the same manner as in Example 229 to yield the compounds of Examples 230 to 232.

Example 230

1-Benzyloxy-1,2,3,4-tetrahydro-8,9-dimethyl-6-oxo-11-phenyl-6H-benzo[b]quinolizine Melting point: 133°–134° C. (recrystallized from ethyl ether-hexane)

Example 231

1-(3,5-Dimethylbenzyloxy)-1,2,3,4-tetrahydro-8,9-dimethyl-6-oxo-11-phenyl- 6H-benzo[b]quinolizine Melting point: 146°–147° C. (recrystallized from ethyl acetate-isopropyl ether)

Example 232

1,2,3,4-Tetrahydro-1-(2-methoxybenzyloxy)-8,9-dimethyl-6-oxo-11-phenyl- 6H-benzo[b]quinolizine Melting point: 186°–188° C. (recrystallized from ethyl acetate-isopropyl ether)

Example 233

1-(3,5-Dimethylbenzylamino)-1,2,3,4-tetrahydro-8,9-dimethyl-6-oxo-11-phenyl-6H-benzo[b]quinolizine hydrochloride A mixture of the compound (159 mg) obtained in Reference Example 64, acetic acid (0.03 ml), 3,5-dimethylbenzaldehyde (0.1 ml) and methanol (10 ml) was stirred at room temperature for 15 minutes. After sodium cyanoborohydride (60 mg) was added, the mixture was stirred at room temperature for 30 minutes. After the solvent was distilled off, aqueous sodium hydrogen carbonate was added, and the mixture was extracted with ethyl acetate. The extract was washed with water and then dried, after which the solvent was distilled off, to yield the free form of the title compound as a colorless oily substance. This compound was dissolved in ether (1 ml), and 4N HCl-ethyl acetate (3 ml) was added while ice cooling the solution, followed by solvent removal by distillation, to yield the title compound as colorless crystals (160 mg).

Melting point: 205°–208° C. (recrystallized from ethanol) NMR (200 MHz, CDCl$_3$) ppm: [free base] 1.55–2.05 (4H, m), 2.22 (3H, s), 2.25 (6H, s), 2.36 (3H, s), 3.20 (1H, d, J=12.4 Hz), 3.40 (1H, d, J=12.4 Hz), 3.91 (1H, bs), 4.30 (1H, m), 4.59 (1H, m), 6.70 (2H, s), 6.74 (1H, s), 6.83 (1H, s), 7.21–7.32 (2H, m), 7.48 (3H, m), 8.24 (1H, s) Elemental analysis (for C$_{30}$H$_{32}$N$_2$O.HCl.0.2H$_2$O): Calculated: C, 75.59; H, 7.06; N, 5.88 Found: C, 75.42; H, 7.29; N, 5.72

Example 234

1,2,3,4-Tetrahydro-8,9-dimethyl-1-[N-methyl-(3,5-dimethylbenzyl)amino]- 6-oxo-11-phenyl-6H-benzo[b]quinolizine The compound obtained in Example 233 and formalin were reacted and treated with sodium borohydride in the same manner as in Example 233 to yield the title compound as colorless crystals.

Melting point: 144°–145° C. (recrystallized from ethyl acetate-isopropyl ether)

Amine compounds having respective corresponding substituents and aldehydes were reacted and treated with sodium borohydride in the same manner as in Examples 233 and 234 to yield the compounds of Example 235 to 239 (free form or hydrochloride).

Example 235

1-[3,5-Bis(trifluoromethyl)benzylamino]-1,2,3,4-tetrahydro-8,9-dimethyl- 6-oxo-11-phenyl-6H-benzo[b]quinolizine Melting point: 189.5°–191.5° C. (recrystallized from isopropyl ether) NMR (200 MHz, CDCl$_3$) ppm: 1.70–2.00 (4H, m), 2.22 (3H, s), 2.38 (3H, s), 3.36 (1H, d, J=13.4 Hz), 3.56 (1H, d, J=13.4 Hz), 3.94 (1H, bs), 4.27 (1H, m), 4.56 (1H, m), 6.74 (1H, s), 7.25 (2H, m), 7.47 (3H, m), 7.57 (2H, s), 7.71 (1H, s), 8.25 (1H, s) Elemental analysis (for C$_{30}$H$_{26}$N$_2$OF$_6$): Calculated: C, 66.17; H, 4.81; N, 5.14 Found: C, 65.83; H, 4.79; N, 5.01

Example 236

1,2,3,4-Tetrahydro-8,9-dimethyl-1-[N-methyl-[3,5-bis(trifluoromethyl)benzyl]amino]- 6-oxo-11-phenyl-6H-benzo[b]quinolizine hydrochloride Melting point: 116°–119° C. (recrystallized from ethanol)

Example 237

1-(2-Chlorobenzylamino)-1,2,3,4-tetrahydro-8,9-dimethyl-6-oxo-11-phenyl- 6H-benzo[b]quinolizine hydrochloride Melting point: 201°–204° C. (recrystallized from ethanol)

Example 238

1,2,3,4-Tetrahydro-1-(2-methoxybenzylamino)-8,9-dimethyl-6-oxo-11-phenyl- 6H-benzo[b]quinoiizine hydrochloride Melting point: 211°–215° C. (recrystallized from methanol-ethanol)

Example 239

1,2,3,4-Tetrahydro-1-(2-methoxybenzylamino)-6-oxo-11-phenyl-6H-benzo[b]quinolizine Melting point: 135°–137° C. (recrystallized from ethyl acetate-isopropyl ether)

Example 240

N-[3,5-Bis(trifluoromethyl)benzyl]-1,2,3,4-tetrahydro-1,6-dioxo-11-phenyl- 6H-pyrazino[1,2-b]isoquinoline A solution of the compound obtained in Reference Example 66 (103 mg) in DMF (5 ml) was added sodium hydride (60% in oil) (16 mg), and the mixture was stirred for 30 minutes at room temperature, followed by addition of 3,5-bis(trifluoromethyl)benzyl bromide (74 µl) with ice cooling and the mixture was stirred for 1 hour at room temperature. Water was added to the mixture, which was extracted with ethyl acetate. The extract was washed with water, dried and evaporated to yield the title compound as colorless crystals (65 mg).

Melting point: 204°–206° C. (recrystallized from ethyl acetate-ethyl ether) NMR (200 MHz, CDCl$_3$) ppm: 3.63 (2H, m), 4.44 (2H, m), 4.78 (2H, s), 7.18–7.27 (3H, m), 7.44–7.66 (5H, m), 7.68 (2H, s), 7.82 (2H, s), 8.52 (1H, m)

Example 241

N-[3,5-Bis(trifluoromethyl)benzyl]-1,2,3,4-tetrahydro-1,6-dioxo-11-phenyl- 6H-pyrazino[1,2-b]isoquinoline A solution of the compound obtained in Reference Example 67 (140 mg) in DMF (5 ml) were added potassium carbonate (76 mg) and 3,5-bis(trifluoromethyl)benzyl bromide (111 pl), and the mixture was stirred for 30 minutes at 70°–80° C. Water was added to the mixture, which was extracted with ethyl acetate. The extract was washed with water, dried and evaporated to yield the title compound as colorless crystals (170 mg).

Melting point: 194°–196° C. (recrystallized from ethyl acetate)

Example 242

N-[3,5-Bis(trifluoromethyl)benzyl]-6-chloro-N-methyl-1-oxo-4-phenyl-1H-2-benzopyran-3-carboxamide 6-Chloro-1-oxo-4-phenyl-1H-2-benzopyran-3-carboxylic acid was reacted with N-[3,5-bis(trifluoromethyl)benzyl] methylamine by a method similar to Example 101 (amidation) to yield the title compound.

Melting point: 170°–171° C. (recrystallized from ethyl acetate-hexane) NMR (200 MHz, CDCl$_3$) ppm: 2.78 (3/5H, s), 2.91 (3x4/5H, s), 4.59 (2H, s), 7.18(1H, s), 7.27–7.57 (8H, m), 7.80(1H, s), 8.33 (1H, d, J=8.6 Hz)

The compounds of Example 243–247 were obtained from the 1-oxo-1H-2-benzopyran-3-carboxylic acids and amines, which have substituents corresponding to each Example, by a method similar to Example 242 (amidation).

Example 243

N-[3,5-Bis(trifluoromethyl)benzyl]-N-methyl-1-oxo-4-phenyl-1H-2-benzopyran- 3-carboxamide Melting point: 151°–152° C. (recrystallized from ethyl acetate-hexane) NMR (200 MHz, CDCl$_3$) ppm: 2.78 (3/5H, s), 2.92 (3×4/5H, s), 4.60 (2H, s), 7.22–7.75 (10H, m), 7.80 (1H, s), 8.39–8.43 (1H, m)

Example 244

N-[3,5-Bis(trifluoromethyl)benzyl]-4-(2-methoxyphenyl)-N-methyl-1-oxo- 1H-2-benzopyran-3-carboxamide Melting point: 153°–154° C. (recrystallized from ethyl acetate-hexane) NMR (200 MHz, CDCl$_3$) ppm: 2.91 (3/4H, s), 3.06 (3×3/4H, s), 3.56 (3/4H, s), 3.74 (3×3/4H, s), 4.42 (1H, d, J=14.6 Hz), 5.01 (1H, d, J=14.6 Hz), 6.95–7.80 (9H, m), 7.91 (1H, s), 8.48–8.53 (1H, m)

Example 245

N-[3,5-Bis(trifluoromethyl)benzyl]-4-(4-fluorophenyl)-1-oxo-1H-2-benzopyran- 3-carboxamide Melting point: 166°–167° C. (recrystallized from ethyl ether)

Example 246

N-[3,5-Bis(trifluoromethyl)benzyl]-4-(4-fluorophenyl)-N-methyl-1-oxo-1H-2-benzopyran-3-carboxamide Melting point: 132°–133° C. (recrystallized from ethyl ether-isopropyl ether) NMR (200 MHz, CDCl$_3$) ppm: 2.96 (3H, s), 4.61 (2H, s), 7.08 (1H, d, J=8.6 Hz), 7.13–7.22 (2H, m), 7.30 (1H, dd, J=7.2, 3.6 Hz), 7.32 (1H, m), 7.52 (2H, s), 7.58–7.76 (2H, m), 7.82 (1H, s), 8.41 (1H, dd, J=7.2, 1.2 Hz)

Example 247

N-[3,5-Bis(trifluoroethyl)benzyl]-N,6-dimethyl-1-oxo-4-phenyl-1H-2-benzopyran-3-carboxamide Melting point: 162°–163° C. (recrystallized from isopropyl ether-hexane) NMR (200 MHz, CDCl$_3$) ppm: 2.38, 2.39 (total 3H, each s), 2.77 (1/4×3H, s), 2.91 (3/4×3H, s), 4.58 (2H, s), 6.99 (1H, s), 7.25–7.42 (6H, m), 7.49 (2H, s) 7.78 (1H, s), 8.29 (1H, d, J=8.0 Hz)

Example 248

N-[3,5-Bis(trifluoromethyl)benzyl]-6-chloro-N-methyl-4-(2-methylphenyl)- 2-oxo-4H-1-benzopyran-3-carboxamide 6-Chloro-4-(2-methylphenyl)-2-oxo-2H-1-benzopyran-3-carboxylic acid was reacted with N-[3,5-bis(trifluoromethyl)benzyl]methylamine by a method similar to Example 101 (amidation) to yield the title compound.

Melting point: 148°–149° C. (recrystallized from ethyl acetate-hexane) NMR (200 MHz, CDCl$_3$) ppm: 2.08 (1H, s), 2.20 (2H, s), 2.86 (1H, s), 3.00 (2H, s), 4.37 (1H, d, J=15.2 Hz), 4.88 (2/3H, d, J=15.2 Hz), 4.92 (1/3H, d, J=15.2 Hz), 6.89–7.56 (9H, m), 7.76 (1H, s)

The compounds of Example 249–253 were obtained from the 2-oxo-2H-1-benzopyran-3-carboxylic acids and amines, which have substituents corresponding to each Example, by a method similar to Example 248 (amidation).

Example 249

N-[3,5-Bis(trifluoromethyl)benzyl]-6-chloro-N-methyl-2-oxo-4-phenyl- 2H-1-benzopyran-3-carboxamide Melting point: 172°–173° C. (recrystallized from ethyl acetate-isopropyl ether) NMR (200 MHz, CDCl$_3$) ppm: 2.74 (0.57H, s), 2.85 (2.43H, s), 4.18 (0.19H, d, J=15.6 Hz), 4.40 (0.81H, d, J=15.4 Hz), 4.63 (0.19H, d, J=16.2 Hz), 4.88 (0.81H, d, J=15.0 Hz), 7.12–7.70 (10H, m), 7.78 (1H, s)

Example 250

N-[3,5-Bis(trifluoromethyl)benzyl]-N-methyl-2-oxo-4-phenyl-2H-1-benzopyran- 3-carboxamide Melting point: 146°–147° C. (recrystallized from ethyl acetate hexane) NMR (200 MHz, CDCl$_3$) ppm: 2.74 (3/5H, s), 2.86 (3×4/5H, s), 4.22 (1/5H, d, J=15.6 Hz), 4.39 (4/5H, d, J=15.2 Hz), 4.69 (1/5H, d, J=15.6 Hz), 4.91 (4/5H, d, J=15.2 Hz), 7.14–7.70 (11H, m), 7.78 (1H, s)

Example 251

N-[3,5-Bis(trifluoromethyl)benzyl]-6-chloro-4-(2-methoxyphenyl)-N-methyl- 2-oxo-2H-1-benzopyran-3-carboxamide Melting point: 121°–122° C. (recrystallized from isopropyl ether-ethyl acetate) NMR (200 MHz, CDCl$_3$) ppm: 2.85 (3H, s), 3.63 (3H, s), 4.29 (1H, d, J=15.4 Hz), 4.98 (1H, d, J=15.0 Hz), 6.90–7.09 (3H, m), 7.30–7.64 (6H, m), 7.77 (1H, s)

Example 252

N-[3,5-Bis(trifluoromethyl)benzyl]-6-chloro-N-methyl-2-oxo-4-(2-trifluoromethylphenyl)- 2H-1-benzopyran-3-carboxamide Melting point: 206°–207° C. (recrystallized from ethyl acetate) NMR (200 MHz, CDCl$_3$) ppm: 2.92 (3H, s), 4.33 (1H, d, J=15.2Hz), 4.92 (1H, d, J=15.4 Hz), 6.77 (1H, d, J=2.2 Hz), 7.38 (1H, d, J=8.8 Hz), 7.46–7.58 (3H, m), 7.60–7.88 (5H, m)

Example 253

6-Chloro-N-(2,6-dimethoxybenzyl)-4-(2-methyl phenyl)-2-oxo-2H-1-benzopyran-3-carboxamide Melting point: 190°–191° C. (recrystallized from ethanol)

Example 254

N-[3,5-Bis(trifluoromethyl)benzyl]-N-methyl-4-(2-methyl phenyl)-2-oxo- 2H-1-benzopyran-3-carboxamide The compound obtained in Reference 248 was reacted by a method similar to Example 224 (catalytic reduction) to yield the title compound.

Melting point: 130°–131° C. (recrystallized from ethyl acetate-hexane) NMR (200 MHz, CDCl$_3$) ppm: 2.07 (1H, s), 2.22 (2H, s), 2.87 (1H, s), 3.01 (2H, s), 4.36 (1H, d, J=15.2 Hz), 4.90 (2/3H, d, J=15.2 Hz), 4.95 (1/3H, d, J=15.2 Hz), 6.92–7.57 (10H, m), 7.76(1H, s)

The compounds of Example 255 and 256 were obtained from the compounds of Example 251 and 252, respectively, by a method similar to Example 254.

Example 255

N-[3,5-Bis(trifluoromethyl)benzyl]-4-(2-methoxyphenyl)-N-methyl-2-oxo- 2H-1-benzopyran-3-carboxamide Melting point: 140°–142° C. (recrystallized from isopropyl ether-ethyl acetate) NMR (200 MHz, CDCl$_3$) ppm: 2.87 (3H, s), 3.61 (3H, s), 4.28 (1H, d, J=15.2 Hz), 5.01 (1H, d, J=15.2Hz), 6.85–7.22 (4H, m), 7.30–7.62 (6H, m), 7.77 (1H, s)

Example 256

N-[3,5-Bis(trifluoromethyl)benzyl]-N-methyl-2-oxo-4-(2trifluoromethylphenyl)- 2H-1-benzopyran-3-carboxamide Melting point: 135°–137° C. (recrystallized from isopropyl ether-ethyl acetate) NMR (200 MHz, CDCl$_3$) ppm: 2.94 (3H, s), 4.33 (1H, d, J=15.4 Hz), 4.95 (1H, d, J=15.0 Hz), 6.84 (1H, dd, J=1.4, 8.0 Hz), 7.20 (1H, dr, J=1.4, 7.2 Hz), 7.43 (1H, dd, J=1.0, 8.4 Hz), 7.52–7.82 (8H, m)

Example 257

N-[3,5-Bis(trifluoromethyl)benzyl]-1,2-dihydro-2-oxo-4-phenyl-3-quinolinecarboxamide 1,2-Dihydro-2-oxo-4-phenyl-3-quinolinecarboxylic acid was reacted with 3,5-bis(trifluoromethyl)benzylamine by a method similar to Example 101 (amidation) to yield the title compound.

Melting point: 251°–252° C. (recrystallized from ethyl acetate-isopropyl ether)

The compounds of Example 258–263 were obtained from the 1,2-dihydro- 2-oxo-3-quinolinecarboxylic acids and amines, which have substituents corresponding to each Example, by a method similar to Example 257 (amidation).

Example 258

N-[3,5-Bis(trifluoromethyl)benzyl]-1,2-dihydro-N-methyl-2-oxo-4-phenyl- 3-quinolinecarboxamide Melting point: 262°–264° C. (recrystallized from ethyl acetate hexane) NMR (200 MHz, CDCl$_3$) ppm: 2.87 (3H, s), 4.61 (1H, d, J=15 Hz), 4.75 (1H, d, J=15 Hz), 7.10–7.60 (9H, m), 7.66 (2H, s), 7.78 (1H, s), 12.44 (1H, bs)

Example 259

N-[3,5-Bis(trifluoromethyl)benzyl]-1,2-dihydro-1-methyl-2-oxo-4-phenyl- 3-quinolinecarboxamide Melting point: 191°–192° C. (recrystallized from ethyl acetate-isopropyl ether)

Example 260

N-[3,5-Bis(trifluoromethyl)benzyl]-1,2-dihydro-N,1-dimethyl-2-oxo-4-phenyl- 3-quinolinecarboxamide Melting point: 163°–164° C. (recrystallized from ethyl ether-hexane) NMR (200 MHz, CDCl$_3$) ppm: 2.83 (3H, s), 3.83 (3H, s), 4.29 (1H, d, J=15 Hz), 5.00 (1H, d, J=15 Hz), 7.16 (2H, m), 7.24–7.70 (9H, m), 7.75 (1H, s)

Example 261

N-[3,5-Bis(trifluoromethyl)benzyl]-4-(2-chlorophenyl)-1,2-dihydro-1-methyl- 2-oxo-3-quinolinecarboxamide A white form NMR (200 MHz, CDCl$_3$) ppm: 3.87 (3H, s), 4.54 (1H, dd, J=16, 5.6 Hz), 4.69 (1H, dd, J=16, 6.5 Hz), 7.05–7.53 (7H, m), 7.68 (1H, m), 7.69 (2H, s), 7.73 (1H, s), 9.17 (1H, bs)

Example 262

N-[3,5-Bis(trifluoromethyl)benzyl]-4-(2-chlorophenyl)-1,2-dihydro-N,1-dimethyl- 2-oxo-3-quinolinecarboxamide Melting point: 189°–190° C. (recrystallized from ethyl acetate-hexane) NMR (200 MHz, CDCl$_3$) ppm: 2.94 (3H, s), 3.84 (3H, s), 4.25 (1H, d, J=15 Hz), 5.08 (1H, d, J=15 Hz), 7.03–7.23 (2H, m), 7.32–7.65 (8H, m), 7.75 (1H, s)

Example 263

N-[3,5-Bis(trifluoromethyl)benzyl]-4-(2-chlorophenyl)-1,2-dihydro-N,1,6-trimethyl-2-oxo-3-quinolinecarboxamide Melting point: 226°–227° C. (recrystallized from ethyl acetate-isopropyl ether)

Example 264

N-[3,5-Bis(trifluoromethyl)benzyl]-6-chloro-N-methyl-4-phenyl-3-quinolinecarboxamide 6-Chloro-4-phenylquinolin-3-carboxylic acid was reacted with N-[3,5-bis(trifluoromethyl)benzyl]methylamine by a method similar to Example 101 (amidation) to yield the title compound.

Melting point: 105°–106° C. (recrystallized from ethyl acetate-hexane) NMR (200 MHz, CDCl$_3$) ppm: 2.60 (3×4/5H, s), 2.81 (3/5H, s), 4.0–5.2 (2H, b), 7.29–7.81 (10H, m), 8.16 (1H, d, J=8.8 Hz), 8.91 (1H,s)

Example 265

N-[3,5-Bis(trifluoromethyl)benzyl]-N-methyl-4-phenyl-3-quinolinecarboxamide

The compound obtained in Example 264 was reacted by a method similar to Example 224 (catalytic reduction) to yield the title compound.

Melting point: 96°–97° C. (recrystallized from ethyl acetate-hexane) NMR (200 MHz, CDCl$_3$) ppm: 2.61 (3×6/7H, s), 2.81 (3/7H, s), 4.0–5.2 (2H, b), 7.28–7.83 (11H, m), 8.22 (1H, d, J=8.8 Hz), 8.93 (1H, s)

The compounds of Example 266–268 were obtained from the quinoline-3-carboxylic acids and amines, which have substituents corresponding to each Example, by a method similar to Example 264 (amidation)

Example 266

N-[3,5-Bis(trifluoromethyl)benzyl]-2-methyl-4-phenyl-3-quinolinecarboxamide

Melting point: 191°–192° C. (recrystallized from ethyl ether-hexane)

Example 267

N-[3,5-Bis(trifluoromethyl)benzyl]-N,2-dimethyl-4-phenyl-3-quinolinecarboxamide

Melting point: 146°–147° C. (recrystallized from ethyl ether-hexane) NMR (200 MHz, CDCl$_3$) ppm: 2.61 (3H, s), 2.74 (3H, s), 4.42 (1H, d, J=15 Hz), 4.77 (1H, d, J=15 Hz), 7.20–7.85 (11H, m), 8.09 (1H, d, J=8.8 Hz)

Example 268

N-[3,5-Bis(trifluoromethyl)benzyl]-2,6,7-trimethoxy-N-methyl-4-phenyl- 3-quinolinecarboxamide Melting point: 88°–89° C. (recrystallized from isopropyl ether-hexane)

Example 269

N-[3,5-Bis(trifluoromethyl)benzyl]-2-chloro-N-methyl-4-phenyl-3-quinolinecarboxamide A mixture of the compound obtained in Example 258 (2.55 g) and phosphorus oxychloride (60 ml) was stirred for 2 hours with heating under reflux. The solvent was evaporated and the residue was dissolved in ethyl acetate. The solution was washed with cooled aqueous sodium hydrogen carbonate and water, dried and evaporated to yield the title compound as colorless crystals (2.45 g).

Melting point: 147°–148° C. (recrystallized from ether acetate-isopropyl ether) NMR (200 MHz, CDCl$_3$) ppm: 2.71 (3H, s), 4.54 (1H, d, J=14.9 Hz), 4.71 (1H, d, J=14.9 Hz), 7.20–8.13 (h, m), 8.11 (1H, d, J=8.4 Hz)

Example 270

N-[3,5-Bis(trifluoromethyl)benzyl]-2-methoxy-N-methyl-4-phenyl-3-quinolinecarboxamide To a solution of the compound obtained in Example 269 (100 mg) in methanol (2 ml) was added 28% NaOMe-methanol (2 ml), and the mixture was stirred for 3 hours with heating under reflux. The solvent was evaporated and the residue was dissolved in ethyl acetate. The solution was washed with water, dried and evaporated to yield the title compound as colorless crystals (85 mg).

Melting point: 146°–147° C. (recrystallized from ether acetate-hexane) NMR (200 MHz, CDCl$_3$) ppm: 2.70 (2H, s), 2.72 (1H, s), 3.82 (1/3H, d, J=15.7 Hz), 4.15 (1H, s), 4.18 (2H, s), 4.39 (2/3H, d, J=15 Hz), 4.62 (1/3H, d, J=15.7 Hz), 4.89 (2/3H, d, J=15.6 Hz), 17.7–7.95 (12H, m)

Example 271

N-[3,5-Bis(trifluoromethyl)benzyl]-N-methyl-2-methylamino-4-phenyl- 3-quinolinecarboxamide To a solution of the compound obtained in Example 269 (100 mg) in ethanol (4 ml) was added 40% MeNH$_2$-methanol (12 ml), and the mixture was stirred for 4 hours with heating under reflux. The solvent was evaporated and the residue was dissolved in ethyl acetate. The solution was washed with water, dried and evaporated to yield the title compound as colorless crystals (65 mg).

Melting point: 173°–174° C. (recrystallized from ethyl acetate-hexane) NMR (200 MHz, CDCl$_3$) ppm: 2.57 (2H, s), 2.62 (1H, s), 3.13 (2H, d, J=4.8 Hz), 3.14 (1H, d, J=5 Hz), 3.52 (1/3H, d, J=15.SHz), 4.39 (2/3H, d, J=14.5 Hz), 4.60 (1/3H, d, J=15.8 Hz), 4.69 (2/3H, d, J=14.5 Hz), 5.14 (2/3H, b), 5.32 (1/3H, b), 7.12–7.85 (12H, m)

Example 272

N-[3,5-Bis(trifluoromethyl)benzyl]-N-methyl-2-methylthio-4-phenyl-3-quinolinecarboxamide To a solution of the compound obtained in Example 269 (100 mg) in THF (6 ml)-methanol (2 ml) was added 15% MeSNa in water (4 ml), and the mixture was stirred for 8 hours with heating under reflux. The solvent was evaporated and the residue was dissolved in ethyl acetate. The solution was washed with water, dried and evaporated to yield the title compound as colorless crystals (55 mg).

Melting point: 144°–145° C. (recrystallized from ethyl acetate-hexane) NMR (200 MHz, CDCl$_3$) ppm: 2.65 (3H, s), 2.77 (3H, s), 4.50 (1H, d, J=15 HZ), 4.70 (1H, d, J=15 Hz), 7.29–8.05 (12H, m)

Example 273

N-[3,5-Bis(trifluoromethyl)benzyl]-1-chloro-4-(4-fluorophenyl)-N-methyl- 3-isoquinolinecarboxamide The compound obtained in Example 178 (200 mg) was reacted with phosphorus oxychloride (3 ml) by a method similar to Example 269 to yield the title compound as colorless crystals (165 mg).

Melting point: 142°–143° C. (recrystallized from ethyl acetate-isopropyl ether) NMR (200 MHz, CDCl$_3$) ppm: 2.79 (2H, s), 2.86 (1H, s), 4.43 (2/3H, s), 4.69 (4/3H, s), 7.06–7.81 (10H, m), 8.44–8.49 (1H, m)

Example 274

N-[3,5-Bis(trifluoromethyl)benzyl]-4-(4-fluorophenyl)-N-methyl-3-isoquinolinecarboxamide The compound obtained in Example 273 was reacted by a method similar to Example 224 (catalytic reduction) to yield the title compound as colorless crystals.

Melting point: 134°–135° C., (recrystallized from ethyl acetate-isopropyl ether) NMR (200 MHz, CDCl$_3$) ppm: 2.76 (3×5/7H, s), 2.85 (3×2/7H, s), 4.39 (2×2/7, s), 4.71 (2×5/7H, s), 7.07–7.81 (10H, m), 8.07–8.12 (1H, m), 9.28 (2/7H, s), 9.32 (5/7H, s)

Example 275

N-[3,5-Bis(trifluoromethyl)benzyl]-1-chloro-N-methyl-4-phenyl-3-isoquinolinecarboxamide The compound obtained in Example 172 was reacted with phosphorus oxychloride by a method similar to Example 269 to yield the title compound as colorless crystals.

Melting point: 176°–177° C. (recrystallized from ethyl acetate-hexane),. NMR (200 MHz, CDCl$_3$) ppm: 2.75 (3×3/4H, s), 2.82 (3/411, s), 4.42 (1/2H, s), 4.67 (3/2H, s), 7.30–7.83 (11H, m), 8.46 (1H, m)

Example 276

N-[3,5-Bis(trifluoromethyl)benzyl]-N-methyl-4-phenyl-3-isoquinolinecarboxamide

The compound obtained in Example 275 was reacted by a method similar to Example 224 (catalytic reduction) to yield the title compound as colorless crystals.

Melting point: 139°–140° C. (recrystallized from hexane) NMR (200 MHz, CDCl$_3$) ppm: 2.73 (3×3/4H, s), 2.82 (3/411H, s), 4.36 (1/2H, s), 4.70 (3/2H, s), 7.33–7.82 (11H, m), 8.10 (1H, m), 9.32 (1H, m)

Example 277

N-[3,5-Bis(trifluoromethyl)benzyl]-1-methoxy-N-methyl-4-phenyl-3-isoquinolinecarboxamide The compound obtained in Example 275 was reacted with sodium methoxide by a method similar to Example 270 to yield the title compound as colorless crystals.

Melting point: 129°–130° C. (recrystallized from isopropyl ether-hexane) NMR (200 MHz, CDCl$_3$) ppm: 2.75, 2.77 (total 3H, each s), 4.07 (2/5×3H, s), 4.19 (3/5×3H, s), 4.36 (2/5×2H, s), 4.68(3/5×2H, s), 7.28–7.70 (9H, m), 7.78 (2H, m), 8.31 (1H, m)

Example 278

N-[3,5-Bis(trifluoromethyl)benzyl]-N-methyl-1-methylamino-4-phenyl- 3-isoquinolinecarboxamide The compound obtained in Example 275 was reacted with methylamine by a method similar to Example 271 to yield the title compound as colorless crystals.

Melting point: 213°–214° C. (recrystallized from ethyl acetate-isopropyl ether) NMR (200 MHz, CDCl$_3$) ppm: 2.74, 2.77 (total 3H, each s), 3.11 (3/7×3H, d, J=5.0 Hz), 3.22 (4/7×3H, d, J=4.8 Hz), 4.39 (3/7×2H, s), 4.68 (4/7×2H, s), 5.44 (1H, m), 7.33–7.67 (10H, m), 7.79 (2H, bs)

Example 279

3,4-cis-N-[3,5-Bis(trifluoromethyl)benzyl]-1,2,3,4-tetrahydro-N-2-dimethyl- 1-oxo-4-phenyl-3-isoquinolinecarboxamide 3,4-cis-1,2,3,4-Tetrahydro-2-methyl-1-oxo-4-phenyl-3-isoquinolinecarboxlic acid [prepared from 2-methyl-4-phenyl-1(2H)-isoquinolinone-3-carboxylic acid methyl ester, by converting to the reduced compound (3,4-cis) by stirring for 6 hours at 90° C. in the presence of 10% palladium-carbon in acetic acid in a hydrogen atmosphere, followed by hydrolysis in hydrochloric acid-acetic acid at 110° C.] was reacted with N-[3,5-bis(trifluoromethyl)benzyl]methylamine by a method similar to Example 101 to yield the title compound.

Melting point: 226°–227° C. (recrystallized from ethyl acetate-ethyl ether)

Example 280

3,4-trans-N-[3,5-Bis(trifluoromethyl)benzyl]-4-(4-fluorophenyl)-1,2,3,4-tetrahydro-N,2-dimethyl-1-oxo-3-isoquinolinecarboxamide The compound obtained in Reference Example 2 was reacted with N-[3,5-bis(trifluoromethyl)benzyl]methylamine by a method similar to Example 101 to yield the title compound.

Melting point: 171°–172° C. (recrystallized from ethyl acetate-isopropyl ether)

Example 281

3,4-cis-N-[3,5-Bis(trifluoromethyl)benzyl]-3,4-dihydro-N-methyl-1-oxo-4-phenyl-1H-2-benzopyran-3-carboxamide 3,4-cis-3,4-Dihydro-1-oxo-4-phenyl-1H-2-benzopyran-3-carboxylic acid [prepared from 1-oxo-4-phenyl-1H-2-benzopyran-3-carboxylic acid by stirring for 4 hours at 90° C. in the presence of 10% palladium-carbon in acetic acid in a hydrogen atmosphere] was reacted with N-[3,5-bis(trifluoromethyl)benzyl]methylamine by a method similar to Example 101 to yield the title compound.

Melting point: 160°–161° C. (recrystallized from ethyl acetate-isopropyl ether)

Example 282

N-[3,5-Bis(trifluoromethyl)benzyl]-1,2-dihydro-N-methyl-1-oxo-4-phenyl- 2-[2-(N,N,N-trimethylammonium)ethyl]-3-isoquinolinecarboxamide A solution of the compound obtained in Example 184 (free form) (65 mg) in methanol (2 ml) was added methyl iodide (0.5 ml), and the mixture was stirred at room temperature for 1.5 hours. Evaporation of the solvent yielded the title compound as colorless crystals (72 mg).

Melting point: 242°–243° C. (recrystallized from methanol-dichloromethaneethyl ether) NMR (200 MHz, CDCl$_3$) ppm: 3.02 (3H, s), 3.65 (9H, s), 3.70–4.05 (2H, b), 4.34 (1H, d, J=14.2 Hz), 4.52–4.80 (1H, b), 4.90–5.15 (1H, b), 5.42 (1H, d, J=14.2 Hz), 7.05–7.30 (6H, m), 7.42 (2H, s), 7.58 (2H, m), 7.76 (1H, s), 8.44 (1H, m)

Example 283

N-[3,5-Bis(trifluoromethyl)phenyl]-6-chloro-1,2-dihydro-N-methyl-1-oxo- 4-phenyl-3-isoquinolineacetamide The compound obtained Example 223 was reacted by a method similar to Example 102(C) to yield the title compound.

Melting point: 181°–182° C. (recrystallized from ethyl acetate-isopropyl ether) NMR (200 MHz, CDCl$_3$) ppm: 2.51 (2H, b), 3.30 (3H, s), 3.67 (3H, s), 6.92 (1H, bd, J=1.8 Hz), 7.10–7.65 (8H, m), 7.76 (1H, bs), 8.44 (1H, d, J=8.6 Hz)

Example 284

3,5-Bis(trifluoromethyl)benzyl 1,2-dihydro-2-methyl-1-oxo-4-phenyl-3-isoquinolinecarboxylate A mixture of 2-methyl-4-phenyl-1(2H)-isoquinolinone-3-carboxylic acid (140 mg), acetone (5 ml), DMF (1 ml), potassium carbonate (70 mg) and 3,5-bis(trifluoromethyl)benzyl bromide (0.11 ml) was stirred with heating under reflux for 1 hour, and then concentrated. To the concentrate

Example 285

N-[3,5-Bis(trifluoromethyl)benzyl]-1,2-dihydro-N,2-dimethyl-4-phenyl-1-thioxo-3-isoquinolinecarboxamide A mixture of the compound obtained in Example 157 (52 mg), dioxane (3 ml) and phosphorus pentasulfide (44 mg) was refluxed for 4 hours. To the mixture was added water, and extracted with ethyl acetate. The extract was washed with aqueous sodium hydrogen carbonate and water, dried and evaporated. The residue was purified by silica gel column chromatography to yield the titdle compound as colorless crystals (35 mg).

Melting point: 145°–147° C. (recrystallized from ethyl acetate-hexane) NMR (200 MHz, CDCl$_3$) ppm: 2.79 (3H, s), 4.13 (3H, s), 4.24 (1H, d, J=14.6 Hz), 4.80 (1H, d, J=14.6 Hz), 7.16–7.39 (6H, m), 7.51 (2H, s), 7.60 (2H, m), 7.81 (1H, s), 9.23 (1H, m)

The compounds of Example 286 to 289 were obtained using the corresponding 2-oxo-2H-1-benzopyran-3-acetic acids and anilides by a method similar to Example 1(A).

Example 286

N-[2,6-Bis(2,2,2-trifluoroethoxy)phenyl]-6-chloro-4-(2-methylphenyl)-2-oxo-2H-1-benzopyran-3-acetamide Melting point: 214°–216° C. (recrystallized from isopropyl ether-ethyl acetate) NMR (200 MHz, CDCl$_3$) ppm: 2.07 (3H, s), 3.34 (1H, d, J=14.0 Hz), 3.54 (1H, d, J=13.6 Hz), 4.33 (4H, q, J=8.2 Hz), 6.67 (2H, d, J=8.4 Hz), 6.85 (1H, J=2.2 Hz), 7.17 (1H, d, J=8.4 Hz), 7.23–7.51 (6H, m), 7.60 (1H, bs)

Example 287

6-Chloro-4-(2-methylphenyl)-2-oxo-N-(2,4,6-trifluolophenyl)-2H-1-benzopyran-3-acetamide Melting point: 225°–227° C. (recrystallized from isopropyl ether-ethyl acetate) NMR (200 MHz, CDCl$_3$) ppm: 2.08 (3H, s), 3.38 (1H, d, J=13.6 Hz), 3.54 (1H, d, J=14.2 Hz), 6.70 (2H, ddd, J=1.2, 8.6, 8.6 Hz), 6.87 (1H, d, J=2.4 Hz), 7.10–7.19 (1H, m), 7.33–7.53 (8H, m), 7.65 (1H, bs)

Example 288

6-Chloro-2-oxo-4-(2-trifluoromethylphenyl)-N-(2,4,6-trifluolophenyl)-2H-1-benzopyran-3-acetamide Melting point: 247°–249° C. (recrystallized from ethyl acetate) NMR (200 MHz, CDCl$_3$) ppm: 3.10 (1H, d, J=14.4 Hz), 3.73 (1H, d, J=14.2 Hz), 6.65–6.76 (3H, m), 7.34–7.50 (3H, m), 7.59 (1H, bs), 7.62–7.80 (2H, m), 7.90 (1H, dd, J=1.6, 7.0 Hz)

Example 289

N-[2,6-Bis(2,2,2,-trifluoroethoxy)phenyl]-6-chloro-4-(2-methoxyphenyl)-2-oxo-2H-1-benzopyran-3-acetamide Melting point: 243°–245° C. (recrystallized from ethyl acetate) NMR (200 MHz, CDCl$_3$) ppm: 3.35 (1H, d, J=14.0 Hz), 3.63 (1H, d, J=14.2 Hz), 3.70 (3H, s), 4.22–4.38 (4H, m), 6.69 (2H, d, J=8.4 Hz), 6.94 (1H, d, J=2.2 Hz), 7.08 (1H, d, J=8.6 Hz), 7.13–7.35 (4H, m), 7.42–7.58 (2H, m), 7.63 (1H, bs)

was added water, and the mixture was extracted with ethyl acetate. The extract was washed with water, dried, and evaporated to yield the title compound as colorless crystals (185 mg).

Melting point: 153°–154° C. (recrystallized from methanol-ethyl ether)

Reference Example 1

4-(2-Chlorophenyl)-6,7-dimethyl-2-(1-methylethyloxy)-3-quinolinecarboxylic acid

Process 1

To a solution of 4-(2-chlorophenyl)-1,2-dihydro-6,7-dimethyl-2-oxo-3-quinolinecarboxylic acid ethyl ester (2.0 g) in DMF (20 ml) was added sodium hydride (60% in oil) (270 mg), followed by stirring at room temperature for 30 minutes. To this solution was added isopropyl iodide (0.9 ml), followed by stirring at 70° C. for 5 hours. After the mixture was cooled, ethyl acetate was added, and this mixture was washed successively with dilute hydrochloric acid, aqueous potassium carbonate and water and then dried, after which the solvent was distilled off. The residue was subjected to silica gel column chromatography (hexane:ethyl acetate= 5:1), to yield 4-(2-chlorophenyl)-6,7-dimethyl-2-(1-methylethyloxy)-3-quinolinecarboxylic acid ethyl ester as colorless crystals (1.72 g).

Melting point: 96°–97° C. (recrystallized from ethyl ether-hexane) NMR (200 MHz, CDCl$_3$) ppm: 1.01 (3H, t, J=7.1 Hz), 1.42 (6H, d, J=6.2 Hz), 2.26 (3H, s), 2.41 (3H, s), 4.00–4.16 (2H, m), 5.57 (1H, m), 6.92 (1H, s), 7.20–7.55 (4H, m), 7.64 (1H, s) Elemental analysis (for C$_{23}$H$_{24}$NO$_3$Cl): Calculated (%): C, 69.43; H, 6.08; N, 3.52 Found (%): C, 69.19; H, 5.99; N, 3.40

Process 2

To the compound obtained in Process 1 (1.64 g) were added ethanol (28 ml), water (7 ml) and potassium hydroxide (1.09 g), followed by heating under reflux for 1 hour. After the solvent was distilled off, the residue was acidified with dilute hydrochloric acid and then extracted with ethyl acetate. The extract was washed with saturated aqueous sodium chloride and dried, after which the solvent was distilled off, to yield the title compound as colorless crystals (1.31 g).

Melting point: 184°–186° C. (recrystallized from ethyl acetate-hexane) NMR (200 MHz, CDCl$_3$) ppm: 1.49 (6H, d, J=6.2 Hz), 2.26 (3H, s), 2.43 (3H, s), 5.73 (1H, m), 6.92 (1H, s), 7.10–7.60 (4H, m), 7.66 (1H, s) Elemental analysis (for C$_{21}$H$_{20}$NO$_3$Cl): Calculated (%): C, 68.20; H, 5.45; N, 3.79 Found (%): C, 68.23; H, 5.47; N, 3.78

Reference Example 2

3,4-trans-4-(4-Fluorophenyl)-1,2,3,4-tetrahydro-2-methyl-1-oxo-3-isoquinolinecarboxy acid

Process 1

A mixture of 2-(4-fluorobenzoyl)benzoic acid (3.00 g), 1-hydroxybenzotriazole (2.07 g), 1,3-dicyclohexylcarbodiimide (3.00 g) and anhydrous THF (50 ml) was stirred at room temperature for 1 hour. To this mixture were added N-methylglycine ethyl ester hydrochloride (2.84 g) and triethylamine (2.58 ml), followed by stirring at room temperature for 16 hours and with heating and refluxing for 4 hours. After the solvent was distilled off, ethyl acetate was added to the residue, and the insoluble crystals were separated by filtration. The filtrate was washed successively with water, aqueous sodium hydrogen carbonate, water, dilute hydrochloric acid and water and then dried, after which the solvent was distilled off, to yield N-[2-(4-fluorobenzoyl)benzoyl]-N-methylglycine ethyl ester as a colorless oily substance (4.2 g).

[NMR (200 MHz, CDCl$_3$) ppm: 1.27, 1.30 (total 3H, each t, J=7.0 Hz), 3.01, 3.06 (total 3H, each s), 4.01, 4.17 (total 2H, each s), 4.15–4.20 (2H, m), 7.0– 7.9 (8H, m)]

To a solution of this oily substance in toluene (100 ml) was added 1,8-diazabicyclo[5.4.0]undec-7-en (3.0 ml), followed by heating under reflux for 2 hours. After the solvent was distilled off, ethyl acetate was added to the residue. This mixture was washed successively with water, 10% aqueous potassium hydrogen sulfate and water and then dried, after which the solvent was distilled off, to yield 4-(4-fluorophenyl)-3,4-dihydro-4-hydroxy-2-methyl-1(2H)-isoquinoline-3-carboxylic acid ethyl ester as colorless crystals. To a suspension of the crystals in toluene (100 ml) was added p-toluenesulfonic acid hydrate (3.0 g), followed by heating under reflux for 14 hours with a water separator. The solvent was distilled off, and ethyl acetate was added to the residue. This mixture was washed successively with water, aqueous sodium hydrogen carbonate and water and then dried, after which the solvent was distilled off, to yield 4-(4-fluorophenyl)-2-methyl-1(2H)-isoquinoline-3-carboxylic acid ethyl ester as colorless crystals (3.12 g).

Melting point: 172°–173° C. (recrystallized from ethyl acetate-hexane) NMR (200 MHz, CDCl$_3$) ppm: 1.00 (3H, t, J=7.0 Hz), 3.62 (3H, s), 4.07 (2H, q, J=7.0 Hz), 7.11–7.35 (8H, m), 7.53–7.60 (2H, m), 8.50–8.55 (1H, m) Elemental analysis (for C$_{19}$H$_{16}$NO$_3$F): Calculated (%): C, 70.15; H, 4.96; N, 4.31 Found (%): C, 70.01; H, 4.86; N, 4.20

Process 2

A mixture of the compound obtained in Process 1 (2.70 g), acetic acid (50 ml) and 5% palladium-carbon (2.00 g) was stirred at 70° C. in a hydrogen atmosphere for 1 hour. After the mixture was cooled and then filtered, the filtrate was distilled to remove the solvent. The residue was dissolved in ethyl acetate and washed successively with water, aqueous potassium carbonate and water and then dried, after which the solvent was distilled off, to yield 3,4-cis-4-(4-fluorophenyl)-1,2,3,4-tetrahydro-2-methyl-1-oxo-3-isoquinolinecarboxylic acid ethyl ester as colorless crystals (2.43 g).

Melting point: 15 1°–153° C. (recrystallized from ethyl acetate-isopropyl ether) NMR (200 MHz, CDCl$_3$) ppm: 0.98 (3H, t, J=7.2 Hz), 3.12 (3H, s), 3.78–4.03 (2H, m), 4.25 (1H, d, J=7.0 Hz), 4.92 (1H, d, J=7.0 Hz), 6.90–7.41 (7H, m), 8.20–8.26 (1H, m) Elemental analysis (for C$_{19}$H$_{18}$NO$_3$F): Calculated (%): C, 69.71; H, 5.54; N, 4.28 Found (%): C, 69.44; H, 5.19; N, 4.31

Process 3

To a suspension of the compound obtained in Process 2 (2.43 g) in ethanol (50 ml) and THF (15 ml) was added 2N-NaOH (14 ml) at 0° C. After this mixture was stirred at room temperature for 1 hour, the solvent was distilled off. Water was added to the residue, which was then washed with ethyl ether, after which the water layer was acidified with 2N-HCl. This mixture was extracted with ethyl acetate, the extract being washed with water and dried, followed by solvent removal by distillation, to yield the title compound as colorless crystals (2.12 g).

Melting point: 248°–250° C. (recrystallized from ethyl acetate-ethyl ether) NMR (200 MHz, CDCl$_3$+DMSO-d$_6$) ppm: 3.04 (3H, s), 4.16 (1H, s), 4.73 (1H, s), 6.90–7.17 (5H, m), 7.41–7.44 (2H, m), 8.16–8.21 (1H, m) Elemental analysis (for C$_{17}$H$_{14}$NO$_3$F): Calculated (%): C, 68.22; H, 4.71; N, 4.68 Found (%): C, 68.02; H, 4.72; N, 4.58

Reference Example 3

3,4-trans-4-(2-Chlorophenyl)-1,2,3,4-tetrahydro-1,6,7-trimethyl-2-oxo-3-quinolinecarboxylic acid

Process 1

To a suspension of lithium aluminum hydride (1.4 g) in THF (50 ml) was added dropwise a solution of 4-(2-chlorophenyl)-1,2,-dihydro-1,6,7-trimethyl- 2-oxo-3-quinolinecarboxylic acid ethyl ester (10.0 g) in THF (100 ml) at 0° C. After this mixture was stirred at 0° C. for 30 minutes, water (4 ml) was added, followed by stirring at room temperature for 30 minutes. The insoluble material was filtered off, the filtrate being concentrated. After ethyl acetate was added, the residue was washed successively with dilute hydrochloric acid and water and then dried, followed by solvent removal by distillation. The residue was subjected to silica gel column chromatography (hexane:ethyl acetate=3:1) to yield 3,4-trans-4-(2-chlorophenyl)-1,2,3,4-tetrahydro- 1,6,7- trimethyl-2-oxo-3-quinolinecarboxylic acid ethyl ester as colorless crystals (2.94 g).

Melting point: 147°–148° C. (recrystallized from ethyl acetate-isopropyl ester) NMR (200 MHz, CDCl$_3$) ppm: 1.10 (3H, t, J=7.0 Hz), 2.14 (3H, s), 2.29 (3H, s), 3.43 (3H, s), 3.97 (1H, d, J=7.2 Hz), 4.09 (2H, q, J=7.0 Hz), 5.07 (1H, d, J=7.2 Hz), 6.64 (1H, s), 6.80–6.90 (1H, m), 6.89 (1H, s), 7.10–7.30 (2H, m), 7.40–7.50 (1H, m) Elemental analysis (for C$_{21}$H$_{22}$NO$_3$Cl): Calculated (%): C, 67.83; H, 5.96; N, 3.77 Found (%): C, 67.98; H, 6.05; N, 3.98

Process 2

A mixture of the compound obtained in Process 1 (1.50 g), THF (10 ml), ethanol (20 ml), water (2 ml) and sodium hydroxide (0.75 g) was stirred at room temperature for 3 hours, after which the solvent was distilled off to an about half amount. After water was added, the residue was washed with ether. The water layer was acidified with dilute hydrochloric acid and extracted with ethyl acetate. The extract was washed with saturated aqueous sodium chloride and then dried, after which the solvent was distilled off, to yield the title compound as colorless crystals (1.26 g).

Melting point: 128°–129° C. (recrystallized from ethyl acetate-isopropyl ether) NMR (200 MHz, CDCl$_3$) ppm: 2.15 (3H, s), 2.29 (3H, s), 3.42 (3H, s), 3.93 (1H, d, J=5.2 Hz), 5.07 (1H, d, J=5.2 Hz), 6.70–6.80 (1H, m), 6.74 (1H, s), 6.89 (1H, s), 7.03–7.45 (3H, m) Elemental analysis (for C$_{19}$H$_{18}$NO$_3$Cl): Calculated (%): C, 66.38; H, 5.28; N, 4.07 Found (%): C, 66.22; H, 5.16; N, 4.03

Reference Example 4

3,4-trans-6-Chloro-1,2,3,4-tetrahydro-1-methyl-2-oxo-4-phenyl-3-quinolinecarboxylic acid

Process 1

6-Chloro-1,2-dihydro-1-methyl-2-oxo-4-phenyl-3-quinolinecarboxylic acid ethyl ester was reacted in substantially the same manner as in Process 1 of Reference Example 3 to yield 3,4-trans-6-chloro-1,2,3,4-tetrahydro-1-methyl-2-oxo-4-phenyl-3-quinolinecarboxylic acid ethyl ester as colorless crystals.

Melting point: 83°–84° C. (recrystallized from ethyl ether-hexane) NMR (200 MHz, CDCl$_3$) ppm: 1.05 (3H, t, J=7.11 Hz), 3.41 (3H, s), 3.89 (1H, d, J=9.4 Hz), 4.00–4.15 (2H, m), 4.58 (1H, d, J=9.4 Hz), 6.85 (1H, d, J=1.8 Hz), 7.00

(1H, d, J=8.6 Hz), 7.10–7.40 (6H, m) Elemental analysis (for $C_{19}H_{18}NO_3Cl$): Calculated (%): C, 66.38; H, 5.28; N, 4.07 Found (%): C, 66.36; H, 5.16; N, 4.12

Process 2

The compound obtained in Process 1 was reacted in substantially the same manner as in Process 2 of Reference Example 3 to yield the title compound as colorless crystals.

Melting point: 138°–139° C. (recrystallized from ethyl acetate-isopropyl ether) NMR (200 MHz, $CDCl_3$) ppm: 3.41 (3H, s), 3.93 (1H, d, J=8.0 Hz), 4.58 (1H, d, J=8.0 Hz), 5.20 (1H, bs), 6.80–7.40 (8H, m) Elemental analysis (for $C_{17}H_{14}NO_3Cl$): Calculated (%): C, 64.67; H, 4.47; N, 4.44 Found (%): C, 64.35; H, 4.52; N, 4.57

Reference Example 5

3,4-trans-4-(2-Chlorophenyl)-1,2,3,4-tetrahydro-1,6,7-trimethyl-3-quinolinecarboxylic acid Process 1

To a mixture of 4-(2-chlorophenyl)-6,7-dimethyl-3-quinolinecarboxylic acid ethyl ester (26.5 g), sodium borohydride (6.0 g) and ethanol (150 ml) was heated under reflux for 2 hours. After the solvent was distilled off, water was added to the residue, followed by extraction with ethyl acetate. After the extract was washed with water and dried, the solvent was distilled off. The residue was subjected to silica gel column chromatography (ethyl acetate:hexane= 3:1) to yield 4-(2-chlorophenyl)-1,4-dihydro-6,7-dimethyl-3-quinolinecarboxylic acid ethyl ester as colorless crystals (5.0 g).

Melting point: 204°–209° C. (recrystallized from ethyl acetate-isopropyl ether) NMR (200 MHz, $CDCl_3$) ppm: 1.13 (3H, t, J=7.2 Hz), 2.07 (3H, s), 2.12 (3H, s), 3.95–4.15 (2H, m), 5.74 (1H, s), 6.34 (1H, d, J=5.4 Hz), 6.46 (1H, s), 6.94 (1H, s), 6.95–7.20 (2H, m), 7.25–7.35 (2H, m), 7.61 (1H, d, J=6.2 Hz) Elemental analysis (for $C_{20}H_{20}NO_2Cl$): Calculated (%): C, 70.27; H, 5.90; N, 4.10 Found (%): C, 70.02; H, 5.84; N, 4.07

Process 2

To a solution of the compound obtained in Process 1 (2.65 g) in DMF (40 ml) was added 60% sodium hydride (60% in oil) (0.35 g), followed by stirring at room temperature for 15 minutes. After this mixture was cooled to 0° C., 3 ml of methyl iodide was added, followed by stirring at 0° C. for 30 minutes. After dilute hydrochloric acid was added, the mixture was extracted with ethyl acetate. The extract was washed with water and then dried, after which the solvent was distilled off, to yield 4-(2-chlorophenyl)-1,4-dihydro-1, 6,7-trimethyl- 3-quinolinecarboxylic acid ethyl ester as colorless crystals (2.32 g).

Melting point: 200°–201° C. (recrystallized from ethyl acetate-isopropyl ether) NMR (200 MHz, $CDCl_3$) ppm: 1.12 (3H, t, J=7.2 Hz), 2.09 (3H, s), 2.19 (3H, s), 3.35 (3H, s), 3.95–4.10(2H, m), 5.74 (1H, s), 6.62 (1H, s), 6.97 (1H, s), 6.98–7.15 (2H, m), 7.20–7.35 (2H, m), 7.52 (1H, s) Elemental analysis (for $C_{21}H_{22}NO_2Cl.0.1H_2O$): Calculated (%): C, 70.52; H, 6.26; N, 3.92 Found (%): C, 70.39; H, 6.32; N, 3.82

Process 3

While stirring at room temperature a mixture of the compound obtained in Process 2 (2.2 g), methanol (30 ml), methanol containing 20% hydrogen chloride (10 ml) and THF (10 ml), a solution of sodium cyanoborohydride (1.0 g) in methanol (15 ml) was gradually added dropwise. After stirring at room temperature for 1 hour, the mixture was alkalinized with aqueous potassium carbonate and then extracted with ethyl acetate. The extract was washed with saturated aqueous sodium chloride and dried, after which the solvent was distilled off, to yield 4-(2-chlorophenyl)-1,2,3, 4-tetrahydro- 1,6,7-trimethyl-3-quinolinecarboxylic acid ethyl ester as a pale yellow oily substance (2.44 g).

NMR (200 MHz, $CDCl_3$) ppm: 1.13 (3H, t, J=7.1 Hz), 2.04 (3H, s), 2.21 (3H, s), 2.93 (2.5H, s), 3.00–3.50 (3H, m), 3.01 (0.5H, s), 4.00–4.18 (2H, m), 4.95 (0.87H, d, J=5.8 Hz), 5.09 (0.13H, d, J=5.4 Hz), 6.45–6.66 (2H, m), 6.85–7.45 (4H, m)

Process 4

To the compound obtained in Process 3 (2.37 g) were added ethanol (40 ml), water (10 ml) and potassium hydroxide (2.0 g), followed by stirring at room temperature overnight. After the solvent was distilled off, the residue was weakly acidified (pH 3 to 4) with dilute hydrochloric acid and then extracted with ethyl acetate. The extract was washed with saturated aqueous sodium chloride and dried, after which the solvent was distilled off, to yield the title compound as colorless crystals (1.51 g).

Melting point: 196°–199° C. (recrystallized from ethyl acetate-ethyl ether) NMR (200 MHz, $CDCl_3$) ppm: 2.08 (3H, s), 2.23 (3H, s), 3.09 (3H, s), 3.25–3.60 (3H, m), 4.92 (1H, d, J=5.6 Hz), 5.50–6.80 (1H, brs), 6.59 (1H, s), 6.90 (1H, s), 6.95 (1H, m), 7.10–7.45 (3H, m) Elemental analysis (for $C_{19}H_{20}NO_2Cl.0.7H_2O$): Calculated (%): C, 66.64; H, 6.30; N, 4.09 Found (%): C, 66.53; H, 6.00; N, 3.85

Reference Example 6

1,2,3,4-Tetrahydro-1-methyl-2-oxo-4-phenyl-3-quinolineacetic acid

Process 1

A mixture of 1,2-dihydro-1-methyl-2-oxo-4-phenyl-3-quinolinecarboxylic acid ethyl ester (30.7 g), 10% palladium-carbon (2.0 g) and acetic acid (150 ml) was stirred at 80° C. for 24 hours in a hydrogen atmosphere (5 atm). After the catalyst was filtered off, the filtrate was concentrated. After ethyl acetate was added, the residue was washed successively with potassium carbonate and water and then dried, after which the solvent was distilled off, to yield 3,4-trans-1,2,3,4-tetrahydro-1-methyl-2-oxo- 4-phenyl-3-quinolinecarboxylic acid ethyl ester as colorless crystals (27.9 g).

Melting point: 80°–81° C. (recrystallized from ethyl acetate-isopropyl ether) NMR (200 MHz, $CDCl_3$) ppm: 1.04 (3H, t, J=7.1 Hz), 3.43 (3H, s), 3.91 (1H, d, J=9.6 Hz), 4.00–4.15 (2H, m), 4.16 (1H, d, J=9.6 Hz), 6.80–7.40 (9H, m) Elemental analysis (for $C_{19}H_{19}NO_3$): Calculated (%): C, 73.77; H, 6.19; N, 4.53 Found (%): C, 73.53; H, 6.12; N, 4.52

Process 2

A mixture of the compound obtained in Process 1 (20 g), sodium hydride (60% in oil) (2.72 g) and DMF (200 ml) was stirred at room temperature for 30 minutes. After methyl bromoacetate (6.73 ml) was added, the mixture was stirred at room temperature overnight. After dilute hydrochloric acid was added, the mixture was extracted with ethyl acetate. The extract was washed with aqueous potassium carbonate and water and then dried, followed by solvent removal by distillation. The residue was subjected to silica gel column chromatography (hexane:ethyl acetate=3:1) to yield 3-ethoxycarbonyl- 1,2,3,4-tetrahydro-1-methyl-2-oxo-4-phenyl-3-quinolinecarboxylic acid methyl ester as a pale yellow oily substance. To this oily substance were added ethanol (160 ml), water (40 ml) and potassium hydroxide (10 g), followed by overnight heating and refluxing. After the solvent was distilled off, dilute hydrochloric acid was added, and the mixture was extracted with ethyl acetate. The extract was washed with saturated aqueous sodium chloride and then dried, after which the solvent was distilled off. After pyridine (100 ml) was added, the residue was heated under reflux for 30 minutes. After the solvent was distilled off, the residue was acidified with dilute hydrochloric acid and then extracted with ethyl acetate. The extract was washed with saturated aqueous sodium chloride and then dried, after which the solvent was distilled off, to yield the title compound (trans:cis= about 3:2 mixture) as a white foamy substance (19.1 g).

NMR (200 MHz, CDCl$_3$) ppm: 2.27–2.65 (1.6H, m), 2.75–3.00 (0.4H, m), 3.25– 3.60 (1H, m), 3.44 (1.8H, s), 3.48 (1.2H, s), 4.16 (0.6H, d, J=13.0 Hz), 4.19 (0.4H, d, J=6.8 Hz), 6.60–6.70 (0.6H, m), 6.90–7.45 (8.4H, m)

Reference Example 7

4-(2-Chlorophenyl)-1,2,3,4-tetrahydro-1-methyl-2-oxo-3-quinolineacetic acid

Process 1

4-(2-Chlorophenyl)-1,2-dihydro-1-methyl-2-oxo-3-quinolineacetic acid ethyl ester was reacted in substantially the same manner as in Process 1 of Reference Example 3 to yield 3,4-trans-4-(2-chlorophenyl)-1,2,3,4-tetrahydro-1-methyl-2-oxo-3-quinolinecarboxylic acid ethyl ester as colorless crystals.

Melting point: 131°–133° C. (recrystallized from ethyl acetate-isopropyl ether) NMR (200 MHz, CDCl$_3$) ppm: 1.08 (3H, t, J=7.2 Hz), 3.45 (3H, s), 4.00:–4.20 (2H, m),4.03(1H, d,J=8.0 Hz),5.14(1H, d,J=8.0 Hz),6.80–7.50(8H, m) Elemental analysis (for C$_{19}$H$_{18}$NO$_3$Cl): Calculated (%): C, 66.38; H, 5.28; N, 4.07 Found (%): C, 66.03; H, 5.17; N, 4.06

Process 2

The compound obtained in Process 1 was reacted in substantially the same manner as in Process 2 of Reference Example 6 to yield the title compound (trans:cis=about 6:1 mixture) as colorless crystals.

Melting point: 177°–180° C. (recrystallized from ethyl acetate-isopropyl ether) NMR (200 MHz, CDCl$_3$) ppm: 2.34 (0.86, dd, J=16.0, 3.8 Hz), 2.45–2.80 (0.28, m),2.67 (0.86H, dd, J=16.0, 8.8 Hz),3.35–3.70(1H, m),3.45(2.58H, s), 3.49 (0.42H, s), 4.77 (0.86H, d, J=13 Hz), 5.00 (0.14H, d, J=7.0 Hz), 6.58 (0.86H, d, J=7.4 Hz), 6.90–7.55 (7.14H, m) Elemental analysis (for C$_{18}$H$_{16}$NO$_3$Cl.0.2H$_2$O): Calculated (%): C, 64.85; H, 4.96; N, 4.20 Found (%): C, 64.80; H, 4.74; N, 4.23

Reference Example 8

1,2,3,4-Tetrahydro-6,7-dimethoxy-1-methyl-2-oxo-4-phenyl-3-quinolineacetic acid

Process 1

1,2-Dihydro-6,7-dimethoxy-1-methyl-2-oxo-4-phenyl-3-quinolinecarboxylic acid ethyl ester was reacted in substantially the same manner as in Process 1 of Reference Example 7 to yield 3,4-trans-1,2,3,4-tetrahydro- 6,7-dimethoxy-1-methyl-2-oxo-4-phenyl-3-quinolinecarboxylic acid ethyl ester as colorless crystals.

Melting point: 157°–159° C. (recrystallized from ethyl acetate-isopropyl ether) NMR (200 MHz, CDCl$_3$) ppm: 1.07 (3H, t, J=7.1 Hz), 3.43 (3H, s), 3.71 (3H, s), 3.86 (1H, d, J=8.0 Hz), 3.93 (3H, s), 4.00–4.20 (2H, m), 4.55 (1H, d, J=8.0 Hz), 6.44 (1H, s), 6.65 (1H, s), 7.10–7.40 (8H, m) Elemental analysis (for C$_{21}$H$_{23}$NO$_5$): Calculated (%): C, 68.28; H, 6.28; N, 3.79 Found (%): C, 68.11; H, 6.36; N, 3.77

Process 2

The compound obtained in Process 1 was reacted in substantially the same manner as in Process 2 of Reference Example 7 to yield the title compound a white foamy substance.

NMR (200 MHz, CDCl$_3$) ppm: 2.32 (0.33H, dd, J=17.0, 6.2 Hz), 2.39 (0.67H, dd, J=16.0, 5.0 Hz), 2.57 (0.67H, dd, J=16.0, 7.4 Hz), 2.83 (0.33H, dd, J=17.0, 7.6 Hz), 3.20–3.60 (1H, m), 3.42 (2H, s), 3.48 (1H, s), 3.62 (2H, s) 3.81 (1H, s), 3.92 (3H, s), 4.09 (0.67H, d, J=11.0 Hz), 4.09 (0.33H, d, J=6.2 Hz), 6.22 (0.67H, s), 6.60–6.67 (1.33H, m), 6.90–7.40 (5H, m)

Reference Example 9

6-Chloro-1,2,3,4-tetrahydro-1,4-dimethyl-2-oxo-4-phenyl-3-quinolineacetic acid

Process 1

To a solution of 6-chloro-1,2,3,4-tetrahydro-4-methyl-2-oxo-4-phenylquinolin (6.0 g) in DMF (50 ml) was added sodium hydride (60% in oil) (0.98 g), followed by stirring at room temperature for 30 minutes. After this mixture was cooled to 0° C., methyl iodide (3 ml) was added, followed by stirring at room temperature for further 30 minutes. After dilute hydrochloric acid was added, the mixture was extracted with ethyl acetate. The extract was washed with water and then dried, after which the solvent was distilled off, to yield 6-chloro-1,2,3,4-tetrahydro-1,4-dimethyl-2-oxo-4-phenylquinolin as colorless crystals (5.58 g).

Melting point: 125°–126° C. (recrystallized from ethyl acetate-isopropyl ether) NMR (200 MHz, CDCl$_3$) ppm: 1.66 (3H, s), 2.70 (1H, d, J=16.0 Hz), 3.20 (1H, d, J=16.0 Hz), 3.24 (3H, s), 6.95 (1H, d, J=8.4 Hz), 7.10–7.35 (7H, m) Elemental analysis (for C$_{17}$H$_{16}$NOCl): Calculated (%): C, 71.45; H, 5.64; N, 4.90 Found (%): C, 71.46; H, 5.66; N, 4.88

Process 2

While stirring at −78° C. in an argon atmosphere a solution of the compound obtained in Process 1 (5.0 g) in THF (60 ml), a solution of 2M lithium sodium isopropylamide in THF-heptane (14.6 ml) was added dropwise. After the mixture was stirred for 30 minutes, a solution of methyl bromoacetate (2.9 ml) in THF (15 ml) was added dropwise, followed by stirring at −78° C. for 30 more minutes. After saturated aqueous ammonium chloride was added, the mixture was extracted with ethyl acetate. The extract was washed successively with dilute hydrochloric acid and water and then dried, followed by solvent removal by distillation. The residue was subjected to silica gel column chromatography (hexane:ethyl acetate=2:1) to yield 6-chloro-1,2,3,4-tetrahydro-1,4-dimethyl-2-oxo-4-phenyl-3-quinolineacetic acid methyl ester as a colorless oily substance. To this oily substance were added methanol (64 ml), water (26 ml) and sodium hydroxide (8 g), followed by stirring overnight at room temperature. After the solvent was distilled off, water was added, and the mixture was washed with ether. The aqueous layer was acidified with dilute hydrochloric acid and then extracted with ethyl acetate. The extract was washed with saturated aqueous sodium chloride and then dried, after which the solvent was distilled off, to yield the title compound as colorless crystals (5.27 g).

Melting point: 166°–168° C. (recrystallized from ethyl acetate-hexane) NMR (200 MHz, CDCl$_3$) ppm: 1.42 (3H, s), 1.88 (1H, dd, J=16.0, 2.6 Hz), 2.69 (1H, dd, J=16.0, 10.0 Hz), 3.42 (3H, s), 3.68 (1H, dd, J=10.0, 2.6 Hz), 6.52 (1H, d, J=2.4 Hz), 6.96 (1H, d, J=8.6 Hz), 7.15–7.50 (6H, m) Elemental analysis (for C$_{19}$H$_{18}$NO$_3$Cl): Calculated (%): C, 66.38; H, 5.28; N, 4.07 Found (%): C, 66.40; H, 5.12; N, 4.30

Reference Example 10

4-(2-Chlorophenyl)-1,2,3,4-tetrahydro-1,6,7-trimethyl-2-oxo-3-quinolineacetic acid The compound obtained in Process 1 of Reference Example 3 was reacted in substantially the same manner as in Process 2 of Reference Example 6 to yield the titte compound (trans:cis=about 5:1 mixture) as colorless crystals.

Melting point: 210°–215° C. (recrystallized from ethyl acetate-isopropyl ether) NMR (200 MHz, CDCl$_3$) ppm: 2.09 (2.5H, s), 2.16 (0.5H, s), 2.27 (3H, s), 2.33 (0.83H, dd, J=16.0, 4.2 Hz), 2.35–2.80 (0.34H, m), 2.66 (0.83H, dd, J=16.0, 8.0 Hz), 3.30–3.70 (1H, m), 3.43 (2.5H, s), 3.47 (0.5H, s), 4.68 (0.83H, d, J=12.0 Hz), 4.91 (0.17H, d, J=7.0 Hz), 6.33 (0.83H, s), 6.80–7.50 (5.17H, m) Elemental analysis (for C$_{20}$H$_{20}$NO$_3$Cl): Calculated (%): C, 67.13; H, 5.63; N, 3.91 Found (%): C, 66.88; H, 5.71; N, 3.81

Reference Example 11

6-Chloro-4-(2-chloro phenyl)-1,2,3,4-tetrahydro-1-methyl-2-oxo-3-quinolineacetic acid Process 1

6-Chloro-4-(2-chlorophenyl)-1,2-dihydro-1-methyl-2-oxo-3-quinolinecarboxylic acid ethyl ester was reacted in substantially the same manner as in Process 1 of Reference Example 3 to yield 3,4-trans-6-chloro-4-( 2-chlorophenyl)-1,2,3,4-tetrahydro-1-methyl-2-oxo-3-quinolinecarboxylic acid ethyl ester as colorless crystals.

Melting point: 103°–104° C. (recrystallized from ethyl acetate-isopropyl ether) NMR (200 MHz, CDCl$_3$) ppm: 1.10 (3H, t, J=7.1 Hz), 3.43 (3H, s), 4.00–4.20 (2H,m), 4.01 (1H, d, J=8.2. Hz), 5.11 (1H, d, J=8.2 Hz), 6.80–7.50 (7H, m) Elemental analysis (for C$_{19}$H$_{17}$NO$_3$Cl$_2$): Calculated (%): C, 60.33; H, 4.53; N, 3.70 Found (%): C, 60.28; H, 4.35; N, 3.78

Process 2

The compound obtained in Process 1 was reacted in substantially the same manner as in Process 2 of Reference Example 6 to yield the title compound (trans:cis=about 4:1 mixture) as a white foamy substance.

NMR (200 MHz, CDCl$_3$) ppm: 2.34 (0.SH, dd, J=16.0, 4.2 Hz), 2.36–2.80 (0.4H, m), 2.63 (0.8SH, dd, J=16.0, 8.0 Hz), 3.35–3.70 (1H, m), 3.42 (2.4H, s) 3.46 (0.6H, s), 4.78 (0.8H, d, J=13 Hz), 4.98 (0.2H, d, J=6.8 Hz), 6.54 (0.8H, s), 6.75–7.60 (6.2H, m)

Reference Example 12

6-Chloro-1,2,3,4-tetrahydro-1-methyl-2-oxo-4-phenyl-3-quinolineacetic acid

The compound obtained in Process 1 of Reference Example 4 was reacted in substantially the same manner as in Process 2 of Reference Example 6 to yield the title compound (trans:cis=about 4:1 mixture) as a white foamy substance.

NMR (200 MHz, CDCl$_3$) ppm: 2.25–2.60 (1.8H, m), 2.80–2.95 (0.2H, m), 3.20– 3.60 (1H, m), 3.41 (2.4H, s), 3.45 (0.6H, s), 4.14 (0.2H, d, J=7.0 Hz), 4.16 (0.8H, d, J=12 Hz), 6.63 (0.8H, s), 6.90–7.50 (7.2H, m) Elemental analysis (for C$_{18}$H$_{16}$NO$_3$Cl): Calculated (%): C, 65.56; H, 4.89; N, 4.25 Found (%): C, 65.75; H, 4.98; N, 4.18

Reference Example 13

3,4-cis-6-Chloro-3,4-dihydro-2-oxo-4-phenyl-2H-1-benzopyran-3-acetic acid

Process 1

To a solution of 6-chloro-2-oxo-4-phenyl-2H-1-benzopyran-3-carboxylic acid ethyl ester (4.4 g) in ethanol (300 ml) was added platinum oxide (0.30 g), followed by stirring at room temperature in a hydrogen atmosphere (3 to 4 atm) for 3 hours. After the catalyst was filtered off, the filtrate was distilled to remove the solvent, followed by treatment of the residue with isopropyl ether, to yield 6-chloro-3,4-dihydro-2-oxo-4-phenyl-2H-1-benzopyran-3-carboxylic acid ethyl ester as colorless crystals (2.24 g).

Melting point: 93°–95° C. (recrystallized from isopropyl ether) NMR (200 MHz, CDCl$_3$) ppm: 1.09 (3H, t, J=7.0 Hz), 3.95 (1H, d, J=8.2 Hz), 4.11 (2H, q, J=7.0 Hz), 6.94 (1H, d, J=2.4 Hz), 7.0–7.3 (7H, m) Elemental analysis (for C$_{18}$H$_{15}$O$_4$Cl): Calculated (%): C, 65.36; H, 4.57 Found (%): C, 65.75; H, 4.61

Process 2

To a solution of the compound obtained in Process 1 (2.20 g) in DMF (20 ml) was added sodium hydride (60% in oil) (0.35 g) at room temperature, followed by stirring for 0.5 hours. After methyl bromoacetate (1.4 ml) was added, this mixture was stirred at room temperature for 2 hours, after which dilute hydrochloric acid was added, followed by extraction with ethyl acetate. The extract was washed with water and dried, after which the solvent was distilled off, followed by treatment of the residue with isopropyl ether, to yield 6-chloro-3-ethoxycarbonyl-3,4-dihydro-3-methoxycarbonylmethyl-2-oxo-4-phenyl- 2H-1-benzopyran as colorless crystals.

Melting point: 134°–136° C. (recrystallized from isopropyl ether) NMR (200 MHz, CDCl$_3$) ppm: 0.99 (3 H, t, J=7.0 Hz), 2.69 (1H, d, J=17.8 Hz), 3.27 (1H, d, J=17.8 Hz), 4.00

(2H, m), 5.12 (1H, s), 6.82 (1H, bs), 7.0–7.1 (3H, m), 7.2–7.3 (1H, m), 7.4–7.5 (3H, m) Elemental analysis (for $C_{21}H_{19}O_6Cl$): Calculated (%): C, 62.61; H, 4.75 Found (%): C, 62.31.; H, 4.70

Process 3

A mixture of the compound obtained in Process 2 (1.5 g), acetic acid (10 ml) and hydrochloric acid (5 ml) was heated for 3 hours under reflux, followed by solvent removal by distillation, to yield a mixture of the title compound and its stereo isomer as an oily substance. This oily substance was treated with ethyl acetate-isopropyl ether to yield the title compound as colorless crystals (0.7 g).

Melting point: 117°–119° C. (recrystallized from isopropyl ether) NMR (200 MHz, CDCl$_3$) ppm: 2.37 (1H, dd, J=18.0 Hz, J=7.2 Hz), 2.86 (1H, dd, J=17.6 Hz, J=6.4 Hz), 3.62 (1H, m), 4.31 (1H, d, J=6.6 Hz), 7.0–7.4 (8H, m) Elemental analysis (for $C_{17}H_{13}O_4Cl$): Calculated (%): C, 64.47; H, 4.14 Found (%): C, 64.35; H, 3.95

Reference Example 14

3,4-Dihydro-6-methyl-2-oxo-4-phenyl-2H-1-benzopyran-3-acetic acid

Process 1

To a solution of 6-methyl-2-oxo-4-phenyl-2H-1-benzopyran-3-carboxylic acid ethyl ester (15.0 g) in acetic acid (150 ml) was added 10% palladium-carbon (3.0 g), followed by stirring at 80° C. in a hydrogen atmosphere (4 to 5 atm) for 4.5 hours. After the catalyst was filtered off, the filtrate was distilled to remove the solvent, followed by treatment of the residue with isopropyl ether, to yield 3,4-dihydro-6-methyl-2-oxo-4-phenyl-2H-1-benzopyran- 3-carboxylic acid ethyl ester as colorless crystals (12.5 g).

Melting point: 206°–208° C. (recrystallized from isopropyl ether) NMR (200 MHz, CDCl$_3$) ppm: 1.07 (3H, t, J=7.0 Hz), 2.25 (3H, s), 3.94 (1H, d, J=7.6 Hz), 4.10 (2H, qd, J=7.0 Hz, J=2.0 Hz), 4.68 (1H, d, J=7.6 Hz), 6.75 (1H, bs), 7.0–7.4 (7H, m) Elemental analysis (for $C_{19}H_{18}O_4 \cdot 1/4H_2O$): Calculated (%): C, 72.48; H, 5.92 Found (%): C, 72.24; H, 5.97

Process 2

The compound obtained in Process 1 was reacted in substantially the same manner as in Process 2 of Reference Example 13 to yield 3-ethoxycarbonyl- 3,4-dihydro-3-methoxycarbonylmethyl-6-methyl-2-oxo-4-phenyl- 2H-1-benzopyran as colorless crystals.

Melting point: 123°–125° C. (recrystallized from isopropyl ether) NMR (200 MHz, CDCl$_3$) ppm: 0.95 (3H, t, J=7 Hz), 2.21 (3H, s), 2.71 (1H, d, J=17.8 Hz), 3.23 (1H, d, J=17.8 Hz), 3.73 (3H, s), 3.97 (2H, m), 5.04 (1H, s), 6.63 (1H, bs), 7.0–7.2 (4H, m), 7.3–7.4 (3H, m) Elemental analysis (for $C_{22}H_{22}O_6$): Calculated (%): C, 69.10; H, 5.80 Found (%): C, 68.77; H, 5.87

Process 3

The compound obtained in Process 2 was reacted in substantially the same manner as in Process 3 of Reference Example 13 to yield a mixture of the trans and cis configurations of the title compound (trans:cis=about 2.5:1 mixture) as colorless crystals.

Melting point: 152°–154° C. (recrystallized from ethyl acetate-isopropyl ether) NMR (200 MHz, CDCl$_3$) ppm: 2.19 (3H, s), 2.55 (2H, m), 3.36 (1H, m), 4.27 (1H, d, J=12.6 Hz), 6.44 (1H, brs), 7.0–7.5 (7H, m), 2.27 (3H, s), 2.34 (1H, dd, J=17.8 Hz, J=7.6 Hz), 2.86 (1H, dd, J=18.0 Hz, J=6.6 Hz), 3.50 (1H, m) 4.27 (1H, d, J=6.8 Hz), 7.0–7.5 (8H, m) Elemental analysis (for $C_{18}H_{16}O_4$): Calculated (%): C, 72.96; H, 5.44 Found (%): C, 72.94; H, 5.59

Reference Example 15

3,4-cis-6-Chloro-1,2,3,4-tetrahydro-1-methyl-4-phenyl-3-quinolineacetic acid

Process 1

6-Chloro-4-phenyl-3-quinolinecarboxylic acid ethyl ester was reacted in substantially the same manner as in Process 1 of Reference Example 5 to yield 6-chloro-1,4-dihydro-4-phenyl-3-quinolinecarboxylic acid ethyl ester as colorless crystals.

Melting point: 167°–168° C. (recrystallized from ethyl acetate-isopropyl ether) NMR (200 MHz, CDCl$_3$) ppm: 1.18 (3H, t, J=7.1 Hz), 4.00–4.20 (2H, m), 5.08 (1H, s), 6.44 (1H, bd, J=6.2 Hz), 6.65 (1H, d, J=9.4 Hz), 7.00–7.30 (7H, m), 7.54 (1H, d, J=6.2 Hz) Elemental analysis (for $C_{18}H_{16}NO_2Cl$): Calculated (%): C, 68.90; H, 5.14; N, 4.46 Found (%): C, 68.66; H, 5.23; N, 4.56

Process 2

The compound obtained in Process 1 was reacted in substantially the same manner as in Process 2 of Reference Example 5 to yield 6-chloro-1,4-dihydro- 1-methyl-4-phenyl-3-quinolinecarboxylic acid ethyl ester as a colorless crystals.

Melting point: 159°–161° C. (recrystallized from ethyl acetate-isopropyl ether) NMR (200 MHz, CDCl$_3$) ppm: 1.19 (3H, t, J=7.1 Hz), 3.34 (3H, s), 4.00–4.20 (2H, m), 5.08 (1H, s), 6.80 (1H, d, J=8.4 Hz), 7.05–7.30 (7H, m), 7.45 (1H, s) Elemental analysis (for $C_{19}H_{18}NO_2Cl$): Calculated (%): C, 69.62; H, 5.53; N, 4.27 Found (%): C, 69.60; H, 5.54; N, 4.44

Process 3

The compound obtained in Process 2 was reacted in substantially the same manner as in Process 3 of Reference Example 5 to yield 6-chloro-1,2,3,4-tetrahydro- 1-methyl-4-phenyl-3-quinolinecarboxylic acid ethyl ester as a mixture of stereo isomers. From this mixture, the 3,4-cis isomer was obtained as colorless crystals.

Melting point: 138°–139° C. (recrystallized from ethyl acetate-isopropyl ether) NMR (200 MHz, CDCl$_3$) ppm: 1.20 (3H, t, J=7.1 Hz), 3.01 (3H, s), 3.10–3.55 (3H, m), 4.06 (2H, q, J=7.1 Hz), 4.52 (1H, d, J=5.6 Hz), 6.62 (1H, d, J=9.0 Hz), 6.85–7.30 (7H, m) Elemental analysis (for $C_{19}H_{20}NO_2Cl$): Calculated (%): C, 69.19; H, 6.11; N, 4.25 Found (%): C, 68.94; H, 5.84; N, 4.22

Process 4

To a suspension of lithium aluminum hydride (2.0 g) in THF (50 ml) was added dropwise a solution of the compound (cis isomer) obtained in Process 3 (4.85 g) in THF (25 ml) at room temperature, followed by stirring at room temperature for 15 minutes. Water (2 ml) was added, followed by stirring for 15 more minutes. After the insoluble material was filtered off, the filtrate was concentrated. After ethyl acetate was added, the residue was washed with water and dried, after which the solvent was distilled off, to yield 3,4-cis-6-chloro-1,2,3,4-tetrahydro-3-hydroxymethyl-1-methyl-4-phenylquinolin as colorless crystals (3.91 g).

Melting point: 108°–110° C. (recrystallized from ethyl ether-hexane) NMR (200 MHz, CDCl$_3$) ppm: 2.41 (1H, m), 2.99 (3H, s), 3.00–3.22 (2H, m), 3.27 (1H, dd, J=11.0, 7.2 Hz), 3.49 (1H, dd, J=11.0, 7.0 Hz), 4.20 (1H, d, J=5.2 Hz), 6.61 (1H, d, J=8.8 Hz), 6.86 (1H, d, J=2.4 Hz), 7.00–7.35 (6H, m) Elemental analysis (for C$_{17}$H$_{18}$NOCl): Calculated (%): C, 70.95; H, 6.30; N, 4.87 Found (%): C, 70.52; H, 6.43; N, 5.08

Process 5

The compound obtained in Process 4 was reacted in substantially the same manner as in Process 2 of Reference Example 18 to yield 3,4-cis-6-chloro- 3-cyanomethyl-1,2,3,4-tetrahydro-1-methyl-4-phenylquinolin as colorless crystals.

Melting point: 166°–168° C. (recrystallized from ethyl ether-isopropyl ether) NMR (200 MHz, CDCl$_3$) ppm: 2.03 (1H, dd, J=17.0, 8.4 Hz), 2.14 (1H, dd, J=17.0, 7.2 Hz), 2.61 (1H, m), 3.00 (3H, s), 3.05–3.40 (2H, m), 4.23 (1H, d, J=5.0 Hz), 6.62 (1H, d, J=8.8 Hz), 6.86 (1H, d, J=1.8 Hz), 7.00–7.4 (6H, m) Elemental analysis (for C$_{18}$H$_{17}$N$_2$Cl): Calculated (%): C, 72.84; H, 5.77; N, 9.44 Found (%): C, 72.49; H, 5.79; N, 9.23

Process 6

The compound obtained in Process 5 was reacted in substantially the same manner as in Process 3 of Reference Example 18 to yield the title compound as colorless crystals.

Melting point: 192°–195° C. (recrystallized from ethyl acetate-isopropyl ether) NMR (200 MHz, CDCl$_3$) ppm: 1.96 (1H, dd, J=17.0, 8.0 Hz), 2.28 (1H, dd, J=17.0, 6.6 Hz), 2.75 (1H, m), 2.98 (3H, s), 3.05–3.20 (2H, m), 4.16 (1H, d, J=5.2Hz), 6.61(1H, d, J=8.8 Hz), 6.86 (1H, d, J=2.6 Hz), 6.95–7.35 (6H, m) Elemental analysis (for C$_{18}$H$_{18}$NO$_2$Cl): Calculated (%): C, 68.46; H, 5.75; N, 4.44 Found (%): C, 68.44; H, 5.96; N, 4.24

Reference Example 16

3,4-trans-1,2,3,4-1Tetrahydro-2,6,7-trimethyl-1-oxo-4-phenyl-3-isoquinolineacetic acid Process 1

A mixture of 2-benzoyl-4,5-dimethylbenzoic acid (11.4 g), acetone (300 ml), DMF (10 ml), potassium carbonate (6.83 g) and diethyl bromomalonate (12.84 g) was stirred at room temperature for 60 hours. After the solvent was distilled off, ethyl acetate was added to the residue. This mixture was washed with water and dried, after which the solvent was distilled off. To the residue were added acetic acid (180 ml) and hydrochloric acid (180 ml), followed by heating at 110° C. for 5 hours. After the reaction mixture was concentrated, water was added to the concentrate, followed by extraction with ethyl acetate. The extract was washed with water and then dried, after which the solvent was distilled off, to yield colorless crystals, which were recrystallized from ethyl acetate-isopropyl ether, to yield 6,7-dimethyl-1-oxo-4-phenyl-1H-2-benzopyran- 3-carboxylic acid.

Melting point: 265°–268° C.

Process 2

To a solution of the compound obtained in Process 1 (3.75 g) in methanol (50 ml) was added a 40% methylamine-methanol solution (25 ml), followed by stirring at room temperature for 2 hours. After the solvent was distilled off, 4N-HCl-ethyl acetate (50 ml) was added to the residue, followed by stirring at room temperature for 2 hours. After the solvent was distilled off, water was added to the residue, the precipitated crystals were collected by filtration and washed with water, acetone and ethyl ether, to yield 4-phenyl-2,6,7-trimethyl-1(2H)-isoquinolinone-3-carboxylic acid as colorless crystals (3.51 g).

Melting point: >300° C. (recrystallized from ethanol) NMR (200 MHz, CDC$_{13}$ +DMSO-d$_6$) ppm: 2.25 (3H, s), 2.39 (3H, s), 3.67 (3H, s), 6.91 (1H, s), 7.39–7.42 (5H, m), 8.24 (1H, s) Elemental analysis (for C$_{19}$H$_{17}$NO$_3$): Calculated (%): C, 74.25; H, 5.58; N, 4.56 Found (%): C, 74.40; H, 5.50; N, 4.41

Process 3

To a solution of the compound obtained in Process 2 (3.2 g) in DMF (30 ml) was added sodium hydride (60% in oil) (0.50 g) while stirring the solution, followed by addition of ethyl iodide (1.5 ml) and stirring at room temperature for 16 hours. After the reaction mixture was concentrated, ethyl acetate was added to the concentrate. This mixture was washed with water, after which the solvent was distilled off, to yield 2,6,7-trimethyl-4-phenyl-1(2H)-isoquinolinone-3-carboxylic acid ethyl ester as colorless crystals (3.3 g).

Melting point: 151°–153° C. (recrystallized from ethyl acetate-isopropyl ether) NMR (200 MHz, CDCl$_3$) ppm: 0.92 (3H, t, J=7.2 Hz), 2.26 (3H, s), 2.40 (3H, s), 3.61 (3H, s), 4.01 (2H, q, J=7.2 Hz), 6.96 (1H, s), 7.30–7.46 (5H, m), 8.27 (1H, s) Elemental analysis (for C$_{21}$H$_{21}$NO$_3$): Calculated (%): C, 75.20; H, 6.31; N, 4.18 Found (%): C, 74.91; H, 6.29; N, 4.13

Process 4

The compound obtained in Process 3 (1.0 g) was reacted in substantially the same manner as in Process 2 of Reference Example 2 to yield 3,4-cis-1,2,3,4-tetrahydro-2,6,7-trimethyl-1-oxo-4-phenyl-3-isoquinolinecarboxylic acid ethyl ester as colorless crystals (730 mg).

NMR (200 MHz, CDCl$_3$) ppm: 0.94 (3H, t, J=7.2 Hz), 2.17 (3H, s), 2.29 (3H, s), 3.09 (3H, s), 3.72–4.02 (2H, m), 4.24 (1H, d, J=7.0 Hz), 4.84 (1H, d, J=7.0 Hz), 6.72 (1H, s), 7.24–7.38 (5H, m), 7.98 (1H, s)

Process 5

The compound obtained in Process 4 (690 mg) was reacted in substantially the same manner as in Process 3 of Reference Example 2 to yield 3,4-trans-1,2,3,4-tetrahydro2,6,7-trimethyl-1-oxo-4-phenyl-3-isoquinoline carboxylic acid as colorless crystals (610 mg).

Melting point: 248°–250° C. (recrystallized from ethyl acetate-ethyl ether) NMR (200 MHz, CDCl$_3$) ppm: 2.22 (3H, s), 2.28 (3H, s), 2.99 (3H, s), 4.22 (1H, s), 4.61 (1H, s), 6.89 (1H, s), 7.05–7.25 (5H, m), 7.94 (1H, s) Elemental analysis (for C$_{19}$H$_{19}$NO$_3$.1/5H$_2$O): Calculated (%): C, 72.92; H, 6.25; N, 4.48 Found (%): C, 72.84; H, 6.31; N, 4.42

Process 6

The compound obtained in Process 5 was reacted in substantially the same manner as in Process 1 of Reference Example 18 to yield 3,4-trans-1,2,3,4-tetrahydro-3-hydroxymethyl-2,6,7-trimethyl-1-oxo-4-phenylisoquinoline as colorless crystals.

Melting point: 180°–182° C. (recrystallized from ethyl acetate-isopropyl ether) NMR (200 MHz, CDCl$_3$) ppm: 2.23 (3H, s), 2.29 (3H, s), 3.03 (3H, s), 3.63 (1H, s), 3.55–3.75 (1H, m), 3.80–3.85 (1H, m), 4.27 (1H, s), 6.92 (1H, s), 7.02–7.25 (5H, m), 7.88 (1H, s) Elemental analysis (for C$_{19}$H$_{21}$NO$_2$): Calculated (%): C, 77.26; H, 7.17; N, 4.74 Found (%): C, 77.02; H, 7.27; N, 4.66

Process 7

The compound obtained in Process 6 was reacted in substantially the same manner as in Process 2 of Reference Example 18 to yield 3,4-trans-3-cyanomethyl-1,2,3,4-tetrahydro-2,6,7-trimethyl-1-oxo-4-phenylisoquinoline as colorless crystals.

Melting point: 183°–184° C. (recrystallized from ethyl acetate-isopropyl ether) NMR (200 MHz, CDCl$_3$) ppm: 2.27 (3H, s), 2.33 (3H, s), 2.56 (1H, dd, J=17.0, 9.2 Hz), 2.74 (1H, dd, J=17.0, 5.4 Hz), 3.01 (3H, s), 3.85–3.98 (1H, m), 4.23 (1H, s like), 6.98 (1H, s), 7.00–7.05 (2H, m), 7.20–7.30 (3H, m), 7.93 (1H, s), Elemental analysis (for C$_{20}$H$_{20}$N$_2$O): Calculated (%): C, 78.92; H, 6.62; N, 9.20 Found (%): C, 79.08; H, 6.58; N, 9.35

Process 8

The compound obtained in Process 7 was reacted in substantially the same manner as in Process 3 of Reference Example 18 to yield the title compound as colorless crystals.

Melting point: 225°–227° C. (recrystallized from THF-isopropyl ether) NMR (200 MHz, CDCl$_3$) ppm: 2.25 (3H, s), 2.32 (3H, s), 2.65 (1H, dd, J=16.0, 8.8 Hz), 2.76 (1H, dd, J=16.0, 5.0 Hz), 2.97 (3H, s), 4.00–4.12 (1H, m), 4.15 (1H, s like), 6.93 (1H, s), 6.95–7.10 (2H, m), 7.15–7.30 (3H, m), 7.93 (1H, s) Elemental analysis (for C$_{20}$H$_{21}$NO$_3$): Calculated (%): C, 74.28; H, 6.55; N, 4.33 Found (%): C, 74.24; H, 6.49; N, 4.59

Reference Example 17

6-Chloro-1,2,3,4-tetrahydro-1-methyl-2-oxo-4-phenyl-3-quinolineacetic acid

Process 1

6-Chloro-1,2,3,4-tetrahydro-2-oxo-4-phenylquinoxaline [N-(4-chlorophenyl)-1,2-phenylenediamine was chloroacetylated with chloroacetyl chloride, after which it was thermally reacted with potassium carbonate in DMF in the presence of sodium iodide: Melting point: 210°–212° C. (recrystallized from ethyl acetate-isopropyl ether): NMR (200 MHz, CDCl$_3$) ppm: 4.26 (2H, s), 6.75–6.85 (3H, m), 7.10–7.25 (3H, m), 7.35–7.50 (2H, m), 9.26 (1H, bs)]

To a solution of this compound (4.70 g) in DMF (50 ml) was added sodium hydride (60% in oil) (0.89 g), followed by stirring at room temperature for 30 minutes. After the mixture was cooled to 0° C., methyl iodide (5 ml) was added, followed by stirring at room temperature overnight. After dilute hydrochloric acid was added, the mixture was extracted with ethyl acetate. The extract was washed with water and dried, after which the solvent was distilled off, to yield 6-chloro-1,2,3,4-tetrahydro-1-methyl-2-oxo-4-phenylquinoxaline as colorless crystals (1.88 g).

Melting point: 112°–114° C. (recrystallized from ethyl acetate-isopropyl ether) NMR (200 MHz, CDCl$_3$) ppm: 3.42 (3H, s), 4.25 (2H, s), 6.84–7.00 (3H, m), 7.13–7.25 (3H, m), 7.35 o 7.50 (2H, m) Elemental analysis (for C$_{15}$H$_{13}$N$_2$OCl): Calculated (%): C, 66.06; H, 4.80; N, 10.27 Found (%): C, 66.21; H, 4.62; N, 10.44

Process 2

While stirring a solution of the compound obtained in Process 1 (1.8 g) in THF (40 ml) at −78° C. in an argon atmosphere, a solution of 2M lithium diisopropylamide in THF-heptane (5 ml) was added dropwise. After the mixture was stirred for 30 minutes, a solution of t-butyl bromoacetate (1.4 ml) in THF (5 ml) was added dropwise, followed by stirring at −78° C. for further 30 minutes. After saturated aqueous ammonium chloride was added, the mixture was extracted with ethyl acetate. The extract was washed successively with aqueous potassium hydrogen sulfate, aqueous potassium carbonate and water and then dried, after which the solvent was distilled off, to yield 6-chloro-1,2,3,4-tetrahydro-1-methyl-2-oxo-4-phenyl-3-quinolineacetic acid t-butyl ester as a pale yellow oily substance. To this oily substance were added a 3N aqueous sodium hydroxide solution (10 ml) and methanol (40 ml), followed by heating under reflux for 2 hours. After the solvent was distilled off, water was added to the residue, which was washed with ether. The water layer was weakly acidified with dilute hydrochloric acid and then extracted with ethyl acetate. The extract was washed with water and dried, after which the solvent was distilled off, to yield the title compound as colorless crystals (1.03 g).

Melting point: 152°–153° C. (recrystallized from ethyl acetate-isopropyl ether) NMR (200 MHz, CDCl$_3$) ppm: 2.69 (2H, d, J=6.6 Hz), 3.42 (3H, s), 4.60–5.80 (1H, bs), 4.93 (1H, t, J=6.6 Hz), 6.88 (1H, s like), 6.97 (2H, s like), 7.10–7.40 (5H, m) Elemental analysis (for C$_{17}$H$_{15}$N$_2$O$_3$Cl): Calculated (%): C, 61.73; H, 4.57; N, 8.47 Found (%): C, 61.96; H, 4.61; N, 8.75

Reference Example 18

6-Chloro-1,2-dihydro-1-methyl-2-oxo-4-phenyl-3-quinolineacetic acid

Process 1

To a solution of 6-chloro-1,2-dihydro-1-methyl-2-oxo-4-phenyl-3-quinolinecarboxylic acid (4.41 g) in anhydrous THF (50 ml) were added oxalyl chloride (1.83 ml) and DMF (one drop), followed by stirring at room temperature for 1.5 hours. Upon solvent removal by distillation, the acid chloride was obtained as colorless crystals (4.60 g). To a solution of this acid chloride (4.0 g) in THF (65 ml) was added sodium borohydride (NaBH$_4$) (1.30 g) at room temperature, followed by stirring for 0.5 hours. Then to this solution was added 1,2-dimethoxyethane (50 ml) and then NaBH$_4$ (0.30 g), followed by stirring at 50° C. for 1 hour. Then, NaBH$_4$ (0.20 g) was added to the solution, followed by stirring at the room temperature for 1 hour. The separated precipitate was filtered off, and the filtrate was added to a dilute hydrochloric acid solution under cooling conditions, followed by extraction with ethyl acetate. The extract was washed with water and dried, after which the solvent was distilled off. The residue was purified by silica gel column chromatography (hexane:ethyl acetate=2:1→1:1) to yield 6-chloro-1, 2-dihydro-3-hydroxymethyl-1-methyl-2-oxo-4-phenylquinolin as colorless crystals (1.90 g).

Melting point: 141°–142° C. (recrystallized from ethyl acetate-isopropyl ether) NMR (200 MHz, CDCl$_3$) ppm: 3.81 (3H, s), 3.96 (1H, b), 4.40 (2H, s), 7.17 (1H, d, J=2.4 Hz), 7.23–7.27 (2H, m), 7.38 (1H, d, J=9.2 Hz), 7.49–7.54 (4H, m) Elemental analysis (for C$_{17}$H$_{15}$NO$_2$Cl): Calculated (%): C, 67.89; H, 5.03; N, 4.66 Found (%): C, 67.63; H, 4.79; N, 4.55

Process 2

While stirring a solution of 3-hydroxymethyl derivative obtained in Process 1 (1.80 g) in dichloromethane (45 ml) at 0° C., triethylamine (1.08 ml) and methanesulfonyl chloride (0.61 ml) were added, followed by stirring at for 1 hour. The reaction mixture was concentrated, and ethyl acetate was added to the residue. This mixture was washed with water and dried, after which the solvent was distilled off, to yield 6-chloro-1,2-dihydro-3-methanesulfonyloxymethyl- 1-methyl-2-oxo-4-phenylquinolin as colorless crystals (2.0 g) [NMR (200 MHz, CDCl$_3$) ppm: 3.14 (3H, s), 3.81 (3H, s), 5.00 (2H, s), 7.17–7.58 (8H, m)].

Without purification, this compound was dissolved in DMSO (20 ml), and sodium cyanide (2.0 g) was added, followed by stirring at room temperature for 1 hour. To this reaction mixture was added ethyl acetate, and the resulting mixture was washed with water and dried, after which the solvent was distilled off, to yield 6-chloro-3-cyanomethyl-1,2-dihydro-1-methyl- 2-oxo-4-phenylquinolin as colorless crystals (1.43 g).

Melting point: 160°–161° C. (recrystallized from ethyl acetate-isopropyl ether) NMR (200 MHz, CDCl3) ppm: 3.47 (2H, s), 3.84 (3H, s), 7.12 (1H, d, J=3.0 Hz), 7.21–7.31 (2H, m), 7.39 (1H, d, J=9.0 Hz), 7.53–7.61 (4H, m) Elemental analysis (for C$_{18}$sH$_{13}$N$_2$OCl): Calculated (%): C, 70.02; H, 4.24; N, 9.07 Found (%): C, 69.75; H, 4.36; N, 8.81

Process 3

A mixture of the compound obtained in Process 2 (1.10 g), acetic acid (10 ml) and hydrochloric acid (10 ml) was heated at 110° C. for 2 hours. After the solvent was distilled off, ethyl acetate was added to the residue. The mixture was washed with water and dried, after which the solvent was distilled off, to yield the title compound as colorless crystals (1.06 g).

Melting point: 195°–199° C. (recrystallized from ethyl acetate-ethyl ether) NMR (200 MHz, CDCl$_3$) ppm: 3.50 (2H, s), 3.89 (3H, s), 7.18–7.59 (8H, m) Elemental analysis (for C$_{18}$H$_{14}$NO$_3$Cl): Calculated (%): C, 65.96; H, 4.31; N, 4.27 Found (%): C, 65.75; H, 4.34; N, 4.15

Reference Example 19

1,2-Dihydro-2,6,7- trimethyl-1-oxo-4-phenyl-3-isoquinolineacetic acid

The isoquinoline-3-carboxylic acid obtained in Process 2 of Reference Example 16 was reacted in substantially the same manner as in Process 1 and 2 of Reference Example 21 to yield the title compound as colorless crystals.

Melting point: 217°–220° C. (recrystallized from ethyl acetate-isopropyl ether) NMR (200 MHz, CDCls) ppm: 2.22 (3H, s), 2.37 (3H, s), 3.63 (2H, s), 3.67 (3H, s), 5.90 (1H, brs), 6.75 (1H, s), 7.20–7.35 (2H, m), 7.40–7.55 (3H, m), 8.24 (1H, s) Elemental analysis (for C$_{20}$H$_{19}$NO$_3$): Calculated (%): C, 74.75; H, 5.96; N, 4.36 Found (%): C, 74.69; H, 6.08; N, 4.23

Reference Example 20

6-Chloro-1-oxo-4-phenyl-1H-2-benzopyran-3-acetic acid

Process 1

6-Chloro-1-oxo-4-phenyl-1H-2-benzopyran-3-carboxylic acid was reacted in substantially the same manner as in Process 1 of Reference Example 18 to yield 6-chloro-3-hydroxymethyl-1-oxo-4-phenyl-1H-2-benzopyran as colorless crystals.

Melting point: 161°–164° C. (recrystallized from ethyl acetate-ethyl ether) NMR (200 MHz, CDCl$_3$) ppm: 2.20 (1H, b), 4.30 (2H, s), 7.05 (1H, d, J=2.2 Hz), 7.28–7.53 (1H, d, J=2.0 Hz), 8.30 (1H, d, J=8.6 Hz) Elemental analysis (for C$_{16}$H$_{11}$O$_3$Cl): Calculated (%): C, 67.03; H, 3.87 Found (%): C, 66.85; H, 3.95

Process 2

The compound obtained in Process 1 was reacted with methanesulfonyl chloride in the same manner as the reaction in Process 2 of Reference Example 18 to yield 6-chloro-3-methanesulfonyloxymethyl-1-oxo-4-phenyl- 1H-2-benzopyran as colorless crystals.

Melting point: 179°–180° C. (recrystallized from ethyl acetate-isopropyl ether) NMR (200 MHz, CDCl$_3$) ppm: 3.10 (3H, s), 4.86 (2H, s), 7.08 (1H, d, J=2.0 Hz), 7.30–7.34 (2H, m), 7.53–7.58 (4H, m), 8.33 (1H, d, J=8.4 Hz) Elemental analysis (for C$_{17}$H$_{13}$O$_5$ClS): Calculated (%): C, 55.97; H, 3.59 Found (%): C, 55.69; H, 3.79

Process 3

The compound obtained in Process 2 was reacted with sodium cyanide in the same manner as the reaction in Process 2 of Reference Example 18 to yield 6-chloro-3-cyanomethyl-1-oxo-4-phenyl-1H-2-benzopyran as a pale yellow oily substance.

NMR (200 MHz, CDCl$_3$)ppm: 3.45 (2H, s), 7.01 (1H, d, J=2.2 Hz), 7.29–7.60 (6H, m), 8.31 (1H, d, J=8.6 Hz)

Process 4

The compound obtained in Process 3 was reacted in the same manner as in Process 3 of Reference Example 18 to yield the title compound as colorless crystals.

Melting point: 211°–215° C. (recrystallized from ethyl acetate-ethyl ether) NMR (200 MHz, CDCl$_3$) ppm: 3.46 (2H, s), 6.99 (1H, d, J=2.0 Hz), 7.28–7.56 (6H, m), 8.28 (1H, d, J=8.4 Hz) Elemental analysis (for C$_{17}$H$_{11}$O$_4$Cl.1/4H$_2$O): Calculated (%): C, 63.96; H, 3.63 Found (%): C, 64.09; H, 3.64

Reference Example 21

6-Chloro-2-oxo-4-phenyl-2H-1-benzopyran-3-acetic acid

Process 1

To a solution of 6-chloro-2-oxo-4-phenyl-2H-1-benzopyran-3-carboxylic acid (6.1 g) in anhydrous THF (100 ml) were added oxalyl chloride (2.7 ml) and DMF (several drops), followed by stirring at room temperature for 3 hours. Upon solvent removal by distillation, an acid chloride was obtained as colorless crystals. To a solution of this acid chloride in anhydrous THF (100 ml) was added a solution of diazomethane in ethyl ether (prepared from 12.0 g of N-nitrosomethyleurea), followed by stirring at room temperature for 0.5 hours. Upon solvent removal by distillation, a diazoketone derivative was obtained as an oily substance [NMR (200 MHz, CDCl$_3$) ppm: 5.4 (1H, bs), 7.19 (1H, d, J=2.2 Hz), 7.3–7.4 (3H, m), 7.5–7.6 (4H, m); IR$\nu_{max}$ (Neat)cm$^{-1}$: 2100, 1720, 1620].

This diazoketone derivative was dissolved in methanol (300 ml). While stirring this solution with heating at 50° C., silver oxide (Ag$_2$O) (3.0 g) was added portionwise. After this mixture was stirred for 3 hours with heating under reflux, it was filtered through Celite, and the filtrate was distilled to remove the solvent. The residue was fractionated and purified by silica gel column chromatography (hexane-:ethyl acetate=3:1) to yield 6-chloro-2-oxo-4-phenyl-2H-1-benzopyran-3-acetic acid ethyl ester as an orange oily substance (4.14 g). This oily substance becomes colorless crystals upon addition of ethyl acetate-hexane.

Melting point: 98°–99° C. (recrystallized from ethyl acetate-hexane) NMR (200 MHz, CDCl$_3$) ppm: 3.40 (2H, s), 3.68 (3H, s), 6.99 (1H, d, J=2.2 Hz), 7.2–7.6 (7H, m) Elemental analysis (for C$_{18}$H$_{13}$O$_4$Cl): Calculated (%): C, 65.76; H, 3.99 Found (%): C, 65.92; H, 3.84

Process 2

A mixture of the crude compound obtained in Process 1 (4.1 g), acetic acid (48 ml) and hydrochloric acid (24 ml) was heated under reflux for 1 hour. After the solvent was distilled off, ethyl acetate was added to the residue. This mixture was washed with water and dried, after which the solvent was distilled off, followed by treatment of the residue with isopropyl ether, to yield the title compound as pale yellow crystals (2.32 g).

Melting point: 174°–177° C. (recrystallized from isopropyl ether) NMR (200 MHz, CDCl$_3$) ppm: 3.44 (2H, s), 7.01 (1H, d, J=2.4 Hz), 7.2–7.6 (7H, m) Elemental analysis (for C$_{17}$H$_{11}$O$_4$Cl): Calculated (%): C, 64.88; H, 3.52 Found (%): C, 65.13; H, 3.54

Reference. Example 22

6-Methyl-2-oxo-4-phenyl-2H-1-benzopyran-3-acetic acid

Process 1

A mixture of 6-methyl-2-oxo-4-phenyl-2H-1-benzopyran-3-carboxylic acid ethyl ester [prepared by heating 2-hydroxy-5-methylbenzophenone and diethyl malonate in the presence of 1,8-diazabicyclo[5.4.0]undec-7-en; melting point: 129°–131° C.; NMR (200 MHz, CDCl$_3$) ppm: 0.96 (3H, t, J=7.2 Hz), 2.31 (3H, s), 4.07 (2H, q, J=7.2 Hz), 7.01 (1H, bs), 7.2–7.4 (4H, m), 7.5–7.6 (3H, m)](10.0 g), acetic acid (100 ml) and hydrochloric acid (60 ml) was heated under reflux at 110° C. for 15 hours. After the solvent was distilled off, ethyl acetate was added to the residue. The mixture was washed with water and dried, after which the solvent was distilled off, to yield 6-methyl-2ooxo-4-phenyl-2H-1-benzopyran-3-carboxylic acid as colorless crystals (8.7 g).

Melting point: 260°–262° C. (recrystallized from ethyl acetate-isopropyl ether) NMR (200 MHz, CDCl$_3$) ppm: 2.31 (3H, s), 6.95 (1H, bs), 7.2–7.3 (2H, m), 7.39 (H, d, J=8.6 Hz), 7.5–7.6 (4H, m) Elemental analysis (for C$_{17}$H$_{12}$O$_4$): Calculated (%): C, 72.85; H, 4.32 Found (%): C, 73.13; H, 4.45

Process 2

The compound obtained in Process 1 was reacted in substantially the same manner as in Process 1 of Reference Example 21 to yield 6-methyl-2-oxo- 4-phenyl-2H-1-benzopyran-3-acetic acid methyl ester as colorless crystals.

Melting point: 142°–144° C. (recrystallized from ethyl acetate-isopropyl ether) NMR (200 MHz, CDCl$_3$) ppm: 2.72 (3H, s), 3.39 (2H, s), 3.67 (3H, s), 6.79 (1H, brs), 7.2–7.3 (4H, m), 7.5–7.6 (3H, m) Elemental analysis (for C$_{19}$H$_{16}$O$_4$): Calculated (%): C, 74.01; 11, 5.23 Found (%): C, 73.75; 11, 5.23

Process 3

The compound obtained in Process 2 was reacted in substantially the same manner as in Process 2 of Reference Example 21 to yield the title compound as colorless crystals.

Melting point: 214°–217° C. (recrystallized from chloroform-isopropyl ether) NMR (200 MHz, CDCl$_3$) ppm: 2.27 (3H, s), 3.42 (2H, s), 6.80 (1H, brs), 7.2–7.3 (4H, m), 7.5–7.6 (3H, m) Elemental analysis (for C$_{18}$H$_{14}$O$_4$): Calculated (%): C, 73.46; 11, 4.79 Found (%): C, 73.37; 11, 4.79

Reference Example 23

6-Chloro-4-phenyl-3-quinolineacetic acid

Process 1

While stirring a mixture of 6-chloro-4-phenyl-3-quinolinecarboxylic acid methyl ester (8.0 g) and ethyl ether (100 ml) at 0° C., lithium aluminum hydride (1.0 g) was added, followed by stirring for 30 minutes. After water (5 ml) was added, the mixture was stirred at room temperature for 30 more minutes. After ethyl acetate was added, the insoluble material was altered off. The filtrate was washed by successively with aqueous potassium carbonate and saturated aqueous sodium chloride and then dried, after which the solvent was distilled off, to yield 6-chloro-3-hydroxymethyl-4-phenylquinolin as colorless crystals (6.05 g).

Melting point: 169°–170° C. (recrystallized from ethyl acetate-isopropyl ether) NMR (200 MHz, CDCl$_3$) ppm: 4.63 (2H, s), 7.20–7.35 (2H, m), 7.40–7.65 (5H, m), 8.07 (1H, d, J=8.8 Hz), 9.09 (1H, s) Elemental analysis (for C$_{16}$H$_{12}$NOCl): Calculated (%): C. 71.25; H, 4.48; N, 5.19 Found (%): C, 71.44; H, 4.51; N, 5.30

Process 2

The compound obtained in Process 1 was reacted in substantially the same manner as in Process 2 of Reference Example 18 to yield 6-chloro-3-cyanomethyl- 4-phenylquinolin as colorless crystals.

Melting point: 149°–151° C. (recrystallized from ethyl acetate-isopropyl ether) NMR (200 MHz, CDCl$_3$) ppm: 3.65 (2H, s), 7.25–7.35 (2H, m), 7.43 (1H, d, J=2.2 Hz), 7.58–7.75 (4H, m), 8.12 (1H, d, J=9.0 Hz), 9.04 (1H, s) Elemental analysis (for C$_{17}$H$_{11}$N$_2$Cl): Calculated (%): C, 73.25; H, 3.98; N, 10.05 Found (%): C, 72.86; H, 3.93; N, 10.36

Process 3

The compound obtained in Process 2 was reacted in substantially the same manner as in Process 3 of Reference Example 18 to yield the title compound as colorless crystals.

Melting point: 211°–213° C. (recrystallized from tetrahydrofuran-isopropyl ether) NMR (200 MHz, CDCl$_3$) ppm: 3.61 (2H, s), 4.10 (1H, bs), 7.25–7.35 (2H, m), 7.43 (1H, d, J=2.2 Hz), 7.50–7.70 (4H, m), 8.19 (1H, d, J=8.8 Hz), 8.95 (1H, s) Elemental analysis (for C$_{17}$H$_{12}$NO$_2$Cl.0.8H$_2$O): Calculated (%): C, 65.41; H, 4.39; N, 4.49 Found (%): C, 65.42; H, 4.16; N, 4.66

Reference Example 24

4-(2-Methoxyphenyl)-1-oxo-1H-2-benzopyran-3-acetic acid 4-(2-Methoxyphenyl)-1-oxo-1H-2-benzopyran-3-carboxylic acid was reacted in substantially the same manner as in Process 1 and 2 of Reference Example 21 to yield the title compound as colorless crystals.

Melting point: 143°–144° C. (recrystallized from ethyl acetate-isopropyl ether) NMR (200 MHz, CDCl$_3$) ppm: 3.44 (2H, s), 3.72 (3H, s), 6.9–7.6 (7H, m), 8.34 (1H, m)

Reference Example 25

6-Chloro-4-(2-methylphenyl)-2-oxo-2H-1-benzopyran-3-carboxylic acid

Process 1

A mixture of 5-Chloro-2-hydroxy-2-methylbenzophenone [prepared by reaction of 4-chloroanisole with orthotolyl chloride in 1,1,2,2,-tetrachloroethane in the presence of aluminum chloride (150° C., 7 hours): melting point 65°–66° C.] (71.9 g), diethyl malonate (70 ml) and 1,8diazabicyclo[5.4.0]undec-7-ene (4 ml) was stirred at 170° C. for 6 hours. The reaction mixture was purified by silica gel column chromatography (hexane) to yield 6-chloro-4-(2-methylphenyl)-2-oxo-2H-1-benzopyran-3-carboxylic acid ethyl ester as colorless crystals (73.2 g).

Melting point: 93°–95° C. (recrystallized from isopropyl ether-hexane)

Process 2

The compound obtained in Process 1 was reacted by a method similar to Process 1 of Reference Example 22 to yield the title compound as colorless crystals.

Melting point: 211°–214° C. (recrystallized from ethyl acetate-isopropyl ether) NMR (200 MHz, CDCl$_3$) ppm: 2.09 (3H, s), 6.9–7.1 (2H, m), 7.3–7.5 (4H, m), 7.64 (1H, dd, J=8.8, 2.2 Hz)

Reference Example 26

6-Chloro-4-(2-methylphenyl)-2-oxo-2H-1-benzopyran-3-acetic acid

The compound obtained in Reference Example 25 was reacted by a method similar to Process 1 of Reference Example 21 to yield the methyl ester of the title compound as an oil.

NMR (200 MHz, CDCl$_3$) ppm: 2.09 (3H, s), 3.24 (1H, d, J=16.5 Hz), 3.43 (1H, d, J=16.5 Hz), 3.66 (3H, s), 6.83 (1H, d, J=2.2 Hz), 7.10 (1H, m), 7.3–7.5 (8H,m)]

This compound was reacted by a method similar to Process 2 of Reference Example 21 to yield the title compound as colorless crystals.

Melting point: 180°–183° C. (recrystallized from ethyl acetate-isopropyl ether) NMR (200 MHz, CDCl$_3$) ppm: 2.05 (3H, s), 3.27 (1H, d, J=16.8 Hz), 3.45 (1H, d, J=16.8 Hz), 6.83 (1H, d, J=2.2 Hz), 7.10 (1H, d, J=6.6 Hz), 7.3–7.5 (5H, m)

Reference Example 27

6-Chloro-4-(2-methoxyphenyl)-2-oxo-2H-1-benzopyran-3-acetic acid

Process 1

A mixture of 5-chloro-2-hydroxy-2-methoxybenzophenone [prepared from 2-bromo-4-chloro-(2-methoxyethoxy)methoxybenzene and orthoanisaldehyde as the starting materials: melting point, 94°–95° C. (recrystallized from isopropyl ether)] (11.8 g), diethyl malonate (13.6 g) and potassium fluoride (2.61 g) was heated at 180° C. for 8.5 hours. After cooling, ethyl acetate was added to the mixture, washed with water, dried and evaporated. The residue was subjected to silica gel column chromatography (ethyl acetate:hexane: 1:10) to yield 6-chloro-4-(2-methoxyphenyl)-2-oxo-2H-1-benzopyran-3-carboxylic acid ethyl ester as colorless crystals (7.73 g).

Melting point: 108°–109° C. (recrystallized from ethyl acetate-ethyl ether)

Process 2

The compound obtained in Process 1 was subjected to hydrolysis by a method similar to Process 2 of Reference Example 25 to yield 6-chloro-4-(2-methoxyphenyl)- 2-oxo-2H-1-benzopyran-3-carboxylic acid as colorless crystals.

Melting point: 197°–199° C. (recrystallized from ethyl acetate-methanol)

Process 3

The compound obtained in Process 2 was subjected to carbon-elongation by a method similar to Process 1 of Reference Example 26 to yield 6-chloro-4-(2-methoxyphenyl)-2-oxo-2H-1-benzopyran-3-acetic acid methyl ester as colorless crystals.

Melting point: 132°–133° C. (recrystallized from ethyl acetate)

Process 4

The compound obtained in Process 3 was subjected to hydrolysis by a method similar to Process 2 of Reference Example 26 to yield the title compound as colorless crystals.

Melting point: 200°–202° C. (recrystallized from ethyl acetate)

Reference Example 28

6-Chloro-2-oxo-4-[2-(trifluoromethyl)phenyl)-2H-1-benzopyran-3-acetic acid

Process 1

5-Chloro-2-hydroxy-2-(trifluoromethyl)benzophenone [prepared from 2-bromo-4-chloro-(2-methyoxyethoxy)methoxybenzene and ortho(trifluoromethyl)benzaldehyde as the starting materials: melting point, 71°–72° C. (recrystallized from hexane-isopropyl ether)] was reacted by a method similar to Process 1 of Reference Example 25 to yield 6-chloro-2-oxo-4-[ 2-(trifluoromethyl)phenyl)-2H-1-benzopyran-3-carboxylic acid ethyl ester as an oily substance.

NMR (200 MHz, CDCl$_3$) ppm: 0.95 (3H, t, J=7.2 Hz), 4.05 (2H, q, J=7.2 Hz), 6.81 (1H, d, J=2.4 Hz), 7.30–7.38 (2H, m), 7.54 (1H, dd, J=2.6, 8.8 Hz), 7.71 (2H, t, J=4.2 Hz), 7.82–7.90 (1H, m)

Process 2

The compound obtained in Process 1 was reacted by a method similar to Process 2 of Reference Example 25 to yield 6-chloro-2-oxo-4-[2-(trifluoromethyl)phenyl]- 2H-1-benzopyran-3-carboxylic acid as colorless crystals.

Melting point: 205°–209° C. (recrystallized from ethyl acetate)

Process 3

The compound obtained in Process 2 was subjected to carbon-elongation by a method similar to Process 1 of Reference Example 26 to yield 6-chloro-2-oxo-4-[2-(trifluoromethyl)phenyl)-2H-1-benzopyran-3-acetic acid methyl ester as colorless crystals.

Melting point: 146°–147° C. (recrystallized from ethyl acetate)

Process 4

The compound obtained in Process 3 was reacted by a method similar to Process 2 of Reference Example 26 to yield the title compound as colorless crystals.

Melting point: 167°–169° C. (recrystallized from isopropyl ether)

Reference Example 29

2,6,7-Trimethyl-4-phenyl-1(2H)-isoquinolinone-3-carboxylic acid

Process 1

A mixture of 2-benzoyl-4,5-dimethylbenzoic acid (11.4 g), acetone (300 ml), DMF (10 ml), potassium carbonate (6.83 g) and diethyl bromomalonate (12.84 g) was stirred at room temperature for 60 hours. After the solvent was distilled off, ethyl acetate was added to the residue. This mixture was washed with water and then dried, after which the solvent was distilled off. To the residue were added acetic acid (180 ml) and hydrochloric acid (180 ml), followed by heating at 110° C. for 5 hours. The reaction mixture was concentrated, and water was added to the concentrate, followed by extraction with ethyl acetate. The extract was washed with water and then dried, after which the solvent was distilled off, to yield colorless crystals. The crystals were recrystallized from ethyl acetate-isopropyl ether to yield 6,7-dimethyl- 4-phenylisocoumarin-3-carboxylic acid (≡6,7-dimethyl-1-oxo-4-phenyl- 1H-2-benzopyran-3-carboxylic acid).

Melting point: 265°–268° C.

Process 2

To a solution of the compound (3.75 g) obtained in Process 1 in methanol (50 ml) was added a 40% methylamine-methanol solution (25 ml), followed by stirring at room temperature for 2 hours. After the solvent was distilled off, 4 N-HCl-ethyl acetate (50 ml) was added to the residue, followed by stirring at room temperature for 2 hours. After the solvent was distilled off, water was added to the residue, and the precipitated crystals were collected by filtration and then washed with water, acetone and ethyl ether to yield the title compound as colorless crystals (3.51 g).

Melting point: >300° C. (recrystallized from ethanol) NMR (200 MHz, CDCl$_3$+DMSO-d$_6$) ppm: 2.25 (3H, s), 2.39 (3H, s), 3.67 (3H, s), 6.91 (1H, s), 7.39–7.42(5H, m),8.24(1H, s) Elemental analysis (for C$_{19}$H$_{17}$NO$_3$): Calculated: C, 74.25; H, 5.58; N, 4.56 Found: C, 74.40; H, 5.50; N, 4.41

The compound obtained in Process 1 of Reference Example 29 was reacted with ethylamine, n-butylamine, N,N-dimethylaminoethylenediamine or ammonia, in place of methylamine, in the same manner as in Process 2, to yield the compounds of Reference Examples 30 through 33 as colorless crystals.

Reference Example 30

2-Ethyl-6,7-dimethyl-4-phenyl-1(2H)-isoquinolinone-3-carboxylic acid

Melting point: 254°–256° C. (recrystallized from ethyl acetate-methanol)

Reference Example 31

2-n-Butyl-6,7-dimethyl-4-phenyl-1(2H)-isoquinolinone-3-carboxylic acid

Melting point: 218°–219° C. (recrystallized from ethyl acetate-isopropyl ether)

Reference Example 32

2-(2-Dimethylaminoethyl)-6,7-dimethyl-4-phenyl-1(2H)-isoquinolinone- 3-carboxylic acid Melting point: 291°–293° C. (recrystallized from chloroform-methanol)

Reference Example 33

6,7-Dimethyl-4-phenyl-1(2H)-isoquinolinone-3-carboxylic acid

Melting point: 325°–327° C. (recrystallized from chloroform-methanol)

Reference Example 34

4-(4-Fluorophenyl)-2,6,7-trimethyl-1(2H)-isoquinolinone-3-carboxylic acid 4,5-Dimethyl-2-(4-fluorobenzoyl)benzoic acid, in place of 2-benzoyl-4,5-dimethylbenzoic acid, was reacted and treated in the same manner as in Process 1 of Reference Example 29 to yield 4-(2-fluorophenyl)-6,7-dimethylisocoumarin- 3-carboxylic acid [melting point 214°–217° C. (recrystallized from ethyl acetate)]. This compound was reacted in the same manner as in Process 2 of Reference Example 29 to yield the title compound as colorless crystals.

Melting point: 309°–312° C. (recrystallized from chloroform-methanol)

Reference Example 35

5-Fluoro-4-(4-fluorophenyl)-2-methyl-1 (2H)-isoquinolinone-3-carboxylic acid

5-Fluoro-4-(4-fluorophenyl)isocoumarin-3-carboxylic acid and methylamine were reacted in the same manner as in Process 2 of Reference Example 29 to yield the title compound as colorless crystals.

Melting point: 256°–257° C. (recrystallized from acetone-isopropyl ether)

Reference Example 36

6,7-Dichloro-2-methyl-4-phenyl-1(2H)-isoquinolinone-3-carboxylic acid

2-Benzoyl-4,5-dichlorobenzoic acid, in place of 2-benzoyl-4,5-dimethylbenzoic acid, was reacted and treated in the same manner as in Process 1 of Reference Example 29 to yield 6,7-dichloro-4-phenylisocoumarin-3-carboxylic acid [melting point 243°–244° C. (recrystallized from ethyl acetate-isopropyl ether)]. This compound was reacted and treated in the same manner as in Process 2 of Reference Example 29 to yield the title compound as colorless crystals.

Melting point: >300° C. (recrystallized from chloroform-methanol)

Reference Example 37

2-[2-(N,N-Dimethylamino)ethyl]-4-phenyl-1-(2H)-isoquinolinone-3-carboxylic acid

1-Oxo-4-phenyl-1H-2-benzopyran-3-carboxylic acid and N,N-dimethylaminoethylenediamine were reacted by a method similar to Process 1 and 2 of Reference Example 29 to yield the title compound as colorless crystals.

Melting point: 295°–296° C. (recrystallized from chloroform methanoldichloromethane-ethyl ether)

Reference Example 38

2,6,7-Trimethyl-4-(2-methylphenyl)-1(2H)-isoquinolinone-3-carboxylic acid

Process 1

A mixture of 4,5-dimethyl-2-(2-methylbenzoyl)benzoic acid (7.7 g), dichloromethane (100 ml), oxalyl chloride (2.74 ml) and DMF (3 drops) was stirred at room temperature for 2 hours. After the solvent was distilled off, dichloromethane (50 ml) was added to the residue. This mixture was added dropwise to a mixture of N-methylaminoacetonitrile hydrochloride (4.86 g), triethylamine (12.0 ml) and dichloromethane (70 ml), while stirring with ice cooling. This mixture was stirred at room temperature for 12 hours. After the solvent was distilled off, ethyl acetate was added to the residue. The mixture was washed successively with water, dilute hydrochloric acid, sodium hydrogen carbonate and water and then dried, after which the solvent was distilled off, to yield 4,5-dimethyl-2-(2-methylbenzoyl)benzoic acid-N-cyanomethyl-N-methylamide as a colorless oily substance (9.2 g).

NMR (200 MHz, CDCl$_3$) ppm: 2.26 (3H, s), 2.35 (3H, s), 2.37 (3H, s), 2.99 (3H, s), 4.47 (2H, s), 7.05–7.40 (6H, m)

Process 2

A mixture of the compound (9.1 g) obtained in Process 1, toluene (200 ml) and 1,8-diazabicyclo[5.4.0]undec-7-ene (8 ml) was stirred for 7 hours under refluxing. After ethyl acetate was added, the reaction mixture was washed successively with water, dilute hydrochloric acid, aqueous sodium hydrogen carbonate and water and then dried, after which the solvent was distilled off, to yield 3-cyano-2,6,7-trimethyl-4-(2-methylphenyl)-1(2H)-isoquinolinone as colorless crystals (6.3 g).

Melting point: 217°–218° C. (recrystallized from ethyl acetate)

Process 3

The compound (5.8 g) obtained in Process 2, ethanol (20 ml) and 1N sodium hydroxide (25 ml) were stirred for 3 hours under refluxing. The reaction mixture was concentrated, dilute hydrochloric acid was added to the concentrate, and the precipitated crystals were collected by filtration. The crystals were washed with water, acetone and ethyl ether to yield 2,6,7-trimethyl- 4-(2-methylphenyl)-1(2H)-isoquinolinone-3-carboxylic acid amide as colorless crystals (6.1 g).

Melting point: 296°–299° C. (recrystallized from methanol)

Process 4

To a mixture of the compound (1.0 g) obtained in Process 3, acetic acid (15 ml) and concentrate hydrochloric acid (30 ml) was added portionwise sodium nitrite (6.2 g) at room temperature, followed by stirring for 5 hours. To the reaction mixture was added water, and the precipitated crystals were collected by filtration, which were then washed with water, acetone and ethyl ether, to yield the title compound as colorless crystals (0.97 g).

Melting point: 291°–292.5° C. (recrystallized from ethyl acetate)

2-Benzoylbenzoic acids having respective corresponding substituents, in place of 4,5-dimethyl-2-(2-methylbenzoyl)benzoic acid of Process 1 of Reference Example 38, were reacted and treated in the same manner as in processes 2 through 4 to yield the compounds of Reference Example 39 to 45 as colorless crystals.

Reference Example 39

4-(2,6-Dimethylphenyl)-2-methyl-1(2H)-isoquinolinone-3-carboxylic acid

Melting point: 284°–285.5° C. (recrystallized from methanol-ethanol)

Reference Example 40

4-(4-Fluoro-2-methylphenyl)-2-methyl-1(2H)-isoquinolinone-3-carboxylic acid

Melting point: 257.5°–260° C. (recrystallized from ethyl acetate-ethanol)

Reference Example 41

2-Methyl-4-(2-methylphenyl)-1(2H)-isoquinolinone-3-carboxylic acid

Melting point: 225°–227° C. (recrystallized from ethyl acetate-ethanol)

Reference Example 42

4-(2-Ethylphenyl)-2-methyl-1(2H)-isoquinolinone-3-carboxylic acid

Melting point: 100°–102° C. [2/3 hydrate] (recrystallized from ethyl acetate-isopropyl ether)

Reference Example 43

4-(2-Ethylphenyl).2,6,7-trimethyl-1(2H)-isoquinolinone-3-carboxylic acid

Melting point: 214°–215° C. (recrystallized from ethyl acetate-ethanol)

Reference Example 44

4-(2,6-Dimethylphenyl)-2,6,7-trimethyl-1 (2H)-isoquinolinone-3-carboxylic acid

Melting point: >300° C. (recrystallized from ethyl acetate-ethanol)

Reference Example 45

2-Methyl-4-[2-(trifluoromethyl)phenyl]-1-(2H)-isoquinolinone-3-carboxylic acid

Melting point: 250°–253° C. (recrystallized from ethyl acetate-THF)

Reference Example 46

5,6,7,8-Tetrahydro-2-methyl-4-phenyl-1(2H)-isoquinolinone-3-carboxylic acid

Process 1

To a solution of 2-benzoyl-1-cyclohexenecarboxylic acid [prepared from 3,4,5,6-tetrahydrophtalic anhydride by reacting with aluminum chloride in benzene] (7.05 g) in THF (100 ml) were added DMF (a few drops) and oxalyl chloride (3.20 ml) at room temperature, and the mixture was stirred for 2 hours. The solvent was evaporated, and the residue was dissolved in THF (50 ml). The solution was added dropwise to a stirred mixture of N-methylglycine ethyl ester hydrochloride (5.64 g), THF (100 ml) and triethylamine (12.0 ml) at 0° C. The mixture was stirred at room temperature for 2 hours and under reflux for 4 hours, and the solvent was evaporated. To the residue was added ethyl acetate. The mixture was washed successively with water, diluted hydrochloric acid, water, aqueous sodium hydrogen carbonate and water, dried, and the solvent was evaporated to yield N-(2-benzoyl-1-cyclohexenecarbonyl)-N-methylglycine ethyl ester as a pale yellow oil (9.73 g). To the solution of this compound in THF (250 ml) was added pottasium t-butoxide (3.97 g) at 0° C. with stirring, and the mixture was stirred for 10 minutes at room temperature. The solvent was evaporated, and to the residue was added ethyl acetate. The mixture was washed with water, dried and the solvent was evaporated to yield 5,6,7,8-tetrahydro-2-methyl-4-phenyl-1(2H)-isoquinolinone- 3-carboxylic acid ethyl ester as colorless crystals (1.86 g).

Melting point: 131°–132° (7 (recrystallized from isopropyl ether)

Process 2

A mixture of the compound obtained in Process 1 (1.00 g), dioxane (20 ml), and 1N-NaOH (20 ml) was refluxed for 2 hours. The solvent was evaporated, and to the residue was added water. The mixture was acidified with hydrochloric acid, and extracted with ethyl acetate. The extract was washed with water, dried, and the solvent was evaporated to yield the title compound as colorless crystals (519 mg).

Melting point: 226°–227° C. (recrystallized from ethyl acetate-isopropyl ether)

Reference Example 47

1,2-Dihydro-3-hydroxymethyl-2,6,7-trimethyl-1-oxo-4-phenylisoquinoline

To a solution of the compound (9.27 g) obtained in Reference Example 29 in THF (100 ml) were added oxalyl chloride (3.7 ml) and DMF (10 drops) at room temperature, followed by stirring for 30 minutes. After the solvent was distilled off, the residue was dissolved in THF (50 ml). This solution was gradually added at 0° C. to a suspension of sodium borohydride (5.0 g) in dimethoxyethane (100 ml). After stirring at 0° C. for 30 minutes, the reaction mixture was added to 2 N hydrochloric acid at 0° C., followed by extraction with ethyl acetate. The extract was washed with aqueous sodium hydrogen carbonate and water and then dried, after which the solvent was distilled off, to yield the title compound as a colorless crystals (7.18 g).

Melting point: 209°–210° C. (recrystallized from ethyl acetate-isopropyl ether) NMR (200 MHz, CDCl$_3$) ppm: 2.09 (1H, bt, J=5.8 Hz), 2.20 (3H, s), 2.34 (3H, s), 3.81 (3H, s), 4.43 (2H, d, J=5.8 Hz), 6.73 (1H, s), 7.25–7.35 (2H, m), 7.45–7.55 (3H, m), 8.19 (1H, s)

1(2H)-Isoquinolinone-3-carboxylic acids having respective corresponding substituents were reduced in the same manner as in Reference Example 47 to yield the compounds of Reference Examples 48 to 51 as colorless crystals.

Reference Example 48

1,2-Dihydro-3-hydroxymethyl-2-methyl-1-oxo-4-phenylisoquinoline

Melting point: 158°–159° C. (recrystallized from ethyl acetate-isopropyl ether)

Reference Example 49

1,2-Dihydro-3-hydroxymethyl-2-methyl-4-(2-methylphenyl)-1-oxoisoquinoline

Melting point: 167°–168° C. (recrystallized from ethyl acetate-isopropyl ether)

Reference Example 50

6-Chloro-1,2-dihydro-3-hydroxymethyl-2-methyl-1-oxo-4-phenylisoquinoline

Melting point: 193°–195° C. (recrystallized from ethyl acetate-ethyl ether)

Reference Example 51

2-Ethoxycarbonylethyl-1,2-dihydro-3-hydroxymethyl-6,7-dimethyl-1-oxo-4-phenylisoquinoline Melting point: 176°–178° C. (recrystallized from ethyl acetate)

Reference Example 52

1,2-Dihydro-3-methanesulfonyloxymethyl-2,6,7-trimethyl-1-oxo-4-phenylisoquinoline To a solution of the compound (3.0 g) obtained in Reference Example 47 in dichloromethane (1()0 ml) were added triethylamine (3.8 ml) and methanesulfonyl chloride(1.3 ml), while stirring the solution at 0° C., followed by stirring for 30 minutes. After dichloromethane was added, the reaction mixture was washed with a 5% aqueous phosphoric acid solution and water and then dried, after which the solvent was distilled off, to yield the title compound as colorless crystals (2.98 g).

Melting point: 150°–151° C. (recrystallized from ethyl acetate-isopropyl ether) NMR (200 MHz, CDCl$_3$) ppm: 2.25 (3H, s), 2.40 (3H, s), 2.86 (3H, s), 3.77 (3H, s), 5.01 (2H, s), 6.82 (1H, s), 7.25–7.35 (2H, m), 7.45–7.60 (3H, m), 8.27 (1H, s) Elemental analysis (for C$_{20}$H$_{21}$NO$_4$S): Calculated: C, 64.67; H, 5.70; N, 3.77 Found: C, 64.59; Y, 5.69; N, 3.67

3-Hydroxylmethytisoquinolines having respective corresponding substituents were reacted with methanesulfonyl chloride in the same manner as in Reference Example 52 to yield the compounds of Reference Example 53 to 55 as colorless crystals.

Reference Example 53

1,2-Dihydro-3-methanesulfonyloxymethyl-2-methyl-1-oxo-4-phenylisoquinoline

Melting point: 149°–150° C. (recrystallized from ethyl acetate-isopropyl ether)

Reference Example 54

1,2-Dihydro-3-methanesulfonyloxymethyl-2-methyl-4-(2-methylphenyl)- 1-oxoisoquinoline Melting point: 149°–150° C. (recrystallized from ethyl acetate-isopropyl ether)

Reference Example 55

6-Chloro-1,2-dihydro-3-methanesulfonyloxymethyl-2-methyl-1-oxo-4-phenylisoquinoline Melting points: 163°–165° C. (recrystallized from ethyl acetate-isopropyl ether)

Reference Example 56

1,2-Dihydro-2,6,7-trimethyl-1-oxo-4-phenyl-3-isoquinolineacetic acid

Process 1

The compound (6.4 g) obtained in Reference Example 52 was dissolved in DMSO (80 ml), and sodium cyanide (5.0 g) was added, followed by stirring at room temperature for 30 minutes. After ethyl acetate was added, this reaction mixture was washed with water and then dried, after which the solvent was distilled off, to yield 3-cyanomethyl-1,2-dihydro-2,6,7-trimethyl-1-oxo-4-phenylisoquinoline as colorless crystals (4.7 g).

Melting point: 186°–188° C. (recrystallized from ethyl acetate-isopropyl ether)

Process 2

A mixture of the compound (4.7 g) obtained in Process 1, acetic acid (150 ml) and hydrochloric acid (150 ml) was heated at 110° C. for 7 hours. After the solvent was distilled off, ethyl acetate was added to the residue. The mixture was washed with water and then dried, after which the solvent was distilled off, to yield the title compound as colorless crystals (3.7 g).

The physico-chemical data of this compound were identical with those of the compound obtained in Reference Example 19.

Reference Example 57

The compound obtained in Reference Example 55 was reacted by a method similar to Process 1 and 2 of Reference Example 56 to yield the following compounds.

Process 1

6-Chloro-3-cyanomethyl-1,2-dihydro-2-methyl-1-oxo-4-phenylisoquinoline

Melting point: 229°–231° (3 (recrystallized from ethyl acetate)

Process 2

6-Chloro-1,2-dihydro-2-methyl-1-oxo-4-phenyl-3-isoquinolineacetic acid

Melting point: 216°–217° C. (recrystallized from ethyl acetate-acetone)

Reference Example 58

1,2-Dihydro-3-(2-hydroxyethyl)-2,6,7-trimethyl-1-oxo-4-phenylisoquinoline

To a solution of the compound (700 mg) obtained in Reference Example 56 in THF (10 ml) were added oxalyl chloride (0.3 ml) and DMF (one drop) at room temperature, followed by stirring for 30 minutes. After the solvent was distilled off, the residue was dissolved in THF (5 ml). This solution was gradually added at 0° C. to a suspension of sodium borohydride (0.5 g) in dimethoxyethane (10 ml). After stirring at 0° C. for 20 minutes, the reaction mixture was added to 2N hydrochloric acid at 0° C., followed by extraction with ethyl acetate. The extract was washed with aqueous sodium hydrogen carbonate and water and then dried, after which the solvent was distilled off, to yield the title compound as colorless crystals (571 mg).

Melting point: 204°–207° C. (recrystallized from ethyl acetate-isopropyl ether) NMR (200 MHz, $CDCl_3$) ppm: 1.90 (1H, bs), 2.19 (3H, s), 2.34 (3H, s), 2.84 (2H, t, J=7.1 Hz), 3.60–3.80 (2H, m), 3.73 (3H, s), 6.62 (1H, s) 7.20–7.30 (2H, m), 7.35–7.50 (3H, m), 8.16 (1H, s)

Reference Example 59

2-Ethoxycarbonylmethyl-6,7-dimethyl-4-phenyl-1 (2H)-isoquinolinone-3-carboxylic acid

Process 1

To a solution of the compound (1.172 g) of Reference Example 33 in acetone (20 ml)-DMF (5 ml) were added benzyl bromide (0.536 ml) and potassium carbonate (608 mg), followed by heating under reflux for 2.5 hours. After the solvent was distilled off, ethyl acetate was added to the residue, which was then washed with water and then dried, followed by solvent removal by distillation, to yield 6,7-dimethyl-4-phenyl-1(2H)-isoquinolinone-3-carboxylic acid benzyl ester as colorless crystals (700 mg).

Melting point: 166°–169° C. (recrystallized from ethyl acetate)

Process 2

To a solution of the compound (700 mg) obtained in Process 1 in DMF (5 ml) was added sodium hydride (60% in oil) (80 mg), followed by stirring at room temperature for 15 minutes. To this mixture was added ethyl bromoacetate (0.222 ml) with ice cooling, followed by stirring at room temperature for 30 minutes. The reaction mixture was poured into water and extracted with ethyl acetate, after which the extract was washed with water and then dried. After the solvent was distilled off, the residue was subjected to silica gel column chromatography (hexane:ethyl acetate=9:1) to yield 2-ethoxycarbonylmethyl- 6,7-dimethyl-4-phenyl-1(2H)-isoquinolinone-3-carboxylic acid benzyl ester as colorless crystals (450 mg).

Melting point: 139.5°–140.5° C. (recrystallized from ethyl acetate-hexane)

Process 3

To a solution of the compound (400 mg) obtained in Process 2 in ethanol (15 ml) was added 10% palladium carbon (100 mg), followed by stirring at room temperature in a hydrogen atmosphere for 1.5 hours. The catalyst was filtered off, and the filtrate was distilled to remove the solvent. The residue was subjected to silica get column chromatography (chloroform:methanol=4:1) to yield the title compound as colorless crystals (280 mg).

Melting point: 210°–213° C. (recrystallized from methanol)

Reference Example 60

2-(3-Ethoxycarbonylpropyl)-4-phenyl-1(2H)-isoquinolinone-3-carboxylic acid

A mixture of 4-phenylisocoumarin-3-carboxylic acid (1.30 g), 4-amino-n-butyric acid ethyl ester (2.75 g) and ethanol (8 ml) was heated under reflux for 14 hours while stirring. After the solvent was distilled off, ethyl acetate was added to the residue. This mixture was washed with dilute hydrochloric acid and water and then dried, after which the solvent was distilled off. To the residue were added ethyl acetate (10 ml) and 4N HCl-ethyl acetate (20 ml), followed by stirring at room temperature for 3 hours. After ethyl acetate was added, the reaction mixture was washed with water and then dried, followed by solvent removal by distillation, to yield the title compound as colorless crystals (1.83 g).

Melting point: 154°–156° C. (recrystallized from ethyl acetate-ethyl ether)

Reference Example 61

1-Amino-1,2,3,4-tetrahydro-6-oxo-11-phenyl-6H-benzo[b]quinolizine

Process 1

The compound (393 mg) obtained in Reference Example 60 was dissolved in DMF (2 ml). While stirring this solution with ice cooling, sodium hydride (60% in oil) (50 mg) was added, followed by stirring for 15 minutes. To this mixture was added ethyl iodide (0.15 ml), followed by stirring at room temperature for 2 hours, after which the solvent was distilled off. To the residue was added ethyl acetate, and the mixture was washed with water and then dried, after which the solvent was distilled off, to yield 2-(3- ethoxycarbonylpropyl)-4-phenyl-1(2H)-isoquinolinone-3-carboxylic acid ethyl ester as colorless crystals(390 mg).

Melting point: 98°–99° C. (recrystallized from ethyl acetate-isopropyl ether)

Process 2

The compound (6.75 g) obtained in Process 1 was dissolved in dry THF (150 ml). While stirring this solution at room temperature, sodium hydride (60% in oil) (1.50 g) was added. This mixture was heated under reflux for 1 hour. After the reaction mixture was concentrated, ethyl acetate was added to the concentrate, which was then washed successively with dilute hydrochloric acid, water and aqueous sodium hydrogen carbonate and then dried, after which the solvent was distilled off, to yield 2-ethoxycarbonyl-1,2,3,4-tetrahydro-1,6-dioxo-11-phenyl-6H-benzo[b]quinolizine as pale yellow crystals (5.25 g).

Melting point: 167°–169° C. (recrystallized from ethyl acetate) NMR (200 MHz, CDCl$_3$) ppm: 1.33 (3H, t, J=7 Hz), 2.67 (2H, t, J=6 Hz), 4.27 (4H, m), 7.06–7.55 (8H, m), 8.51 (1H, m), 12.04 (1H, s) [This product has an enol structure.]

Process 3

A mixture of the compound (2.0 g) obtained in Process 2, acetic acid (15 ml), concentrate hydrochloric acid (4 ml), ethanol (3 ml) and water (3 ml) was heated under reflux for 5 hours while stirring, followed by solvent removal by distillation. To the residue was added water, and the precipitated crystals were collected by filtration and then washed with water, ethanol and ether, to yield 1,2,3,4-tetrahydro-1,6-dioxo-11-phenyl-6H-benzo[b]quinolizine as yellow crystals (1.48 g).

Melting point: 223°–225° C. (recrystallized from ethyl acetate) NMR (200 MHz, CDCl$_3$) ppm: 2.27 (2H, m), 2.67 (2H, t, J=6.5 Hz), 4.37 (2H, m), 7.15–7.62 (8H, m), 8.55 (1H, m) Elemental analysis (for $C_{19}H_{15}NO_2$): Calculated: C, 78.87; H, 5.23; N, 4.84 Found: C, 78.65; H, 5.36; N, 4.88

Process 4

A mixture of the compound (1.16 g) obtained in Process 3, hydroxylamine hydrochloride (2.78 g), sodium acetate (3.28 g) and ethanol (50 ml) was heated under reflux for 4 hours, followed by solvent removal by distillation. To the residue was added water, and the precipitated colorless crystals were collected by filtration and then washed with water, ethanol and ether, to yield an oxime derivative as colorless crystals (1.18 g).

Melting point: 277°–279° C. (decomposed) (recrystallized from chloroformmethanol) NMR (200 MHz, CDCl$_3$) ppm: 2.04 (2H, m), 2.80 (2H, t, J=7.4 Hz), 2.23 (2H, m), 7.20–7.55 (8H, m), 8.52 (1H, m)

Process 5

To a suspension of the compound (500 mg) obtained in Process 4 in ethanol (20 ml) were added ammonium acetate (138 mg), zinc powder (520 mg) and 40% aqueous ammonia (10 ml), followed by heating under reflux for 5 hours. The precipitate was filtered off, and the filtrate was distilled to remove the solvent. After ethyl acetate was added, the residue was washed with water. The ethyl acetate layer was extracted with 2N HCl. The extract was alkalinized by addition of potassium carbonate and then extracted with ethyl acetate, washed with water and then dried, after which the solvent was distilled off, to yield the title compound as colorless crystals (205 mg).

Melting point: 183°–185° C. (recrystallized from ethyl acetate-ether) NMR (200 MHz, CDCl$_3$)ppm: 1.7–2.3 (4H, m), 4.13 (1H, t, J=3 Hz), 4.32 (2H, t, J=7 Hz), 6.96 (1H, m), 7.26–7.55 (7H,m), 8.49 (1H, m)

Reference Example 62

1,2,3,4-Tetrahydro-1-hydroxy-6-oxo-11-phenyl-6H -benzo[b]quinolizine

To a suspension of the compound (250 mg) obtained in process 3 of Reference Example 61 in methanol (15 ml) was added sodium borohydride (40 mg) at room temperature, followed by stirring for 1 hour. The reaction mixture was concentrated, and dilute hydrochloric acid was added to the concentrate, followed by extraction with ethyl acetate. The extract was washed with water and then dried, after which the solvent was distilled off, to yield the title compound as pale yellow crystals (235 mg).

Melting point: 220°–222° C. (recrystallized from ethyl acetate) NMR (200 MHz, CDCl$_3$) ppm:. 1.70–2.30 (4H, m), 4.10–4.45 (2H, m), 4.75 (1H, t, J=3.2 Hz), 6.99–7.03 (1H, m), 7.25–7.53 (7H, m), 8.49 (1H, m)

Reference Example 63

2-(3-Ethoxycarbonylpropyl)-6,7-dimethyl-4-phenyl-1 (2H)-isoquinolinone-3-carboxylic acid The compound obtained in Process 1 of Reference Example 29 and 4-amino-n-butyric acid ethyl ester were reacted and treated in the same manner as in Reference Example 60 to yield the title compound as a colorless oily substance. NMR (200 MHz, CDCl$_3$) ppm: 1.13 (3H, t, J=7.2 Hz), 2.16 (2H, m), 2.26 (3H, s), 2.39 (3H, s), 2.42 (2H, m), 3.97 (2H, q, J=7.2 Hz), 4.16 (2H, m), 6.92 (1H, s), 7.32–7.48 (5H, m), 8.23 (1H, s)

Reference Example 64

1-Amino-1,2,3,4-tetrahydro-6-oxo-11-phenyl-6H-benzo[b]quinolizine

The compound obtained in Reference Example 63 was reacted and treated in the same manner as in Process 1 through 5 of Reference Example 61 to yield the title compound. The intermediate compounds obtained in the respective process and their physico-chemical constants are given below.

Process 1

2-(3-Ethoxycarbonylpropyl)-6,7-dimethyl-4-phenyl-1(2H)-isoquinolinone- 3-carboxylic acid ethyl ester A colorless oily substance NMR (200 MHz, CDCl$_3$) ppm: 0.90 (3H, t, J=7.2 Hz), 1.25 (3H, t, J=7.2 Hz), 2.12 (2H, m), 2.26 (3H, s), 2.39 (2H, m), 2.40 (3H, s), 3.95–4.20 (6H, m), 6.95 (1H, s), 7.24–7.50 (8H, m), 8.25 (1H, s)

Process 2

2-Ethoxycarbonyl-1,2,3,4-tetrahydro-8,9-dimethyl-1,6-dioxo-11-phenyl- 6 H-benzo[b]quinolizine Melting point: 166°–168° C. (recrystallized from ethyl acetate)

Process 3

1,2,3,4-Tetrahydro-8,9-dimethyl-1,6-dioxo-11-phenyl-6H-benzo[b]quinolizine

Melting point: 203°–206° C. (recrystallized from ethyl acetate)

Process 4

1,2,3,4-Tetrahydro-1-hydroxyamino-8,9-dimethyl-1,6-dioxo-11-phenyl-6H-benzo[b]quinolizine Melting point: 247°–250° C. (decomposed) (recrystallized from ethanol)

Process 5

Title compound (recrystallized from ethyl acetate)

Melting point: 175°–177° C. (recrystallized from ethyl acetate)

Reference Example 65

1,2,3,4-Tetrahydro-1-hydroxy-8,9-dimethyl-6-oxo-11-phenyl-6H-benzo[b]quinolizine The compound obtained in Process 3 of Reference Example 64 was reacted (reduced) and treated in the same manner as in Reference Example 62 to yield the title compound as colorless crystals.

Melting point: 210°–212° C. (recrystallized from ethyl acetate)

Reference Example 66

1,2,3,4-Tetrahydro-1,6-dioxo-11-phenyl-6H-pyrazino[1,2b]isoquinoline

A mixture of 1-oxo-4-phenyl-1H-2-benzopyran-3-carboxylic acid (500 mg) and ethylenediamine (15 ml) was stirred at room temperature overnight. After evaporation of the solvent, concentrated hydrochloric acid (10 ml) and acetic acid (10 ml) were added to the residue. The mixture was heated under reflux for 48 hours. To the mixture was added water, and extracted with ethyl acetate. The extract was washed successively with water, aqueous sodium hydrogen carbonate and water, dried, and evaporated to yield the title compound as colorless crystals (115 mg).

Melting point: >300° C. (recrystallized from ethyl acetate)

Reference Example 67

1,2,3,4-Tetrahydro-6-oxo-11-phenyl-6H-pyrazino[1,2-b]isoquinoline

Process 1

1-Oxo-4-phenyl-1H-2-benzopyran-3-carboxylic acid (3.0 g) was subjected to reduction by a method similar to Reference Example 47 to yield 3-hydroxymethyl-1-oxo-4-phenyl-1H-2-benzopyran as colorless crystals (2.6 g).

Melting point: 109°–110° C. (recrystallized from ethyl acetate-hexane)

Process 2

The compound obtained in Process 1 (2.5 g) was oxidized with SO$_3$-pyridine complex in DMSO in the presence of triethylamine to yield 1-oxo-4-phenyl- 1H-2-benzopyran-3-carboxyaldehyde as colorless crystals (2.38 g).

Melting point: 179°–181° C. (recrystallized from ethyl acetate-THF)

Process 3

A mixture of the compound obtained in Process 2 (500 mg) and ethylenediamine (15 ml) was stirred at room temperature for 5 hours. After evaporation of the solvent, water was added to the residue, and the mixture was extracted with ethyl acetate. The extract was washed with water, dried, and evaporated. To the residue was added concentrated hydrochloric acid (5 ml) and the mixture was stirred at room temperature overnight. After neutralization, the mixture was extracted with ethyl acetate. The extract was washed with water, dried, and evaporated to yield 3,4-dihydro-6-oxo-11-phenyl- 6H-pyrazino[1,2-b]isoquinoline as color crystals (280 mg).

Melting point: 181°–183° C. (recrystallized from ethyl acetate)

Process 4

To a mixture of the compound obtained in Process 3 (260 mg), acetic acid (60 μl) and methanol (10 ml) was added sodium cyanoborohydride (120 mg), and the mixture was stirred for 80 minutes at room temperature. After evaporation of the solvent, aqueous sodium hydrogen carbonate was added to the residue, and the mixture was extracted with ethyl acetate. The extract was washed with water, dried, and evaporated to yield the title compound as colorless crystals (240 mg).

Melting point: 154°–156° C. (recrystallized from ethyl acetate)

Reference Example 68

1,2-Dihydro-3-mercaptomethyl-2-methyl-4-(2-methylphenyl)-1-oxoisoquinoline

A mixture of the compound obtained in Reference Example 54 (1.8 g), sodium hydrosulfide-methanol solution (2.73M) (3 ml), THF (25 ml), and methanol (10 ml) was stirred for 1 hour at room temperature. After evaporation of the solvent, dilute hydrochloric acid was added to the residue, and the mixture was extracted with ethyl acetate. The extract was washed with dilute hydrochloric acid and water, dried, and evaporated. The residue was subjected to silica gel column chromatography (ethyl acetate:hexane= 3:1) to yield the title compound as colorless crystals (503 mg).

Melting point: 184°–186° C. (recrystallized from ethyl acetate-isopropyl ether)

FORMULATION EXAMPLE

Tablets

Of the components given below, to the compound of Example 101, corn starch and lactose were added with aqueous hydroxypropylcellulose, and the mixture was kneaded, then dried and crushed to give granules.

To this was added magnesium stearate and, after admixing, the whole mixture was made up into tablets each weighing 200 mg on a rotary tableting machine.

| Composition per tablet: | |
| --- | --- |
| Compound of Example 101 | 50 mg |
| Lactose | 100 mg |
| Corn starch | 43.4 mg |
| Hydroxypropylcellulose | 6 mg |
| Magnesium stearate | 0.6 mg |
| Total | 200 mg |

We claim:
1. A compound represented by the general formula:

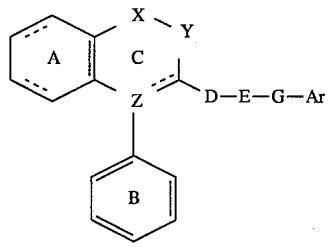

wherein ring A may be substituted by one to four substituents selected from the group consisting of (i) a halogen, (ii) an optionally halogenated $C_{1-6}$ alkyl, (iii) an optionally halogenated $C_{1-6}$ alkoxy, (iv) an optionally halogenated $C_{1-6}$ alkylthio, (v) a $C_{1-7}$ alkylamino, (vi) a $C_{1-3}$ acyloxy, (vii) a hydroxyl, (viii) a nitro (ix) a cyano, (x) an amino, (xi) a mono- or di-$C_{1-4}$ alkylamino, (xii) a pyrrolidino, (xiii) a piperidino, (xiv) a morpholino, (xv) a carboxyl, (xvi) a $C_{1-4}$ alkyl-carbonylamino, (xvii) a $C_{1-4}$ alkyl-carbonyl, (xx) a carbamoyl, (xxi) a mono- or di-$C_{1-4}$ alkylcarbamoyl and (xxii) a $C_{1-6}$ alkylsulfonyl;

ring B represents a benzene ring which may be substituted by one to four substituents selected from the group consisting of (i) a halogen, (ii) an optionally halogenated $C_{1-6}$ alkoxy, (iv) an optionally halogenated $C_{1-6}$ alkylthio, (v) a $C_{1-7}$ alkylamino, (vi) a $C_{1-3}$ acyloxy, (vii) a hydroxyl, (viii) a nitro, (ix) a cyano, (x) an amino, (xi) a mono- or di-$C_{1-4}$ alkylamino, (xii) a pyrrolidino, (xiii) a piperidino, (xiv) a morpholino, (xv) a carboxyl, (xvi) a $C_{1-4}$ alkyl-carbonylamino, (xvii) a $C_{1-4}$ alkyl-carbonyl, (xx) a carbamoyl, (xxi) a mono- or di-$C_{1-4}$ alkylcarbamoyl and (xxii) a $C_{1-6}$ alkylsulfonyl;

—X—Y— represents —O—CO— or —CO—O—;

$\equiv$ represents one of a single and double bond;

(1) when $\equiv$ adjacent to Z is a single bond, Z represents $CR^4$ ($R^4$ represents a hydrogen atom, hydroxyl group or a $C_{1-6}$ alkyl, $C_{2-6}$ alkenyl, $C_{2-6}$ alkynyl, $C_{3-8}$ cycloalkyl or $C_{6-14}$ aryl group which may be substituted by one to four substituents selected from the group consisting of (i) a halogen, (ii) a $C_{3-6}$ cycloalkyl, (iii) a $C_{6-10}$ aryl, (iv) an amino which may have a substituent selected from $C_{1-4}$ alkyl, a $C_{2-4}$ alkenyl, $C_{3-6}$ cycloalkyl or $C_{6-10}$ aryl, (v) a hydroxyl, (vi) a $C_{1-4}$ alkoxy which may have one to three halogen atoms, (vii) a $C_{1-4}$ acyl, (viii) a $C_{1-4}$ alkyl or a $C_{7-11}$ aralkyl, (ix) a cyano, (x) a carboxyl which may be protected by a $C_{1-4}$ alkyl or a $C_{7-11}$ aralkyl, (xi) a carbamoyl, (xii) a mercapto, (xiii) a $C_{1-4}$ alkylthio, (xiv) a sulfo and (xv) a $C_{1-4}$ alkylsulfonyl) , or (2 ) when $\equiv$ is adjacent to Z is a double bond, Z represents a carbon atom;

D represents a $C_{1-3}$ alkylene group which may be substituted by an oxo group or a thioxo group;

E represents a —$NR^5$— ($R^5$ represents a hydrogen atom or a $C_{1-6}$ alkyl, $C_{2-6}$ alkenyl, $C_{2-6}$ alkynyl, $C_{3-8}$ cycloalkyl or $C_{6-14}$ aryl group which may be substituted by one to four substituents selected from the group consisting of (i) a halogen, (ii) a $C_{3-6}$ cycloalkyl, (iii) a $C_{6-10}$ aryl, (iv) an amino which may have a substituent selected from $C_{1-4}$ alkyl, a $C_{2-4}$ alkenyl, $C_{3-6}$ cycloalkyl or $C_{6-10}$ aryl, (v) a hydroxyl, (vi) a $C_{1-4}$ alkoxy which may have one to three halogen atoms, (vii) a $C_{1-4}$ acyl, (viii) a $C_{1-4}$ acyloxy, (ix) a cyano, (x) a carboxyl which may be protected by a $C_{1-4}$ acyloxy, (xi) a carbamoyl, (xii) a mercapto, (xiii) a $C_{1-4}$ alkylthio, (xiv) a sulfo and (xv) a $C_{1-4}$ alkylsulfonyl), —O— or —$S(O)_n$— (n is 0, 1 or 2)

G represents a bond or a $C_{1-3}$ group;

Ar represents a $C_{6-10}$ aryl group which may be substituted by one to five substituents selected from the group consisting of (i) a $C_{1-4}$ alkyl which may be substituted by one to three halogen atoms, (ii) a $C_{1-4}$ alkyl substituted by an amino, (iii) a $C_{1-4}$ alkyl substituted by a mono- or di-$C_{1-4}$ alkylamino, (iv) a $C_{1-4}$ alkyl substituted by a carboxyl, (v) a $C_{1-4}$ alkyl substituted by a $C_{1-4}$ alkoxycarbonyl, (vi) a $C_{1-4}$2 alkyl substituted by a hydroxyl, (vii) a $C_{1-4}$ alkyl substituted by a $C_{1-4}$ alkoxycarbonyl, (viii) a $C_{3-6}$ cycloalkyl, (ix) a halogen, (x) a nitro, (xi) a cyano, (xii) a hydroxyl, (xiii) a $C_{1-4}$ alkoxy which may be substituted by one to three halogen atoms, (xiv) a $C_{1-4}$ alkylthio which may be substituted by one to three halogen atoms, (xv) an amino, (xvi) a mono- or di-$C_{1-4}$ alkylamino, (xvii) a pyrrolidino, (xviii) a piperidino, (xix) a morpholino, (xx) a $C_{1-4}$ alkylcarbonylamino, (xxi) an aminocarbonyloxy, (xxii) a mono- or di-$C_{1-4}$ alkylaminocarbonyloxy, (xxiii) $C_{1-4}$ alkylsulfonylamino, (xxiv) a $C_{1-4}$ alkoxy-carbonyl, (xxv) a benzyloxycarbonyl, (xxvi) a carboxyl, (xxvii) a $C_{1-6}$ alkylcarbonyl, (xxviii) a $C_{3-6}$ cycloalkyl-carbonyl, (xxix) a carbamoyl, (xxx) a mono- or di-$C_{1-4}$ alkylcarbamoyl, (xxxii) a $C_{1-6}$ alkylsulfonyl and (xxxiii) a furyl, thienyl, oxazolyl, isolxazolyl, thiazolyl, isothiazolyl, imidazolyl, pyrazolyl, 1,2,3-oxadiazolyl, 1,2-4-oxadiazolyl, 1,3-4-oxadiazolyl, furazanyl, 1,2,3-thiadiazolyl, 1,2,4-thiadiazolyl 1,3,4-thiadiazolyl, 1,2,3-triazolyl, 1,2,4-triazolyl, tetrazolyl, pyridyl, pyridazinyl, pyrimidinyl, pyrazinyl or triazinyl which may be substituted by one to three substituents selected from the group consisting of a $C_{1-4}$ alkyl which may have one to three halogen atoms, a $C_{3-6}$ cycloalkyl, a halogen, a hydroxyl, a $C_{1-4}$ alkoxy which may have one to three halogen atoms, a $C_{1-4}$ alkylthio which may have one to three halogen atoms, an amino, a mono- or di-$C_{1-4}$ alkylamino, a $C_{1-4}$ alkoxy-carbonyl, a carboxyl and a $C_{1-6}$ alkyl-carbonyl; or a pharmaceutically acceptable salt thereof, provided that when D represents —CO— and E represents —NR$^5$—, either G represents a $C_{1-3}$ alkylene group and AR represents a substituted aryl group, or G represents a bond and R$^5$ represents a hydrocarbon group.

2. A composition for inhibiting acyl-CoA: cholesterol acyl transferase which comprises an effective amount of a compound of the formula:

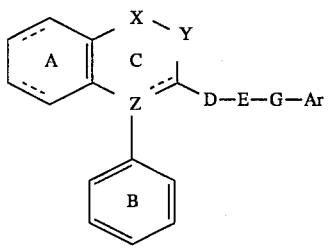

wherein all symbols are, the same meanings as defined in claim 1, or a pharmaceutically acceptable salt and physiologically acceptable carrier.

3. A compound as claimed in claim 1, which is the general formula:

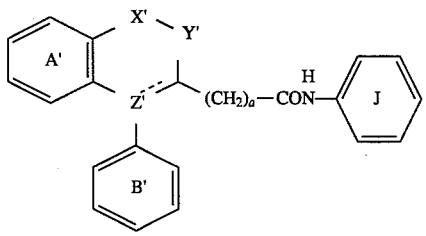

wherein rings A', B' and J independently represent a benzene ring which may be substituted by one to four substituents selected from the group consisting of (i) a halogen, (ii) an optionally halogenated $C_{1-6}$ alkyl group, (iii) a $C_{1-6}$ alkoxy group, (iv) a hydroxyl group, (v) an amino group which may be substituted by a $C_{1-4}$ alkyl group or (vi) a $C_{1-3}$ acyloxy group;

—X'—Y'— represents —O—CO— or —CO—O; ⇌ represents one of a single and double bond;

(a) when ⇌ is a single bond, Z' represents —CR$^{4a}$— (R$^{4a}$ represents a hydrogen atom, a $C_{1-6}$ alkyl, $C_{2-6}$ alkenyl, $C_{2-6}$ alkynyl, $C_{3-8}$ cycloalkyl or $C_{6-14}$ aryl group which may be substituted by one to four substituents selected from the group consisting of (i) a halogen, (ii) a $C_{3-6}$ cycloalkyl, (iii) a $C_{6-10}$ aryl, (iv) an amino which may have a $C_{1-4}$ alkyl, $C_{2-4}$ alkenyl, $C_{3-6}$ cycloalkyl or $C_{6-10}$ aryl, (v) a hydroxyl, (vi) a $C_{1-4}$ alkoxy which may have one to three halogen atoms, (vii) a $C_{1-4}$ acyl, (viii) a $C_{1-4}$ acyloxy, (ix) a cyano, (x) a carboxyl which may be protected by a $C_{1-4}$ alkyl or a $C_{7-11}$ aralkyl, (xi) a carbamoyl, (xii) a mercapto, (xiii) a $C_{1-4}$ alkylthio, (xiv) a sulfo and (xv) a $C_{1-4}$ alkylsulfonyl), or (b) when ⇌ is a double bond, Z represents a carbon atom;

α represents 0, 1 or 2, with proviso that when —X'Y'— is —O—CO—,

α represents 1 or 2, or a pharmaceutically acceptable salt thereof.

4. A composition for inhibiting acyl-CoA: cholesterol acyl transferase which comprises an effective amount of the compound of claim 3 or a pharmaceutically acceptable salt therefore and a physiologically acceptable carrier therefore.

5. A compound of claim 1 which is 6-chloro-N-(2,6-diethoxyphenyl)- 4-(2-methylphenyl)-2-oxo-2H-1-benzopyran-3-acetamide or a pharmaceutically acceptable salt thereof.

6. A compound as claimed in claim 1, wherein the ring A and B respectively represent a ring which may be substituted with one to four substituents selected from the group consisting of (i) a halogen, (ii) an optionally halogenated $C_{1-4}$ alkyl, (iii) an optionally halogenated $C_{1-4}$ alkoxy, (iv) an optionally halogenated $C_{1-4}$ alkylthio, (v) a $C_{1-3}$ acyloxy, (vi) a hydroxyl, (vii) an amino, (viii) a mono- or di-$C_{1-4}$ alkylamino, (ix) a carboxyl and (x) a $C_{1-4}$ alkoxy-carbonyl.

7. A compound as claimed in claim 1, wherein the ring A and B respectively represent a ring which may be substituted by one to four substituents selected from the group consisting of (i) a halogen, (ii) an optionally halogenated $C_{1-4}$ alkyl and (iii) an optionally halogenated $C_{1-4}$ alkoxy.

8. A compound as claimed in claim 1, wherein the ring A represents an unsubstituted ring.

9. A compound as claimed in claim 1, wherein the ring B represents an unsubstituted benzene ring.

10. A compound as claimed in claim 1, wherein —X—Y— represents —O—CO—.

11. A compound as claimed in claim 1, wherein —X—Y— represents —CO—O—.

12. A compound as claimed in claim 1, wherein ⇌ on the ring C represents a single bond; and Z represents a —CR$^4$— wherein R$^4$ represents the same meaning as defined in claim 1.

13. A compound as claimed in claim 1, wherein ⇌ on the ring C represents a double bond; and Z represents a carbon atom.

14. A compound as claimed in claim 1, wherein D represents a $C_{1-3}$ alkylene group which may be substituted by an oxo group.

15. A compound as claimed in claim 1, wherein D represents —CO—.

16. A compound as claimed in claim 1, wherein D represents —CH$_2$CO— or —CH$_2$CH$_2$CO—.

17. A compound as claimed in claim 1, wherein D represents —CH$_2$— or —CH$_2$CH$_2$—.

18. A compound as claimed in claim 1, wherein E represents —NR$^5$— wherein R$^5$ represents the same meaning as defined in claim 1.

19. A compound as claimed in claim 1, wherein E represents —O—.

20. A compound as claimed in claim 1, wherein E represents —S— or —SO—.

21. A compound as claimed in claim 1, wherein G represents a bond.

22. A compound as claimed in claim 1, wherein G represents a $C_{1-3}$ alkylene group.

23. A compound as claimed in claim 1, wherein D represents —CO—; E represents —NR$^5$— wherein R$^5$ represent the same meaning as defined in claim 1 and G represents —CH$_2$— or —CH$_2$CH$_2$—.

24. A compound as claimed in claim 1, wherein D represents —CO—; E represents —NR$^5$— wherein R$^5$ represent the same meaning as defined in claim 1; and G represents a bond.

25. A compound as claimed in claim 1, wherein D represents —CH$_2$CO— or —CH$_2$CH$_2$CO—; E represents —NR$^5$— wherein R$^5$ represent the same meaning as defined in claim 1; and G represents a bond.

26. A compound as claimed in claim 1, wherein D represents —CH$_2$CO— or —CH$_2$CH$_2$CO—; E represents —NR$^5$— wherein R$^5$ represent the same meaning as defined in claim 1; and G represents —CH$_2$— or —CH$_2$CH$_2$—.

27. A compound as claimed in claim 1, wherein D represents —CH$_2$— or —CH$_2$CH$_2$—; E represents —O—; and G represents —CH$_2$— or —CH$_2$CH$_2$—.

28. A compound as claimed in claim 1, wherein D represents —CH$_2$— or —CH$_2$CH$_2$—; E represents —NR$^5$— wherein R$^5$ represent the same meaning as defined in claim 1; and G represents —CH$_2$— or —CH$_2$CH$_2$—.

29. A compound as claimed in claim 1, wherein D represents —CH$_2$— or —CH$_2$CH$_2$—; E represents —S— or —SO—; and G represents —CH$_2$— or —CH$_2$CH$_2$—.

30. A compound as claimed in claim 1, wherein R$^1$ represents a $C_{1-4}$ alkyl group which may be substituted by a substituent selected from the group consisting of (i) a mono-, di- or tri-$C_{1-4}$ alkyl amino group, (ii) a $C_{1-4}$ alkoxy-carbonyl group, (iii) a carbamoyl group and (iv) a carboxyl group.

31. A compound as claimed in claim 1, wherein R$^1$ represents a hydrogen atom.

32. A compound as claimed in claim 1, wherein R$^2$ and R$^{2a}$ respectively represent a hydrogen atom.

33. A compound as claimed in claim 1, wherein R$^3$ represents a hydrogen atom.

34. A compound as claimed in claim 1, wherein R$^3$ represents a halogen atom, a $C_{1-4}$ alkyl group, $C_{1-4}$ alkoxy group, a $C_{1-4}$ alkylthio group or a mono- or di-$C_{1-4}$ alkyl amino group.

35. A compound as claimed in claim 1, wherein R$^3$ represents a halogen atom or a mono-$C_{1-4}$ alkylamino group.

36. A compound as claimed in claim 1, wherein R$^4$ represents a $C_{1-4}$ alkyl group, a hydroxyl group or a halogen atom.

37. A compound as claimed in claim 1, wherein R$^4$ represents a hydrogen atom.

38. A compound as claimed in claim 1, wherein R$^5$ represents a hydrogen atom.

39. A compound as claimed in claim 1, wherein R$^5$ represents a $C_{1-4}$ alkyl group which may be substituted by one or two substituents selected from the group consisting of a hydroxyl group, a $C_{1-4}$ alkoxy group, an amino group, a mono- or di-$C_{1-4}$ alkylamino group, a $C_{1-4}$ alkoxy-carbonyl group, a carboxyl group, a carbamoyl group and a phenyl group.

40. A compound as claimed in claim 1, wherein Ar represents a $C_{6-10}$ aryl group which may be substituted by one to three substituents selected from the group consisting of (i) an optionally halogenated $C_{1-4}$ alkyl, (ii) a halogen, (iii) a nitro, (iv) a hydroxyl, (v) an optionally halogenated $C_{1-4}$ alkoxy, (vi) an amino, (vii) a mono- or di-$C_{1-4}$ alkylamino, (viii) a $C_{1-4}$ alkoxy-carbonyl, (ix) a carboxyl and (x) a carbamoyl.

41. A compound as claimed in claim 1, wherein Ar represents a phenyl group which may be substituted by one to three substituents selected from the group consisting of (i) an optionally halogenated $C_{1-4}$ alkyl, (ii) a halogen, (iii) an optionally halogenated $C_{1-4}$ alkoxy.

42. A composition for lowering cholesterol in blood which comprises an effective amount of a compound as claimed in claim 2, or a pharmaceutically acceptable salt and a physiologically acceptable carrier.

43. Method for inhibiting acyl-CoA: cholesterol transferase in mammals which comprises administrating to a subject in need an effective amount of a composition as claimed in claim 2 or a pharmaceutically acceptable salt and a physiologically acceptable carrier.

44. A compound as claimed in claim 1, wherein ring A represents a benzene ring which may be substituted by a halogen atom;

ring B represents a benzene ring which may be substituted by a $C_{1-4}$ alkyl group or a halogen atom;

—X—Y— represents —CO—O— or —O—CO—;

Z represents a carbon atom;

╌╌╌ represents a double bond;

—D—E—G— represents —CON(CH$_3$)—CH$_2$—; and

Ar represents a phenyl group substituted by two optionally halogenated $C_{1-4}$ alkyl groups.

45. A compound as claimed in claim 1, wherein ring A represents a benzene ring which may be substituted by one or two halogen atom(s) or $C_{1-4}$ alkyl group(s);

ring B represents a benzene ring which may be substituted by one to three $C_{1-4}$ alkyl group(s), $C_{1-4}$ alkoxy group(s) or a halogen atom(s);

—X—Y— represents —CO—O— or —O—CO—;

Z represents a carbon atom;

╌╌╌ represents a double bond;

—D—E—G— represents —CON(CH$_3$)—CH$_2$—; and

Ar represents a phenyl group substituted by two optionally halogenated $C_{1-4}$ alkyl groups.

46. A compound as claimed in claim 1, wherein ring A represents a benzene ring which may be substituted by one or two halogen atom(s) or $C_{1-4}$ alkyl group(s);

ring B represents a benzene ring which may be substituted by one to three $C_{1-4}$ alkyl group(s) or halogen atom(s);

—X—Y— represents —CO—O— or —O—CO—;

Z represents a carbon atom;

╌╌╌ represents a single bond or a double bond;

—D—E—G— represents —CH$_2$—CONH—; and

Ar represents a phenyl group substituted by one to three optionally halogenated $C_{1-4}$ alkyl group(s), $C_{1-4}$ alkoxy group(s) or halogen atom(s).

47. A compound as claimed in claim 3, wherein the ring A' is a benzene ring which may be substituted by one to four substituents selected from the group consisting of a halogen, a $C_{1-4}$ alkyl group, a $C_{1-4}$ alkoxy group and a halogeno $C_{1-4}$ alkyl group.

48. A compound as claimed in claim 3, wherein the ring A' is a represented by the formula:

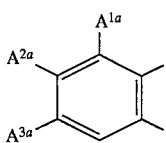

wherein $A^{1a}$, $A^{2a}$ and $A^{3a}$, independently represent a hydrogen, a halogen, a $C_{1-4}$ alkyl group, a $C_{1-4}$ alkoxy group or a halogeno-$C_{1-4}$ alkyl group.

49. A compound as claimed in claim 3, wherein the ring B' is a benzene ring which may be substituted by one to four substituents selected from the group consisting of a halogen, a $C_{1-4}$ alkyl group and a $C_{1-4}$ alkoxy group.

50. A compound as claimed in claim 3, wherein the ring B' is represented by the formula:

wherein $B^{1b}$, $B^{2b}$ and $B^{3b}$, independently represent hydrogen, a halogen, a $C_{1-4}$ alkyl group or a $C_{1-4}$ alkoxy group.

51. A compound as claimed in claim 3, wherein the ring J is a benzene ring which may be substituted by one to four substituents selected from the group consisting of a halogen, a $C_{1-4}$ alkyl group, a $C_{1-4}$ alkoxy group, a di-$C_{1-4}$ alkylamino group, a $C_{1-3}$ acyloxy group and a hydroxyl group.

52. A compound as claimed in claim 3, wherein the ring J is represented by the formula:

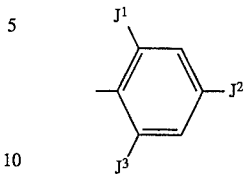

wherein $J^1$, $J^2$ and $J^3$, independently represent a hydrogen, a halogen, a $C_{1-4}$ alkyl group, a $C_{1-4}$ alkoxy group or a di-$C_{1-4}$ alkylamino group, or by the formula:

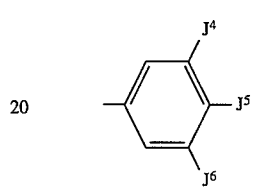

wherein $J^4$, $J^5$ and $J^6$, independently represent hydrogen, a $C_{1-4}$ alkyl group, a $C_{1-3}$ acyloxy group or a hydroxyl group.

53. The compound as claimed in claim 3, wherein $\alpha$ is 1.

54. A composition for lowering cholesterol in blood which comprises an effective amount of a compound as claimed in claim 4, or a pharmaceutically acceptable salt and a physiologically acceptable carrier.

* * * * *

UNITED STATES PATENT AND TRADEMARK OFFICE
CERTIFICATE OF CORRECTION

PATENT NO. : 5,482,967
DATED : Jan. 9, 1996
INVENTOR(S) : NATSUGARI et al.

It is certified that error appears in the above-indentified patent and that said Letters Patent is hereby corrected as shown below:

In the abstract, lines 3 and 4, the compound "6-Chloro-N-(2,6-diethoxyphenyl)-4-(2-methylphenyl-2-oxo-2H-1-benzopyran-3-acetamide" should read
--6-Chloro-N-(2,6-diethoxyphenyl)-4-(2-methylphenyl)-2-oxo-2H-1-benzopyran-3-acetamide--.

Signed and Sealed this

Twenty-seventh Day of May, 1997

Attest:

BRUCE LEHMAN

*Attesting Officer*　　*Commissioner of Patents and Trademarks*